US010767211B2

(12) United States Patent
Ichiyanagi et al.

(10) Patent No.: US 10,767,211 B2
(45) Date of Patent: Sep. 8, 2020

(54) MODIFIED AMADORIASE REACTING WITH FRUCTOSYL HEXAPEPTIDE

(71) Applicant: KIKKOMAN CORPORATION, Noda-shi, Chiba (JP)

(72) Inventors: Atsushi Ichiyanagi, Noda (JP); Yosuke Masakari, Noda (JP)

(73) Assignee: Kikkoman Corporation, Chiba (JP)

( * ) Notice: Subject to any disclaimer, the term of this patent is extended or adjusted under 35 U.S.C. 154(b) by 0 days.

(21) Appl. No.: 14/396,855

(22) PCT Filed: Apr. 26, 2013

(86) PCT No.: PCT/JP2013/062508

§ 371 (c)(1),
(2) Date: Oct. 24, 2014

(87) PCT Pub. No.: WO2013/162035

PCT Pub. Date: Oct. 31, 2013

(65) Prior Publication Data

US 2015/0118700 A1 Apr. 30, 2015

(30) Foreign Application Priority Data

Apr. 27, 2012 (JP) ................................ 2012-102771

(51) Int. Cl.
*C12N 9/06* (2006.01)
*C12Q 1/26* (2006.01)
*G01N 33/72* (2006.01)

(52) U.S. Cl.
CPC ............ *C12Q 1/26* (2013.01); *C12N 9/0032* (2013.01); *G01N 33/723* (2013.01); *G01N 2333/90672* (2013.01)

(58) Field of Classification Search
CPC ................................ C12N 9/0032; C12N 9/06
USPC ........................................................ 435/183
See application file for complete search history.

(56) References Cited

U.S. PATENT DOCUMENTS

| | | | |
|---|---|---|---|
| 5,370,990 A | 12/1994 | Staniford et al. | |
| 6,767,701 B1 * | 7/2004 | Vind ........................ | C12N 9/20 435/183 |
| 7,070,948 B1 | 7/2006 | Sakaue et al. | |
| 8,497,083 B2 * | 7/2013 | Ikebukuro ............ | C12N 9/0022 204/403.14 |
| 9,062,286 B2 * | 6/2015 | Ichiyanagi ........... | C12N 9/0032 |
| 2006/0240501 A1 | 10/2006 | Ebinuma | |
| 2007/0037243 A1 | 2/2007 | Hirokawa et al. | |
| 2008/0113381 A1 | 5/2008 | Matsuoka et al. | |
| 2008/0233605 A1 | 9/2008 | Taniguchi et al. | |
| 2009/0239239 A1 | 9/2009 | Hirokawa et al. | |
| 2011/0003361 A1 | 1/2011 | Kurosawa et al. | |
| 2011/0195444 A1 | 8/2011 | Hirao et al. | |
| 2014/0234886 A1 | 8/2014 | Aisaka et al. | |

FOREIGN PATENT DOCUMENTS

| | | |
|---|---|---|
| JP | 05-033997 B2 | 5/1993 |
| JP | 11-127895 A | 5/1999 |
| JP | 2001-095598 A | 4/2001 |
| JP | 2003-235585 A | 8/2003 |
| JP | 2004-275013 A | 10/2004 |
| JP | 2004-275063 A | 10/2004 |
| JP | 2005-110657 A | 4/2005 |
| JP | 2010-035469 A | 2/2010 |
| JP | 2010-057474 A | 3/2010 |
| JP | 2011-229526 A | 11/2011 |
| WO | WO 97/13872 A1 | 4/1997 |
| WO | WO 2004/038034 A1 | 5/2004 |
| WO | WO 2004/104203 A1 | 12/2004 |
| WO | WO 2005/049857 A1 | 6/2005 |
| WO | WO 2007/125779 A1 | 11/2007 |
| WO | WO 2008/108385 A1 | 9/2008 |
| WO | WO 2010/041419 A1 | 4/2010 |
| WO | WO 2010/041715 A1 | 4/2010 |
| WO | WO 2011/015325 A1 | 2/2011 |
| WO | WO 2011/015326 A2 | 2/2011 |

OTHER PUBLICATIONS

Miura et al., Biotechnol. Lett., 1895-1900, 2006.*
Ferri et al., "Cloning and Expression of Fructosyl-amine Oxidase from Marine Yeast *Pichia* Species N1-1," Mar. Biotechnol., 2004, 6:625-632.
Ferri et al., "Isolation and characterization of a fructosyl-amine oxidase from an *Arthrobacter* sp.," Biotechnology Letters, 2005, 27:27-32.
Ferri et al., "Engineering Fructosyl Peptide Oxidase to Improve Activity Toward the Fructosyl Hexapeptide Standard for HbA1c Measurement," Mol. Biotechnol., 2013, 54:939-943.
Fujiwara et al., "Alteration of Substrate Specificity of Fructosyl-Amino Acid Oxidase from *Ulocladium* sp. JS-103," Journal of Bioscience and Bioengineering, 2006, 102(3):241-243.
Fujiwara et al., "Alteration of substrate specificity of fructosyl-amino acid oxidase from *Fusarium oxysporum*," Appl. Microbiol. Biotechnol., 2007, 74:813-819.
Hirokawa et al., "Recombinant *Agrobacterium* AgaE-like Protein with Fructosyl Amino Acid Oxidase Activity," Biosci. Biotechnol. Biochem., 2002, 66(11):2323-2329.

(Continued)

*Primary Examiner* — Maryam Monshipouri
(74) *Attorney, Agent, or Firm* — Foley & Lardner LLP

(57) ABSTRACT

This invention provides an amadoriase having high reactivity with α-fructosyl hexapeptide (αF6P) derived from the β-chain amino terminus of glycated hemoglobin (HbAlc), which enables satisfactory quantification of αF6P cleaved from HbAlc. A novel amadoriase is derived from the amadoriase of the genus *Coniochaeta* by substitution of one or more amino acids at positions selected from the group consisting of positions 62, 63, 102, 106, 110, 113, 355, and 419. Such amadoriase enables rapid, simple, accurate, and satisfactory quantification of αF6P cleaved from HbAlc. With the use of such amadoriase, a method for measurement of HbAlc by an enzymatic method and a kit for measurement of HbAlc that are based on the same principle as used in the conventional standard method and excellent in terms of the relevance with the standard method.

4 Claims, 24 Drawing Sheets

Specification includes a Sequence Listing.

(56) References Cited

OTHER PUBLICATIONS

Hirokawa et al., "Molecular cloning and expression of novel fructosyl peptide oxidases and their application for the measurement of glycated protein," Biochemical and Biophysical Research Communications, 2003, 311:104-111.
Jeppsson et al., "Approved IFCC Reference Method for the Measurement of $HbA_{1c}$ in Human Blood," Clin. Chem. Lab. Med., 2002, 40(1):78-89.
Kim et al., "Motif-Based Search for a Novel Fructosyl Peptide Oxidase from Genome Databases," Biotechnology and Bioengineering, Jun. 15, 2010, 106(3):358-366.
Sakaue et al., "Cloning and Expression of Fructosyl-amino Acid Oxidase Gene from *Corynebacterium* sp. 2-4-1 in *Escherichia coli*," Biosci. Biotechnol. Biochem., 2002, 66(6):1256-1261.
Yoshida et al., "Primary structures of fungal fructosyl amino acid oxidases and their application to the measurement of glycated proteins," Eur. J. Biochem., 1996, 242:499-505.
Office Action dated Aug. 6, 2019, in JP 2018-166687.

* cited by examiner

Fig. 1-1

```
Co   1  MTSNRADTRVIVVGGGGTIGSSTALHLVRSGYAPANITVLDTFEIPSAQS  50
Et   1  MAHSRASTKVVVVGGGGTIGSSTALHLIRSGYTPSNITVLDVYKTPSLQS  50
Py   1  MAASRAKTTVIVVGGGGTIGSSTALHLLRSGYTPSNITVLDTYPIPSLQS  50
Ar   1  MAASRKTTKVIVVGGGGTIGSSTALHLLRSGYTATNITVLDTYPIPSAQS  50
Cc   1  MAPSRANTSVIVVGGGGTIGSSTALHLVRSGYTPSNITVLDTYPIPSAQS  50
Nv   1  MTTPRKETTVLIIGGGGTIGSSTALHLLRAGYTPSNITVLDTYPIPSAQS  50
Cn   1  MPPSRASTKVIVIGGGGTLGSSTALHLLRAGYTPSNITVLDTYLIPSAQS  50
Pn   1  MAPSRANTSVIVVGGGGTIGSSTALHLVRSGYTPSNVTVLDAYPIPSSQS  50
An   1  MTP-RANTKIIVVGGGGTMGSSTALHLLRAGYTPSNITVLDTCPIPSAQS  49
En   1  MAP-RANTKIIVVGGGGTMGSSTALHLLRAGYTPSNITVLDTYPIPSAQS  49
Ul   1  MAPNRANISVIVVGGGGTIGSSTALHLVRSGYTPSNITVLDTYPIPSAQS  50
Pj   1  MAHSRESTKIVIVGGGGTMGSSTALHLIRSGYTPSNITVLDVYPIPSLQS  50

Co  51  AGHDLNKIMGIRLRNKVDLQMSLEARQMWKEDELFQPFFHNTGRMDCEHT  100
Et  51  AGHDLNKIMGIRLRNGPDLQLSLESLDMWQNDELFKPFFHQVGMIDCSSS  100
Py  51  AGNDLNKIMGIRLRNKVDLQLSLEAREMWREDELFRDFFHNTGRLDCAHG  100
Ar  51  AGNDLNKIMGIRLRNPVDKQLSLEAQDMWCHDELFKPYFHNTGRMDCEGT  100
Cc  51  AGNDLNKIMGIRLRNKVDLQLSLEARQMWREDDLFKEYFHNTGRLDCAHG  100
Nv  51  AGNDLNKIMGIRLRNKVDLQLSLEARDMWRNDALFRPFFHNTGRLDCESS  100
Cn  51  AGNDLNKIMGIRIRNPVDKQLSLEARDMWRNDEVFKPYFHNTGRLDCAHT  100
Pn  51  AGNDLNKIMGVSLRNPVDLQLALEARQMWNEDELFKKFFHNTGRLDCAHG  100
An  50  AGYDLNKIMSIRLRNKPDLQLSLEALDMWKNDPLFKPFFHNVGMIDVSST  99
En  50  AGYDLNKIFGIRLRNKPDLQLYLEALDMWKNDPLFKPFFHNVGQMDVSST  99
Ul  51  AGNDLNKIMGIRLRNKVDLQLSLEARQMWTEDDLFKEYFHKTGRLDCAHG  100
Pj  51  AGYDLNKIMSIRLRNGPDLQLSLEALDMWKNDPLFKPFFHNVGMLDCSSS  100
```

Fig. 1-3

```
Co  200  CIGVETADGTKYYADKVVLAAGAWSPTLVDLEDQCCSKAWVYAHIQLTPE  249
Et  200  CIGLETTDGTKYFADKVVLAAGAWSPTLVDLEDQCVSKAWVFAHIQLTPK  249
Py  198  CIGVETTDGTRYYADKVVLAAGAWSPALVDLEDQCVSKAWVYAHMQLTPK  247
Ar  200  CIGVETVDGTKYYGDKVVLAAGAWSPALVDLEEQCCSKAWVYAHMQLTPH  249
Cc  198  CIGVETVDGTRYYADKVVLAAGAWSPVLVDLEDQCVSKAWVYAHIQLTPE  247
Nv  200  CIGVETVDGTQYHADKVVLAAGAWSPALVDLEEQCCSKAWVYAHMQLTPE  249
Cn  200  AIGIETVDGTQYFADKVVLAAGAWSPTLVDLEGQCCSKAWVYAHMQLTPE  249
Pn  196  CIGVETVDGTRYYADKVVLAAGAWSPTLVELHEQCVSKAWVYGHIQLTPE  245
An  200  CIGVETVDGTKYYADKVVLAAGAWSSTLVDLEEQCVSKAWVFAHIQLTPA  249
En  200  CIGVETVDGTKYYADKVVLAAGAWSSTLVDLEEQCVSKAWVFAHIQLTPA  249
Ul  198  CVGVETVDGTRYYADKVVLAAGAWSPALVDLQDQCVSKAWVYAHIQLSPS  247
Pj  200  CSGVETVDGTKYFADKVVLAAGAWSSTLVDLEDQCVSKAWVFAHIQLTPQ  249

Co  250  EAAEYKGVPVVYNGEFGFFFEPDEFGVIKVCDEFPGFSRF-KEHQPYGAP  298
Et  250  EADAYKNVPVVYDGEYGFFFEPNEYGVIKVCDEFPGFSRF-KLHQPYGAA  298
Py  248  EAAAYKDTPVVYNGDLGFFFEPNEHGVIKVCDEFPGFTRF-KKHQPFGAR  296
Ar  250  EAAEYQGCPVVYHGDLGFFFEPNEHGVIKVCDEFPGFTRFLEQHQSYGAP  299
Cc  248  EAAEYKNVPVVYNGDVGFFFEPDEHGVIKVCDEFPGFTRF-KQHQPYGAK  296
Nv  250  EAAVYKGCPVVYHGDVGFFFEPNENGVIKVCDEFPGFTRF-KQHQPYGAP  298
Cn  250  EAAEYKECPVVYNSELGFFFEPNEKGVIKVCDEFPGFTRF-KQHQPYGAS  298
Pn  246  EAARYKNSPVVYNGDVGFFFEPNEHGVIKVCDEFPGFTRF-KMHQPFGAK  294
An  250  EAAAYKNTPVIYDGDYGFFFEPNENGIIKVCDEFPGFTHF-KMHQPYGSP  298
En  250  EAAAYKNTPVIYDGDYGFFIEPDENGIIKVCDEFPGFTHF-KMHQPYGSP  298
Ul  248  EAAEYKNVPVVYNGDVGFFFEPDEYGVIKVCDEFPGFTRF-KQHQPFGAS  296
Pj  250  ESAQYKDVPVVYDGDYGFFFEPNEHGVIKVCDEFPGFSRF-KLHQPYGAT  298
```

Fig. 1-4

| | | | |
|---|---|---|---|
| Co | 299 | SPKRISVPRSHAKHPTDTYPDASEVSIKKAIATFLPRFQDKELFNRALCW | 348 |
| Et | 299 | SPKMISVPRSHAKHPTDTYPDASEVTIRKAIARFLPEFKDKELFNRTMCW | 348 |
| Py | 297 | APKRISVPRSHAKHPTDTYPHASEASIKKAIAAFLPQFKDKELFNRAMCW | 346 |
| Ar | 300 | APTRVSVPRSHAKHPTDTYPDASEQSIRRAVAAFLPRFQSKELFNRAMCW | 349 |
| Cc | 297 | APKRISVPRSAAKHPTDTYPDASEKSIRKAIATFLPKFTEKELFNRHLCW | 346 |
| Nv | 299 | APKPVSVPRSHAKHPTDTYPDASEESIKRAVSTFLPRFKDKPLFNRALCW | 348 |
| Cn | 299 | STKHISFPRSHAKHPTDTIPDESDASIRRAISAFLPRFKEKELFNRALCW | 348 |
| Pn | 295 | APKRISVPRSHAKHPTDTIPDASDVSIRRAIATFMPQFKNKKMFNQAMCW | 344 |
| An | 299 | APKPISVPRSHAKHPTDTYPHASEVTIKKAINRFLPRFNDKELFNRAMCW | 348 |
| En | 299 | VPKLISVPRSHAKHPTDTYPHASEVTIKKAINRFLPRFNDKELFNRAMCW | 348 |
| Ul | 297 | APKRISVPRSAAKHPTDTYPDASEVSIRKAIATFLPKFTEKEVFNRHLCW | 346 |
| Pj | 299 | SPKLISVPRSHAKHPTDTYPDSSEETIRKAIARFMPRFKDKELFNRSMCW | 348 |

| | | | |
|---|---|---|---|
| Co | 349 | CTDTADAALLMCEHPKWKNFILATGDSGHSFKILPNVGKRVVELIEGRLP | 398 |
| Et | 349 | CTDTADANLLICEHPKWKNFILATGDSGHSFKLLPNIGKHVVELLEGSLS | 398 |
| Py | 347 | CTDTADAALLICEHPQWKNFMLATGDSGHSFKLLPNIGKHVVELIEGTLA | 396 |
| Ar | 350 | CTDTADAALLICEHPRWRNFILATGDSGHSFKLLPNIGKHVVELLEGRLA | 399 |
| Cc | 347 | CTDTADAALLMCEHPEWKNFVLATGDSGHTFKLLPNIGKHVVELLEGTLA | 396 |
| Nv | 349 | CTDTADSALLICEHPRWKNFILATGDSGHSFKLLPIIGKHVVELVEGRLA | 398 |
| Cn | 349 | CTDTADANLLICEHPKWKNFILATGDSGHSFKILPNIGKHVVELIEGTLA | 398 |
| Pn | 345 | CTDTADAALLICEHPEWKNFVLATGDSGHSFKLLPNIGKHVVELLEGTLA | 394 |
| An | 349 | CTDTADANLLVCEHPRWKGFYLATGDSGHSFKLLPNIGKHVVELLEERLE | 398 |
| En | 349 | CTDTADANLLVCEHPRWKGFYLATGDSGHSFKLLPNIGKHVVELLEGRLE | 398 |
| Ul | 347 | CTDTADAALLMCEHPEWKNFVLATGDSGHTFKLLPNIGKHVVELLEGTLA | 396 |
| Pj | 349 | CTDTADANLLICEHPKWKNFILATGDSGHSFKVLPNIGKHVVELIEGRLP | 398 |

Fig. 1-5

```
Co 399 EEMAYQWRWRPG-GDALKSRRAAPPKDLADMPGWKHDPKL---------- 437
Et 399 QEMAGAWRWRPG-GDALRSRRGAPAKDLAEMPGWKHDAHL---------- 437
Py 397 ADLAHAWRWRPGIGDALQSRRAAPAKDLADMPGWNHD-ESPRAKL----- 440
Ar 400 DDLAQAWRWRPGQGDALKSRRAAPAKDLADMPGWNHDGDSGNATSGTSSE 449
Cc 397 EDLAHAWRWRPGTGDALKSRRAAPAKDLADMPGWKHD-DVVKSKL----- 440
Nv 399 DDLAEAWRWRPGQGDARKSIRAAPAKDLADMPGWKHDQDSESR------- 441
Cn 399 EDLAESWRWRPGSGDPLISRRAAPARDLADLPGWNHDEPSDDDMDVKDVA 448
Pn 395 DDLAHAWRWRPGSGDALKSRRSAPAKDLADMPGWNHD--KPRANL----- 437
An 399 SVFKDAWRWRPGSGDALKSRRAAPAKDLADMPGWRNEAKM---------- 438
En 399 SVFKDAWRWRPGSGDALKSRRAAPAKDLADMPGWRNEAKM---------- 438
Ul 397 DDLAHAWRWRPGTGDALKSRRAARAKDLADMPGWNHDGEAPRAKL----- 441
Pj 399 QDLAGAWRWRPG-GDALKSKRSAPAKDLAEMPGWKHDAKL---------- 437

Co 437 ----------------------------- 437 (SEQ ID NO 1)
Et 437 ----------------------------- 437 (SEQ ID NO 145)
Py 440 ----------------------------- 440 (SEQ ID NO 113)
Ar 450 HKL-------------------------- 452 (SEQ ID NO 115)
Cc 440 ----------------------------- 440 (SEQ ID NO 117)
Nv 441 ----------------------------- 441 (SEQ ID NO 54)
Cn 449 VSLASVKIGENIGEKVVEDGARVGVKVLA 477 (SEQ ID NO 149)
Pn 437 ----------------------------- 437 (SEQ ID NO 38)
An 438 ----------------------------- 438 (SEQ ID NO 147)
En 438 ----------------------------- 438 (SEQ ID NO 119)
Ul 441 ----------------------------- 441 (SEQ ID NO 121)
Pj 437 ----------------------------- 437 (SEQ ID NO 123)
```

Fig. 2-2

```
Co  101  PEGIEDLKKQYQALHDAGAGLEKTHAWLDNEDEILSKMPLLQRDQIQGWK  150
Et  101  KEGIENLRRKYQTLLDAGIGLEKTNVWLESEDEILAKAPNFTREQVKGWK  150
Py  101  EKGINDLRQAYQTLLDANAGLEETNEWLDSEDEILARMPLLSREQIKGWK  150
Ar  101  EKGIAALKQQYQTLLDADVGLEKTTEWLDSEDAILAKMPLLERDQIKGWK  150
Cc  101  EEGLADLRQAYQALLDANAGLEETTEWLDSEDEILKKMPLLDREQIKGWK  150
Nv  101  AEGVEGLRREYQKLVEAGVGLEETHEWLDSEEAILEKAPLLQREEIEGWK  150
Cn  101  PESIASLRKSYEAILKAGSGLEKTHHWLSTEDEILARAPLLDRKQIKGWK  150
Pn  101  EKDIADLKSGYQALVDA--GLDATNEWLDSEDEILKRMPLLSRDQIKGWK  148
An  100  EEGIEGLRKKYQSLLDAGIGLEKTNFMLESEDEILAKAPHFTQEQIKGWK  149
En  100  EEGIKKLRMRYQSLLDAGIGLEKTNFLLESEDEILAKAPHFTREQIKGWK  149
Ul  101  EKGLADLKQAYQALLDANAGLEATTEWLDSEDKILEKMPLLNRDQIKGWK  150
Pj  101  QEGIASLRRKHQDLIDANIGLEKTNIWLESEDDILAKAPHFTREQIKGWK  150

Co  151  AIWSQDGGWLAAAKAINAIGQFLKERGVKFGFGGAGSFKQPLFD-DEGTT  199
Et  151  GLFCTDGGWLAAAKAINAIGIFLQDKGVKFGFGGAGTFQQPLFA-ADGKT  199
Py  151  AVFSRDGGWLAAGKAINAIGEYLRKEGVKFGFGGAGSFQQPLLA-EG--I  197
Ar  151  AIFSQDGGWLAAAKAINAIGEELKRQGVNFGFGGAGAFKKPLFA-PDGST  199
Cc  151  AVYSQDGGWLAAAKAINAIGEYLRAQGVKFGFGGAGSFKQPLLA-EG--V  197
Nv  151  AIWSEEGGWLAAAKAINAIGEELQRQGVRFGFGGAGSFKRPLFA-DDGTT  199
Cn  151  AIYSEDGGWLAAAKAINSIGQVLKEKGVTFGFGSAGSFKKPLFD-EDGTK  199
Pn  149  AIFSKDGGWLAAAKAINAVGEYLRDQGVRFGFYGAGSFKAPLLA-EG--V  195
An  150  GLFCGDGGWLAAAKAINAIGQFLKEQGVKFGFGGAGTFKKPLFADAHEKT  199
En  150  GLFCGDGGWLAAAKAINAIGQFLKEQGVKFGFGEAGTFKKPLFADADEKT  199
Ul  151  AVFSEDGGWLAAAKAINAIGRFLRDQGVKFGFGGAGSFKQPLLA-EG--V  197
Pj  151  GLFCGDGGWLAAAKAINAIGTFLKSQGVKFGFGSAGTFKRPLFA-PDGAT  199
```

Fig. 2-3

```
Co 200 CIGVETADGTKYYADKVVLAAGAWSPTLVDLEDQCCSKAWVYAHIQLTPE 249
Et 200 CIGLETTDGTKYFADKVVLAAGAWSPTLVDLEDQCVSKAWVFAHIQLTPK 249
Py 198 CIGVETTDGTRYYADKVVLAAGAWSPALVDLEDQCVSKAWVYAHMQLTPK 247
Ar 200 CIGVETVDGTKYYGDKVVLAAGAWSPALVDLEEQCCSKAWVYAHMQLTPH 249
Cc 198 CIGVETVDGTRYYADKVVLAAGAWSPVLVDLEDQCVSKAWVYAHIQLTPE 247
Nv 200 CIGVETVDGTQYHADKVVLAAGAWSPALVDLEEQCCSKAWVYAHMQLTPE 249
Cn 200 AIGIETVDGTQYFADKVVLAAGAWSPTLVDLEGQCCSKAWVYAHMQLTPE 249
Pn 196 CIGVETVDGTRYYADKVVLAAGAWSPTLVELHEQCVSKAWVYGHIQLTPE 245
An 200 CIGVETVDGTKYYADKVVLAAGAWSSTLVDLEEQCVSKAWVFAHIQLTPA 249
En 200 CIGVETVDGTKYYADKVVLAAGAWSSTLVDLEEQCVSKAWVFAHIQLTPA 249
Ul 198 CVGVETVDGTRYYADKVVLAAGAWSPALVDLQDQCVSKAWVYAHIQLSPS 247
Pj 200 CSGVETVDGTKYFADKVVLAAGAWSSTLVDLEDQCVSKAWVFAHIQLTPQ 249

Co 250 EAAEYKGVPVVYNGEFGFFFEPDEFGVIKVCDEFPGFSRF-KEHQPYGAP 298
Et 250 EADAYKNVPVVYDGEYGFFFEPNEYGVIKVCDEFPGFSRF-KLHQPYGAA 298
Py 248 EAAAYKDTPVVYNGDLGFFFEPNEHGVIKVCDEFPGFTRF-KKHQPFGAR 296
Ar 250 EAAEYQGCPVVYHGDLGFFFEPNEHGVIKVCDEFPGFTRFLEQHQSYGAP 299
Cc 248 EAAEYKNVPVVYNGDVGFFFEPDEHGVIKVCDEFPGFTRF-KQHQPYGAK 296
Nv 250 EAAVYKGCPVVYHGDVGFFFEPNENGVIKVCDEFPGFTRF-KQHQPYGAP 298
Cn 250 EAAEYKECPVVYNSELGFFFEPNEKGVIKVCDEFPGFTRF-KQHQPYGAS 298
Pn 246 EAARYKNSPVVYNGDVGFFFEPNEHGVIKVCDEFPGFTRF-KMHQPFGAK 294
An 250 EAAAYKNTPVIYDGDYGFFFEPNENGIIKVCDEFPGFTHF-KMHQPYGSP 298
En 250 EAAAYKNTPVIYDGDYGFFIEPDENGIIKVCDEFPGFTHF-KMHQPYGSP 298
Ul 248 EAAEYKNVPVVYNGDVGFFFEPDEYGVIKVCDEFPGFTRF-KQHQPFGAS 296
Pj 250 ESAQYKDVPVVYDGDYGFFFEPNEHGVIKVCDEFPGFSRF-KLHQPYGAT 298
```

Fig. 2-5

```
Co  399  EEMAYQWRWRPG-GDALKSRRAAPPKDLADMPGWKHDPKL----------  437
Et  399  QEMAGAWRWRPG-GDALRSRRGAPAKDLAEMPGWKHDAHL----------  437
Py  397  ADLAHAWRWRPGIGDALQSRRAAPAKDLADMPGWNHD-ESPRAKL-----  440
Ar  400  DDLAQAWRWRPGQGDALKSRRAAPAKDLADMPGWNHDGDSGNATSGTSSE  449
Cc  397  EDLAHAWRWRPGTGDALKSRRAAPAKDLADMPGWKHD-DVVKSKL-----  440
Nv  399  DDLAEAWRWRPGQGDARKSIRAAPAKDLADMPGWKHDQDSESR-------  441
Cn  399  EDLAESWRWRPGSGDPLISRRAAPARDLADLPGWNHDEPSDDDMDVKDVA  448
Pn  395  DDLAHAWRWRPGSGDALKSRRSAPAKDLADMPGWNHD--KPRANL-----  437
An  399  SVFKDAWRWRPGSGDALKSRRAAPAKDLADMPGWRNEAKM----------  438
En  399  SVFKDAWRWRPGSGDALKSRRAAPAKDLADMPGWRNEAKM----------  438
Ul  397  DDLAHAWRWRPGTGDALKSRRAARAKDLADMPGWNHDGEAPRAKL-----  441
Pj  399  QDLAGAWRWRPG-GDALKSKRSAPAKDLAEMPGWKHDAKL----------  437

Co  437  -----------------------------  437 (SEQ ID NO 1)
Et  437  -----------------------------  437 (SEQ ID NO 145)
Py  440  -----------------------------  440 (SEQ ID NO 113)
Ar  450  HKL--------------------------  452 (SEQ ID NO 115)
Cc  440  -----------------------------  440 (SEQ ID NO 117)
Nv  441  -----------------------------  441 (SEQ ID NO 54)
Cn  449  VSLASVKIGENIGEKVVEDGARVGVKVLA  477 (SEQ ID NO 149)
Pn  437  -----------------------------  437 (SEQ ID NO 38)
An  438  -----------------------------  438 (SEQ ID NO 147)
En  438  -----------------------------  438 (SEQ ID NO 119)
Ul  441  -----------------------------  441 (SEQ ID NO 121)
Pj  437  -----------------------------  437 (SEQ ID NO 123)
```

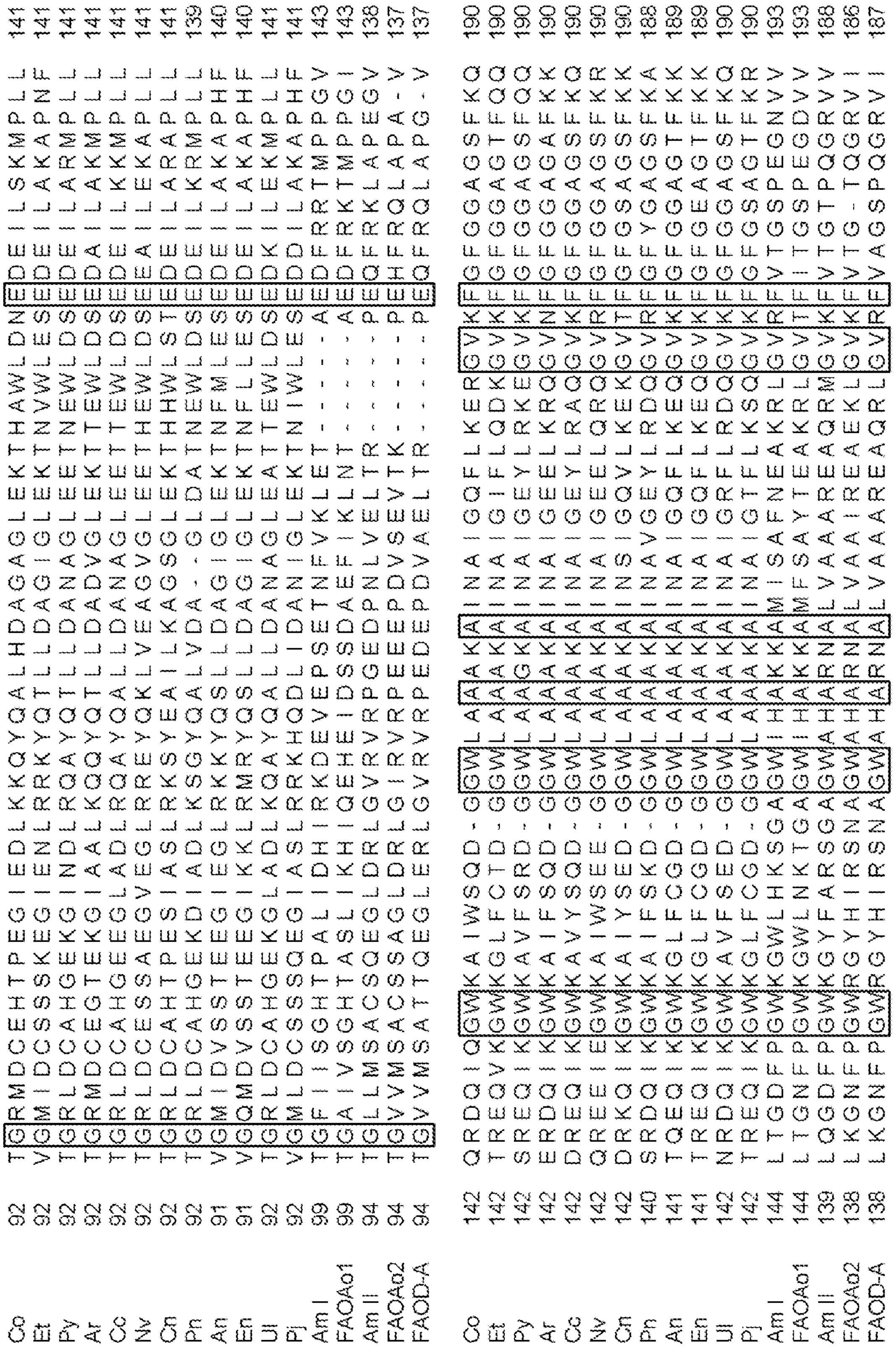

Fig. 3-2

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
Co | 92 | T G R M D C E H T P E G - - I E D L K K Q Y Q A L H D A G L E K T H A W L D N E D E I L S K M P L L | 141
Et | 92 | V G M I D C S S K E G - - I E N D L R R Q A A L L D A D V W L E K T N V W L E S E E D E I L A K A P N F | 141
Py | 92 | T G R L D C A H G E K G - - I A A L K R Q K Y Q T L L D A N A G L E K T T E W L D S E E D A I L L K K M P L L | 141
Ar | 92 | T G R M D C E G T E E G - - I A D L R R R E Y Q A Y Q T L L D A D V G L E K T H E W L D S E E D A I L A R A P L L | 141
Cc | 92 | T G R L D C E S S A E G - - I A S L R R K S Y E A L L D A N E W L D S E E D E I L A K A P L L | 141
Nv | 92 | T G R L D C A H P E S G - - I A D L R R R E Y Q A L V E K Y Q A L L D A N E W L D S E E D E I L A K R M P L L | 141
Cn | 92 | T G R L D C E S S A H G E K D - - I E G L R R K S Y Q A L L D A D V G L E K T H H W L S T E E D E I L A K A P H F | 141
Pn | 92 | V G M I D V S S T E E G - - I K K L R M R Y Q S L L D A N I G L E K T N F M L L E S E E D E I L A K A P H F | 139
An | 91 | V G Q M D V S S T E E G - - I K K L R M R Y Q S L L D A G - - G L D A I G L E E S E E D E I L A K A P L L | 140
En | 92 | T G R L D C A H G E K G - - I A S L K K L R M R Q A Y Q A L L D A N I G L E K T N F M L L E S E E D E I L A K A P H F | 140
Ui | 92 | V G M L D V S S T E E G - - I K K L R Q E H R - - - - - - - - - - L - - - - L - - - - L - - - L | 141
Pj | 99 | T G F - - I S G H T P A L - - I D H I R K D E V E P S E T N F V K L - - L V E L T R - - - - - - A E D F R K L A P A - V | 143
Aml | 99 | T G L L M S A C S S Q E G - - I A S L L I K H I Q E H F R - - - - L - - - - L - - - - L | 143
FAOAo1 | 94 | T G V V M S A C S S Q E G L A D L D R L G - - I R - - R R V K D E P S E T N F V K L | 138
AmII | 94 | T G V V M S A T T Q E G L E R L G V R P G E E E U R P - - - - L D V A E L T R - - - - - - A E Q F R Q L A P G - V | 137
FAOAo2 | 94 | T G V V M S A T T Q E G L E R L G V R P E D - - - - I R V R P E D - - - - - - - L V E L T R - - - - - - P E H F R K L A P A - V | 137
FAOD-A | 94 | T G V V M S A T T Q E G L E R L G V R P E D - - - - - - - - - - - - - - - - - - - - - - - - - P E Q F R Q L A P G - V | 137

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
Co | 142 | Q R D Q - I Q G W K A I W S Q D - Q G D - I K E R G V K F G F F G G A G S F K Q Q | 190
Et | 142 | T R E Q V K G W K G L F C T D - D V K G V V K F G F F G G A G S F Q Q Q | 190
Py | 142 | S R E Q - I K G W R D A V F S R D - D K G R A Q G V N F G F F G G A G S F K K K | 190
Ar | 142 | E R D D - I R E E Q A I F S Q D - D L R A Q G V R F G F F G G A G S F K K Q | 190
Cc | 142 | Q R E E - I R E E K G L F S Q D - D K R A Q G V K F G F F G G A G S F K K K | 190
Nv | 142 | D R K Q - I K G W K A V Y S Q D - D L R D Q G V K F G F F G G A G S F K K K | 190
Cn | 142 | S R D Q - I K G W K A I F S K D - D L K E R Q G V R F G F F G G A G S F K K A | 188
Pn | 140 | Q R E D - I E G W K K A I W S E E - D L K E K Q G V T F G F F G G A G S F K Q Q | 189
An | 141 | T R E Q - I K G W K A V F S E D - D L K R D Q G V R F G F F G G A G S F Q Q Q | 190
En | 141 | N R D Q - I K G W K G L F S K D - D L R D Q G V K F G F F G G A G S F K Q K | 190
Ui | 142 | T R E Q V K G W K G L F C G D - D L K S Q G V R L G F F G G E A G S F K K R | 190
Pj | 144 | L T G D F P G W L H K S G A G W - - H A K L G V T F G F Y G G S P E G D S F K A | 193
AmI | 144 | L T G N F P G W L N K T G A G W - - H A K R N V K F G F V T G S P Q G G T F N E N | 193
FAOAo1 | 139 | L Q G D F P G W K G Y F A R S G A G W A H A R L G M Q G V R F V T G - T Q G G R V V | 188
FAOAo2 | 138 | L K G N F P G W R G Y H I R S N A G W A H A R N A L G V K F V T G - T Q G G R V V | 186
FAOD-A | 138 | L K G N F P G W R G Y H I R S N A G W A H A R N A L G V R L G V A G S P Q G G R V I | 187

Fig. 3-3

```
Co      191 PLFD-DEGTTCIGVETADGTKYYADKVVLAAGAWSPTLVDLEDQCCSKAW 239
Et      191 PLFA-ADGKTCIGLETTDGTKYFADKVVLAAGAWSPTLVDLEDQCVSKAW 239
Py      191 PLLA-EG--ICIGVETTDGTRYYADKVVLAAGAWSPALVDLEDQCVSKAW 237
Ar      191 PLFA-PDGSTCIGVETVDGTKYYGDKVVLAAGAWSPALVDLEEQCCSKAW 239
Cc      191 PLLA-EG--VCIGVETVDGTRYYADKVVLAAGAWSPVLVDLEDQCVSKAW 237
Nv      191 PLFA-DDGTTCIGVETVDGTQYHADKVVLAAGAWSPALVDLEEQCCSKAW 239
Cn      191 PLFD-EDGTKAIGIETVDGTQYFADKVVLAAGAWSPTLVDLEGQCCSKAW 239
Pn      189 PLLA-EG--VCIGVETVDGTRYYADKVVLAAGAWSPTLVELHEQCVSKAW 235
An      190 PLFADAHEKTCIGVETVDGTKYYADKVVLAAGAWSSTLVDLEEQCVSKAW 239
En      190 PLFADADEKTCIGVETVDGTKYYADKVVLAAGAWSSTLVDLEEQCVSKAW 239
Ul      191 PLLA-EG--VCVGVETVDGTRYYADKVVLAAGAWSPALVDLQDQCVSKAW 237
Pj      191 PLFA-PDGATCSGVETVDGTKYFADKVVLAAGAWSSTLVDLEDQCVSKAW 239
Am I    194 SLVY--EDGDVVGARTADGRVHKAHRTILSAGAGSDSLLDFKKQLRPTAW 241
FAOAo1  194 SLIY--ENGDVVGARTADGTVHRADHTILSAGAGSDRLLDFKKQLRPTAW 241
Am II   189 TLIF--ENNDVKGAVTGDGKIWRAERTFLCAGASAGQFLDFKNQLRPTAW 236
FAOAo2  187 TLIF--ENNDVKGAVTADGKIWRAEQTVLCAGANAAQFLDFKDQLRPTAW 234
FAOD-A  188 TLIF--ENNDVKGAVTADGKIWRAEQTILCAGAAAGQFLDFKDQLRPTAW 235

Co      240 VYAHIQLTPEEAAEYKGVPVVYNGEFGFFFEPDE-FGVIKVCDEFPGFSR 288
Et      240 VFAHIQLTPKEADAYKNVPVVYDGEYGFFFEPNE-YGVIKVCDEFPGFSR 288
Py      238 VYAHMQLTPKEAAAYKDTPVVYNGDLGFFFEPNE-HGVIKVCDEFPGFTR 286
Ar      240 VYAHMQLTPHEAAEYQGCPVVYHGDLGFFFEPNE-HGVIKVCDEFPGFTR 288
Cc      238 VYAHIQLTPEEAAEYKNVPVVYNGDVGFFFEPDE-HGVIKVCDEFPGFTR 286
Nv      240 VYAHMQLTPEEAAVYKGCPVVYHGDVGFFFEPNE-NGVIKVCDEFPGFTR 288
Cn      240 VYAHMQLTPEEAAEYKECPVVYNSELGFFFEPNE-KGVIKVCDEFPGFTR 288
Pn      236 VYGHIQLTPEEAARYKNSPVVYNGDVGFFFEPNE-HGVIKVCDEFPGFTR 284
An      240 VFAHIQLTPAEAAAYKNTPVIYDGDYGFFFEPNE-NGIIKVCDEFPGFTH 288
En      240 VFAHIQLTPAEAAAYKNTPVIYDGDYGFFIEPDE-NGIIKVCDEFPGFTH 288
Ul      238 VYAHIQLSPSEAAEYKNVPVVYNGDVGFFFEPDE-YGVIKVCDEFPGFTR 286
Pj      240 VFAHIQLTPQESAQYKDVPVVYDGDYGFFFEPNE-HGVIKVCDEFPGFSR 288
Am I    242 TLCHIQMGPEEVKQYRNLPVLFNIAKGFFMEPDEDKHELKICDEHPGYCN 291
FAOAo1  242 TLCHIRMTPDEAKKYRNLPVLFNVAKGFFMEPDEDNHELKICDEHPGYCN 291
Am II   237 TLVHIALKPEERALYKNIPVIFNIERGFFFEPDEERGEIKICDEHPGYTN 286
FAOAo2  235 TLAHIRLKPEERALYKNLPVIFNIEKGFFFEPDEERGEIKICDEHPGYTN 284
FAOD-A  236 TLVHIQLKPEERAQYKNMPVVFNIEKGFFFEPDEERGEIKICDEHPGYTN 285
```

Fig. 3-5

```
Co      388 RVVELIEGRLPEEMAYQWRWRPG-GDALKSR----RAAPPKDLADMPGWK 432
Et      388 HVVELLEGSLSQEMAGAWRWRPG-GDALRSR----RGAPAKDLAEMPGWK 432
Py      386 HVVELIEGTLAADLAHAWRWRPGIGDALQSR----RAAPAKDLADMPGWN 431
Ar      389 HVVELLEGRLADDLAQAWRWRPGQGDALKSR----RAAPAKDLADMPGWN 434
Cc      386 HVVELLEGTLAEDLAHAWRWRPGTGDALKSR----RAAPAKDLADMPGWK 431
Nv      388 HVVELVEGRLADDLAEAWRWRPGQGDARKSI----RAAPAKDLADMPGWK 433
Cn      388 HVVELIEGTLAEDLAESWRWRPGSGDPLISR----RAAPARDLADLPGWN 433
Pn      384 HVVELLEGTLADDLAHAWRWRPGSGDALKSR----RSAPAKDLADMPGWN 429
An      388 HVVELLEERLESVFKDAWRWRPGSGDALKSR----RAAPAKDLADMPGWR 433
En      388 HVVELLEGRLESVFKDAWRWRPGSGDALKSR----RAAPAKDLADMPGWR 433
Ul      386 HVVELLEGTLADDLAHAWRWRPGTGDALKSR----RAARAKDLADMPGWN 431
Pj      388 HVVELIEGRLPQDLAGAWRWRPG-GDALKSK----RSAPAKDLAEMPGWK 432
Am I    383 FIADALESKLQKEVKDIVRWRPETAVDRDWRATQNRFGGPDRIMDFQQVG 432
FAOAo1  383 FIADALEGNLQKELKHALRWRPEIAAQRDWKDTQNRFGGPNKVMDFQKVG 432
Am II   376 LIVDAMEGKVPQKIHELIKWNPDIAANRNWRDTLGRFGGPNRVMDFHDVK 425
FAOAo2  374 LIVDAIEDKVPEKVHKLTRWSPDIAVDRKWRDTLGRFGGPNRVMDFHDVK 423
FAOD-A  375 IIADAMEDKTPAKIHKLIRWSPEIAINRNWGDRLGRFGGPNRVMDFNEVK 424

Co      433 HDPKL--------------------------------------- 437 (SEQ ID NO 1)
Et      433 HDAHL--------------------------------------- 437 (SEQ ID NO 145)
Py      432 HD-ESPRAKL---------------------------------- 440 (SEQ ID NO 113)
Ar      435 HDGDSGNATSGTSSEHKL-------------------------- 452 (SEQ ID NO 115)
Cc      432 HD-DVVKSKL---------------------------------- 440 (SEQ ID NO 117)
Nv      434 HDQDSESR------------------------------------ 441 (SEQ ID NO 54)
Cn      434 HDEPSDDDMDVKDVAVSLASVKIGENIGEKVVEDGARVGVKVLA 477 (SEQ ID NO 149)
Pn      430 HD--KPRANL---------------------------------- 437 (SEQ ID NO 38)
An      434 NEAKM--------------------------------------- 438 (SEQ ID NO 147)
En      434 NEAKM--------------------------------------- 438 (SEQ ID NO 119)
Ul      432 HDGEAPRAKL---------------------------------- 441 (SEQ ID NO 121)
Pj      433 HDAKL--------------------------------------- 437 (SEQ ID NO 123)
Am I    433 EDQWTKIGESRGP------------------------------- 445 (SEQ ID NO 125)
FAOAo1  433 ENEWTKIGDKSRL------------------------------- 445 (SEQ ID NO 127)
Am II   426 EWTNVQYRDISKL------------------------------- 438 (SEQ ID NO 129)
FAOAo2  424 EWTNVQNKDTAKL------------------------------- 436 (SEQ ID NO 36)
FAOD-A  425 EWTNVTQRDISKL------------------------------- 437 (SEQ ID NO 131)
```

Fig. 4-1

```
Co      1   -MTSNRADTRVIVVGGGGTIGSSTALHLVRSGYAPANITVLDTFEIPSAQ  49
Et      1   -MAHSRASTKVVVVGGGGTIGSSTALHLIRSGYTPSNITVLDVYKTPSLQ  49
Py      1   -MAASRAKTTVIVVGGGGTIGSSTALHLLRSGYTPSNITVLDTYPIPSLQ  49
Ar      1   -MAASRKTTKVIVVGGGGTIGSSTALHLLRSGYTATNITVLDTYPIPSAQ  49
Cc      1   -MAPSRANTSVIVVGGGGTIGSSTALHLVRSGYTPSNITVLDTYPIPSAQ  49
Nv      1   -MTTPRKETTVLIIGGGGTIGSSTALHLLRAGYTPSNITVLDTYPIPSAQ  49
Cn      1   -MPPSRASTKVIVIGGGGTLGSSTALHLLRAGYTPSNITVLDTYLIPSAQ  49
Pn      1   -MAPSRANTSVIVVGGGGTIGSSTALHLVRSGYTPSNVTVLDAYPIPSSQ  49
An      1   --MTPRANTKIIVVGGGGTMGSSTALHLLRAGYTPSNITVLDTCPIPSAQ  48
En      1   --MAPRANTKIIVVGGGGTMGSSTALHLLRAGYTPSNITVLDTYPIPSAQ  48
Ul      1   -MAPNRANISVIVVGGGGTIGSSTALHLVRSGYTPSNITVLDTYPIPSAQ  49
Pj      1   -MAHSRESTKIVIVGGGGTMGSSTALHLIRSGYTPSNITVLDVYPIPSLQ  49
Am I    1   MAPSILSTESSIIVIGAGTWGCSTALHLARRGYK--DVTVLDPHPVPSPI  48
FAOAo1  1   MTSSKLTPTSSILIVGAGTWGCSTALHLARRGYK--NVTVLDPHPVPSPI  48
Am II   1   ---MAVTKSSSLLIVGAGTWGTSTALHLARRGYT--NVTVLDPYPVPSAI  45
FAOAo2  1   ---MTVAKSSSILIIGAGTWGASTALHLGRRGYT--NVTVLDPYTVPSAI  45
FAOD-A  1   ---MPVTKSSSILIIGAGTWGCSTALHLARRGYT--NVTVLDPYPVPSAI  45

Co      50  SAGHDLNKIMGIRLRN--------KVDLQMSLEARQMWKEDELFQPFFHN  91
Et      50  SAGHDLNKIMGIRLRN--------GPDLQLSLESLDMWQNDELFKPFFHQ  91
Py      50  SAGNDLNKIMGIRLRN--------KVDLQLSLEAREMWREDELFRDFFHN  91
Ar      50  SAGNDLNKIMGIRLRN--------PVDKQLSLEAQDMWCHDELFKPYFHN  91
Cc      50  SAGNDLNKIMGIRLRN--------KVDLQLSLEARQMWREDDLFKEYFHN  91
Nv      50  SAGNDLNKIMGIRLRN--------KVDLQLSLEARDMWRNDALFRPFFHN  91
Cn      50  SAGNDLNKIMGIRIRN--------PVDKQLSLEARDMWRNDEVFKPYFHN  91
Pn      50  SAGNDLNKIMGVSLRN--------PVDLQLALEARQMWNEDELFKKFFHN  91
An      49  SAGYDLNKIMSIRLRN--------KPDLQLSLEALDMWKNDPLFKPFFHN  90
En      49  SAGYDLNKIFGIRLRN--------KPDLQLYLEALDMWKNDPLFKPFFHN  90
Ul      50  SAGNDLNKIMGIRLRN--------KVDLQLSLEARQMWTEDDLFKEYFHK  91
Pj      50  SAGYDLNKIMSIRLRN--------GPDLQLSLEALDMWKNDPLFKPFFHN  91
Am I    49  AAGNDINKIMEHSELKDGSSDPRSAAFSTFTRAALKAWKTDPVFQPYFHE  98
FAOAo1  49  AAGNDINKIMEHREVKASETDPWSIAFSTCTRAALKGWKNDPVFQPYFHE  98
Am II   46  SAGNDVNKVISSGQYSNNKDE--IEVNEILAEEAFNGWKNDPLFKPYYHD  93
FAOAo2  46  SAGNDVNKIISSGQYSNKKDE--IEVNEILAEEAFKGWTTDPLFKPYYHD  93
FAOD-A  46  SAGNDVNKIISSGQYSSKKDE--VEVNEIIAEQAFNGWKNDPIFKPYYHD  93
```

Fig. 4-2

```
Co       92  TGRMDCEHTPEGIEDLKKQYQALHDAGAGLEKTHAWLDNEDEILSKMPLL  141
Et       92  VGMIDCSSSKEGIENLRRKYQTLLDAGIGLEKTNVWLESEDEILAKAPNF  141
Py       92  TGRLDCAHGEKGINDLRQAYQTLLDANAGLEETNEWLDSEDEILARMPLL  141
Ar       92  TGRMDCEGTEKGIAALKQQYQTLLDADVGLEKTTEWLDSEDAILAKMPLL  141
Cc       92  TGRLDCAHGEEGLADLRQAYQALLDANAGLEETTEWLDSEDEILKKMPLL  141
Nv       92  TGRLDCESSAEGVEGLRREYQKLVEAGVGLEETHEWLDSEEAILEKAPLL  141
Cn       92  TGRLDCAHTPESIASLRKSYEAILKAGSGLEKTHHWLSTEDEILARAPLL  141
Pn       92  TGRLDCAHGEKDIADLKSGYQALVDA--GLDATNEWLDSEDEILKRMPLL  139
An       91  VGMIDVSSTEEGIEGLRKKYQSLLDAGIGLEKTNFMLESEDEILAKAPHF  140
En       91  VGQMDVSSTEEGIKKLRMRYQSLLDAGIGLEKTNFLLESEDEILAKAPHF  140
Ul       92  TGRLDCAHGEKGLADLKQAYQALLDANAGLEATTEWLDSEDKILEKMPLL  141
Pj       92  VGMLDCSSSQEGIASLRRKHQDLIDANIGLEKTNIWLESEDDILAKAPHF  141
Am I     99  TGFIISGHTPALIDHIRKDEVEPSETNFVKLET-----AEDFRRTMPPGV  143
FAOAo1   99  TGAIVSGHTASLIKHIQEHEIDSSDAEFIKLNT-----AEDFRKTMPPGI  143
Am II    94  TGLLMSACSQEGLDRLGVRVRPGEDPNLVELTR-----PEQFRKLAPEGV  138
FAOAo2   94  TGVVMSACSSAGLDRLGIRVRPEEEPDVSEVTK-----PEHFRQLAPA-V  137
FAOD-A   94  TGVVMSATTQEGLERLGVRVRPEDEPDVAELTR-----PEQFRQLAPG-V  137

Co      142  QRDQIQGWKAIWSQD-GGWLAAAKAINAIGQFLKERGVKFGFGGAGSFKQ  190
Et      142  TREQVKGWKGLFCTD-GGWLAAAKAINAIGIFLQDKGVKFGFGGAGTFQQ  190
Py      142  SREQIKGWKAVFSRD-GGWLAAGKAINAIGEYLRKEGVKFGFGGAGSFQQ  190
Ar      142  ERDQIKGWKAIFSQD-GGWLAAAKAINAIGEELKRQGVNFGFGGAGAFKK  190
Cc      142  DREQIKGWKAVYSQD-GGWLAAAKAINAIGEYLRAQGVKFGFGGAGSFKQ  190
Nv      142  QREEIEGWKAIWSEE-GGWLAAAKAINAIGEELQRQGVRFGFGGAGSFKR  190
Cn      142  DRKQIKGWKAIYSED-GGWLAAAKAINSIGQVLKEKGVTFGFGSAGSFKK  190
Pn      140  SRDQIKGWKAIFSKD-GGWLAAAKAINAVGEYLRDQGVRFGFYGAGSFKA  188
An      141  TQEQIKGWKGLFCGD-GGWLAAAKAINAIGQFLKEQGVKFGFGGAGTFKK  189
En      141  TREQIKGWKGLFCGD-GGWLAAAKAINAIGQFLKEQGVKFGFGEAGTFKK  189
Ul      142  NRDQIKGWKAVFSED-GGWLAAAKAINAIGRFLRDQGVKFGFGGAGSFKQ  190
Pj      142  TREQIKGWKGLFCGD-GGWLAAAKAINAIGTFLKSQGVKFGFGSAGTFKR  190
Am I    144  LTGDFPGWKGWLHKSGAGWIHAKKAMISAFNEAKRLGVRFVTGSPEGNVV  193
FAOAo1  144  LTGNFPGWKGWLNKTGAGWIHAKKAMFSAYTEAKRLGVTFITGSPEGDVV  193
Am II   139  LQGDFPGWKGYFARSGAGWAHARNALVAAAREAQRMGVKFVTGTPQGRVV  188
FAOAo2  138  LKGNFPGWRGYHIRSNAGWAHARNALVAAIREAEKLGVKFVTG-TQGRVI  186
FAOD-A  138  LKGNFPGWRGYHIRSNAGWAHARNALVAAAREAQRLGVRFVAGSPQGRVI  187
```

Fig. 4-3

| | | | |
|---|---|---|---|
| Co | 191 | PLFD-DEGTTCIGVETADGTKYYADKVVLAAGAWSPTLVDLEDQCCSKAW | 239 |
| Et | 191 | PLFA-ADGKTCIGLETTDGTKYFADKVVLAAGAWSPTLVDLEDQCVSKAW | 239 |
| Py | 191 | PLLA-EG--ICIGVETTDGTRYYADKVVLAAGAWSPALVDLEDQCVSKAW | 237 |
| Ar | 191 | PLFA-PDGSTCIGVETVDGTKYYGDKVVLAAGAWSPALVDLEEQCCSKAW | 239 |
| Cc | 191 | PLLA-EG--VCIGVETVDGTRYYADKVVLAAGAWSPVLVDLEDQCVSKAW | 237 |
| Nv | 191 | PLFA-DDGTTCIGVETVDGTQYHADKVVLAAGAWSPALVDLEEQCCSKAW | 239 |
| Cn | 191 | PLFD-EDGTKAIGIETVDGTQYFADKVVLAAGAWSPTLVDLEGQCCSKAW | 239 |
| Pn | 189 | PLLA-EG--VCIGVETVDGTRYYADKVVLAAGAWSPTLVELHEQCVSKAW | 235 |
| An | 190 | PLFADAHEKTCIGVETVDGTKYYADKVVLAAGAWSSTLVDLEEQCVSKAW | 239 |
| En | 190 | PLFADADEKTCIGVETVDGTKYYADKVVLAAGAWSSTLVDLEEQCVSKAW | 239 |
| Ul | 191 | PLLA-EG--VCVGVETVDGTRYYADKVVLAAGAWSPALVDLQDQCVSKAW | 237 |
| Pj | 191 | PLFA-PDGATCSGVETVDGTKYFADKVVLAAGAWSSTLVDLEDQCVSKAW | 239 |
| Am I | 194 | SLVY--EDGDVVGARTADGRVHKAHRTILSAGAGSDSLLDFKKQLRPTAW | 241 |
| FAOAo1 | 194 | SLIY--ENGDVVGARTADGTVHRADHTILSAGAGSDRLLDFKKQLRPTAW | 241 |
| Am II | 189 | TLIF--ENNDVKGAVTGDGKIWRAERTFLCAGASAGQFLDFKNQLRPTAW | 236 |
| FAOAo2 | 187 | TLIF--ENNDVKGAVTADGKIWRAEQTVLCAGANAAQFLDFKDQLRPTAW | 234 |
| FAOD-A | 188 | TLIF--ENNDVKGAVTADGKIWRAEQTILCAGAAAGQFLDFKDQLRPTAW | 235 |

| | | | |
|---|---|---|---|
| Co | 240 | VYAHIQLTPEEAAEYKGVPVVYNGEFGFFFEPDE-FGVIKVCDEFPGFSR | 288 |
| Et | 240 | VFAHIQLTPKEADAYKNVPVVYDGEYGFFFEPNE-YGVIKVCDEFPGFSR | 288 |
| Py | 238 | VYAHMQLTPKEAAAYKDTPVVYNGDLGFFFEPNE-HGVIKVCDEFPGFTR | 286 |
| Ar | 240 | VYAHMQLTPHEAAEYQGCPVVYHGDLGFFFEPNE-HGVIKVCDEFPGFTR | 288 |
| Cc | 238 | VYAHIQLTPEEAAEYKNVPVVYNGDVGFFFEPDE-HGVIKVCDEFPGFTR | 286 |
| Nv | 240 | VYAHMQLTPEEAAVYKGCPVVYHGDVGFFFEPNE-NGVIKVCDEFPGFTR | 288 |
| Cn | 240 | VYAHMQLTPEEAAEYKECPVVYNSELGFFFEPNE-KGVIKVCDEFPGFTR | 288 |
| Pn | 236 | VYGHIQLTPEEAARYKNSPVVYNGDVGFFFEPNE-HGVIKVCDEFPGFTR | 284 |
| An | 240 | VFAHIQLTPAEAAAYKNTPVIYDGDYGFFFEPNE-NGIIKVCDEFPGFTH | 288 |
| En | 240 | VFAHIQLTPAEAAAYKNTPVIYDGDYGFFIEPDE-NGIIKVCDEFPGFTH | 288 |
| Ul | 238 | VYAHIQLSPSEAAEYKNVPVVYNGDVGFFFEPDE-YGVIKVCDEFPGFTR | 286 |
| Pj | 240 | VFAHIQLTPQESAQYKDVPVVYDGDYGFFFEPNE-HGVIKVCDEFPGFSR | 288 |
| Am I | 242 | TLCHIQMGPEEVKQYRNLPVLFNIAKGFFMEPDEDKHELKICDEHPGYCN | 291 |
| FAOAo1 | 242 | TLCHIRMTPDEAKKYRNLPVLFNVAKGFFMEPDEDNHELKICDEHPGYCN | 291 |
| Am II | 237 | TLVHIALKPEERALYKNIPVIFNIERGFFFEPDEERGEIKICDEHPGYTN | 286 |
| FAOAo2 | 235 | TLAHIRLKPEERALYKNLPVIFNIEKGFFFEPDEERGEIKICDEHPGYTN | 284 |
| FAOD-A | 236 | TLVHIQLKPEERAQYKNMPVVFNIEKGFFFEPDEERGEIKICDEHPGYTN | 285 |

Fig. 4-5

```
Co       388  RVVELIEGRLPEEMAYQWRWRPG-GDALKSR----RAAPPKDLADMPGWK  432
Et       388  HVVELLEGSLSQEMAGAWRWRPG-GDALRSR----RGAPAKDLAEMPGWK  432
Py       386  HVVELIEGTLAADLAHAWRWRPGIGDALQSR----RAAPAKDLADMPGWN  431
Ar       389  HVVELLEGRLADDLAQAWRWRPGQGDALKSR----RAAPAKDLADMPGWN  434
Cc       386  HVVELLEGTLAEDLAHAWRWRPGTGDALKSR----RAAPAKDLADMPGWK  431
Nv       388  HVVELVEGRLADDLAEAWRWRPGQGDARKSI----RAAPAKDLADMPGWK  433
Cn       388  HVVELIEGTLAEDLAESWRWRPGSGDPLISR----RAAPARDLADLPGWN  433
Pn       384  HVVELLEGTLADDLAHAWRWRPGSGDALKSR----RSAPAKDLADMPGWN  429
An       388  HVVELLEERLESVFKDAWRWRPGSGDALKSR----RAAPAKDLADMPGWR  433
En       388  HVVELLEGRLESVFKDAWRWRPGSGDALKSR----RAAPAKDLADMPGWR  433
Ul       386  HVVELLEGTLADDLAHAWRWRPGTGDALKSR----RAARAKDLADMPGWN  431
Pj       388  HVVELIEGRLPQDLAGAWRWRPG-GDALKSK----RSAPAKDLAEMPGWK  432
Am I     383  FIADALESKLQKEVKDIVRWRPETAVDRDWRATQNRFGGPDRIMDFQQVG  432
FAOAo1   383  FIADALEGNLQKELKHALRWRPEIAAQRDWKDTQNRFGGPNKVMDFQKVG  432
Am II    376  LIVDAMEGKVPQKIHELIKWNPDIAANRNWRDTLGRFGGPNRVMDFHDVK  425
FAOAo2   374  LIVDAIEDKVPEKVHKLTRWSPDIAVDRKWRDTLGRFGGPNRVMDFHDVK  423
FAOD-A   375  IIADAMEDKTPAKIHKLIRWSPEIAINRNWGDRLGRFGGPNRVMDFNEVK  424

Co       433  HDPKL---------------------------------------  437 (SEQ ID NO 1)
Et       433  HDAHL---------------------------------------  437 (SEQ ID NO 145)
Py       432  HD-ESPRAKL----------------------------------  440 (SEQ ID NO 113)
Ar       435  HDGDSGNATSGTSSEHKL--------------------------  452 (SEQ ID NO 115)
Cc       432  HD-DVVKSKL----------------------------------  440 (SEQ ID NO 117)
Nv       434  HDQDSESR------------------------------------  441 (SEQ ID NO 54)
Cn       434  HDEPSDDDMDVKDVAVSLASVKIGENIGEKVVEDGARVGVKVLA  477 (SEQ ID NO 149)
Pn       430  HD--KPRANL----------------------------------  437 (SEQ ID NO 38)
An       434  NEAKM---------------------------------------  438 (SEQ ID NO 147)
En       434  NEAKM---------------------------------------  438 (SEQ ID NO 119)
Ul       432  HDGEAPRAKL----------------------------------  441 (SEQ ID NO 121)
Pj       433  HDAKL---------------------------------------  437 (SEQ ID NO 123)
Am I     433  EDQWTKIGESRGP-------------------------------  445 (SEQ ID NO 125)
FAOAo1   433  ENEWTKIGDKSRL-------------------------------  445 (SEQ ID NO 127)
Am II    426  EWTNVQYRDISKL-------------------------------  438 (SEQ ID NO 129)
FAOAo2   424  EWTNVQNKDTAKL-------------------------------  436 (SEQ ID NO 36)
FAOD-A   425  EWTNVTQRDISKL-------------------------------  437 (SEQ ID NO 131)
```

MODIFIED AMADORIASE REACTING WITH FRUCTOSYL HEXAPEPTIDE

CROSS-REFERENCE TO RELATED APPLICATIONS

This application is a National Stage application of PCT/JP2013/062508, filed Apr. 26, 2013, which claims priority from Japanese application JP 2012-102771, filed Apr. 27, 2012.

TECHNICAL FIELD

The present invention relates to an amadoriase reacting with fructosyl hexapeptide, a gene and recombinant DNA thereof, and a process for producing an amadoriase having altered substrate specificity.

BACKGROUND ART

Glycated proteins are generated by non-enzymatic covalent bonding between aldehyde groups in aldoses, such as glucose (monosaccharides potentially containing aldehyde groups and derivatives thereof), and amino groups in proteins, followed by Amadori rearrangement. Examples of amino groups in proteins include α-amino groups of the amino terminus and side chain ε-amino groups of the lysine residue in proteins. Examples of known glycated proteins generated in vivo include glycated hemoglobin resulting from glycation of hemoglobin and glycated albumin resulting from glycation of albumin in the blood.

Among such glycated proteins generated in vivo, hemoglobin Ale (HbAlc) has drawn attention as a glycemic control marker significant for diagnosis of diabetic patients and control of conditions in the field of clinical diagnosis of diabetes mellitus. HbAlc is a protein comprising glucose bound to the α-amino group at the N-terminal (amino-terminal) valine (Val) residue of the hemoglobin "β chain." The blood HbAlc level reflects the average blood glucose level for a given period of time in the past, and the measured value thereof serves as a significant indicator for diagnosis and control of diabetes conditions.

Several types of enzymatic methods involving the use of amadoriases have heretofore been known as methods for rapidly and simply measuring HbAlc.

Enzymes that oxidize iminodiacetic acid or a derivative thereof (also referred to as an "Amadori compound") in the presence of oxygen to catalyze a reaction to generate glyoxylic acid or α-ketoaldehyde, amino acid or peptide, and hydrogen peroxide are collectively referred to as "amadoriases." Amadoriases are known to be useful for measuring HbAlc by an enzymatic method. Amadoriases have been found in bacteria, yeast, and fungi. For example, amadoriases derived from the genera *Coniochaeta. Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Debaryomyces, Corynebacterium, Agrobacterium*, and *Arthrobacter* have been reported (e.g., Patent Documents 1 and 6 to 15 and Non-Patent Documents 1 to 9). These genera may be referred to as the genera *Coniochaeta* etc. in this description. In some of the aforementioned documents, amadoriase is occasionally referred to as, for example, ketoamine oxidase, fructosyl amino acid oxidase, fructosyl peptide oxidase, or fructosyl amine oxidase.

As a method for rapidly and readily measuring HbAlc with the use of various types of amadoriases as described above, a method in which HbAlc is degraded with a cleavage enzyme such as a protease and a particular target substance released from the β-chain amino terminus of HbAlc is quantified with the use of amadoriases as described above is known (e.g., Patent Documents 1 to 7).

Specifically, a method in which HbAlc is degraded with a particular protease or the like, α-fructosyl valyl histidine (hereafter referred to as "αFVH") is released from the β-chain amino terminus thereof, and the released αFVH is quantified has been known. At present, such method is a major technique for measuring HbAlc by an enzymatic method.

According to another method that has been proposed as a method for quantifying HbAlc, α-fructosyl valine (hereafter referred to as "αFV") is released and the released αFV is quantified. According to this method, however, various contaminants are disadvantageously cleaved from various sites other than the N-terminus of the target HbAlc hemoglobin "β-chain" in the process of cleavage of αFV from HbAlc. Thus, such method is problematic in terms of accuracy.

When implementing such methods for measuring HbAlc, it is important to select, search for, or create amadoriases exhibiting the maximal reaction specificity to a particular target substance in order to perform accurate measurement. Such attempts are been continuously made to this day.

According to a third method for measuring HbAlc by an enzymatic method involving the use of amadoriases, α-fructosyl hexapeptide comprising 6 amino acids including valine at the glycated β-chain amino terminus (α-fructosyl-valyl-histidyl-leucyl-threonyl-propyl-glutamic acid, hereafter referred to as "αF6P") is released and then quantified (e.g., Patent Documents 17 and 18).

According to a conventional technique for measuring HbAlc defined by the International Federation of Clinical Chemistry and Laboratory Medicine (IFCC), the HbAlc β-chain is digested with the use of a Glu-C protease to release αF6P, and the released αF6P is measured via HPLC-CE (HPLC capillary electrophoresis) or HPLC-MS (HPLC-mass analysis) to determine the HbAlc level (Non-Patent Document 10).

Because a special apparatus and complicated procedures at the time of detection is needed for this method, development of an enzymatic method had been desired. However, the aforementioned method defined by IFCC has heretofore been widely recognized as a reference method excellent in specificity to this day and before an enzymatic method of HbAlc measurement became widespread. Accordingly, such technique has been employed in laboratory institutions at which equipment and techniques necessary for such method are available.

When comparing the major enzymatic method comprising measuring αFVH using amadoriases which is the mainstream method for measuring HbAlc at this day with the reference method for the measurement of HbAlc via HPLC-CE or HPLC-MS defined by IFCC, the former method focuses on α-fructosyl dipeptide; that is, αFVH, as the target of measurement, whereas, the latter method focuses on α-fructosyl hexapeptide; that is, αF6P, as the target of measurement. If a method of enzymatic measurement based on the same principle as the reference method in which HbAlc is measured through quantification of αF6P is realized, the relevance between the reference method and the method of enzymatic measurement can be enhanced. Accordingly, such technique has a great significance at the industrial level. However, most of known amadoriases show reactivity selectively to relatively short α-fructosyl peptides, and, unfortunately, practical amadoriases that can satisfactorily react with αF6P released from the β-chain amino terminus of HbAlc and rapidly quantify the released αF6P (hereafter referred to as "fructosyl hexapeptide oxidase" (F6P oxidase)) have not yet been discovered.

According to the IFCC reference method, a cleavage enzyme, i.e., Glu-C protease, is applied to HbAlc to cleave αF6P from the β-chain amino terminus of HbAlc (Non-Patent Document 10). However, neither α-fructosyl amino acid nor α-fructosyl dipeptide is substantially cleaved even if Glu-C protease is allowed to react with αF6P (Patent Document 16). Accordingly, substantially all of glycated peptides cleaved from the β-chain N terminus glycated upon cleavage of HbAlc with Glu-C protease remain in the form of αF6P, and substantially no peptides are degraded to peptides of shorter chains. Most known amadoriases show high-level reactivity selectively with relatively short α-fructosyl peptides, and accordingly it is not possible to quantify αF6P.

Examples of amadoriases capable of reacting with αF6P that have been disclosed include amadoriases derived from plants belonging to the family Zingiberaceae (Patent Document 17), amadoriases derived from *Aspergillus oryzae* (Patent Document 18), and amadoriases derived from *Phaeosphaeria nodorum* (Patent Documents 15 and 19).

Fructosyl peptide oxidase derived from plants belonging to the family Zingiberaceae was reported as the first amadoriase reacting with αF6P (Patent Document 17). However, it would take as long as about 16 hours in order to detect αF6P with the use of a crude enzyme solution. Thus, this can hardly serve as a practical αF6P oxidase. Since this enzyme is unpurified and derived from a plant, also, it is predicted that various technical problems would arise when such enzyme is applied to a general procedure of enzyme mass-production utilizing genetically engineered microorganisms. In fact, there is no report that such enzyme is purified, mass-produced, or put to practical applications.

As a different approach, it has been reported that a plurality of amadoriases derived from the genus *Aspergillus* are capable of reacting with αF6P (Patent Document 18). However, it takes as long as 4 hours to conduct a reaction so as to detect αF6P oxidation activity in a crude enzyme solution. Accordingly, it is deduced that the productivity of αF6P oxidases derived from the genus *Aspergillus* is very low or reactivity per amadoriase molecule; i.e., specific activity, is very low. Low productivity is not favorable from the viewpoint of industrial applicability. In addition, a lower specific activity would necessitate the use of a larger amount of enzyme when preparing a composition or kit for αF6P measurement.

In addition to amadoriases derived from the genus *Aspergillus*, amadoriases derived from *Phaeosphaeria nodorum* were found to be reactive with αF6P (Patent Document 15). However, practicality of such enzyme is still at the developmental stage, and its specific activity is as low as 0.0013 U/mg. This specific activity is less than 1/18,300 of the specific activity of amadoriase derived from the genus *Coniochaeta* with αFVH (i.e., 23.8 U/mg) that are commonly used for a method, which is a currently major enzymatic measurement technique, in which αFVH is released from HbAlc and quantified (Non-Patent Document 1). This necessitates the use of considerably large amounts of enzymes so as to measure αF6P with the use of amadoriases derived from *Phaeosphaeria nodorum*, and accordingly, use of such enzyme is not realistic.

PRIOR ART DOCUMENTS

Patent Documents

Patent Document 1: WO 2004/104203
Patent Document 2: WO 2005/49857
Patent Document 3: JP 2001-95598 A
Patent Document 4: JP H05-33997 B (1993)
Patent Document 5: JP H11-127895 A (1999)
Patent Document 6: WO 97/13872
Patent Document 7: JP 2011-229526 A
Patent Document 8: JP 2003-235585 A
Patent Document 9: JP 2004-275013 A
Patent Document 10: JP 2004-275063 A
Patent Document 11: JP 2010-35469 A
Patent Document 12: JP 2010-57474 A
Patent Document 13: WO 2010/41715
Patent Document 14: WO 2010/41419
Patent Document 15: WO 2011/15325
Patent Document 16: JP 2005-110657 A
Patent Document 17: WO 2004/38034
Patent Document 18: WO 2008/108385
Patent Document 19: WO 2011/15326

Non-Patent Documents

Non-Patent Document 1: Biochem. Biophys. Res. Commun. 311, 104-11, 2003
Non-Patent Document 2: Biotechnol. Bioeng. 106, 358-66, 2010
Non-Patent Document 3: J. Biosci. Bioeng. 102, 241-3, 2006
Non-Patent Document 4: Appl. Microbiol. Biotechnol. 74, 813-9, 2007
Non-Patent Document 5: Eur. J. Biochem. 242, 499-505, 1996
Non-Patent Document 6: Mar. Biotechnol. 6, 625-32, 2004
Non-Patent Document 7: Biosci. Biotechnol. Biochem. 66, 1256-61, 2002
Non-Patent Document 8: Biosci. Biotechnol. Biochem. 66, 2323-29, 2002
Non-Patent Document 9: Biotechnol. Letters 27, 27-32, 2005
Non-Patent Document 10: Jeppsson J O, et al, Approved IFCC reference method for the measurement of HbAlc in human blood, Clin. Chem. Lab. Med. 40, 78-89, 2002

SUMMARY OF THE INVENTION

Object to be Attained by the Invention

It is an object of the present invention to provide an amadoriase that shows high reactivity with αF6P and enables satisfactory quantification of αF6P cleaved from HbAlc.

Means for Attaining the Object

The present inventors have conducted concentrated studies in order to attain the above object. As a result, they discovered that such object could be attained by substituting a specific amino acid residue in the amadoriase derived from the genus *Coniochaeta* with another specific amino acid residue, thereby completing the present invention.

Based on the finding concerning substitution of a particular amino acid residue in an amadoriase derived from the genus *Coniochaeta*, the present inventors found that the above object could be attained by introducing similar amino acid substitutions into an amadoriase derived from the genus *Phaeosphaeria*, an amadoriase derived from the genus *Neocosmospora*, an amadoriase derived from the genus *Aspergillus*, an amadoriase derived from the genus *Cryptococcus*, an amadoriase derived from the genus *Curvularia*, and an amadoriase derived from the genus *Eupenicillium* at the position corresponding to the position in the amadoriase derived from the genus *Coniochaeta*, thereby completing the present invention.

The present inventors have also established a quantitative method for measurement of αF6P and a quantitative method for measurement of HbAlc involving the use of amadoriase variants that had acquired reactivity with αF6P. This has led to the completion of the present invention.

Specifically, the present invention concerns the following.

[1] An amadoriase selected from the group consisting of the following:

(i) an amadoriase comprising the amino acid sequence in which, when aligned with the amino acid sequence as shown in SEQ ID NO: 1, the amino acid at the position corresponding to position 62 of the amino acid sequence as shown in SEQ ID NO: 1 is alanine or aspartic acid and having activity on α-fructosyl hexapeptide (αF6P);

(ii) the amadoriase as defined in (i) consisting of an amino acid sequence having a substitution, deletion, or addition of one or several amino acids at positions other than that corresponding to position 62 in the amino acid sequence as shown in SEQ ID NO: 1 and having activity on αF6P; and (iii) the amadoriase as defined in (i) comprising the amino acid sequence in which the amino acid at the position corresponding to position 62 in the amino acid sequence as shown in SEQ ID NO: 1 is alanine or aspartic acid, which exhibits 70% or higher sequence identity with the amino acid sequence as shown in SEQ ID NO: 1 over the full length and 95% or higher sequence identity with the amino acid sequence as shown in SEQ ID NO: 1 in the homologous region consisting of amino acids of positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431, and having activity on αF6P.

[2] The amadoriase according to [1], which comprises an amino acid sequence in which, when aligned with the amino acid sequence as shown in SEQ ID NO: 1, the amino acid at the position corresponding to position 110 in the amino acid sequence as shown in SEQ ID NO: 1 is leucine or tyrosine, and has activity on αF6P.

[3] The amadoriase according to [1] or [2], which comprises an amino acid sequence in which, when aligned with the amino acid sequence as shown in SEQ ID NO: 1, the amino acid at the position corresponding to position 106 in the amino acid sequence as shown in SEQ ID NO: 1 is alanine, lysine, or arginine, and has activity on αF6P.

[4] The amadoriase according to any of [1] to [3], which comprises an amino acid sequence in which, when aligned with the amino acid sequence as shown in SEQ ID NO: 1, the amino acid at the position corresponding to position 113 in the amino acid sequence as shown in SEQ ID NO: 1 is lysine or arginine, and has activity on αF6P.

[5] The amadoriase according to any of [1] to [4], which comprises an amino acid sequence in which, when aligned with the amino acid sequence as shown in SEQ ID NO: 1, the amino acid at the position corresponding to position 63 in the amino acid sequence as shown in SEQ ID NO: 1 is alanine or histidine, and has activity on αF6P.

[6] The amadoriase according to any of [1] to [5], which comprises an amino acid sequence in which, when aligned with the amino acid sequence as shown in SEQ ID NO: 1, the amino acid at the position corresponding to position 102 in the amino acid sequence as shown in SEQ ID NO: 1 is lysine, and has activity on αF6P.

[7] The amadoriase according to any of [1] to [6], which comprises an amino acid sequence in which, when aligned with the amino acid sequence as shown in SEQ ID NO: 1, the amino acid at the position corresponding to position 355 in the amino acid sequence as shown in SEQ ID NO: 1 is serine, and has activity on αF6P.

[8] The amadoriase according to any of [1] to [7], which comprises an amino acid sequence in which, when aligned with the amino acid sequence as shown in SEQ ID NO: 1, the amino acid at the position corresponding to position 419 in the amino acid sequence as shown in SEQ ID NO: 1 is lysine, and has activity on αF6P.

[9] The amadoriase according to any of [1] to [8] comprising the amino acid sequence as shown in SEQ ID NO: 1, SEQ ID NO: 38, SEQ ID NO: 40, SEQ ID NO: 54, SEQ ID NO: 62, SEQ ID NO: 89, SEQ ID NO: 113, SEQ ID NO: 115, SEQ ID NO: 117, SEQ ID NO: 119, SEQ ID NO: 121, or SEQ ID NO: 123, having the amino acid substitution as defined in any of [1] to [8], and having activity on αF6P.

[10] The amadoriase according to any of [1] to [9], which is derived from the genus *Coniochaeta, Eupenicillium Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Debaryomyces, Corynebacterium, Agrobacterium*, or *Arthrobacter*.

[11] An amadoriase selected from the group consisting of the following:

(i) an amadoriase comprising the amino acid sequence as shown in SEQ ID NO: 151, SEQ ID NO: 153, or SEQ ID NO: 155;

(ii) the amadoriase as defined in (i) consisting of an amino acid sequence having a substitution, deletion, or addition of one or several amino acids at positions other than that corresponding to position 62 in the amino acid sequence as shown in SEQ ID NO: 1 and having activity on αF6P; and (iii) the amadoriase as defined in (i) comprising an amino acid sequence, which exhibits 70% or higher sequence identity with the amino acid sequence as shown in SEQ ID NO: 151, SEQ ID NO: 153, or SEQ ID NO: 155 over the full length and 95% or higher sequence identity with the amino acid sequence as shown in SEQ ID NO: 1 in the homologous region consisting of amino acids of positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431, and having activity on αF6P.

[12] An amadoriase selected from the group consisting of the following:

(i) an amadoriase comprising the amino acid sequence as shown in SEQ ID NO: 157, SEQ ID NO: 159, SEQ ID NO: 161, or SEQ ID NO: 163;

(ii) the amadoriase as defined in (i) consisting of an amino acid sequence having a substitution, deletion, or addition of one or several amino acids at positions other than those corresponding to positions 62 and 110 in the amino acid sequence as shown in SEQ ID NO: 1 and having activity on αF6P; and (iii) the amadoriase as defined in (i) comprising an amino acid sequence, which exhibits 70% or higher sequence identity with the amino acid sequence as shown in SEQ ID NO: 157, SEQ ID NO: 159, SEQ ID NO: 161, or SEQ ID NO: 163 over the full length and 95% or higher sequence identity with the amino acid sequence as shown in SEQ ID NO: 1 in the homologous region consisting of amino acids of positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431, and having activity on αF6P.

[13] An amadoriase selected from the group consisting of the following:

(i) an amadoriase comprising the amino acid sequence as shown in SEQ ID NO: 137, SEQ ID NO: 139, SEQ ID NO: 165, SEQ ID NO: 167, SEQ ID NO: 169, SEQ ID NO: 171, or SEQ ID NO: 173;

(ii) the amadoriase as defined in (i) consisting of an amino acid sequence having a substitution, deletion, or addition of one or several amino acids at positions other than those corresponding to positions 62, 110, and 106 or 113 in the amino acid sequence as shown in SEQ ID NO: 1 and having activity on αF6P; and (iii) the amadoriase as defined in (i) comprising an amino acid sequence, which exhibits 70% or higher sequence identity with the amino acid sequence as shown in any of SEQ ID NO: 137, SEQ ID NO: 139, SEQ ID NO: 165, SEQ ID NO: 167. SEQ ID NO: 169, SEQ ID NO: 171, or SEQ ID NO: 173 over the full length and 95% or higher sequence identity with the amino acid sequence as shown in SEQ ID NO: 1 in the homologous region consisting of amino acids of positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431, and having activity on αF6P.

[14] An amadoriase selected from the group consisting of the following:

(i) an amadoriase comprising the amino acid sequence as shown in any of SEQ ID NO: 133, SEQ ID NO: 135, SEQ ID NO: 175, or SEQ ID NO: 189;

(ii) the amadoriase as defined in (i) consisting of an amino acid sequence having a substitution, deletion, or addition of one or several amino acids at positions other than those corresponding to positions 62, 110, 106, and 113 in the amino acid sequence as shown in SEQ ID NO: 1 and having activity on αF6P; and (iii) the amadoriase as defined in (i) comprising an amino acid sequence, which exhibits 70% or higher sequence identity with the amino acid sequence as shown in any of SEQ ID NO: 133, SEQ ID NO: 135, SEQ ID NO: 175, or SEQ ID NO: 189 over the full length and 95% or higher sequence identity with the amino acid sequence as shown in SEQ ID NO: 1 in the homologous region consisting of amino acids of positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431, and having activity on αF6P.

[15] An amadoriase selected from the group consisting of the following:

(i) an amadoriase comprising the amino acid sequence as shown in SEQ ID NO: 177 or SEQ ID NO: 179;

(ii) the amadoriase as defined in (i) consisting of an amino acid sequence having a substitution, deletion, or addition of one or several amino acids at positions other than those corresponding to positions 62, 63, 106, 110, and 113 in the amino acid sequence as shown in SEQ ID NO: 1 and having activity on αF6P; and (iii) the amadoriase as defined in (i) comprising an amino acid sequence, which exhibits 70% or higher sequence identity with the amino acid sequence as shown in SEQ ID NO: 177 or SEQ ID NO: 179 over the full length and 95% or higher sequence identity with the amino acid sequence as shown in SEQ ID NO: 1 in the homologous region consisting of amino acids of positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431, and having activity on αF6P.

[16] An amadoriase selected from the group consisting of the following:

(i) an amadoriase comprising the amino acid sequence as shown in SEQ ID NO: 143, SEQ ID NO: 181, SEQ ID NO: 183, SEQ ID NO: 187, or SEQ ID NO: 191;

(ii) the amadoriase as defined in (i) consisting of an amino acid sequence having a substitution, deletion, or addition of one or several amino acids at positions other than those corresponding to positions 62, 63, 106, 110, 113, and 102, 355, or 419 in the amino acid sequence as shown in SEQ ID NO: 1 and having activity on αF6P; and (iii) the amadoriase as defined in (i) comprising an amino acid sequence, which exhibits 70% or higher sequence identity with the amino acid sequence as shown in any of SEQ ID NO: 143, SEQ ID NO: 181, SEQ ID NO: 183, SEQ ID NO: 187, or SEQ ID NO: 191 over the full length and 95% or higher sequence identity with the amino acid sequence as shown in SEQ ID NO: 1 in the homologous region consisting of amino acids of positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431, and having activity on αF6P.

[17] An amadoriase selected from the group consisting of the following:

(i) an amadoriase comprising the amino acid sequence as shown in SEQ ID NO: 141 or SEQ ID NO: 185;

(ii) the amadoriase as defined in (i) consisting of an amino acid sequence having a substitution, deletion, or addition of one or several amino acids at positions other than those corresponding to positions 62, 63, 102, 106, 110, 113, and 355 in the amino acid sequence as shown in SEQ ID NO: 1 and having activity on αF6P; and (iii) the amadoriase as defined in (i) comprising an amino acid sequence, which exhibits 70% or higher sequence identity with the amino acid sequence as shown in SEQ ID NO: 141 or SEQ ID NO: 185 over the full length and 95% or higher sequence identity with the amino acid sequence as shown in SEQ ID NO: 1 in the homologous region consisting of amino acids of positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431, and having activity on αF6P.

[18] The amadoriase according to any of [1] to [17], which exhibits enhanced reactivity with α-fructosyl hexapeptide relative to reactivity with α-fructosyl valyl histidine, compared with the amadoriase prior to modification.

[19] An amadoriase comprising an amino acid sequence having one or more amino acid substitutions at positions corresponding to the positions of amino acids in the amino acid sequence as shown in SEQ ID NO: 1 selected from the group consisting of the following (a) to (h), when the amino acid sequence of the amadoriase is aligned with the amino acid sequence as shown in SEQ ID NO: 1, and exhibiting enhanced reactivity with α-fructosyl hexapeptide relative to reactivity with α-fructosyl valyl histidine, compared with the amadoriase comprising the amino acid sequence as shown in SEQ ID NO: 1:

(a) arginine at position 62 of SEQ ID NO: 1;
(b) leucine at position 63 of SEQ ID NO: 1;
(c) glutamic acid at position 102 of SEQ ID NO: 1;
(d) aspartic acid at position 106 of SEQ ID NO: 1;
(e) glutamine at position 110 of SEQ ID NO: 1;
(f) alanine at position 113 of SEQ ID NO: 1;
(g) alanine at position 355 of SEQ ID NO: 1; and
(h) alanine at position 419 of SEQ ID NO: 1.

[20] An amadoriase comprising an amino acid sequence comprising one or more amino acid substitutions at positions corresponding to the amino acids in the amino acid sequence as shown in SEQ ID NO: 1 selected from the group consisting of the following (a) to (h), when the amino acid sequence of the amadoriase is aligned with the amino acid sequence as shown in SEQ ID NO: 1, and exhibiting enhanced reactivity with α-fructosyl hexapeptide relative to reactivity with α-fructosyl valyl histidine, compared with the amadoriase comprising the amino acid sequence as shown in SEQ ID NO: 1:

(a) substitution of the amino acid at the position corresponding to arginine at position 62 of SEQ ID NO: 1 with aspartic acid, asparagine, or alanine;

(b) substitution of the amino acid at the position corresponding to leucine at position 63 of SEQ ID NO: 1 with alanine or histidine;

(c) substitution of the amino acid at the position corresponding to glutamic acid at position 102 of SEQ ID NO: 1 with lysine;

(d) substitution of the amino acid at the position corresponding to aspartic acid at position 106 of SEQ ID NO: 1 with alanine, lysine, or arginine;

(e) substitution of the amino acid at the position corresponding to glutamine at position 110 of SEQ ID NO: 1 with leucine or tyrosine;

(f) substitution of the amino acid at the position corresponding to alanine at position 113 of SEQ ID NO: 1 with lysine or arginine;

(g) substitution of the amino acid at the position corresponding to alanine at position 355 of SEQ ID NO: 1 with serine; and (h) substitution of the amino acid at the position corresponding to alanine at position 419 of SEQ ID NO: 1 with lysine.

[21] An amadoriase comprising an amino acid sequence resulting from amino acid substitutions in the amino acid sequence as shown in SEQ ID NO: 1 selected from the group consisting of the following (p) to (u), when the amino acid sequence of the amadoriase is aligned with the amino acid sequence as shown in SEQ ID NO: 1, and exhibiting enhanced reactivity with α-fructosyl hexapeptide relative to reactivity with α-fructosyl valyl histidine, compared with the amadoriase comprising the amino acid sequence as shown in SEQ ID NO: 1:

(p) substitution of the amino acid at the position corresponding to arginine at position 62 of SEQ ID NO: 1 with aspartic acid, substitution of the amino acid at the position corresponding to glutamine at position 110 of SEQ ID NO: 1 with leucine, and substitution of the amino acid at the position corresponding to aspartic acid at position 106 of SEQ ID NO: 1 with lysine or arginine;

(q) substitution of the amino acid at the position corresponding to arginine at position 62 of SEQ ID NO: 1 with aspartic acid, substitution of the amino acid at the position corresponding to aspartic acid at position 106 of SEQ ID NO: 1 with lysine, substitution of the amino acid at the position corresponding to glutamine at position 110 of SEQ ID NO: 1 with leucine, and substitution of the amino acid at the position corresponding to alanine at position 113 of SEQ ID NO: 1 with lysine or arginine;

(r) substitution of the amino acid at the position corresponding to arginine at position 62 of SEQ ID NO: 1 with aspartic acid, substitution of the amino acid at the position corresponding to aspartic acid at position 106 of SEQ ID NO: 1 with lysine, substitution of the amino acid at the position corresponding to glutamine at position 110 of SEQ ID NO: 1 with leucine, substitution of the amino acid at the position corresponding to alanine at position 113 of SEQ ID NO: 1 with lysine, and substitution of the amino acid at the position corresponding to leucine at position 63 of SEQ ID NO: 1 with alanine or histidine;

(s) substitution of the amino acid at the position corresponding to arginine at position 62 of SEQ ID NO: 1 with aspartic acid, substitution of the amino acid at the position corresponding to aspartic acid at position 106 of SEQ ID NO: 1 with lysine, substitution of the amino acid at the position corresponding to glutamine at position 110 of SEQ ID NO: 1 with leucine, substitution of the amino acid at the position corresponding to alanine at position 113 of SEQ ID NO: 1 with lysine, substitution of the amino acid at the position corresponding to leucine at position 63 of SEQ ID NO: 1 with histidine, and substitution of the amino acid at the position corresponding to glutamic acid at position 102 of SEQ ID NO: 1 with lysine;

(t) substitution of the amino acid at the position corresponding to arginine at position 62 of SEQ ID NO: 1 with aspartic acid, substitution of the amino acid at the position corresponding to aspartic acid at position 106 of SEQ ID NO: 1 with lysine, substitution of the amino acid at the position corresponding to glutamine at position 110 of SEQ ID NO: 1 with leucine, substitution of the amino acid at the position corresponding to alanine at position 113 of SEQ ID NO: 1 with lysine, substitution of the amino acid at the position corresponding to leucine at position 63 of SEQ ID NO: 1 with histidine, and substitution of the amino acid at the position corresponding to alanine at position 419 of SEQ ID NO: 1 with lysine; and (u) substitution of the amino acid at the position corresponding to arginine at position 62 of SEQ ID NO: 1 with aspartic acid, substitution of the amino acid at the position corresponding to aspartie acid at position 106 of SEQ ID NO: 1 with lysine, substitution of the amino acid at the position corresponding to glutamine at position 110 of SEQ ID NO: 1 with leucine, substitution of the amino acid at the position corresponding to alanine at position 113 of SEQ ID NO: 1 with lysine, substitution of the amino acid at the position corresponding to leucine at position 63 of SEQ ID NO: 1 with histidine, substitution of the amino acid at the position corresponding to glutamic acid at position 102 of SEQ ID NO: 1 with lysine, and substitution of the amino acid at the position corresponding to alanine at position 355 of SEQ ID NO: 1 with serine.

[22] An amadoriase comprising an amino acid sequence derived from the amino acid sequence as shown in SEQ ID NO: 40 by the following amino acid substitutions (v), when aligned with the amino acid sequence as shown in SEQ ID NO: 40, and exhibiting enhanced reactivity with α-fructosyl hexapeptide relative to reactivity with α-fructosyl valyl histidine compared with the amadoriase comprising the amino acid sequence as shown in SEQ ID NO: 40:

(v) substitution of the amino acid at the position corresponding to arginine at position 62 of SEQ ID NO: 40 with aspartic acid, substitution of the amino acid at the position corresponding to leucine at position 63 of SEQ ID NO: 40 with histidine, substitution of the amino acid at the position corresponding to asparagine at position 106 of SEQ ID NO: 40 with lysine, substitution of the amino acid at the position corresponding to lysine at position 110 of SEQ ID NO: 40 with leucine, substitution of the amino acid at the position corresponding to threonine at position 113 of SEQ ID NO: 40 with lysine, and substitution of the amino acid at the position corresponding to alanine at position 355 of SEQ ID NO: 40 with serine.

[23] An amadoriase gene encoding the amino acid sequence according to any of [1] to [22].

[24] A recombinant vector comprising the amadoriase gene according to [23].

[25] A host cell comprising the recombinant vector according to [24].

[26] A method for producing an amadoriase comprising the following steps:

(i) culturing the host cell according to [25] under conditions where an amadoriase protein can be expressed; and (ii) isolating an amadoriase from a culture product or culture solution.

[27] A kit for use in measurement of HbAlc, said kit comprising the amadoriase according to any of [1] to [22].

[28] A method for measurement of αF6P comprising allowing the amadoriase according to any of [1] to [22] to react with a sample containing HbAlc-derived α-fructosyl hexapeptide (αF6P) and measuring the amount of substance produced or consumed by the reaction.

[29] The method according to [28] comprising quantification of the HbAlc-derived αF6P in the sample.

[30] A method for measurement of HbAlc comprising the following steps:

(i) treating an HbAlc-containing sample with a protease and/or peptidase and releasing αF6P from the β-chain amino terminus of HbAlc; and (ii) allowing the amadoriase according to any of [1] to [22] to react with the released HbAlc-derived αF6P and measuring the amount of substance produced or consumed by the reaction.

[31] The method according to [30] comprising quantification of HbAlc in the sample.

Also, the present invention provides an amadoriase selected from the group consisting of the following:

(i) an amadoriase comprising the amino acid sequence in which, when aligned with the amino acid sequence as shown in SEQ ID NO: 1, the amino acid at the position corresponding to position 62 in the amino acid sequence as shown in SEQ ID NO: 1 is alanine or aspartic acid and having activity on α-fructosyl hexapeptide (αF6P); and (ii) the amadoriase as defined in (i) comprising the amino acid sequence in which the amino acid at the position corresponding to position 62 in the amino acid sequence as shown in SEQ ID NO: 1 is alanine or aspartic acid, which exhibits 50% or higher, preferably 60% or higher, more preferably 70% or higher, further preferably 80% or higher, and still further preferably 90% or higher sequence identity with the amino acid sequence as shown in SEQ ID NO: 1 over the full length and 90% or higher, preferably 95% or higher, and more preferably 98% or higher sequence identity with the amino acid sequence as shown in SEQ ID NO: 1 in the homologous region consisting of amino acids of positions 11 to 18, 20 to 32, 50 to 52, 54 to 58, 266 to 268, 270 to 273, 277 to 286, and 370 to 383, and having activity on αF6P.

When an amino acid sequence of the amadoriase as defined in (ii) above is aligned with the amino acid sequence as shown in SEQ ID NO: 1, the amino acid at the position corresponding to position 110 in the amino acid sequence as shown in SEQ ID NO: 1 may be leucine or tyrosine, the amino acid at the position corresponding to position 106 in the amino acid sequence as shown in SEQ ID NO: 1 may be alanine, lysine, or arginine, the amino acid at the position corresponding to position 113 in the amino acid sequence as shown in SEQ ID NO: 1 may be lysine or arginine, the amino acid at the position corresponding to position 63 in the amino acid sequence as shown in SEQ ID NO: 1 may be alanine or histidine, the amino acid at the position corresponding to position 102 in the amino acid sequence as shown in SEQ ID NO: 1 may be lysine, the amino acid at the position corresponding to position 355 in the amino acid sequence as shown in SEQ ID NO: 1 may be serine, and the amino acid at the position corresponding to position 419 in the amino acid sequence as shown in SEQ ID NO: 1 may be lysine, and the amadoriase may have activity on αF6P.

This description includes part or all of the content as disclosed in the description and/or drawings of Japanese Patent Application No. 2012-102771, which is a priority document of the present application.

Effects of the Invention

The present invention can provide an amadoriase that enables rapid, simple, accurate, and satisfactory quantification of αF6P cleaved from HbAlc. With the use of such amadoriase, based on the same principle as that of the conventional reference method, the present invention can provide a method for measurement of HbAlc by an enzymatic method, which correlates satisfactorily with the reference method, and a kit for measurement of HbAlc.

BRIEF DESCRIPTION OF THE DRAWINGS

FIG. 1-1 is the first diagram exemplifying sequence identity among amino acid sequences of various known amadoriases, showing the results of alignment of Cn, Pn, An, En, Ul, and Pj, in addition to Co, Et, Py, Ar, Cc, and Nv.

FIG. 1-2 is a continuation of FIG. 1-1.

FIG. 1-3 is a continuation of FIG. 1-2.

FIG. 1-4 is a continuation of FIG. 1-3.

FIG. 1-5 is a continuation of FIG. 1-4.

FIG. 2-1 is the second diagram exemplifying sequence identity and similarity among amino acid sequences of various known amadoriases, showing the results of alignment of Co, Et, Py, Ar, Cc, and Nv, in addition to Co, Cn, Pn, An, En, Ul, and Pj.

FIG. 2-2 is a continuation of FIG. 2-1.

FIG. 2-3 is a continuation of FIG. 2-2.

FIG. 2-4 is a continuation of FIG. 2-3.

FIG. 2-5 is a continuation of FIG. 2-4.

FIG. 3-1 is a diagram exemplifying sequence identity among amino acid sequences of 17 types of amadoriases.

FIG. 3-2 is a continuation of FIG. 3-1.

FIG. 3-3 is a continuation of FIG. 3-2.

FIG. 3-4 is a continuation of FIG. 3-3.

FIG. 3-5 is a continuation of FIG. 3-4.

FIG. 4-1 is a diagram exemplifying the identical amino acids and the similar amino acids among amino acid sequences of 17 types of amadoriases.

FIG. 4-2 is a continuation of FIG. 4-1.

FIG. 4-3 is a continuation of FIG. 4-2.

FIG. 4-4 is a continuation of FIG. 4-3.

FIG. 4-5 is a continuation of FIG. 4-4.

FIG. 5-1 shows quantitative measurement of αF6P using the CFP-T7 variant of the present invention.

FIG. 5-2 shows the results of comparative examples.

FIG. 6-1 shows quantitative measurement of HbAlc using the CFP-T7 variant of the present invention.

FIG. 6-2 shows the results of comparative examples.

EMBODIMENTS FOR CARRYING OUT THE INVENTION

Figures 1, 2:
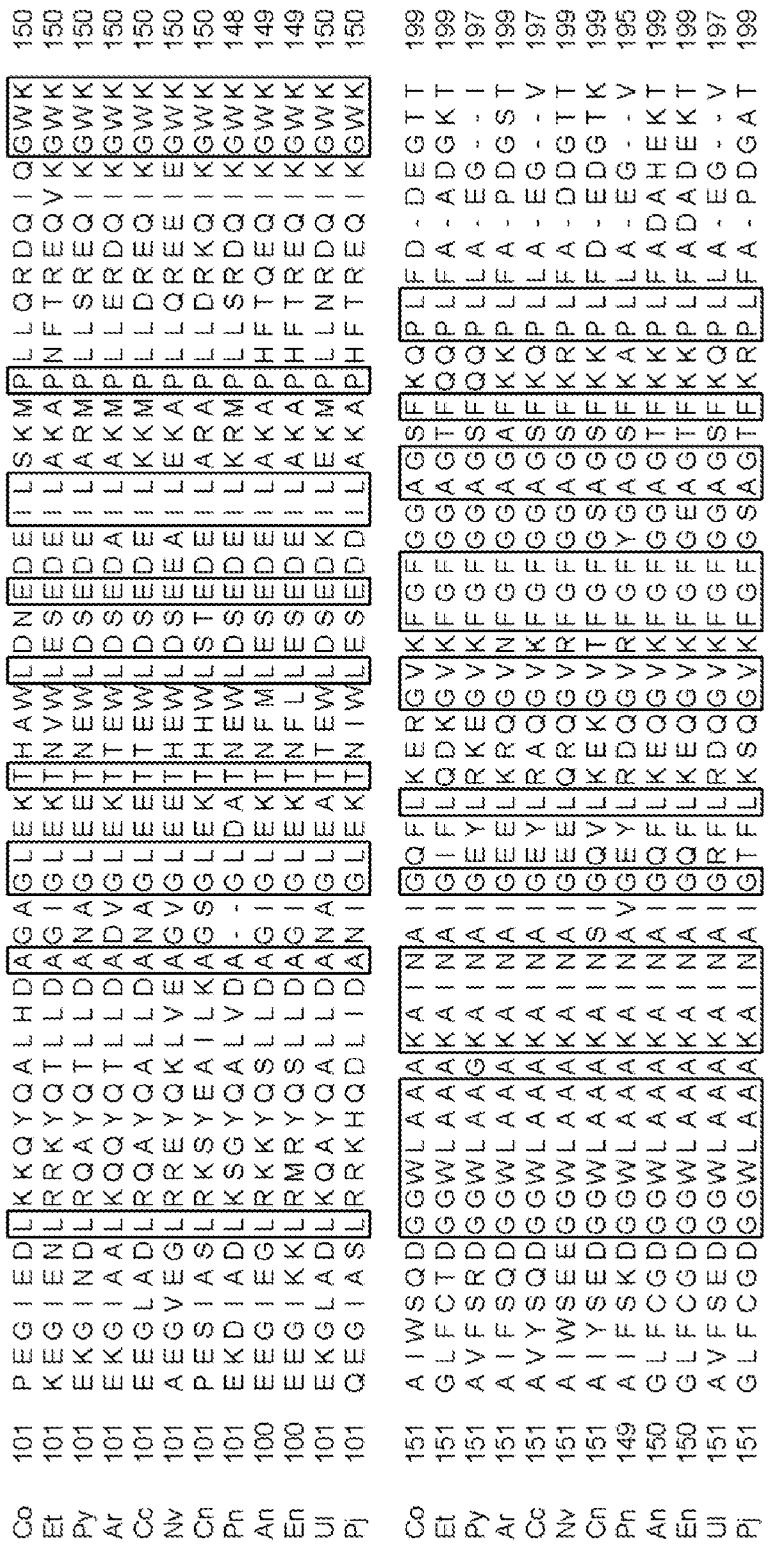
Figures 1, 2:
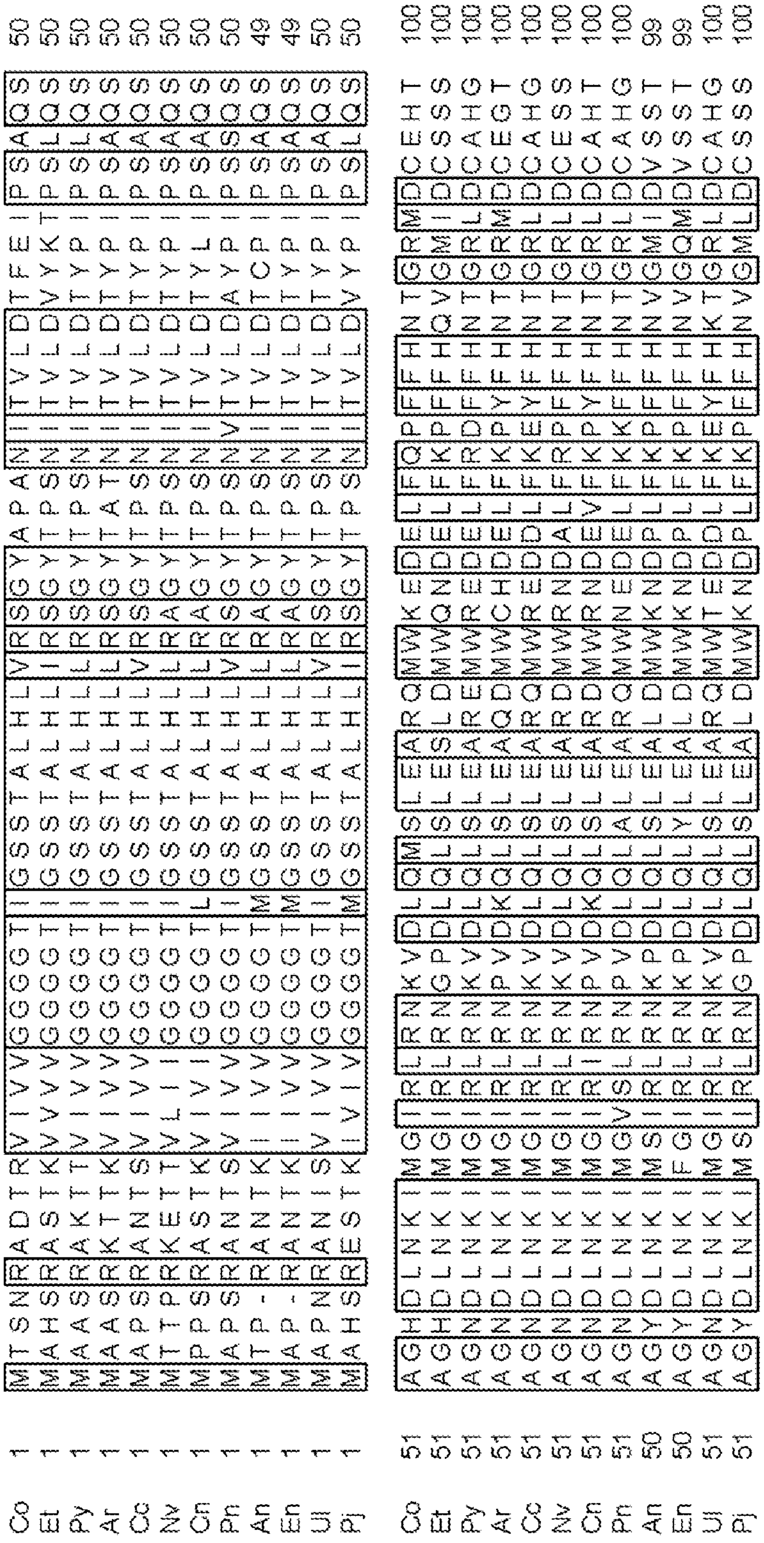
Figures 2, 3, 4:
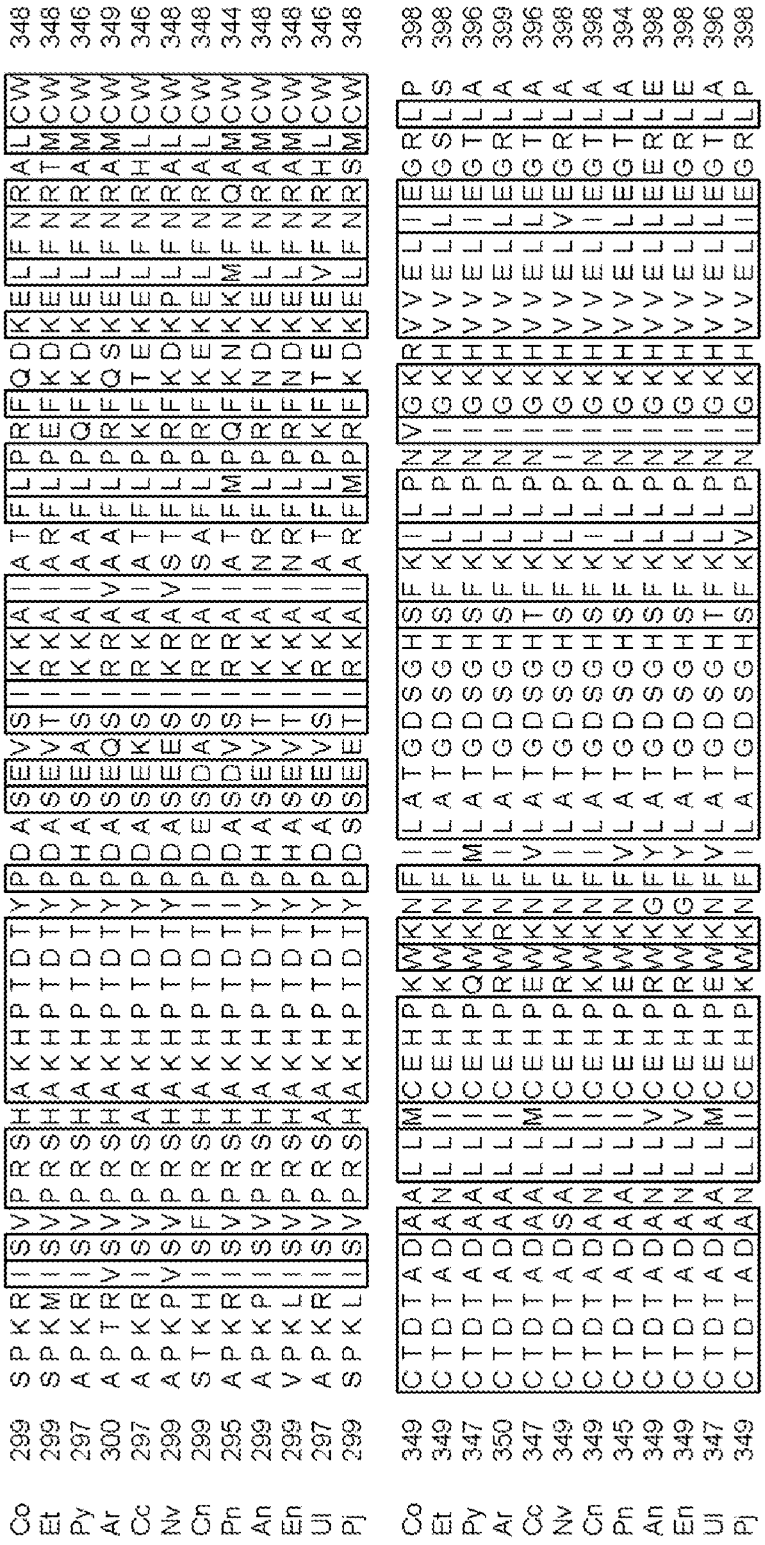
Figures 1, 3:
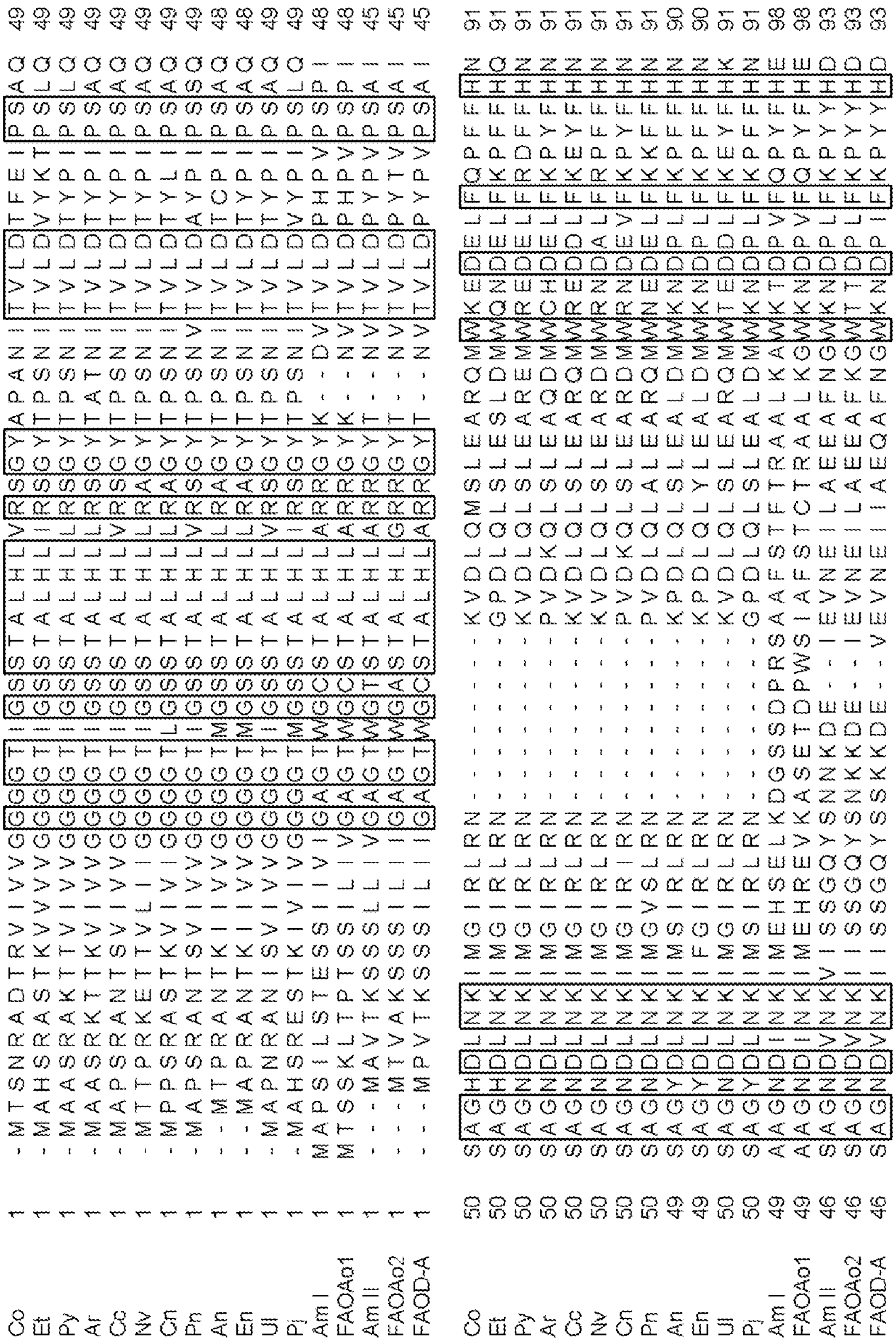
Figures 3, 4:
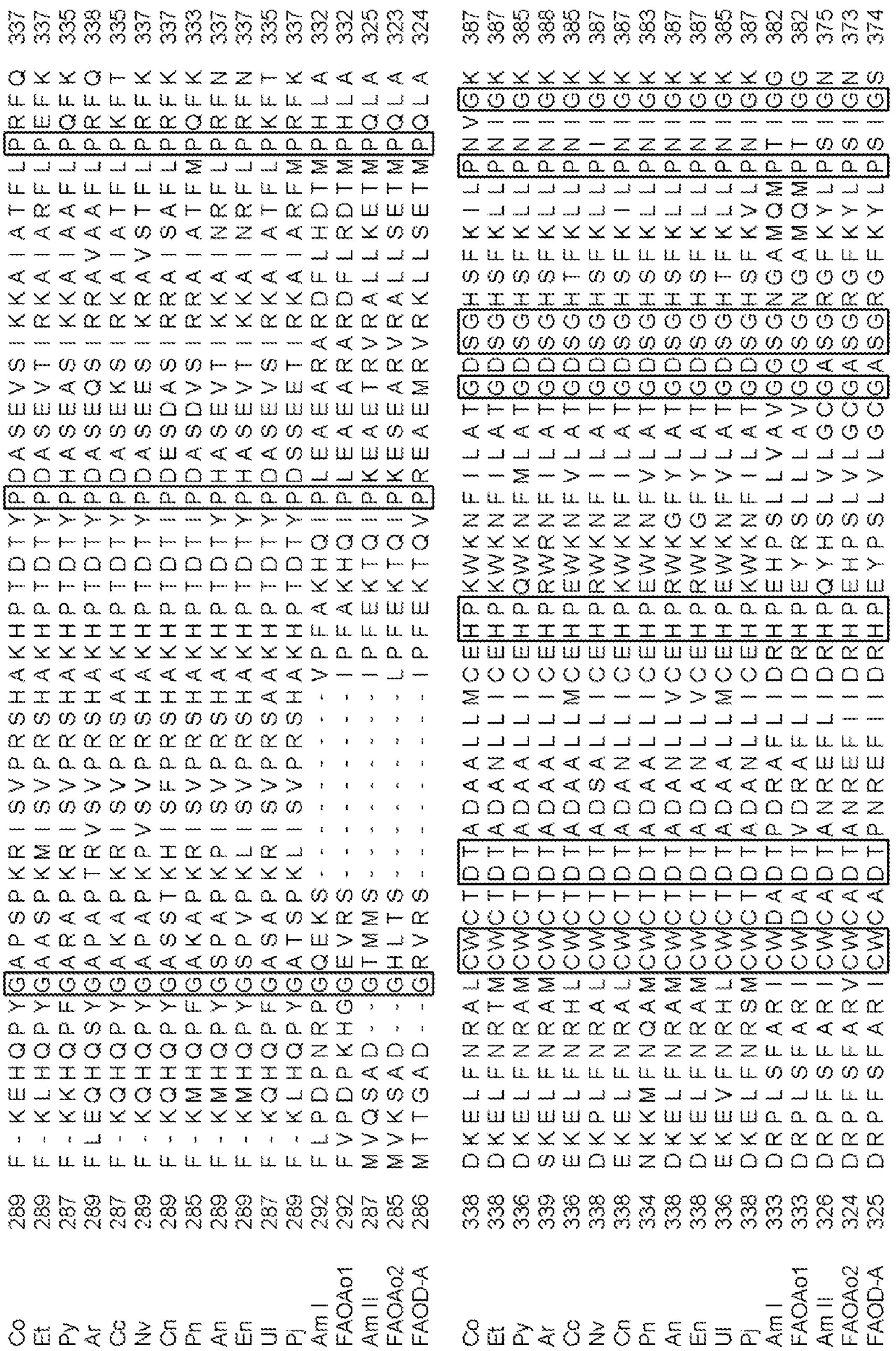
Figure 4:
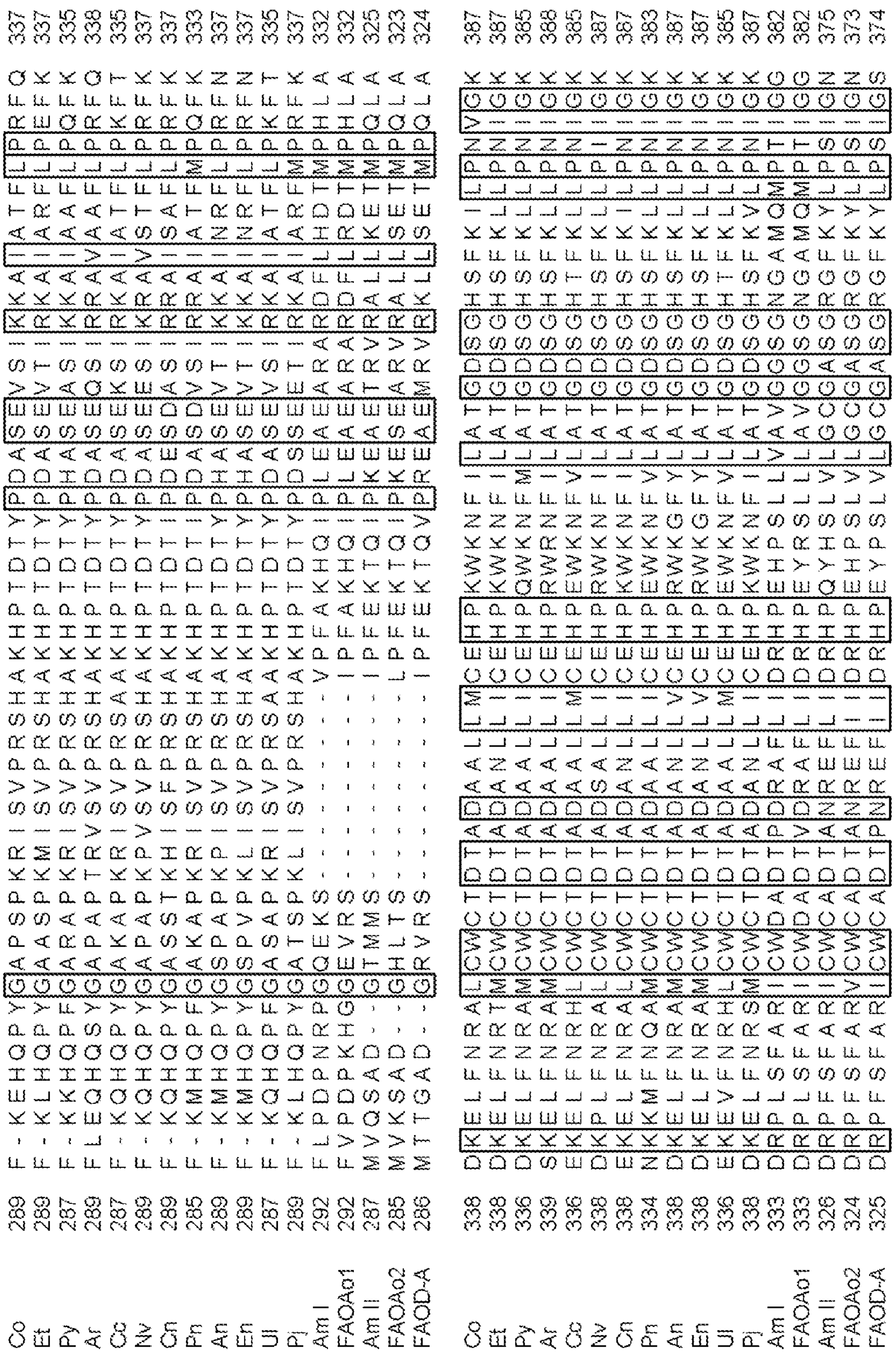

Hereafter, the present invention is described in detail.

(Glycated Protein)

In the present invention, the tem "glycated protein" refers to a protein glycated by a non-enzymatic method. Glycated proteins exist in vivo and ex vivo. Examples of glycated proteins existing in vivo include glycated hemoglobin and glycated albumin in the blood. In particular, glycated hemoglobin comprising glycated valine at the β-chain amino terminus of hemoglobin is referred to as hemoglobin Ale (HbAlc). Examples of glycated proteins existing ex vivo include foods and drinks, such as liquid flavors, and infusion solutions in which a protein or peptide exists together with sugar.

(Fructosyl Hexapeptide and Fructosyl Peptide)

The term "fructosyl peptide" used herein refers to a non-enzymatically-glycated peptide derived from a glycated protein. Peptides that are directly and non-enzymatically glycated and products of degradation of glycated proteins by proteases are within the scope of the fructosyl peptides. In glycated proteins, examples of amino groups in the glycated peptide side chain include an amino terminal α-amino group and a ε-amino group in the lysine side chain in a peptide. In the present invention, more specifically, the fructosyl peptide is an α-glycated peptide (α-fructosyl peptide). The α-fructosyl peptide is released from a glycated protein having a glycated N-terminal α-amino acid by an arbitrary means, such as limited degradation with a protease. When a target glycated protein is hemoglobin Ale (HbAlc), for example, the α-fructosyl peptide is a glycated peptide cleaved from the glycated N-terminus. From the viewpoint of quantification of HbAlc, in particular, the α-fructosyl peptide is a glycated peptide cleaved from the glycated N-terminus of the hemoglobin β-chain.

The target substance with which the amadoriase according to the present invention reacts is an α-fructosyl hexapeptide (αF6P). When αF6P is cleaved from the N-terminus of the HbAlc β-chain, the target substance is, specifically, an α-fructosyl valyl-histidyl-leucyl-threonyl-propyl-glutamic acid.

(Amadoriase)

An amadoriase is also referred to as ketoamine oxidase, fructosyl amino acid oxidase, fructosyl peptide oxidase, or fructosyl amine oxidase, and it is an enzyme that oxidizes iminodiacetic acid or a derivative thereof (Amadori compound) in the presence of oxygen to catalyze a reaction to generate glyoxylic acid or α-ketoaldehyde, amino acid, or peptide, and hydrogen peroxide. Amadoriases are widely distributed in nature and can be obtained by searching for enzymes from sources of microorganisms, animals, or plants. With regard to microorganisms, amadoriases can be obtained from, for example, filamentous fungi, yeast, or bacteria. The amadoriase according to the present invention is characterized by high reactivity with αF6P.

(Modified Amadoriase)

The present invention provides a modified amadoriase having altered substrate specificity, which is prepared from a wild-type amadoriase comprising the amino acid sequence as shown in SEQ ID NO: 1, SEQ ID NO: 38, SEQ ID NO: 40, SEQ ID NO: 54, SEQ ID NO: 62, SEQ ID NO: 89, or SEQ ID NO: 99 and has high reactivity with αF6P. In this description, the term "modified amadoriase" is interchangeably used with the term "amadoriase variant," comprising an amino acid sequence derived from the amino acid sequence of a wild-type amadoriase by substitution, deletion, or addition of some amino acids. The term "addition" used in this context encompasses "insertion."

Also, the present invention provides a modified amadoriase having altered substrate specificity, which is prepared from a wild-type amadoriase comprising the amino acid sequence as shown in SEQ ID NO: 113, SEQ ID NO: 115, SEQ ID NO: 117, SEQ ID NO: 119, SEQ ID NO: 121, SEQ ID NO: 123, SEQ ID NO: 145, or SEQ ID NO: 149 and has high reactivity with αF6P.

On the basis of the finding of the present invention, a modified amadoriase having altered substrate specificity can be obtained from another wild-type amadoriase derived from the genus *Coniochaeta* or the like, which has high reactivity with αF6P.

(Modified Amadoriase Prepared from Amadoriase Derived from *Coniochaeta* sp. NISL 9330)

According to an embodiment of the present invention, the amadoriase has altered substrate specificity, and it is prepared from the amadoriase derived from the genus *Coniochaeta* comprising the amino acid sequence as shown in SEQ ID NO: 1 and has high reactivity with αF6P.

Examples of variants as described above include amadoriases comprising amino acid sequences exhibiting high sequence identity with the amino acid sequences as shown in SEQ ID NO: 151, SEQ ID NO: 153, and SEQ ID NO: 155 (single variants), SEQ ID NO: 157, SEQ ID NO: 159, SEQ ID NO: 161, and SEQ ID NO: 163 (double variants), SEQ ID NO: 137. SEQ ID NO: 139, SEQ ID NO: 165, SEQ ID NO: 167, SEQ ID NO: 169, SEQ ID NO: 171, and SEQ ID NO: 173 (triple variants), SEQ ID NO: 133, SEQ ID NO: 135, SEQ ID NO: 175, and SEQ ID NO: 189 (quadruple variants), SEQ ID NO: 177 and SEQ ID NO: 179 (quintuple variants), SEQ ID NO: 143, SEQ ID NO: 181, SEQ ID NO: 183, SEQ ID NO: 187, and SEQ ID NO: 191 (sextuple variants), and SEQ ID NO: 141 and SEQ ID NO: 185 (septuple variants) (e.g., sequence identity of 50% or higher, preferably 60% or higher, 70% or higher, 75% or higher, or 80% or higher, more preferably 85% or higher, further preferably 90% or higher, 95% or higher, or 98% or higher, and most preferably 99% or higher), and having activity on αF6P.

In addition, examples of such variants include amadoriases comprising amino acid sequences derived from the amino acid sequences as shown in SEQ ID NO: 151, SEQ ID NO: 153, and SEQ ID NO: 155 (single variants), SEQ ID NO: 157, SEQ ID NO: 159, SEQ ID NO: 161, and SEQ ID NO: 163 (double variants), SEQ ID NO: 137, SEQ ID NO: 139, SEQ ID NO: 165, SEQ ID NO: 167, SEQ ID NO: 169, SEQ ID NO: 171, and SEQ ID NO: 173 (triple variants), SEQ ID NO: 133, SEQ ID NO: 135, SEQ ID NO: 175, and SEQ ID NO: 189 (quadruple variants), SEQ ID NO: 177 and SEQ ID NO: 179 (quintuple variants), SEQ ID NO: 143, SEQ ID NO: 181, SEQ ID NO: 183, SEQ ID NO: 187, and SEQ ID NO: 191 (sextuple variants), and SEQ ID NO: 141 and SEQ ID NO: 185 (septuple variants) in which one or several amino acid(s) is(are) modified or mutated or deleted, substituted, added, and/or inserted and having activity on αF6P. The term "one or several amino acids" used herein refers to 1 to 15, preferably 1 to 10, more preferably 1 to 5, still more preferably 1 to 4, further preferably 1 to 3, and still further preferably 1 or 2 amino acids, when the full-length amino acid sequence comprises more than 400 amino acids. Also, the term "one or several amino acids" refers to 1 to 10, preferably 1 to 7, more preferably 1 to 5, still more preferably 1 to 4, further preferably 1 to 3, and still further preferably 1 or 2 amino acids, when the full-length amino acid sequence comprises 200 to 400 amino acids. The term "one or several amino acids" refers to 1 to 5, preferably 1 to 4, more preferably 1 to 3, and further preferably 1 or 2 amino acids, when the full-length amino acid sequence comprises 40 to less than 200 amino acids. The term "one or several amino acids" refers to 1 or 2 amino acids, when the full-length amino acid sequence comprises less than 40 amino acids.

Examples of variants as described above include amadoriases encoded by nucleotide sequences hybridizing under stringent conditions to sequences complementary to the nucleotide sequences as shown in SEQ ID NO: 152, SEQ ID NO: 154, and SEQ ID NO: 156 (single variants), SEQ ID NO: 158, SEQ ID NO: 160, SEQ ID NO: 162, and SEQ ID NO: 164 (double variants), SEQ ID NO: 138, SEQ ID NO: 140, SEQ ID NO: 166, SEQ ID NO: 168, SEQ ID NO: 170, SEQ ID NO: 172, and SEQ ID NO: 174 (triple variants), SEQ ID NO: 134, SEQ ID NO: 136, SEQ ID NO: 176, and SEQ ID NO: 190 (quadruple variants), SEQ ID NO: 178 and SEQ ID NO: 180 (quintuple variants), SEQ ID NO: 144, SEQ ID NO: 182, SEQ ID NO: 184, SEQ ID NO: 188, and SEQ ID NO: 192 (sextuple variants), and SEQ ID NO: 142 and SEQ ID NO: 186 (septuple variants) and having activity on αF6P. Stringent hybridization conditions are described in, for example, Sambrook et al., Molecular Cloning, Vol. 2 (Cold Spring Harbor Laboratory Press) or Current Protocols in Molecular Biology (Frederick, M. Ausubel et al. (ed.), 1987). Under stringent conditions, for example, hybridization is carried out by conducting incubation with the use of a hybridization solution (50% formamide, 6 to 10×SSC (0.15 to 1.5 M NaCl, 15 mM sodium citrate, pH 7.0), 5×Denhardt solution, 1% SDS, 10% dextran sulfate, 10 μg/ml denatured salmon sperm DNA, and 50 mM phosphate buffer (pH 7.5)) at about 42° C. to about 50° C., followed by washing with 0.1×SSC and 0.1% SDS at about 65° C. to about 70° C. Under other stringent conditions, hybridization is carried out with the use of, for example, a hybridization solution of 50% formamide, 5×SSC (0.15 M NaCl, 15 mM sodium citrate, pH 7.0), 1×Denhardt solution, 1% SDS, 10% dextran sulfate, 10 μg/ml denatured salmon sperm DNA, and 50 mM phosphate buffer (pH 7.5).

The variant according to the present invention may be obtained from amadoriases derived from other organism species, such as the genus *Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Corynebacterium, Agrobacterium*, or *Arthrobacter*, provided that the conditions concerning substrate specificity and/or amino acid sequences described in the claims are satisfied.

A modified amadoriase obtained from the amadoriase derived from *Coniochaeta* sp. NISL 9330 (SEQ ID NO: 1) can comprise one or a plurality of amino acid substitutions at the positions described below. The term "one or a plurality of amino acid substitutions" used with regard to the modified amadoriase refers to substitution of 1, 2, 3, 4, 5, 6, 7, or 8 amino acids. Preferably, the term refers to substitution of 1, 2, 3, 4, 5, 6, or 7 amino acids:

(a) arginine at position 62;
(b) leucine at position 63;
(c) glutamic acid at position 102;
(d) aspartic acid at position 106;
(e) glutamine at position 110;
(f) alanine at position 113;
(g) alanine at position 355; and
(h) alanine at position 419.

In the amadoriase derived from *Coniochaeta* sp. NISL 9330 (SEQ ID NO: 1), preferably, (a) arginine at position 62 is substituted with alanine, asparagine, or aspartic acid. Preferably, (b) leucine at position 63 is substituted with histidine or alanine. Preferably, (c) glutamic acid at position 102 is substituted with lysine. Preferably, (d) aspartic acid at position 106 is substituted with alanine, lysine, or arginine. Preferably, (e) glutamine at position 110 is substituted with leucine or tyrosine. Preferably, (f) alanine at position 113 is substituted with lysine or arginine. Preferably, (g) alanine at position 355 is substituted with serine. According to the circumstances, (h) alanine at position 419 may be substituted with lysine.

A modified amadoriase obtained from the amadoriase derived from *Phaeosphaeria nodorum* (PnFX, SEQ ID NO: 38) can contain one or a plurality of amino acid substitutions at the positions described below:

(a) serine at position 62;
(b) leucine at position 63;
(c) lysine at position 102;
(d) aspartic acid at position 106;
(e) glycine at position 110;
(f) alanine at position 113;

(g) alanine at position 351; and (h) serine at position 416.

In the amadoriase derived from *Phaeosphaeria nodorum* (SEQ ID NO: 38), preferably, (a) serine at position 62 is substituted with alanine or aspartic acid. Preferably, (b) leucine at position 63 is substituted with histidine. According to the circumstances, (c) lysine at position 102 may not be substituted. Preferably, (d) aspartic acid at position 106 is substituted with lysine. Preferably, glycine at position 110 is substituted with leucine. Preferably, alanine at position 113 is substituted with lysine. Preferably, alanine at position 351 is substituted with serine. According to the circumstances, (h) serine at position 416 may be substituted with lysine.

A modified amadoriase obtained from the amadoriase derived from *Neocosmospora vasinfecta* (NvFX, SEQ ID NO: 54) can contain one or a plurality of amino acid substitutions at the positions described below:

(a) arginine at position 62;

(b) leucine at position 63;

(c) glutamic acid at position 102;

(d) glycine at position 106;

(e) glutamic acid at position 110;

(f) lysine at position 113;

(g) serine at position 355; and (h) alanine at position 420.

In the amadoriase derived from *Neocosmospora vasinfecta* (SEQ ID NO: 54), preferably, arginine at position 62 is substituted with alanine or aspartic acid. Preferably, (b) leucine at position 63 is substituted with histidine. Preferably, (c) glutamic acid at position 102 is substituted with lysine. Preferably, (d) glycine at position 106 is substituted with lysine. Preferably, glutamic acid at position 110 is substituted with leucine. According to the circumstances, lysine at position 113 may not be substituted, and serine at position 355 may not be substituted. According to the circumstances, (h) alanine at position 420 may be substituted with lysine.

A modified amadoriase obtained from the amadoriase derived from *Aspergillus nidulans* (AnFX, SEQ ID NO: 62) can contain one or a plurality of amino acid substitutions at the positions described below:

(a) arginine at position 61;

(b) leucine at position 62;

(c) glutamic acid at position 101;

(d) glycine at position 105;

(e) lysine at position 109;

(f) serine at position 112;

(g) alanine at position 355; and (h) alanine at position 420.

In the amadoriase derived from *Aspergillus nidulans* (SEQ ID NO: 62), preferably, (a) arginine at position 61 is substituted with alanine or aspartic acid. Preferably, (b) leucine at position 62 is substituted with histidine. Preferably, (c) glutamic acid at position 101 is substituted with lysine. Preferably, (d) glycine at position 105 is substituted with lysine. Preferably, lysine at position 109 is substituted with leucine. Preferably, serine at position 112 is substituted with lysine. Preferably, alanine at position 355 is substituted with serine. According to the circumstances, (h) alanine at position 420 may be substituted with lysine.

A modified amadoriase obtained from the amadoriase derived from *Eupenicillium terrenum* (SEQ ID NO: 40) can contain one or a plurality of amino acid substitutions at the positions described below:

(a) arginine at position 62;

(b) leucine at position 63;

(c) glutamic acid at position 102;

(d) asparagine at position 106;

(e) lysine at position 110;

(f) threonine at position 113;

(g) alanine at position 355; and (h) glycine at position 419.

In the amadoriase derived from EFP-T5 (SEQ ID NO: 40), preferably, (a) arginine at position 62 is substituted with alanine or aspartic acid. Preferably, (b) leucine at position 63 is substituted with histidine. Preferably, (c) glutamic acid at position 102 is substituted with lysine. Preferably, (d) asparagine at position 106 is substituted with lysine. Preferably, lysine at position 110 is substituted with leucine. Preferably, threonine at position 113 is substituted with lysine. Preferably, alanine at position 355 is substituted with serine. According to the circumstances, (h) glycine at position 419 may be substituted with lysine.

A modified amadoriase obtained from fructosyl amino acid oxidase derived from *Cryptococcus neoformans* (SEQ ID NO: 89 or 149) can contain one or a plurality of amino acid substitutions at the positions described below:

(a) arginine at position 62;

(b) isoleucine at position 63;

(c) glutamic acid at position 102;

(d) serine at position 106;

(e) serine at position 110;

(f) alanine at position 113;

(g) alanine at position 355; and (h) alanine at position 420.

In the fructosyl amino acid oxidase derived from *Cryptococcus neoformans* (CnFX, SEQ ID NO: 89 or 149), preferably, (a) arginine at position 62 is substituted with alanine or aspartic acid. Preferably, (b) isoleucine at position 63 is substituted with histidine, Preferably, (c) glutamic acid at position 102 is substituted with lysine. Preferably, (d) serine at position 106 is substituted with lysine. Preferably, serine at position 110 is substituted with leucine. Preferably, alanine at position 113 is substituted with lysine. Preferably, alanine at position 355 is substituted with serine. According to the circumstances, (h) alanine at position 420 may be substituted with lysine.

A modified amadoriase obtained from ketoamine oxidase derived from *Pyrenochaeta* sp. (SEQ ID NO: 113) can contain one or a plurality of amino acid substitutions at the positions described below:

(a) arginine at position 62;

(b) leucine at position 63;

(c) lysine at position 102;

(d) aspartic acid at position 106;

(e) alanine at position 110;

(f) threonine at position 113;

(g) alanine at position 353; and (h) alanine at position 418.

In the ketoamine oxidase derived from *Pyrenochaeta* sp. (SEQ ID NO: 113), preferably, (a) arginine at position 62 is substituted with alanine or aspartic acid. Preferably, (h) leucine at position 63 is substituted with histidine. According to the circumstances, (c) lysine at position 102 may not be substituted. Preferably, (d) aspartic acid at position 106 is substituted with lysine. Preferably, alanine at position 110 is substituted with leucine. Preferably, threonine at position 113 is substituted with lysine. Preferably, alanine at position 353 is substituted with serine. According to the circumstances, (h) alanine at position 418 may be substituted with lysine.

A modified amadoriase obtained from ketoamine oxidase derived from *Arthrinium* sp. (SEQ ID NO: 115) can contain one or a plurality of amino acid substitutions at the positions described below:

(a) arginine at position 62;
(b) leucine at position 63;
(c) lysine at position 102;
(d) alanine at position 106;
(e) glutamine at position 110;
(f) threonine at position 113;
(g) alanine at position 356; and
(h) alanine at position 421.

In the ketoamine oxidase derived from *Arthrinium* sp. (SEQ TD NO: 115), preferably, (a) arginine at position 62 is substituted with alanine or aspartic acid. Preferably, (b) leucine at position 63 is substituted with histidine. According to the circumstances, (c) lysine at position 102 may not be substituted. Preferably, (d) alanine at position 106 is substituted with lysine. Preferably, glutamine at position 110 is substituted with leucine. Preferably, threonine at position 113 is substituted with lysine. Preferably, alanine at position 356 is substituted with serine. According to the circumstances, (h) alanine at position 421 may be substituted with lysine.

A modified amadoriase obtained from ketoamine oxidase derived from *Curvularia clavata* (SEQ ID NO: 117) can contain one or a plurality of amino acid substitutions at the positions described below:

(a) arginine at position 62;
(b) leucine at position 63;
(c) glutamic acid at position 102;
(d) aspartic acid at position 106;
(e) alanine at position 110;
(f) alanine at position 113;
(g) alanine at position 353; and
(h) alanine at position 418.

In the ketoamine oxidase derived from *Curvularia clavata* (SEQ ID NO: 117), preferably, (a) arginine at position 62 is substituted with alanine or aspartic acid. Preferably, (b) leucine at position 63 is substituted with histidine. Preferably, (c) glutamic acid at position 102 is substituted with lysine. Preferably, (d) aspartic acid at position 106 is substituted with lysine. Preferably, alanine at position 110 is substituted with leucine. Preferably, alanine at position 113 is substituted with lysine. Preferably, alanine at position 353 is substituted with serine. According to the circumstances, (h) alanine at position 418 may be substituted with lysine.

A modified amadoriase obtained from ketoamine oxidase (Cc95FX, SEQ ID NO: 99) having 95% amino acid sequence identity with ketoamine oxidase derived from *Curvularia clavata* (SEQ ID NO: 117) can contain one or a plurality of amino acid substitutions at the positions described below:

(a) arginine at position 62;
(b) leucine at position 63;
(c) glutamic acid at position 102;
(d) aspartic acid at position 106;
(e) alanine at position 110;
(f) alanine at position 113;
(g) alanine at position 353; and
(h) serine at position 418.

In the ketoamine oxidase (SEQ ID NO: 99) having 95% amino acid sequence identity with the ketoamine oxidase derived from *Curvularia clavata* (SEQ ID NO: 117), preferably, (a) arginine at position 62 is substituted with alanine or aspartic acid. Preferably, (b) leucine at position 63 is substituted with histidine. Preferably, (c) glutamic acid at position 102 is substituted with lysine. Preferably, (d) aspartic acid at position 106 is substituted with lysine. Preferably, alanine at position 110 is substituted with leucine. Preferably, alanine at position 113 is substituted with lysine. Preferably, alanine at position 353 is substituted with serine. According to the circumstances, (h) serine at position 418 may be substituted with lysine.

A modified amadoriase obtained from fructosyl peptide oxidase derived from *Emericella nidulans* (SEQ ID NO: 119) can contain one or a plurality of amino acid substitutions at the positions described below:

(a) arginine at position 61;
(b) leucine at position 62;
(c) glutamic acid at position 101;
(d) lysine at position 105;
(e) arginine at position 109;
(f) serine at position 112;
(g) alanine at position 355; and
(h) alanine at position 420.

In the fructosyl peptide oxidase derived from *Emericella nidulans* (SEQ ID NO: 119), preferably, (a) arginine at position 61 is substituted with alanine or aspartic acid. Preferably, (b) leucine at position 62 is substituted with histidine. Preferably, (c) glutamic acid at position 101 is substituted with lysine. According to the circumstances, (d) lysine at position 105 may not be substituted. Preferably, arginine at position 109 is substituted with leucine. Preferably, serine at position 112 is substituted with lysine. Preferably, alanine at position 355 is substituted with serine. According to the circumstances, (h) alanine at position 420 may be substituted with lysine.

A modified amadoriase obtained from fructosyl amino acid oxidase derived from *Ulocladium* sp. (SEQ ID NO: 121) can contain one or a plurality of amino acid substitutions at the positions described below:

(a) arginine at position 62;
(b) leucine at position 63;
(c) lysine at position 102;
(d) aspartic acid at position 106;
(e) alanine at position 110;
(f) alanine at position 113;
(g) alanine at position 353; and
(h) alanine at position 418.

In the fructosyl amino acid oxidase derived from *Ulocladium* sp. (SEQ ID NO: 121), preferably, (a) arginine at position 62 is substituted with alanine or aspartic acid. Preferably, (b) Leucine at position 63 is substituted with histidine. According to the circumstances, (c) lysine at position 102 may not be substituted. Preferably (d) aspartic acid at position 106 is substituted with lysine. Preferably, alanine at position 110 is substituted with leucine. Preferably, alanine at position 113 is substituted with lysine. Preferably, alanine at position 353 is substituted with serine. According to the circumstances, (h) alanine at position 418 may be substituted with lysine.

A modified amadoriase obtained from fructosyl amino acid oxidase derived from *Penicillium janthinellum* (SEQ ID NO: 123) can contain one or a plurality of amino acid substitutions at the positions described below:

(a) arginine at position 62;
(b) leucine at position 63;
(c) glutamic acid at position 102;
(d) serine at position 106;
(e) lysine at position 110;
(f) aspartic acid at position 113;
(g) alanine at position 355; and
(h) serine at position 419.

In the fructosyl amino acid oxidase derived from *Penicillium janthinellum* (SEQ ID NO: 123), preferably, (a) arginine at position 62 is substituted with alanine or aspartic acid. Preferably, (b) leucine at position 63 is substituted with histidine. Preferably, (c) glutamic acid at position 102 is substituted with lysine. Preferably, (d) serine at position 106 is substituted with lysine. Preferably, lysine at position 110 is substituted with leucine. Preferably, aspartic acid at position 113 is substituted with lysine. Preferably, alanine at position 355 is substituted with serine. According to the circumstances, (h) serine at position 419 may be substituted with lysine.

Wild-type amadoriases exhibiting no or substantially no activity on αF6P, for example, wild-type amadoriases comprising amino acid sequences as shown in SEQ ID NO: 1, SEQ ID NO: 36, SEQ ID NO: 38, SEQ ID NO: 40, SEQ ID NO: 54, SEQ ID NO: 62, SEQ ID NO: 89, SEQ ID NO: 99, SEQ ID NO: 145, SEQ ID NO: 147, and SEQ ID NO: 149 are excluded from the scope of the amadoriase variant or modified amadoriase of the present invention. Regarding the phrase the amadoriase variant or modified amadoriase of the present invention, unless otherwise specified, wild-type amadoriases exhibiting no or substantially no activity on αF6P are excluded from the scope of the amadoriase variant or modified amadoriase of the present invention.

(Obtaining a Gene Encoding an Amadoriase)

In order to obtain a gene in accordance with the present invention encoding these amadoriases (hereinafter, also referred to as merely "amadoriase gene"), gene cloning methods used in general can be carried out. For example, chromosomal DNA or mRNA can be extracted from a microorganism fungus body or various cells having an ability to produce an amadoriase by a conventional technique, such as a method described in "Current Protocols in Molecular Biology" (WILEY Interscience, 1989). In addition, cDNA can be synthesized using mRNA as a template. A chromosomal DNA or cDNA library can be made using the chromosomal DNA or cDNA obtained in such a manner.

Subsequently, DNA including the entire sequence of a target amadoriase gene can be obtained by a method of synthesizing an appropriate probe DNA based on the amino acid sequence of the aforementioned amadoriase and selecting an amadoriase gene from a chromosomal DNA or cDNA library using the probe DNA. Alternatively, an appropriate primer DNA may be produced based on the aforementioned amino acid sequence, a DNA including the target gene fragment encoding the amadoriase gene may be amplified by using an appropriate polymerase chain reaction (PCR) technique, such as the 5' RACE or 3' RACE method, and the resulting DNA fragments may then be linked.

A preferable example of a gene encoding an amadoriase thus obtained is an amadoriase gene derived from the genus *Coniochaeta* (JP 2003-235585 A).

Other preferable examples include amadoriase genes derived from the genus *Phaeosphaeria*, amadoriase genes derived from the genus *Neocosmospora*, amadoriase genes derived from the genus *Aspergillus*, amadoriase genes derived from the genus *Cryptococcus*, amadoriase genes derived from the genus *Curvularia*, and amadoriase genes derived from the genus *Eupenicillium*.

Such amadoriase genes are preferably linked to various vectors according to a conventional technique from the viewpoint of handleability. For example, a DNA encoding an amadoriase gene can be obtained by subjecting a recombinant plasmid pKK223-3-CFP-T7 including DNA encoding an amadoriase gene derived from a strain of *Coniochaeta* sp. NISL9330 (WO 2007/125779) to extraction and purification using the GenElute Plasmid Miniprep Kit (Sigma-Aldrich). A person skilled in the art would be able to obtain DNA of amadoriase genes derived from other organisms in a similar manner using conventional techniques. More specifically, DNA encoding an amadoriase gene can be obtained by culturing *E. coli* strains carrying the recombinant plasmid pUTE100K'-EFP-T5 including DNA encoding an amadoriase gene derived from a strain of *Eupenicillium terrenum* ATCC 18547 (WO 2007/125779) and extracting and purifying the recombinant plasmid pUTE100K'-EFP-T5 including DNA encoding an amadoriase gene from the cells using the GenElute Plasmid Miniprep Kit. Also, DNA encoding an amadoriase gene can be obtained by culturing *E. coli* strains carrying the recombinant plasmid pET22b-AnFX including DNA encoding an amadoriase gene derived from a strain of *Aspergillus nidulans* FGSC A26 (WO 2012/018094) and extracting and purifying the recombinant plasmid pET22b-AnFX including DNA encoding an amadoriase gene therefrom with the use of the GenElute Plasmid Miniprep Kit. DNA encoding an amadoriase gene can be obtained by culturing *E. coli* strains carrying the recombinant plasmid pET22b-CnFX including DNA encoding an amadoriase gene derived from a strain of *Cryptococcus neoformans* (WO 2012/018094) and extracting and purifying the recombinant plasmid pET22b-CnFX including DNA encoding an amadoriase gene therefrom with the use of the GenElute Plasmid Miniprep Kit. DNA encoding an amadoriase gene can be obtained by culturing *E. coli* strains carrying the recombinant plasmid pET22b-NvFX including DNA encoding an amadoriase gene derived from a strain of *Neocosmospora vasinfecta* (WO 2012/018094) and extracting and purifying the recombinant plasmid pET22b-NvFX including DNA encoding an amadoriase gene therefrom with the use of the GenElute Plasmid Miniprep Kit.

(Vector)

Vectors that can be used in the present invention are not limited to the aforementioned plasmid vectors but include, for example, any other vectors known in the art, such as bacteriophage or cosmid vectors. Specifically, for example, pBluescriptII SK+ (manufactured by Stratagene Corporation) is preferable.

(Mutation of Amadoriase Gene)

Mutation of an amadoriase gene can be performed by any known method depending on an intended form of mutation. More specifically, a method of bringing a chemical mutagen into contact with and allowing to act on an amadoriase gene or recombinant DNA comprising such gene integrated therein; an ultraviolet irradiation method; a genetic engineering technique; a method of making full use of a protein engineering technique; or various other methods can be used.

Examples of chemical mutagens used in the aforementioned mutation include hydroxyl amine, N-methyl-N'-nitro-N-nitrosoguanidine, nitrous acid, sulfurous acid, hydrazine, formic acid, and 5-bromouracil.

Various conditions for the contact/reactions may be employed depending on the type of a drug to be used and are not particularly limited where a desired mutation can be actually induced in an amadoriase gene. In general, the desired mutation can be induced by contact/reactions performed at 20° C. to 80° C. for 10 minutes or longer, and preferably 10 to 180 minutes, with the use of the aforementioned drug at the concentration of 0.5 M to 12 M. The ultraviolet irradiation may be also performed according to a conventional technique as described above (Gendai Kagaku, pp. 24-30, June, 1989).

As the method of making full use of the protein engineering technique, a technique known as site-specific mutagenesis can in general be used, and examples include the Kramer method (Nucleic Acids Res., 12, 9441, 1984; Methods Enzymol., 154, 350, 1987; Gene, 37, 73, 1985), the Eckstein method (Nucleic Acids Res., 13, 8749, 1985; Nucleic Acids Res., 13, 8765, 1985; Nucleic Acids Res, 14, 9679, 1986), and the Kunkel method (Proc. Natl. Acid. Sci. U.S.A., 82, 488, 1985; Methods Enzymol., 154, 367, 1987).

A technique known as a general PCR technique can also be used (Technique, 1, 11, 1989). In addition to the conventional genetic mutation technique, by an organic synthesis method or synthetic method of an enzyme, the modified amadoriase genes of interest can be also directly synthesized.

The DNA nucleotide sequences of amadoriase genes obtained by the aforementioned methods may be determined or verified by, for example, using a multi-capillary DNA analysis system, Applied Biosystems 3130x Genetic Analyzer (Life Technologies).

(Transformation/Transduction)

The amadoriase genes obtained as described above are integrated into a vector such as a bacteriophage vector, a cosmid vector, or a plasmid vector used in transformation of a procaryotic or eucaryotic cell by a conventional technique, and a host corresponding to each vector can be transformed or transduced by a conventional technique. For example, a microorganism belonging to the genus *Escherichia*, such as the obtained recombinant DNA, is used as the host to transform a strain of *E. coli* K-12, and preferably a strain of *E. coli JM*109 or *E. coli* DH5α, (manufactured by Takara Bio Inc.), or such microorganism is transduced into such strain. Thus, transformed or transduced strains of interest can be obtained.

(Amino Acid Sequence Homology, Identity, or Similarity)

The amino acid sequence homology, identity, or similarity can be calculated by a program such as maximum matching or search homology of GENETYX (manufactured by GENETYX), a program such as maximum matching or multiple alignment of DNASIS Pro (manufactured by Hitachi Solutions, Ltd.), or a program such as multiple alignment of CLUSTALW. In order to calculate amino acid sequence identity, two or more amadoriases may be aligned, and the positions of identical amino acids in such two or more amadoriases may be determined. The identical regions in amino acid sequences can be determined based on such information. The percent identity of two or more amino acid sequences is determined by subjecting two or more amino acid sequences to alignment using the algorithm such as Blosum62 by designating the total number of amino acids in the aligned region as the denominator and the number of identical amino acids relative to the total number as the numerator. If no identity is found in parts of the two or more amino acid sequences, for example, an amino acid sequence comprises at its C terminus an additional sequence in which no identity is observed, in general, such regions cannot be aligned. Accordingly, such regions are not used for calculation of the percent identity.

Also, positions of similar amino acids in two or more amadoriases can be inspected. For example, a plurality of amino acid sequences can be subjected to alignment with the use of CLUSTALW. In such a case, Blosum62 is used as the algorithm and a plurality of amino acid sequences are subjected to alignment. Amino acids determined to be similar as a result of alignment may be referred to as "similar amino acids." In the variant of the present invention, amino acid substitution can be carried out between such similar amino acids. Through such alignment, amino acid sequences composed of the identical amino acids or similar amino acids among a plurality of amino acid sequences can be simultaneously investigated. Based on such information, homologous regions (conserved regions) in the amino acid sequences can be determined.

The term "homologous region(s)" used herein refers to the region(s) consisting of identical or similar amino acids at corresponding positions in the reference amadoriase and in the comparative amadoriase, when two or more amadoriases are aligned, such region consisting of 3 or more, 4 or more, 5 or more, 6 or more. 7 or more, 8 or more, 9 or more, or 10 or more continuous amino acids. For example, FIG. 1 shows the alignment of amadoriases exhibiting sequence identity of 74% or higher in full-length amino acid sequences. In such sequences, the region of positions 10 to 32 with reference to the sequence of the amadoriase derived from *Coniochaeta* sp. as shown in SEQ ID NO: 1 consists of identical or similar amino acids, and such region is considered to be a homologous region. Similarly, regions of positions 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 with reference to the sequence of the amadoriase derived from *Coniochaeta* sp. as shown in SEQ ID NO: 1 can be a homologous region(s).

Preferably, the homologous region of amadoriases is the amino acid sequences of positions 11 to 32, 36 to 41, 50 to 52, 54 to 58, 84 to 86, 88 to 90, 145 to 150, 157 to 168, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410 with reference to the sequence of the amadoriase derived from *Coniochaeta* sp. as shown in SEQ ID NO: 1.

More preferably, the homologous region of amadoriases is the amino acid sequences of positions 11 to 18, 20 to 32, 50 to 52, 54 to 58, 266 to 268, 270 to 273, 277 to 286, and 370 to 383 with reference to the sequence of the amadoriase derived from *Coniochaeta* sp. as shown in SEQ ID NO: 1.

When the full-length amino acid sequence of the amadoriase variant of the present invention is aligned with that of the amadoriase comprising the amino acid sequence as shown in SEQ ID NO: 1, the sequence identity is 50% or higher, preferably 60% or higher, 70% or higher, 75% or higher, or 80% or higher, more preferably 90% or higher, or 95% or higher, and most preferably 99% or higher, and such amadoriase variant has high reactivity with αF6P. In addition, the amino acid sequence in the homologous region of the amadoriase variant according to the present invention exhibits 80%, preferably 90%, more preferably 95%, further preferably 98%, and still further preferably 99% or higher sequence identity with the amino acid sequence in the homologous region of SEQ ID NO: 1.

(Specifying a Position Corresponding to an Amino Acid Position)

When an amino acid at a particular position in the reference amino acid sequence correspond to an amino acid at a particular position in another similar amino acid sequence, in the present invention, such amino acid is referred to as a corresponding amino acid, and the position of such amino acid is referred to as the corresponding position or equivalent position. A method of identifying the "position corresponding to an amino acid position" may be also performed by comparing amino acid sequences using a known algorithm such as a Lipman-Pearson method to assign maximum identity to conserved amino acid residues present in the amino acid sequence of each amadoriase. The positions of the homologous amino acid residues in each of the amadoriase sequences can be determined, regardless of insertion or deletion of amino acid residue(s) in the amino acid sequences by aligning the amino acid sequences of the amadoriases by such method. Amino acid residues at homologous positions are thought to exist in similar positions in the three-dimensional structures, and amino acid residues at such homologous positions are expected to exert similar effects in terms of specificity of the amadoriase of interest.

In the present invention, the amino acid at "the position corresponding to arginine at position 62 in the amino acid sequence as shown in SEQ ID NO: 1" is the amino acid corresponding to arginine at position 62 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Thus, the amino acid at "the position corresponding to arginine at position 62 in the amino acid sequence as shown in SEQ ID NO: 1" is arginine at position 62 in the case of the amadoriase derived from *Eupenicillium terrenum* (SEQ ID NOs: 40 and 145), the ketoamine oxidase derived from *Pyrenochaeta* sp. (SEQ ID NO: 113), the ketoamine oxidase derived from *Arthrinium* sp. (SEQ ID NO: 115), the ketoamine oxidase derived from *Curvularia clavata* (SEQ ID NO: 117), the ketoamine oxidase derived from *Neocosmospora vasinfecta* (SEQ ID NO: 54), the fructosyl amino acid oxidase derived from *Cryptococcus neoformans* (SEQ ID NOs: 89 and 149), the fructosyl amino acid oxidase derived from *Ulocladium* sp. (SEQ ID NO: 121), and the fructosyl amino acid oxidase derived from *Penicillium janthinellum* (SEQ ID NO: 123); it is serine at position 62 in the case of the fructosyl peptide oxidase derived from *Phaeosphaeria nodorum* (SEQ ID NO: 38); it is arginine at position 61 in the case of the fructosyl peptide oxidase derived from *Emericella nidulans* (SEQ ID NO: 119); and it is arginine at position 61 in the case of the fructosyl amino acid oxidase derived from *Aspergillus nidulans* (SEQ ID NOs: 62 and 147).

In the present invention, the amino acid at "the position corresponding to leucine at position 63 in the amino acid sequence as shown in SEQ ID NO: 1" is the amino acid corresponding to leucine at position 63 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to leucine at position 63 in the amino acid sequence as shown in SEQ ID NO: 1" is leucine at position 63 in the case of the amadoriase derived from *Eupenicillium terrenum* (SEQ ID NOs: 40 and 145), the ketoamine oxidase derived from *Pyrenochaeta* sp. (SEQ ID NO: 113), the ketoamine oxidase derived from *Arthrinium* sp. (SEQ ID NO: 115), the ketoamine oxidase derived from *Curvularia clavata* (SEQ ID NO: 117), the ketoamine oxidase derived from *Neocosmospora vasinfecta* (SEQ ID NO: 54), the fructosyl peptide oxidase derived from *Phaeosphaeria nodorum* (SEQ ID NO: 38), the fructosyl amino acid oxidase derived from *Ulocladium* sp. (SEQ ID NO: 121), and the fructosyl amino acid oxidase derived from *Penicillium janthinellum* (SEQ ID NO: 123); it is isoleucine at position 63 in the case of the fructosyl amino acid oxidase derived from *Cryptococcus neoformans* (SEQ ID NOs: 89 and 149); and it is leucine at position 62 in the case of the fructosyl amino acid oxidase derived from *Aspergillus nidulans* (SEQ ID NOs: 62 and 147) and the fructosyl peptide oxidase derived from *Emericella nidulans* (SEQ ID NO: 119).

In the present invention, the amino acid at "the position corresponding to glutamic acid at position 102 in the amino acid sequence as shown in SEQ ID NO: 1" is the amino acid corresponding to glutamic acid at position 102 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to glutamic acid at position 102 in the amino acid sequence as shown in SEQ ID NO: 1" is glutamic acid at position 102 in the case of the amadoriase derived from *Eupenicillium terrenum* (SEQ ID NOs: 40 and 145), the ketoamine oxidase derived from *Curvularia clavata* (SEQ ID NO: 117), the ketoamine oxidase derived from *Neocosmospora vasinfecta* (SEQ ID NO: 54), the fructosyl amino acid oxidase derived from *Cryptococcus neoformans* (SEQ ID NOs: 89 and 149), and the fructosyl amino acid oxidase derived from *Penicillium janthinellum* (SEQ ID NO: 123); it is lysine at position 102 in the case of the ketoamine oxidase derived from *Pyrenochaeta* sp. (SEQ ID NO: 113), the ketoamine oxidase derived from *Arthrinium* sp. (SEQ ID NO: 115), the fructosyl peptide oxidase derived from *Phaeosphaeria nodorum* (SEQ ID NO: 38), and the fructosyl amino acid oxidase derived from *Ulocladium* sp. (SEQ ID NO: 121); it is glutamic acid at position 101 in the case of the fructosyl peptide oxidase derived from *Emericella nidulans* (SEQ ID NO: 119) and the fructosyl amino acid oxidase derived from *Aspergillus nidulans* (SEQ ID NOs: 62 and 147).

In the present invention, the amino acid at "the position corresponding to aspartic acid at position 106 in the amino acid sequence as shown in SEQ ID NO: 1" is the amino acid corresponding to aspartic acid at position 106 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to aspartic acid at position 106 in the amino acid sequence as shown in SEQ ID NO: 1" is asparagine at position 106 in the case of the amadoriase derived from *Eupenicillium terrenum* (SEQ ID NOs: 40 and 145); it is aspartic acid at position 106 in the case of the ketoamine oxidase derived from *Pyrenochaeta* sp. (SEQ ID NO: 113), the ketoamine oxidase derived from *Curvularia clavata* (SEQ ID NO: 117), the fructosyl peptide oxidase derived from *Phaeosphaeria nodorum* (SEQ ID NO: 38), and the fructosyl amino acid oxidase derived from *Ulocladium* sp.

(SEQ ID NO: 121); it is alanine at position 106 in the case of the ketoamine oxidase derived from *Arthrinium* sp. (SEQ ID NO: 115); it is glycine at position 106 in the case of the ketoamine oxidase derived from *Neocosmospora vasinfecta* (SEQ ID NO: 54); it is serine at position 106 in the case of the fructosyl amino acid oxidase derived from *Cryptococcus neoformans* (SEQ ID NOs: 89 and 149) and the fructosyl amino acid oxidase derived from *Penicillium janthinellum* (SEQ ID NO: 123); it is lysine at position 105 in the case of the fructosyl peptide oxidase derived from *Emericella nidulans* (SEQ ID NO: 119); and it is glycine at position 105 in the case of the fructosyl amino acid oxidase derived from *Aspergillus nidulans* (SEQ ID NOs: 62 and 147).

In the present invention, the amino acid at the position corresponding to glutamine at position 110 in the amino acid sequence as shown in SEQ ID NO: 1" is the amino acid corresponding to glutamine at position 110 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Thus, the amino acid at "the position corresponding to glutamine at position 110 in the amino acid sequence as shown in SEQ ID NO: 1" is lysine at position 110 in the case of the amadoriase derived from *Eupenicillium terrenum* (SEQ ID NOs: 40 and 145) and the fructosyl amino acid oxidase derived from *Penicillium janthinellum* (SEQ ID NO: 123); it is alanine at position 110 in the case of the ketoamine oxidase derived from *Pyrenochaeta* sp. (SEQ ID NO: 113), the ketoamine oxidase derived from *Curvularia clavata* (SEQ ID NO: 117), and the fructosyl amino acid oxidase derived from *Ulocladium* sp. (SEQ ID NO: 121); it is glutamine at position 110 in the case of the ketoamine oxidase derived from *Arthrinium* sp. (SEQ ID NO: 115); it is glutamic acid at position 110 in the case of the ketoamine oxidase derived from *Neocosmospora vasinfecta* (SEQ ID NO: 54); it is serine at position 110 in the case of the fructosyl amino acid oxidase derived from *Cryptococcus neoformans* (SEQ ID NOs: 89 and 149); it is glycine at position 110 in the case of the fructosyl peptide oxidase derived from *Phaeosphaeria nodorum* (SEQ ID NO: 38); it is arginine at position 109 in the case of the fructosyl peptide oxidase derived from *Emericella nidulans* (SEQ ID NO: 119); and it is lysine at position 109 in the case of the fructosyl amino acid oxidase derived from *Aspergillus nidulans* (SEQ ID NOs: 62 and 147).

In the present invention, the amino acid at "the position corresponding to alanine at position 113 in the amino acid sequence as shown in SEQ ID NO: 1" is the amino acid corresponding to alanine at position 113 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to alanine at position 113 in the amino acid sequence as shown in SEQ ID NO: 1" is threonine at position 113 in the case of the amadoriase derived from *Eupenicillium terrenum* (SEQ ID NOs: 40 and 145), the ketoamine oxidase derived from *Pyrenochaeta* sp. (SEQ ID NO: 113), and the ketoamine oxidase derived from *Arthrinium* sp. (SEQ ID NO: 115); it is alanine at position 113 in the case of the ketoamine oxidase derived from *Curvularia clavata* (SEQ ID NO: 117), the fructosyl amino acid oxidase derived from *Cryptococcus neoformans* (SEQ ID NOs: 89 and 149), the fructosyl peptide oxidase derived from *Phaeosphaeria nodorum* (SEQ ID NO: 38), and the fructosyl amino acid oxidase derived from *Ulocladium* sp. (SEQ ID NO: 121); it is lysine at position 113 in the case of the ketoamine oxidase derived from *Neocosmospora vasinfecta* (SEQ ID NO: 54); it is serine at position 112 in the case of the fructosyl amino acid oxidase derived from *Aspergillus nidulans* (SEQ ID NOs: 62 and 147) and the fructosyl peptide oxidase derived from *Emericella nidulans* (SEQ ID NO: 119); and it is aspartic acid at position 113 in the case of the fructosyl amino acid oxidase derived from *Penicillium janthinellum* (SEQ ID NO: 123).

In the present invention, the amino acid at "the position corresponding to alanine at position 355 in the amino acid sequence as shown in SEQ ID NO: 1" is the amino acid corresponding to alanine at position 355 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to alanine at position 355 in the amino acid sequence as shown in SEQ ID NO: 1" is alanine at position 355 in the case of the amadoriase derived from *Eupenicillium terrenum* (SEQ ID NOs: 40 and 145), the fructosyl amino acid oxidase derived from *Cryptococcus neoformans* (SEQ ID NOs: 89 and 149), the fructosyl amino acid oxidase derived from *Aspergillus nidulans* (SEQ ID NOs: 62 and 147), the fructosyl peptide oxidase derived from *Emericella nidulans* (SEQ ID NO: 119), and the fructosyl amino acid oxidase derived from *Penicillium janthinellum* (SEQ ID NO: 123); it is alanine at position 353 in the case of the ketoamine oxidase derived from *Pyrenochaeta* sp. (SEQ ID NO: 113), the ketoamine oxidase derived from *Curvularia clavata* (SEQ ID NO: 117), and the fructosyl amino acid oxidase derived from *Ulocladium* sp. (SEQ ID NO: 121); it is alanine at position 356 in the case of the ketoamine oxidase derived from *Arthrinium* sp. (SEQ ID NO: 115); it is serine at position 355 in the case of the ketoamine oxidase derived from *Neocosmospora vasinfecta* (SEQ ID NO: 54); and it is alanine at position 351 in the case of the fructosyl peptide oxidase derived from *Phaeosphaeria nodorum* (SEQ ID NO: 38).

In the present invention, the amino acid at "the position corresponding to alanine at position 419 in the amino acid sequence as shown in SEQ ID NO: 1" is the amino acid corresponding to alanine at position 419 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to alanine at position 419 in the amino acid sequence as shown in SEQ ID NO: 1" is glycine at position 419 in the case of the amadoriase derived from *Eupenicillium terrenum* (SEQ ID NOs: 40 and 145); it is alanine at position 418 in the case of the ketoamine oxidase derived from *Pyreno-*

*chaeta* sp. (SEQ ID NO: 113), the ketoamine oxidase derived from *Curvularia clavata* (SEQ ID NO: 117), and the fructosyl amino acid oxidase derived from *Ulocladium* sp. (SEQ ID NO: 121); it is alanine at position 421 in the case of the ketoamine oxidase derived from *Arthrinium* sp. (SEQ ID NO: 115); it is alanine at position 420 in the case of the ketoamine oxidase derived from *Neocosmospora vasinfecta* (SEQ ID NO: 54), the fructosyl amino acid oxidase derived from *Cryptococcus neoformans* (SEQ ID NOs: 89 and 149), and the fructosyl peptide oxidase derived from *Emericella nidulans* (SEQ ID NO: 119); it is serine at position 416 in the case of the fructosyl peptide oxidase derived from *Phaeosphaeria nodorum* (SEQ ID NO: 38); it is serine at position 419 in the case of the fructosyl amino acid oxidase derived from *Penicillium janthinellum* (SEQ ID NO: 123); and it is alanine at position 420 in the case of the fructosyl amino acid oxidase derived from *Aspergillus nidulans* (SEQ ID NOs: 62 and 147). (Synergistic effects of substitution)

The amadoriase variant of the present invention may be a single variant or a multiple variant comprising two or more amino acid substitutions, such as double to octuple variants. The present inventors discovered that an amadoriase comprising an amino acid sequence derived from the amino acid sequence as shown in SEQ ID NO: 1 by substitution of amino acids at positions corresponding to positions 62, 63, 102, 106, 110, 113, 355, and 419 exhibit enhanced activity on αF6P. In particular, it was found that as the number of mutations increases as 1, 2, 3, 4, 5, 6, and 7 mutations, the activity of the resulting variant on αF6P was enhanced accordingly. From the enhanced activity of the amadoriase variant described in the Examples on αF6P, it is clear that such amino acid substitutions yield synergistic effects. In addition, a person skilled in the art can appreciate that various combinations of amino acid substitutions at the positions corresponding to positions 62, 63, 102, 106, 110, 113, 355, and 419 in the amino acid sequence as shown in SEQ ID NO: 1 also enhance activity on αF6P.

(Preparatory Substitution)

When the amino acid at the position corresponding to position 60 in the amino acid sequence as shown in SEQ ID NO: 1 is serine, it may be substituted with glycine, so that the amadoriase that did not show activity on αFVH before substitution would exhibit activity on αFVH after substitution (reported in JP 2010-35469 A and WO 2012/018094). As such, regarding amadoriases of the present invention whose amino acid corresponding to position 60 in the amadoriase sequence as shown in SEQ ID NO: 1 is serine, said serine residue may be substituted with glycine in advance. Alternatively, a wild-type amadoriase comprising a sequence in which the amino acid at the position corresponding to position 60 in the sequence as shown in SEQ ID NO: 1 is glycine may be used to introduce mutations into positions corresponding to positions 62, 63, 102, 106, 110, 113, 355, and 419 in SEQ ID NO: 1. Unless otherwise specified, an amadoriase comprising a sequence in which the amino acid at the position corresponding to position 60 in the sequence as shown in SEQ ID NO: 1 is glycine is within the scope of the amadoriase variant of the present invention. For example, in the case of the amadoriase derived from *Aspergillus nidulans*, the amino acid at position 59 in SEQ ID NO: 147 that corresponds to position 60 in SEQ ID NO: 1 is serine in the wild-type amadoriase. A sequence having a substitution of such serine with glycine (i.e., SEQ ID NO: 62) may be used to obtain the amadoriase variant of the present invention. The same applies to the amadoriase derived from *Penicillium janthinellum* (Pj) (SEQ ID NO: 123).

(Production of the Amadoriase of the Present Invention)

In order to produce an amadoriase having improved substrate specificity using a strain having the ability to produce such amadoriase obtained as described above, the strain may be cultured by a conventional solid culture method, although liquid culture is preferable.

Thus, the present invention provides a method for producing an amadoriase comprising a step of culturing a strain capable of producing an amadoriase with altered substrate specificity under conditions where the amadoriase protein can be expressed and a step of isolating an amadoriase from a culture product or culture solution. In such method, a host cell transformed with a vector comprising a gene encoding the amadoriase of the present invention can be used. By the phrase "under conditions where the amadoriase protein can be expressed" is meant that an amadoriase gene is transcribed, translation is carried out, and a polypeptide encoded by such gene can be produced.

Examples of media to culture the aforementioned strains include media prepared by adding one or more inorganic salts, such as sodium chloride, monopotassium phosphate, dipotassium phosphate, magnesium sulfate, magnesium chloride, ferric chloride, ferric sulfate, and manganese sulfate, to one or more nitrogen sources, such as a yeast extract, tryptone, peptone, a meat extract, a corn steep liquor, and a leaching solution of soybean or wheat bran, and further adding saccharine materials, vitamins, and the like thereto, where necessary.

Further, a substrate with which the amadoriase can react or a compound similar thereto, such as a glycated protein, including a glycated amino acid, a glycated peptide, a degradation product of glycated protein, glycated hemoglobin, or glycated albumin, may be added to the medium, so as to increase the production amount of the enzyme of interest.

It is appropriate to adjust the initial pH of the media to 7 to 9. Culture is preferably performed at 20° C. to 42° C., and more preferably at about 25° C. to 37° C. for 4 to 24 hours, and further preferably at about 25° C. to 37° C. for 8 to 16 hours, by, for example, aeration spinner submerged culture, shake culture, or stationary culture.

Following the completion of culture, amadoriases may be collected from the culture products with conventional enzyme collecting means. For example, a strain may be subjected to ultrasonic disintegration treatment or grinding treatment by a conventional method, the enzyme may be extracted using a lytic enzyme such as lysozyme, or bacteriolysis may be performed via shaking or still standing in the presence of toluene to excrete the enzyme from the microorganism body. The solution is filtered or centrifuged to remove solid content, and according to need, nucleic acid is removed with the aid of streptomycin sulfate, protamine sulfate, or manganese sulfate, and to this ammonium sulfate, alcohol, or acetone is added to the solution so as to fractionate the solution, and sediments are then collected to obtain the crude enzymes of the amadoriases.

The purified amadoriase enzyme preparation can be obtained from: the crude enzyme of the aforementioned amadoriase by a method appropriately selected from gel filtration methods using Sephadex, Superdex, or Ultrogel; adsorption-elution methods using ion exchange carriers, hydrophobic carriers, or hydroxyapatite; electrophoretic methods using polyacrylamide gels, etc.; sedimentation methods such as sucrose density-gradient centrifugation; affinity chromatographic methods; and fractionation methods using a molecular sieve membrane, a hollow-fiber membrane, etc. Alternatively, the aforementioned methods can adequately be performed in combination. The amadoriase having improved specificity with αF6P of interest can thus be obtained.

(Improved Specificity of the Amadoriase of the Present Invention with αF6P)

The amadoriase of the present invention obtained by the means described above has improved reactivity with αF6P and improved substrate specificity as a result of mutation in the amino acid sequence caused by genetic modification or other means. If the amadoriase has "improved substrate reactivity" with αF6P in the present invention, specifically, the ratio of "reactivity with αF6P" relative to "reactivity with αFVH" designated to be "1" is increased, compared with such ratio before modification. The "reactivity with αFVH" may also be referred to as "αFVH oxidation activity."

In order to realize an assay system by an enzymatic method based on the same principle as the reference method for measurement of HbAlc defined by IFCC; that is, a system in which HbAlc is treated with Glu-C protease and resulting αF6P is assayed, it is necessary to acquire an amadoriase that can readily react with αF6P.

Specifically, αF6P/αFVH of the amadoriase of the present invention, indicating the ratio of reactivity with αF6P relative to reactivity with αFVH designated to be 1, is preferably 10% or higher, more preferably 20% or higher, still more preferably 30% or higher, and further preferably 40% or higher, compared with that prior to modification.

Also, αF6P/αFV of the amadoriase of the present invention, indicating the ratio of reactivity with αF6P relative to reactivity with αFV designated to be 1, is preferably 10% or higher, more preferably 20% or higher, still more preferably 30% or higher, and further preferably 40% or higher, compared with that prior to modification. The "reactivity with αFV" may also be referred to as "αFV oxidation activity."

The ratio of reactivity with αF6P relative to reactivity with αFVH (i.e., the ratio of reactivity with αF6P to reactivity with αFVH) can be measured under arbitrary conditions via known techniques for measurement of amadoriases, and the measured values can then be compared with the values before modification. For example, the activity measured with the addition of 1 mM αF6P at pH 6.5 may be divided by the activity measured with the addition of 1 mM αFVH to calculate the ratio of the reactivity with αF6P relative to reactivity with αFVH designated to be 1, and the obtained value may then be compared with that before modification. Also, the activity measured with the addition of 1 mM αF6P at pH 6.5 may be divided by the activity measured with the addition of 1 mM αFV to calculate the ratio of the reactivity with αF6P relative to reactivity with αFV designated to be 1, and the obtained value may then be compared with that before modification.

An example of the amadoriase of the present invention having improved substrate specificity with αF6P compared with that before modification is an amadoriase produced by a strain of *E. coli* JM109 (pKK223-3-CFP-T7-H28). Such amadoriase having altered substrate specificity is very useful at an industrial level because it can realize an assay system by an enzymatic method based on the same principle as the reference method for measurement of HbAlc defined by IFCC in which HbAlc is treated with Glu-C protease and resulting αF6P is assayed.

(Method of Measuring Activity of Amadoriase)

The activity of an amadoriase can be measured by various methods. An example of the method of measuring the activity of an amadoriase as used herein is described below.

Examples of major methods for measuring the enzyme activity of the amadoriase of the present invention include a method of measuring the amount of hydrogen peroxide generated by enzyme reactions and a method of measuring the amount of oxygen consumed in enzyme reactions. An example of the method of measuring the amount of hydrogen peroxide is described below.

For measurement of the activity of the amadoriase of the present invention, αFV, αFVH, or αF6P is used as a substrate, unless otherwise specified. Regarding an enzyme titer, the amount of enzyme used to generate 1 μmol of hydrogen peroxide per minute is defined as 1 U, when measurement is carried out using αFV, αFVH, or αF6P as a substrate.

Specific activity (U/mg) is an enzyme titer (U) per mg of an enzyme.

A fructosyl peptide, such as αFVH, synthesized and purified with reference to the method of, for example, Sakaue et al. can be used (JP 2001-95598 A). Upon treatment of glycated hemoglobin (HbAlc) with endoproteinase Glu-C, for example, α-glycated hexapeptide derived from the β subunit of glycated hemoglobin (HbAlc) (i.e., fructosyl Val-His-Leu-Thr-Pro-Glu) is released (Clin. Chem., 43, 1994-1951, 1997), and it can be used as an αF6P substrate. A substance that is identical with such α-glycated hexapeptide; that is, a synthetic substrate, fructosyl Val-His-Leu-Thr-Pro-Glu (manufactured by Peptide Institute, Inc.), can also be used.

A: Preparation of Reagents (Reagent 1) 0.1 M phosphate buffer (pH 6.5) containing 5 U/ml peroxidase and 0.49 mM 4-aminoantipyrine Peroxidase (5.0 kU, manufactured by Kikkoman Corporation) and 100 mg of 4-aminoantipyrine (manufactured by Wako Pure Chemical Industries. Ltd.) are dissolved in a 0.1 M potassium phosphate buffer (pH 6.5), and the volume of the solution is fixed to 1.000 ml.

(Reagent 2) 15 mM TOOS Solution

TOOS (500 mg, manufactured by Dojindo Laboratories) is dissolved in ion-exchange water, and the volume of the solution is fixed to 100 ml.

(Reagent 3) Substrate Solution (30 mM; Final Concentration: 1 mM)

αF6P (257.1 mg, manufactured by Peptide Institute, Inc.), αFVH (124.9 mg, manufactured by Kikkoman Corporation), or αFV (83.8 mg, manufactured by Kikkoman Corporation) is dissolved in ion-exchange water, and the volume of the solution is fixed to 10 ml.

B: Method for Measuring Activity

Reagent 1 (2.7 ml), 100 μl of Reagent 2, and 100 μl of enzyme solution are mixed, and the mixture is preliminarily heated at 37° C. for 5 minutes. Subsequently, 100 μl of Reagent 3 is added, the resultant is thoroughly mixed, and the absorbance at 555 nm is then measured using a spectrophotometer (U-3010A, manufactured by Hitachi High-Technologies) with the elapse of time to determine the change in absorbance per minute (ΔAs) at 555 nm. A control solution is prepared in the manner as described above, except that 100 μl of ion-exchange water is added instead of 100 μl of Reagent 3, and the change in absorbance per minute (ΔA0) at 555 nm thereof is determined. The number of micromoles of hydrogen peroxide generated per minute at 37° C. is calculated using the equation shown below in terms of the unit of activity (U) in the enzyme solution.

$$\text{Activity(U/ml)}=\{(\Delta As-\Delta A0)\times 3.0\times df\}/(39.2\times 0.5\times 0.1)$$

ΔAs: the change in absorbance of the reaction solution per minute

ΔA0: the change in absorbance of the control solution per minute 39.2: millimole absorbance index of quinoneimine dye generated by the reaction ($mM^{-1} \cdot cm^{-1}$)

0.5: number of moles of quinoneimine dye generated by 1 mol of hydrogen peroxide df: dilution factor (Preparation of αF6P-Containing Sample for Measurement)

According to the method of measurement of the present invention, αF6P oxidase is allowed to react with a sample containing αF6P derived from a glycated protein, and the amount of substance produced or consumed by the reaction is measured. An example of a preferable method for cleaving αF6P from a target glycated protein for the purpose of measurement of a glycated protein, such as HbAlc, is digestion with the use of a protease or peptidase. Any protease or peptidase can be used for releasing αF6P, provided that it can be used for clinical testing and it can effectively cleave at least αF6P from HbAlc. Examples of such protease or peptidase include endoproteinase Glu-C, V8 protease, proteinase K, proteinase P, pronase, thermolysin, subtilisin, carboxy peptidase, chymotrypsin, Dispase, papain, ficin, bromelin, and aminopeptidase. Endoprotease or endopeptidase that specifically cleaves the carboxyl terminus of a glutamic acid residue in a glycated protein is particularly preferable, and examples thereof include endoproteinase Glu-C and V8 protease.

Examples of proteases used for cleaving αF6P from glycated proteins include, but are not limited to: various proteases shown in Table 1 of JP 2005-110657 A, such as IP enzyme (Kikkoman Corporation), AO protease (Kikkoman Corporation), Peptidase (Kikkoman Corporation), Protease A5 (Kyowa Kasei Co., Ltd.), Umamizyme (Amano Enzyme), Protease A (Amano Enzyme), Protease M (Amano Enzyme), Protease P (Amano Enzyme), Sumizyme MP (Shinnihon Chemicals Corporation), Sumizyme LP-20 (Shinnihon Chemicals Corporation), and Proteinase 6 (Fluka) derived from *Aspergillus*; Peptidase R derived from *Rhizopus* (Amano Enzyme); Dispase (Roche), Proteinase N (Fluka), Proteinase Type VII (Sigma), Proteinase Bacterial Subtilisin (Fluka), Protease N (Amano Enzyme), Protease S (Amano Enzyme), Proteinase Type X (Sigma), Thermolysin (Daiwa Kasei), Pronase F (Kaken Kagaku), and Neutral protease (TOYOBO CO., LTD.) derived from *Bacillus*; Pronase (Boehringer), Proteinase Type XIV (Sigma), and alkaline protease (TOYOBO CO., LTD.) derived from *Streptomyces*; Proteinase K (Roche) and Proteinase K (Wako) derived from *Tritirachium*; Papain (Roche), Papain (Wako), Papain (Sigma), Papain W40 (Amano Enzyme), and Papain (Asahi) derived from *Carica papaya*; Ficin (Sigma) derived from *Ficus carica*; Pancreatin (Wako) derived from porcine pancreas; and Cathepsin B (Sigma) derived from bovine pancreas. Further, two or more types of proteases may adequately be used in combination.

A sample can be treated with a protease or peptidase under any conditions, provided that the protease acts on the target glycated protein and efficiently releases an α-glycated hexapeptide within a short period of time. The amount of protease used is adequately determined in accordance with the HbAlc content in the sample, treatment conditions, or other factors. For example, endoproteinase Glu-C (e.g., manufactured by Roche Diagnostics) is added to a final concentration of 0.1 to 50 U/ml, and preferably 1 to 10 U/ml. If necessary, other appropriate proteases may further be added. At the time of treatment with a protease, a pH level may not be adjusted. Alternatively, a pH level may be brought to 2 to 9, and preferably 3 to 8, which is preferable for the protease to be used, with the aid of, for example, an adequate pH adjuster, such as hydrochloric acid, acetic acid, sulfuric acid, sodium hydroxide, or potassium hydroxide. Treatment may be carried out at, for example, 20° C. to 50° C., and treatment may be carried out at higher temperature, such as 45° C. to 70° C., in accordance with the enzyme to be used. The duration of treatment is not particularly limited, provided that HbAlc is sufficiently degraded. For example, it is 5 seconds to 180 minutes, preferably 1 to 60 minutes, and further preferably 1 to 10 minutes. The resulting solution is subjected to a reaction for glycated hexapeptide oxidase as a sample containing αF6P without treatment. Alternatively, the solution is subjected to heating, centrifugation, concentration, dilution, or other processing, according to need, and the resultant is then subjected to the reaction.

(Measurement of Released αF6P)

αF6P oxidase used in the method of measurement according to the present invention is allowed to react with the sample containing αF6P. Cleavage of αF6P and the reaction with αF6P oxidase may be carried out continuously or simultaneously. Alternatively, cleavage of αF6P may be followed by the reaction with αF6P oxidase. The duration of the reaction between αF6P and αF6P oxidase may be, for example, 5 seconds or longer, 10 seconds or longer, or 20 seconds or longer, shorter than 180 minutes or shorter than 150 minutes. More specifically, the duration may be, for example, 0.5 to 120 minutes, preferably 0.5 to 60 minutes, and more preferably 1 to 30 minutes. If the duration of the reaction is too short, glycated hexapeptide in the sample cannot be sufficiently measured. If the duration of the reaction is too long, in contrast, the duration of measurement is prolonged, and measurement efficiency becomes poor. In addition thereto, the sample and the reagent are exposed to the measurement conditions for a long period of time, and this disadvantageously causes problems such as degradation or denaturation of the substrate in the sample or components of the reagent. In the case of a microassay system, in particular, the sample may be dehydrated with the elapse of time, which leads to a decrease in the volume of the sample and a change in the concentration thereof. This may cause an error in the measurement. Accordingly, αF6P oxidase is allowed to react with the sample for preferably 0.5 to 60 minutes, more preferably 1 to 30 minutes, and further preferably 1 to 10 minutes, so that αF6P can be rapidly and sufficiently measured. While the reaction temperature varies depending on the optimal temperature for the enzyme to be used, it is, for example, 20° C. to 45° C., and a temperature that is generally employed for an enzymatic reaction can be adequately selected.

A preferable amount of αF6P oxidase to be used in the present invention varies depending on the amount of αF6P contained in the sample solution. For example, αF6P oxidase may be added, so as to adjust the final concentration of αF6P to 0.1 to 50 U/ml, and preferably 0.2 to 10 U/ml in the solution. A pH level is preferably adjusted to an adequate level for the reaction with the use of a buffer by taking the optimal pH level for αF6P oxidase into consideration, although a pH level is not particularly limited, provided that αF6P oxidase is capable of reaction. For example, it is preferably 3 to 11, and particularly preferably 5 to 9.

In the method of measurement according to the present invention, it is preferable to use various types of buffers, according to need, in order to adjust and/or maintain the pH level for the purpose of stabilization of an enzyme or a reagent or improvement in reactivity. Examples of buffers that can be used include N-[tris(hydroxymethyl)methyl]

glycine, phosphate, acetate, carbonate, tris(hydroxymethyl)-aminomethane, borate, citrate, dimethyl glutamate, Tricine, and HEPES. In addition, solubilizers, stabilizers, reaction-improving agents, or the like, such as surfactants (e.g., n-octyl-β-D-glucoside, n-octyl-β-D-thioglucoside, n-dodecyl-β-D-maltoside, n-octyl-β-D-maltoside, 1-dodecylpyridinium salt, hexadecyl trimethyl ammonium salt, tetradecyl trimethyl ammonium salt, dodecyltrimethyl ammonium salt, triton X-100, Brij 35, Tween 80, or cholate), reducing agents (e.g., dithiothreitol, mercaptoethanol, or L-cysteine), bovine serum albumin, or saccharides (e.g., glycerine, lactose, or sucrose), may be adequately added, according to need.

According to the present invention, αF6P is measured by measuring the amount of substance produced or consumed by the reaction of αF6P oxidase. An example of a product that can be easily measured and is preferable as a target of measurement is hydrogen peroxide. Hydrogen peroxide generated by the action of αF6P oxidase may be detected with the use of a color substrate or the like. Examples of color substrates used in the present invention include, in addition to 4-aminoantipyrine, ADOS (N-ethyl-N-(2-hydroxy-3-sulfopropyl)-m-anisidine), ALOS (N-ethyl-N-(2-hydroxy-3-sulfopropyl)aniline), DA-67 (10-(carboxymethylaminocarbonyl)-3,7-bis(dimethylamino)-phenothiazine), and DA-64 (N-(carboxymethyl am inocarbonyl)-4,4'-bis(dimethylamino)-diphenylamine). In general, it is preferable that measurement of hydrogen peroxide be carried out simultaneously with the step of generating hydrogen peroxide, and it is preferable that measurement be allowed to proceed simultaneously with the reaction with αF6P oxidase. An example of the substance consumed by the reaction to be measured is dissolved oxygen, and the amount of dissolved oxygen in the reaction solution can be measured with the use of a dissolved oxygen meter or the like.

The present invention can provide reagents for measurement of αF6P oxidase and hydrogen peroxide as described above and a reagent for measurement of αF6P supplemented with a buffer or the like, according to need. Such reagent can be adequately supplemented with various known components, such as a surfactant, a salt, a buffer, a pH adjuster, or a preservative. The reagent for measurement of αF6P according to the present invention may be prepared to separately contain various reagents in different containers. For example, it can be provided in the form of a liquid product, a frozen product of a liquid, or a freeze-dried product. Alternatively, such reagent for measurement may be used in a dried or dissolved state, or a carrier on a thin film, such as paper, may be impregnated with such reagent and used. Enzymes used for the reagent for measurement can be solidified and repeatedly used in accordance with a conventional technique. The reagent for measurement of αF6P according to the present invention can constitute a part of a reagent kit comprising a protease used for cleaving αF6P from a glycated protein.

The optimal specification or conditions for the use of the reagent for measurement of αF6P according to the present invention may be selected in accordance with the components thereof or other properties. For example, the reagent can be prepared to be used for measurement conducted at 20° C. to 45° C. The time necessary for measurement can be adequately determined in accordance with various measurement conditions. For example, it is 0.5 to 60 minutes, preferably 0.5 to 30 minutes, and further preferably 1 to 10 minutes. For example, an extent of the reagent colored (i.e., a change in the absorbance) may be measured using a spectrophotometer, and the measured absorbance may be compared with the reference absorbance. Thus, the glycated peptide or glycated protein contained in the sample can be measured. Measurement can be carried out with the use of a common automated analyzer.

(Quantification of α-Fructosyl Hexapeptide)

The method for measurement of αF6P according to the present invention may be a qualitative or quantitative method. According to the quantitative method for measurement of αF6P of the present invention, concentration of αF6P in the sample is determined. Specifically, an aspect of the present invention provides a method for quantifying α-fructosyl hexapeptide in a sample involving the use of an amadoriase variant. This quantitative method comprises a step of bringing a sample containing HbAlc-derived α-fructosyl hexapeptide (αF6P) into contact with the amadoriase of the present invention and a step of measuring the amount of substance produced or consumed by the reaction of the amadoriase with HbAlc-derived αF6P. The "contact" that is carried out in accordance with the method of quantification can be any form of physical contact between the amadoriase of the present invention and a sample, so that the amadoriase can catalyze the oxidation reaction of αF6P. In addition to the case in which a free enzyme is mixed with αF6P in a solution, for example, a liquid sample containing αF6P can be added or added dropwise to the amadoriase of the present invention immobilized to a solid support.

The amount of the amadoriase variant to be used and the duration of reaction are maintained at constant levels, and the amount of αF6P to be added is varied. Under such conditions, the range of αF6P concentration causing the absorbance of the detected luminescent substrate to proportionally lower as the amount of αF6P to be added decreases is investigated. Thus, the lowest αF6P concentration that can be detected with the use of the amadoriase can be determined. Such concentration is occasionally referred to as the "concentration of detection limit" herein. According to the method for quantification of HbAlc-derived αF6P of the present invention, the amount of the enzyme and the duration of reaction are preferably determined so as to adjust the detection limit of αF6P to a level lower than the αF6P concentration in the sample or the glycated hemoglobin level in the blood. When quantitative measurement of a sample with the blood glycated hemoglobin level of about 200 μM is intended, for example, the amount of the enzyme and the duration of reaction are preferably determined so as to bring the detection limit of the amadoriase variant of the present invention to a level lower than the final concentration of 200 μM.

According to the quantitative method of measurement of the present invention, a calibration curve can be prepared in advance by performing regression analysis such as the method of least squares based on the measured absorbance of the control sample containing αF6P at a known concentration. The measured value of the sample containing αF6P at an unknown concentration may be plotted on the prepared calibration curve, so that the αF6P concentration in the sample can be quantified.

Figures 1, 5:
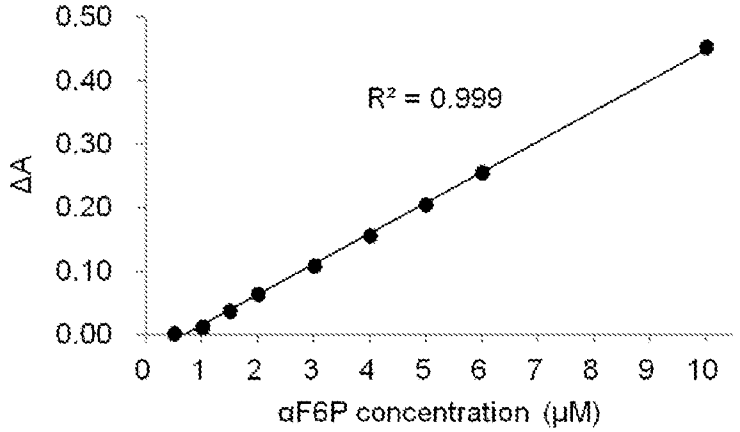
Figures 2, 5:
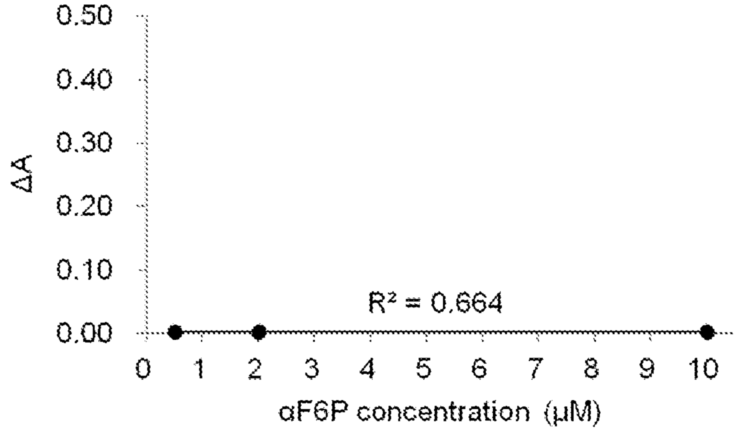
Figures 1, 6:
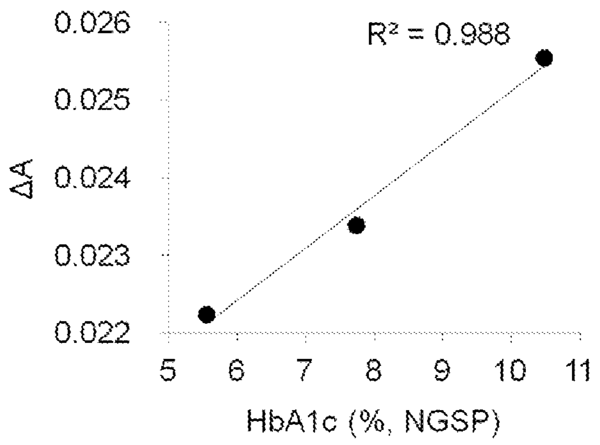
Figures 2, 6:
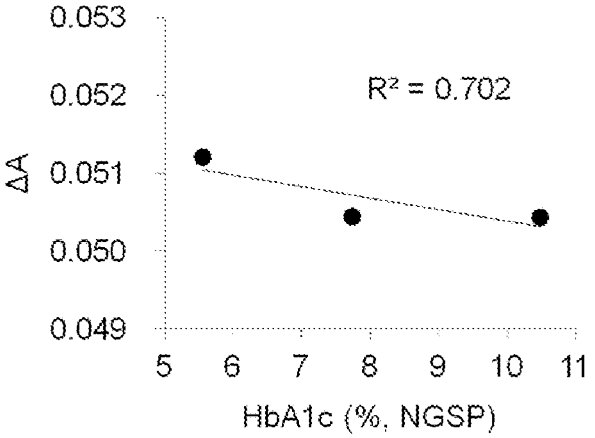

The present inventors had demonstrated that αF6P in the sample could be satisfactorily quantified using an amadoriase variant derived from *Coniochaeta*, such as the variant of the present invention 25 (see FIGS. 5 and 6). Based on such finding, a person skilled in the art would understand that other amadoriase variants of the present invention exhibiting satisfactory activity with αF6P could also be used for quantitative measurement of αF6P. In addition, the amount of enzyme (the concentration of enzyme), the duration of reaction, and other conditions for quantitative assays can be adequately determined.

In addition to the reagent for measurement of αF6P, the kit for measurement of HbAlc according to the present invention may comprise a protease or peptidase used for cleavage and, according to need, other known components, such as a stabilizer or a system for eliminating contaminants. Techniques employed for various reagents or kits aimed at measurement of HbAlc by an enzymatic method can be adequately used for the kit for measurement of HbAlc according to the present invention involving the use of αF6P.

Hereafter, the present invention is described in greater detail with reference to the examples, although the technical scope of the present invention is not limited thereto.

Example 1

(1) Preparation of DNA of Recombinant Plasmid pKK223-3-CFP-T7

A strain of *E. coli* JM109 (pKK223-3-CFP-T7) having the recombinant plasmid of an amadoriase gene derived from the genus *Coniochaeta* (SEQ ID NO: 2) (WO 2007/125779) was inoculated into 3 ml of LB-amp media (1% (w/v) bactotrypton, 0.5% (w/v) peptone, 0.5% (w/v) NaCl, and 50 μg/ml ampicillin) and shake culture was conducted at 37° C. for 16 hours to obtain a culture product.

The culture product was centrifuged at 10,000×g for 1 minute to collect strains. A recombinant plasmid pKK223-3-CFP-T7 was extracted and purified therefrom using the GenElute Plasmid Mini-Prep Kit (manufactured by Sigma-Aldrich Corporation), and 2.5 μg of DNA of the recombinant plasmid pKK223-3-CFP-T7 was obtained.

(2) Site-Directed Modification Operation of DNA of Recombinant Plasmid pKK223-3-CFP-T7

PCR was carried out under conditions described below using DNA of the recombinant plasmid pKK223-3-CFP-T7 as a template, synthetic oligonucleotides of SEQ ID NOs: 3 and 4, and KOD-Plus-(Toyobo Co., Ltd.).

Specifically, 5 μl of 10×KOD-Plus-buffer, 5 μl of a dNTPs mixture in which each dNTP was adjusted at 2 mM, 2 μl of a 25 mM MgSO4 solution, 50 ng of DNA of pKK223-3-CFP-T7 as a template, 15 pmol each of the synthetic oligonucleotides, and 1 unit of KOD-Plus were mixed, and sterilized water was added thereto in order to bring the total amount of the solution to 50 μl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 6 minutes was then repeated 30 times.

A part of the reaction solution was electrophoresed on 1.0% agarose gel, and specific amplification of about 6,000 by DNA was confirmed. The DNAs obtained in such a manner were treated with a restriction enzyme DpnI (manufactured by New England Biolabs), the remaining template DNAs were cleaved, strains of *E. coli* JM109 were transformed, and the transformants were then spread on LB-amp agar media. The grown colonies were inoculated into LB-amp media and shake-cultured therein, and plasmid DNAs were isolated in the same manner as in (1) above. DNA nucleotide sequences encoding amadoriases in plasmids were determined using a multi-capillary DNA analysis system (Applied Biosystems 3130xl Genetic Analyzer; manufactured by Life Technologies). Thus, the recombinant plasmid encoding the modified amadoriase resulting from substitution of arginine at position 62 with alanine in the amino acid sequence as shown in SEQ ID NO: 1 was obtained (pKK223-3-CFP-T7-H1).

(3) Production of Various Types of Modified Amadoriases

Strains of *E. coli* JM109 (pKK223-3-CFP-T7-H1) carrying pKK223-3-CFP-17-H1 were cultured in 3 ml of LB-amp media supplemented with 0.1 mM IPTG (final concentration) at 25° C. for 16 hours. The resulting cultured strains were washed with 10 mM potassium phosphate buffer (pH 7.0), the washed strains were suspended in the same buffer, the resulting suspension was ultrasonically disintegrated, and the resultant was centrifuged at 20,000×g for 10 minutes to prepare 0.6 ml of a crude enzyme solution containing the modified amadoriase (CFP-T7-H1).

(4) Measurement of αF6P/αFVH and αF6P/αFV

The enzyme solution containing CFP-T7-H1 was subjected to measurement of oxidation activity on αFV, αFVH, and αF6P by the method described in the "B: Method of activity measurement" above. For the purpose of comparison, the enzyme solution containing CFP-T7 produced from the *E. coli* JM109 strain (pKK223-3-CFP-T7) was subjected to measurement in the same manner. Table 1 shows the oxidation activity of amadoriases on αFV, αFVH, and αF6P, αF6P/αFVH, and αF6P/αFV, relative to the oxidation activity on αFVH designated to be 100.

TABLE 1

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7 (Comparative Example) | None | 67.1 | 100 | 0 | 0 | 0 |
| CFP-T7-H1 (Present Invention 1) | R62A | 142 | 100 | 0.0316 | 0.000316 | 0.000222 |

As shown in Table 1, CFP-T7 exhibited αFV oxidation activity and αFVH oxidation activity, although it did not exhibit αF6P oxidation activity. This indicates that CFP-T7 has very high specificity with α-fructosyl dipeptide but it does not react with α-fructosyl hexapeptide.

The variant according to the present invention (i.e., CFP-T7-H1) exhibited αF6P oxidation activity, in addition to αFV oxidation activity and αFVH oxidation activity.

Thus, it was found that, as a result of introduction of amino acid substitution (R62A) into CFP-T7, a new trait; i.e., αF6P oxidation activity, could be conferred to CFP-T7, and reactivity (substrate specificity) with αF6P was improved.

Subsequently, in the same manner as in (2) above, PCR was carried out with the use of DNA of the recombinant plasmid pKK223-3-CFP-T7-H1 as a template, oligonucleotides as shown in SEQ ID NOs: 5 to 8, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with alanine and glutamine at position 110 with leucine, phenylalanine, or tyrosine were obtained (pKK223-3-CFP-T7-H2, pKK223-3-CFP-T7-H3, and pKK223-3-CFP-T7-H4).

Strains of *E. coli* JM109 carrying pKK223-3-CFP-T7-H2, pKK223-3-CFP-T7-H3, or pKK223-3-CFP-T7-H4 were cultured in the manner described in (3) above, and crude enzyme solutions (0.6 ml each) containing various types of modified amadoriases (i.e., CFP-T7-H2, CFP-T7-H3, or CFP-T7-H4) were prepared.

The crude enzyme solutions thus prepared were subjected to measurement of oxidation activity on αFV, αFVH, and αF6P by the method described in the "B: Method of activity measurement" above. For the purpose of comparison, the enzyme solution containing CFP-T7-H1 produced from the *E. coli* JM109 strain (pKK223-3-CFP-T7-H1) was subjected to measurement in the same manner. Table 2 shows the oxidation activity of amadoriases on αFV, αFVH, and αF6P, αF6P/αFVH, and αF6P/αFV, relative to the oxidation activity on αFVH designated to be 100.

TABLE 2

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H1 (Present Invention 1) | R62A | 142 | 100 | 0.0316 | 0.000316 | 0.000222 |
| CFP-T7-H2 (Present Invention 2) | R62A, Q110L | 137 | 100 | 0.0735 | 0.000735 | 0.000536 |
| CFP-T7-H3 (Present Invention 3) | R62A, Q110F | 145 | 100 | 0.0298 | 0.000298 | 0.000205 |
| CFP-T7-H4 (Present Invention 4) | R62A, Q110Y | 107 | 100 | 0.0341 | 0.000341 | 0.000319 |

Specifically, CFP-T7-H2 and CFP-T7-H4 were found to have improved reactivity (substrate specificity) with αF6P, compared with that of CFP-T7-H1.

Subsequently, in the same manner as in (2) above, PCR was carried out with the use of DNA of the recombinant plasmid pKK223-3-CFP-T7-H2 as a template, oligonucleotides as shown in SEQ ID NOs: 4 and 9 to 12, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of glutamine at position 110 with leucine and argine at position 62 with asparagine, aspartic acid, glutamine, or glutamic acid (pKK223-3-CFP-T7-H2-62N, pKK223-3-CFP-T7-H6, and pKK223-3-CFP-T7-H2-62Q, and pKK223-3-CFP-T7-H2-62E) were obtained.

Strains of *E. coli* JM109 carrying pKK223-3-CFP-T7-H2-62N, pKK223-3-CFP-T7-H6, pKK223-3-CFP-T7-H2-62Q, or pKK223-3-CFP-T7-H2-62E were cultured in the manner described in (3) above, and crude enzyme solutions (0.6 ml each) containing various types of modified amadoriases (CFP-T7-H2-62N, CFP-T7-H6, CFP-T7-H2-62Q, or CFP-T7-H2-62E) were prepared.

The crude enzyme solutions thus prepared were subjected to measurement of oxidation activity on αF6P by the method described in the "B: Method of activity measurement" above. For the purpose of comparison, the enzyme solution containing CFP-T7-H2 produced from the *E. coli* JM109 strain (pKK223-3-CFP-T7-H2) was subjected to measurement in the same manner. Table 3 shows αF6P oxidation activity of crude enzyme solutions containing amadoriases, relative to αF6P oxidation activity of a crude enzyme solution containing CFP-T7-H2 designated to be 100.

TABLE 3

| Amadoriase | Amino acid substitution | αF6P oxidation activity ratio |
|---|---|---|
| CFP-T7-H2 (Present Invention 2) | R62A, Q110L | 100 |
| CFP-T7-H2-62N (Present Invention 5) | R62N, Q110L | 120 |
| CFP-T7-H6 (Present Invention 6) | R62D, Q110L | 513 |
| CFP-T7-H2-62Q (Present Invention 7) | R62Q, Q110L | 11 |
| CFP-T7-H2-62E (Present Invention 8) | R62E, Q110L | 21 |

Specifically, CFP-T7-H2-62N and CFP-T7-H6 were found to have improved αF6P oxidation activity, compared with that of CFP-T7-H2.

A crude enzyme solution containing CFP-T7-H2 or CFP-T7-H6 was subjected to measurement of oxidation activity on αFV, αFVH, and αF6P by the method described in the "B: Method of activity measurement" above. Table 4 shows oxidation activity on substrates, αF6P/αFVH, and αF6P/FV of amadoriases, relative to αFVH oxidation activity designated to be 100.

TABLE 4

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H2 (Present Invention 2) | R62A, Q110L | 137 | 100 | 0.0735 | 0.000735 | 0.000536 |
| CFP-T7-H6 (Present Invention 6) | R62D, Q110L | 864 | 100 | 3.00 | 0.0300 | 0.00347 |

Specifically, CFP-T7-H6 was found to have significantly improved αF6P oxidation activity and improved reactivity (substrate specificity) with αF6P, compared with those of CFP-T7-H2.

Subsequently, in the same manner as in (2) above, PCR was carried out with the use of DNA of the recombinant plasmid pKK223-3-CFP-T7-H6 as a template, oligonucleotides as shown in SEQ ID NOs: 13 to 24, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with aspartic acid, glutamine at position 110 with leucine, and arginine at position 64 with alanine, glutamic acid, or histidine (pKK223-3-CFP-T7-H7, pKK223-3-CFP-T7-H8, and pKK223-3-CFP-T7-H9), recombinant plasmids encoding modified amadoriases each comprising an amino acid sequence derived from the amino acid sequence as shown in SEQ ID NO: 1 by substitution of arginine at position 62 with aspartic acid, glutamine at position 110 with leucine, and aspartic acid at position 106 with alanine, lysine, or arginine (pKK223-3-CFP-T7-H10, pKK223-3-CFP-T7-H11, and pKK223-3-CFP-T7-H12), and recombinant plasmids encoding modified amadoriases each comprising an amino acid sequence derived from the amino acid sequence as shown in SEQ ID NO: 1 by substitution of arginine at position 62 with aspartic acid, glutamine at position 110 with leucine, and alanine at position 113 with lysine or arginine (pKK223-3-CFP-T7-H13 and pKK223-3-CFP-T7-H14) were obtained.

Strains of *E. coli* JM109 carrying pKK223-3-CFP-T7-H7, pKK223-3-CFP-T7-H8, pKK223-3-CFP-T7-H9, pKK223-3-CFP-T7-H10, pKK223-3-CFP-T7-H11, pKK223-3-CFP-T7-H12, pKK223-3-CFP-T7-H13, or pKK223-3-CFP-T7-H14 were cultured in the manner described in (3) above, and crude enzyme solutions (0.6 ml each) containing various types of modified amadoriases (CFP-T7-H7, CFP-T7-H8, CFP-T7-H9, CFP-T7-H10, CFP-T7-H11, CFP-T7-H12, CFP-T7-H13, or CFP-T7-H14) were prepared.

The crude enzyme solutions thus prepared were subjected to measurement of oxidation activity on αF6P by the method described in the "B: Method of activity measurement" above. For the purpose of comparison, the enzyme solution containing CFP-T7-H6 produced from the *E. coli* JM109 strain (pKK223-3-CFP-T7-H6) was subjected to measurement in the same manner. Table 5 shows αF6P oxidation activity of crude enzyme solutions containing amadoriases, relative to the αF6P oxidation activity of a crude enzyme solution containing CFP-T7-H6 designated to be 100.

TABLE 5

| Amadoriase | Amino acid substitution | αF6P oxidation activity ratio |
|---|---|---|
| CFP-T7-H6 (Present Invention 6) | R62D, Q110L | 100 |
| CFP-T7-H7 (Present Invention 9) | R62D, R64A, Q110L | 17 |
| CFP-T7-H8 (Present Invention 10) | R62D, R64E, Q110L | 2 |
| CFP-T7-H9 (Present Invention 11) | R62D, R64H, Q110L | 44 |
| CFP-T7-H10 (Present Invention 12) | R62D, D106A, Q110L | 301 |
| CFP-T7-H11 (Present Invention 13) | R62D, D106K, Q110L | 951 |
| CFP-T7-H12 (Present Invention 14) | R62D, D106R, Q110L | 636 |
| CFP-T7-H13 (Present Invention 15) | R62D, Q110L, A113K | 207 |
| CFP-T7-H14 (Present Invention 16) | R62D, Q110L, A113R | 183 |

Specifically, CFP-T7-H10, CFP-T7-H11, CFP-T7-H12, CFP-T7-H13, and CFP-T7-H14 were found to have significantly improved αF6P oxidation activity, compared with that of CFP-T7-H6, and the level of improvement in some thereof was remarkable.

Crude enzyme solutions containing CFP-T7-H6, CFP-T7-H11, CFP-T7-H12, CFP-T7-H13, and CFP-T7-H14 were subjected to measurement of oxidation activity on αFV, αFVH, and αF6P by the method described in the "B: Method of activity measurement" above. Table 6 shows oxidation activity on substrates, αF6P/αFVH, and αF6P/FV of amadoriases, relative to αFVH oxidation activity designated to be 100.

TABLE 6

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H6 (Present Invention 6) | R62D, Q110L | 864 | 100 | 3.00 | 0.0300 | 0.00347 |
| CFP-T7-H11 (Present Invention 13) | R62D, D106K, Q110L | 511 | 100 | 12.5 | 0.125 | 0.0245 |
| CFP-T7-H12 (Present Invention 14) | R62D, D106R, Q110L | 700 | 100 | 11.6 | 0.116 | 0.0165 |
| CFP-T7-H13 (Present Invention 15) | R62D, Q110L, A113K | 747 | 100 | 4.33 | 0.0433 | 0.00579 |
| CFP-T7-H14 (Present Invention 16) | R62D, Q110L, A113R | 814 | 100 | 4.22 | 0.0422 | 0.00519 |

As shown in Table 6, specifically, CFP-T7-H11, CFP-T7-H12, CFP-T7-H13, and CFP-T7-H14 were found to have significantly improved reactivity (substrate specificity) with αF6P, compared with that of CFP-T7-H6.

Subsequently, in the same manner as in (2) above, PCR was carried out with the use of DNA of the recombinant plasmid pKK223-3-CFP-T7-H11 as a template, oligonucleotides as shown in SEQ ID NOs: 21 to 24, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with aspartic acid, aspartic acid at position 106 with lysine, glutamine at position 110 with leucine, and alanine at position 113 with lysine or arginine (pKK223-3-CFP-T7-H20 and pKK223-3-CFP-T7-H21) were obtained.

Strains of *E. coli* JM109 carrying pKK223-3-CFP-T7-H20 or pKK223-3-CFP-T7-H21 were cultured in the manner described in (3) above, and crude enzyme solutions (0.6 ml each) containing various types of modified amadoriases (CFP-T7-H20 or CFP-T7-H21) were prepared.

Crude enzyme solutions containing CFP-T7-H11, CFP-T7-H20, and CFP-T7-H21 were subjected to measurement of oxidation activity on αFV, αFVH, and αF6P by the method described in the "B: Method of activity measurement" above. Table 7 shows oxidation activity on substrates, αF6P/αFVH, and αF6P/FV of amadoriases, relative to the αFVH oxidation activity designated to be 100.

TABLE 7

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H11 (Present Invention 13) | R62D, D106K, Q110L | 511 | 100 | 12.5 | 0.125 | 0.0245 |
| CFP-T7-H20 (Present Invention 17) | R62D, D106K, Q110L, A113K | 544 | 100 | 20.5 | 0.205 | 0.0377 |
| CFP-T7-H21 (Present Invention 18) | R62D, D106K, Q110L, A113R | 558 | 100 | 20.8 | 0.208 | 0.0372 |

Specifically, CFP-T7-H20 and CFP-T7-H21 were found to have improved reactivity (substrate specificity) with αF6P, compared with that of CFP-T7-H11.

Subsequently, in the same manner as in (2) above, PCR was carried out with the use of DNA of the recombinant plasmid pKK223-3-CFP-T7-H20 as a template, oligonucleotides as shown in SEQ ID NOs: 25 to 29, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with aspartic acid, aspartic acid at position 106 with lysine, glutamine at position 110 with leucine, alanine at position 113 with lysine, and leucine at position 63 with alanine, aspartic acid, histidine, or lysine (pKK223-3-CFP-T7-H24, pKK223-3-CFP-T7-H25, pKK223-3-CFP-T7-H26, and pKK223-3-CFP-T7-H27) were obtained.

Strains of *E. coli* JM109 carrying pKK223-3-CFP-T7-H24, pKK223-3-CFP-T7-H25, pKK223-3-CFP-T7-H26, or pKK223-3-CFP-T7-H27 were cultured in the manner described in (3) above, and crude enzyme solutions (0.6 ml each) containing various types of modified amadoriases (CFP-T7-H24, CFP-T7-H25, CFP-T7-H26, or CFP-T7-H27) were prepared.

The crude enzyme solutions thus prepared were subjected to measurement of oxidation activity on αF6P by the method described in the "B: Method of activity measurement" above. For the purpose of comparison, the enzyme solution containing CFP-T7-H20 produced from the *E. coli* JM109 strain (pKK223-3-CFP-T7-H20) was subjected to measurement in the same manner. Table 8 shows αF6P oxidation activity of crude enzyme solutions containing amadoriases, relative to the αF6P oxidation activity of a crude enzyme solution containing CFP-T7-H20 designated to be 100.

TABLE 8

| Amadoriase | Amino acid substitution | αF6P oxidation activity ratio |
|---|---|---|
| CFP-T7-H20 (Present Invention 17) | R62D, D106K, Q110L, A113K | 100 |
| CFP-T7-H24 (Present Invention 19) | R62D, L63A, D106K, Q110L, A113K | 123 |
| CFP-T7-H25 (Present Invention 20) | R62D, L63D, D106K, Q110L, A113K | 24 |
| CFP-T7-H26 (Present Invention 21) | R62D, L63H, D106K, Q110L, A113K | 142 |
| CFP-T7-H27 (Present Invention 22) | R62D, L63K, D106K, Q110L, A113K | 7 |

As shown in Table 8, specifically, CFP-T7-H24 and CFP-T7-H26 were found to have improved αF6P oxidation activity, compared with that of CFP-17-H20.

Crude enzyme solutions containing CFP-T7-H20, CFP-T7-H24, or CFP-T7-H26 were subjected to measurement of oxidation activity on αFV, αFVH, and αF6P by the method described in the "B: Method of activity measurement" above. Table 9 shows oxidation activity on substrates, αF6P/αFVH, and αF6P/αFV of amadoriases, relative to the αFVH oxidation activity designated to be 100.

TABLE 9

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H20 (Present Invention 17) | R62D, D106K, Q110L, A113K | 544 | 100 | 20.5 | 0.205 | 0.0377 |
| CFP-T7-H24 (Present Invention 19) | R62D, L63A, D106K, Q110L, A113K | 1880 | 100 | 86.7 | 0.867 | 0.0461 |
| CFP-T7-H26 (Present Invention 21) | R62D, L63H, D106K, Q110L, A113K | 1090 | 100 | 84.3 | 0.843 | 0.0773 |

As shown in Table 9, specifically, CFP-T7-H24 and CFP-T7-H26 were found to have improved reactivity (substrate specificity) with αF6P, compared with that of CFP-T7-H20.

Subsequently, in the same manner as in (2) above, PCR was carried out with the use of DNA of the recombinant plasmid pKK223-3-CFP-T7-H26 as a template, oligonucleotides as shown in SEQ ID NOs: 30 to 33, and KOD-Plus-, strains of *E. coli* JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid, leucine at position 63 with histidine, aspartic acid at position 106 with lysine, glutamine at position 110 with leucine, alanine at position 113 with lysine, and glutamic acid at position 102 with lysine (pKK223-3-CFP-T7-H28) and a recombinant plasmid encoding a modified amadoriase comprising an amino acid sequence derived from the amino acid sequence as shown in SEQ ID NO: 1 by substitution of arginine at position 62 with aspartic acid, leucine at position 63 with histidine, aspartic acid at position 106 with lysine, glutamine at position 110 with leucine, alanine at position 113 with lysine, and alanine at position 419 with lysine (pKK223-3-CFP-T7-H29) were obtained.

Strains of *E. coli* JM109 carrying pKK223-3-CFP-T7-H26, pKK223-3-CFP-T7-H28, or pKK223-3-CFP-T7-H29 were cultured in the manner described in (3) above, and crude enzyme solutions (0.6 ml each) containing various types of modified amadoriases (CFP-T7-H26, CFP-T7-H28, or CFP-T7-H29) were prepared.

The crude enzyme solutions thus prepared were subjected to measurement of oxidation activity on αF6P by the method described in the "B: Method of activity measurement" above. For the purpose of comparison, the enzyme solution containing CFP-T7-H26 produced from the *E. coli* JM109 strain (pKK223-3-CFP-T7-H26) was subjected to measurement in the same manner. Table 10 shows αF6P oxidation activity of crude enzyme solutions containing amadoriases, relative to the αF6P oxidation activity of a crude enzyme solution containing CFP-T7-H26 designated to be 100.

TABLE 10

| Amadoriase | Amino acid substitution | αF6P oxidation activity ratio |
|---|---|---|
| CFP-T7-H26 (Present Invention 21) | R62D, L63H, D106K, Q110L, A113K | 100 |
| CFP-T7-H28 (Present Invention 23) | R62D, L63H, E102K, D106K, Q110L, A113K | 117 |
| CFP-T7-H29 (Present Invention 24) | R62D, L63H, D106K, Q110L, A113K, A419K | 102 |

As shown in Table 10, specifically, CFP-T7-H28 and CFP-T7-H29 were found to have improved αF6P oxidation activity, compared with that of CFP-T7-H26.

Crude enzyme solutions containing CFP-T7-H26, CFP-T7-H28, or CFP-T7-H29 were subjected to measurement of oxidation activity on αFV, αFVH, and αF6P by the method described in the "B: Method of activity measurement" above. Table 11 shows oxidation activity on substrates, αF6P/αFVH, and αF6P/αFV of amadoriases, relative to the αFVH oxidation activity designated to be 100.

TABLE 11

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H26 (Present Invention 21) | R62D, L63H, D106K, Q110L, A113K | 1090 | 100 | 84.3 | 0.843 | 0.0773 |
| CFP-T7-H28 (Present Invention 23) | R62D, L63H, E102K, | 1080 | 100 | 134 | 1.34 | 0.124 |

TABLE 11-continued

| Amadoriase | Amino acid substitution | αFV oxidation activity | αFVH oxidation activity | αF6P oxidation activity | αF6P/ αFVH | αF6P/ αFV |
|---|---|---|---|---|---|---|
| | D106K, Q110L, A113K | | | | | |
| CFP-T7-H29 (Present Invention 24) | R62D, L63H, D106K, Q110L, A113K, A419K | 1000 | 100 | 111 | 1.11 | 0.111 |

As shown in Table 11, specifically, CFP-T7-H28 and CFP-T7-H29 were found to have improved reactivity (substrate specificity) with αF6P, compared with that of CFP-T7-H26.

Subsequently, in the same manner as in (2) above, PCR was carried out with the use of DNA of the recombinant plasmid pKK223-3-CFP-T7-H28 as a template, oligonucleotides as shown in SEQ ID NOs: 34 and 35, and KOD-Plus-, strains of *E. coli* JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid, leucine at position 63 with histidine, glutamic acid at position 102 with lysine, aspartic acid at position 106 with lysine, glutamine at position 110 with leucine, alanine at position 113 with lysine, and alanine at position 355 with serine (pKK223-3-CFP-T7-H35) was obtained.

Strains of *E. coli* JM109 carrying pKK223-3-CFP-T7-H35 were cultured in the manner described in (3) above, and a crude enzyme solution (0.6 ml) containing a modified amadoriase (CFP-T7-H35) was prepared.

The crude enzyme solution thus prepared was subjected to measurement of oxidation activity on αF6P by the method described in the "B: Method of activity measurement" above. For the purpose of comparison, the enzyme solution containing CFP-T7-H20 produced from the strain of *E. coli* JM109 (pKK223-3-CFP-T7-H28) was subjected to measurement in the same manner. Table 12 shows αF6P oxidation activity of the enzyme solution containing the amadoriase, relative to the αF6P oxidation activity of an crude enzyme solution containing CFP-T7-H26 designated to be 100.

TABLE 12

| Amadoriase | Amino acid variation | αF6P oxidation activity ratio |
|---|---|---|
| CFP-T7-H28 (Present Invention 23) | R62D, L63H, E102K, D106K, Q110L, A113K | 100 |
| CFP-T7-H35 (Present Invention 25) | R62D, L63H, E102K, D106K, Q110L, A113K, A355S | 206 |

As shown in Table 12, specifically, CFP-T7-H35 was found to have improved αF6P oxidation activity, compared with that of CFP-T7-H28.

Subsequently, in the same manner as in (2) above, PCR was carried out with the use of DNA of the recombinant plasmid pKK223-3-CFP-T7 as a template, oligonucleotides as shown in SEQ ID NOs: 4 and 10, and KOD-Plus-, strains of *E. coli* JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid (pKK223-3-CFP-T7-62D) was obtained. Subsequently, a strain of *E. coli* JM109 carrying pKK223-3-CFP-T7-62D was prepared.

Example 2

Production and Purification of Various Types of Amadoriases (Production and Purification of Modified Amadoriase Derived from the Genus *Coniochaeta*)

Wild-type amadoriases derived from the genus *Coniochaeta* and the strains of *E. coli* JM109 (pKK223-3-CFP-T7), *E. coli* JM109 (pKK223-3-CFP-T7-62D), *E. coli* JM109 (pKK223-3-CFP-T7-H20), *E. coli* JM109 (pKK223-3-CFP-T7-H21), and *E. coli* JM109 (pKK223-3-CFP-T7-H35) producing modified amadoriases obtained in the manner described above were inoculated into 120 ml of LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare 24 ml of a crude enzyme solution.

The prepared crude enzyme solution was allowed to adsorb to 12 ml of Toyopearl Butyl-650 resin (manufactured by Tosoh) equilibrated with a 10 mM potassium phosphate buffer (pH 7.0) containing 1.35 M $(NH_4)_2SO_4$, the resin was washed with 120 ml of the same buffer, and amadoriases adsorbed to the resin were eluted and collected with the aid of a 10 mM potassium phosphate buffer (pH 7.0) containing 84 ml of 1.05 M $(NH_4)_2SO_4$.

The resulting crude enzyme solution containing amadoriases was introduced into Spectra/Por dialysis tubing (MWCO: 12,000-14,000) and dialyzed against a 10-fold amount of 5 mM potassium phosphate buffer (pH 7.5). This procedure was repeated 3 times to completely remove $(NH_4)_2SO_4$ from the crude enzyme solution containing amadoriases. Subsequently, the crude enzyme solution containing amadoriases was applied to HiScreen Capto Q ImpRes (manufactured by GE Healthcare) equilibrated with a 10 mM potassium phosphate buffer (pH 7.5) to allow amadoriases to bind to anion-exchange resin. Thereafter, the concentration of NaCl contained in a 10 mM potassium phosphate buffer (pH 7.5) was linearly increased from 0 mM to 160 mM to elute proteins bound to the resin, and fractions exhibiting amadoriase activity were collected. The obtained fractions exhibiting amadoriase activity were analyzed by SDS-PAGE to confirm that the fractions were sufficiently purified, so that no other contaminating proteins were present therein. These fractions were designated to be purified samples of CFP-T7, CFP-T7-62D, CFP-T7-H20, CFP-T7-H21, and pKK223-3-CFP-T7-H35.

(Production and Purification of Fructosyl Amino Acid Oxidase Derived from *Aspergillus oryzae* RIB40)

SEQ ID NO: 36 shows the amino acid sequence of fructosyl amino acid oxidase derived from *Aspergillus oryzae* RIB-10 (hereafter referred to as "FAOAo2"), a recombinant plasmid obtained by insertion of the gene (SEQ ID NO: 37) encoding the amino acid sequence as shown in SEQ ID NO: 36 (hereafter referred to as "pUC19-FAOAo2") is allowed to express in *E. coli* DH5α to produce FAOAo2, and FAOAo2 reacts with fructosyl hexapeptide (see WO 2008/108385).

The strains of *E. coli* DH5α capable of producing FAOAo2 (pUC19-FAOAo2) were inoculated into LB-amp media supplemented with IPTG (final concentration: 0.1 mM) and cultured therein at 25° C. for 16 hours. The resulting cultured strains were washed with a 10 mM Tris-HCl buffer (pH 8.5), the washed strains were suspended in the same buffer, the resulting suspension was ultrasonically disintegrated, and the resultant was centrifuged at 20,000×g for 10 minutes to prepare a crude enzyme solution.

The prepared crude enzyme solution was allowed to adsorb to Q Sepharose Fast Flow resin (manufactured by GE Healthcare) equilibrated with a 10 mM Tris-HCl buffer (pH 8.5), the resin was washed with a 10 mM Tris-HCl buffer (pH 8.5) containing 50 mM NaCl, and FAOAo2 adsorbed to the resin was then eluted and collected with the aid of a 10 mM Tris-HCl buffer (pH 8.5) containing 100 mM NaCl.

The resulting crude enzyme solution containing FAOAo2 was applied to the HiLoad 26/600 Superdex 200 column equilibrated with a 20 mM MES-NaOH buffer (pH 7.0) containing 150 mM NaCl so as to elute FAOAo2 with the same buffer, and a fraction exhibiting amadoriase activity was collected. The obtained fraction was analyzed by SDS-PAGE to confirm that the fraction was sufficiently purified, so that no other contaminating proteins were present therein. The fraction was designated to be a purified sample of FAOAo2.

(Preparation of Strain Producing Fructosyl Peptide Oxidase Derived from *Phaeosphaeria nodorum*)

SEQ ID NO: 38 shows the amino acid sequence of fructosyl peptide oxidase derived from *Phaeosphaeria nodorum* (hereafter referred to as "PnFX") (see Biotechnology and Bioengineering, 106, 358-366, 2010). The gene (SEQ ID NO: 39) encoding the amino acid sequence as shown in SEQ ID NO: 38 was obtained via total synthesis of cDNA by a conventional technique of PCR of a gene fragment. The NdeI site and the BamHI were added to the 5' terminus and the 3' terminus of SEQ ID NO: 39, respectively. Also, the full-length amino acid sequence that is deduced based on the cloned gene sequence was confirmed to be consistent with the PnFX sequence as shown in FIG. 1.

In order to express the gene shown in SEQ ID NO: 39 in *E. coli*, subsequently, the following procedures were performed. The gene fully synthesized above was treated with two types of restriction enzymes, NdeI and BamHI (manufactured by Takara Bio Inc.) and inserted into the NdeI-BamHI site of the pET-22b(+) vector (manufactured by Novagen, Inc.). Thus, the recombinant plasmid pET22b-PnFX was obtained. Strains of *E. coli* BL21 (DE3) were transformed under the conditions as described above to obtain a strain of *E. coli* (DE3) (pET22b-PnFX).

(Production and Purification of Fructosyl Peptide Oxidase Derived from *Phaeosphaeria nodorum*)

The strains of *E. coli* BL21 (DE3) (pET22b-PnFX) capable of producing PnFX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The prepared crude enzyme solution containing PnFX was purified in accordance with the method described in the non-patent document (Biotechnology and Bioengineering, 106, 358-366, 2010). Specifically, the crude enzyme solution was fractionated with ammonium sulfate, dialyzed against a 10 mM potassium phosphate buffer (pH8.0), purified via anion-exchange chromatography (Q Sepharose East Flow was used in Example 2), and then purified via gel filtration chromatography (HiLoad 26/600 Superdex 200 was used in Example 2). The obtained fraction was analyzed by SDS-PAGE to confirm that the fraction was sufficiently purified, so that no other contaminating proteins were present therein. The fraction was designated to be a purified sample of PnFX.

With the use of the purified samples of CFP-T7, CFP-T7-62D, CFP-T7-H20, CFP-T7-H21, CFP-T7-H35, FAOAo2, and PnFX, specific activity thereof relative to αFV, αFVH, and αF6P as substrates was measured. The results are shown in Table 13. Concentration of a protein used for calculation of specific activity was determined by the ultraviolet absorption method involving the use of the absorbance at 280 nm (see Protein Sci., 4, 2411-23, 1995).

TABLE 13

| Amadoriase | Amino acid variation | Specific activity (U/mg) 1 mM αFV | 1 mM αFVH | 1 mM αF6P | αF6P/αFVH | αF6P/αFV |
|---|---|---|---|---|---|---|
| CFP-T7 (Comparative Example 1) | None | 11.1 | 16.5 | 0 | 0 | 0 |
| FAOAo2 (Comparative Example 2) | None | Not measured | Not measured | 0.0022 | | |
| PnFX (Comparative Example 3) | None | Not measured | Not measured | 0.0091 | | |

TABLE 13-continued

| Amadoriase | Amino acid variation | Specific activity (U/mg) 1 mM αFV | 1 mM αFVH | 1 mM αF6P | αF6P/ αFVH | αF6P/ αFV |
|---|---|---|---|---|---|---|
| CFP-T7-62D (Present Invention 26) | R62D | 13.6 | 1.62 | 0.018 | 0.00132 | 0.00113 |
| CFP-T7-H20 (Present Invention 17) | R62D, D106K, Q110L, A113K | 21.8 | 4.28 | 0.850 | 0.198 | 0.0389 |
| CFP-T7-H21 (Present Invention 18) | R62D, D106K, Q110L, A113R | 21.0 | 4.05 | 0.795 | 0.196 | 0.0377 |
| CFP-T7-H35 (Present Invention 25) | R62D, L63H, E102K, D106K, Q110L, A113K A355S | 13.2 | 1.90 | 4.27 | 2.25 | 0.323 |

The purified CFP-T7 did not react with αF6P, as expected. In contrast, specific activity of CFP-T7-62D, CFP-T7-H20, CFP-T7-H21, or CFP-T7-H35 relative to αF6P was 0.018 U/mg, 0.850 U/mg, 0.795 U/mg, or 4.27 U/mg, respectively. That is, sufficiently high reactivity with αF6P was observed even by the method of measurement that had eliminated the influence of protease/peptidase derived from the *E. coli* host.

Specific activity of the amadoriase reacting with αF6P (i.e., FAOAo2, see WO 2008/108385) and that of PnFX (see WO 2011/15326, referred to as "P.n FPOX" therein) were 0.0022 U/mg and 0.0091 U/mg, respectively. The modified amadoriase derived from the genus *Coniochaeta* obtained in the present invention exhibited specific activity that is 2 times (Present Invention 26/Comparative Example 3) to 1,940 times (Present Invention 25/Comparative Example 2) greater than that of the amadoriase reacting with αF6P. According to the present invention, thus, a highly practical amadoriase exhibiting reactivity with αF6P, which could not be observed in the past, was obtained.

There were no significant differences between the αF6P/αFVH values of CFP-T7-H20 and CFP-T7-H21 measured with the use of crude enzyme solutions and those measured with the use of purified enzymes.

In the variant of the present invention, improved reactivity with αFV was detected in addition to the reactivity with αF6P, compared with the amadoriase before amino acid substitution. This would not pose any problem in the principle of measurement in which α-glycated hexapeptide derived from the glycated N terminus of the β-chain is cleaved from HbA1c via pretreatment and the cleaved α-glycated hexapeptide is then measured, for the following reason. That is, as described above, in the process of cleaving α-glycated hexapeptide derived from the glycated N terminus of the β-chain from HbA1c via pretreatment, a known enzyme for pretreatment with high cleavage specificity, such as Glu-C, that would not substantially cleave other short-chain α-glycated peptide is used. Thus, substantially all α-glycated peptides to be cleaved are αF6P.

(Evaluation of Substrate Specificity of CFP-T7-H35)

With the use of the purified sample of CFP-T7-H35 obtained in the manner described above, specific activity thereof relative to αFV, αFVH, and αF6P as substrates was measured. The results are shown in Table 14. Concentration of a protein used for calculation of specific activity was determined by the ultraviolet absorption method involving the use of the absorbance at 280 nm (see Protein Sci., 4, 2411-23, 1995).

TABLE 14

| Amadoriase | Amino acid variation | Specific activity (U/mg) 1 mM αFV | 1 mM αFVH | 1 mM αF6P |
|---|---|---|---|---|
| CFP-T7-H35 (Present Invention 25) | R62D, L63H, E102K, D106K, Q110L, A113K A355S | 13.2 | 1.90 | 4.27 |

CFP-T7-H35 showed reactivity with αFV, αFVH, and αF6P used in the measurement of activity. In particular. CFP-T7-H35 showed a greater specific activity to αF6P than to αFVH. This indicates high substrate specificity of CFP-T7-H35.

Example 3

Introduction of Point Mutations into Various Amadoriases

The finding of the present invention was first examined with the use of the amadoriase derived from the genus *Coniochaeta*. The results can suggest that similar effects can be expected by introducing a similar mutation into a corresponding position in the amino acid sequence of the amadoriase derived from another organism species with reference to the information attained by a known sequence alignment processing based on sequence identity. Accordingly, the finding of the present invention was actually applied to a plurality of amadoriases other than the amadoriase derived from the genus *Coniochaeta* in an attempt of verification of such suggestion.

1. Introduction of Point Mutation into Gene of Fructosyl Peptide Oxidase Derived from *Eupenicillium terrenum*

SEQ ID NO: 40 shows the amino acid sequence of fructosyl peptide oxidase derived from *Eupenicillium terrenum* (hereafter referred to as "EFP-T5"), and it can be prepared by *E. coli* strains carrying the recombinant plasmid pUTE100K'-EFP-T5 into which the gene (SEQ ID NO: 41) encoding the amino acid sequence as shown in SEQ ID NO: 40 has been inserted. EFP-T5 is confirmed to exhibit oxidation activity on αFV and αFVH (see WO 2007/125779 and WO 2008/018094).

In order to introduce a mutation aimed at improvement of substrate specificity into EFP-T5, in the same manner as in Example 1, PCR was carried out with the use of the recombinant plasmid pUTE100K'-EFP-T5 as a template, synthetic oligonucleotides as shown in SEQ ID NOs: 42 and 43, and KOD-Plus-(manufactured by TOYOBO CO., LTD.), strains of *E. coli* JM109 were transformed, and a nucleotide sequence of DNA encoding the EFP-T5 variant in the plasmid DNA carried on the grown colonies was determined. As a result, a recombinant plasmid encoding the EFP-T5 gene comprising an amino acid sequence derived from the amino acid sequence as shown in SEQ ID NO: 40 by substitution of arginine at position 62 with aspartic acid (pUTE100K'-EFP-T5-62D) was obtained.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid and asparagine at position 106 with lysine (pUTE100K'-EFP-T5-62D/106K) was obtained with the use of pUTE100K'-EFP-T5-62D as a template and synthetic oligonucleotides as shown in SEQ ID NOs: 44 and 45.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, asparagine at position 106 with lysine, and lysine at position 110 with leucine (pUTE100K'-EFP-T5-62D/106K/110L) was obtained with the use of pUTE100K'-EFP-T5-62D/106K as a template and synthetic oligonucleotides as shown in SEQ ID NOs: 46 and 47.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, asparagine at position 106 with lysine, lysine at position 110 with leucine, and threonine at position 113 with lysine (pUTE100K'-EFP-T5-62D/106K/110L/113K) was obtained with the use of pUTE100K'-EFP-T5-62D/106K/110L as a template and synthetic oligonucleotides as shown in SEQ ID NOs: 48 and 49.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, asparagine at position 106 with lysine, lysine at position 110 with leucine, threonine at position 113 with lysine, and alanine at position 355 with serine (pUTE100K'-EFP-T5-62D/106K/110L/113K/355S) was obtained with the use of pUTE100K'-EFP-T5-62D/106K/110L/113K as a template and synthetic oligonucleotides as shown in SEQ ID NOs: 50 and 51.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, leucine at position 63 with histidine, asparagine at position 106 with lysine, lysine at position 110 with leucine, threonine at position 113 with lysine, and alanine at position 355 with serine (pUTE100K'-EFP-T5-62D/63H/106K/110L/113K/355S) was obtained with the use of pUTE100K'-EFP-T5-62D/106K/110L/113K/355S as a template and synthetic oligonucleotides as shown in SEQ ID NOs: 52 and 53.

2. Introduction of Point Mutation into Gene of Ketoamine Oxidase Derived from *Neocosmospora vasinfecta*

SEQ ID NO: 54 shows the amino acid sequence of ketoamine oxidase derived from *Neocosmospora vasinfecta* (hereafter referred to as "NvFX"), and it can be prepared by *E. coli* strains carrying the recombinant plasmid pET22b-NvFX into which the gene (SEQ ID NO: 55) encoding the amino acid sequence as shown in SEQ ID NO: 54 has been inserted. NvFX is confirmed to exhibit oxidation activity on αFV and αFVH (see WO 2012/018094).

In order to introduce a mutation aimed at improvement of substrate specificity into NvFX, in the same manner as in Example 1, PCR was carried out with the use of the recombinant plasmid pET22b-NvFX as a template, synthetic oligonucleotides as shown in SEQ ID NOs: 56 and 57, and KOD-Plus-(manufactured by TOYOBO CO., LTD.), strains of *E. coli* JM109 were transformed, and a nucleotide sequence of DNA encoding the NvFX variant in the plasmid DNA carried on the grown colonies was determined. As a result, a recombinant plasmid encoding the NvFX gene comprising an amino acid sequence derived from the amino acid sequence as shown in SEQ ID NO: 54 by substitution of arginine at position 62 with aspartic acid (pET22b-NvFX-62D) was obtained.

Subsequently, in the same manner as described above, a recombinant plasmid encoding the NvFX gene comprising an amino acid sequence derived from the amino acid sequence as shown in SEQ ID NO: 54 by substitution of arginine at position 62 with aspartic acid and glycine at position 106 with lysine (pET22b-NvFX-62D/106K) was obtained with the use of pET22b-NvFX-62D as a template and synthetic oligonucleotides as shown in SEQ ID NOs: 58 and 59.

Subsequently, in the same manner as described above, a recombinant plasmid encoding the NvFX gene comprising an amino acid sequence derived from the amino acid sequence as shown in SEQ ID NO: 54 by substitution of arginine at position 62 with aspartic acid, arginine at position 106 with lysine, and glutamic acid at position 110 with leucine (pET22b-NvFX-62D/106K/110L) was obtained with the use of pET22b-NvFX-62D/106K as a template and synthetic oligonucleotides as shown in SEQ ID NOs: 60 and 61.

Strains of *E. coli* BL21 (DE3) were transformed under the same conditions as in Example 1 to obtain strains of *E. coli* BL21 (DE3) (pET22b-NvFX-62D/106K/110L). 3. Introduction of point mutation into gene of fructosyl amino acid oxidase derived from *Aspergillus nidulans*

SEQ ID NO: 62 shows the amino acid sequence of fructosyl amino acid oxidase derived from *Aspergillus nidulans* resulting from substitution of serine at position 59 with glycine so as to impart the activity of fructosyl peptide oxidase (hereafter referred to as "AnFX"), and it can be prepared by *E. coli* strains carrying the recombinant plasmid pET22b-AnFX into which the gene (SEQ ID NO: 63) encoding the amino acid sequence as shown in SEQ ID NO: 62 has been inserted. AnFX is confirmed to exhibit oxidation activity on αFV and αFVH (see WO 2012/018094).

In order to introduce mutations aimed at improvement of substrate specificity into AnFX, in the same manner as in Example 1, PCR was carried out with the use of the recombinant plasmid pET22b-AnFX as a template, synthetic oligonucleotides as shown in SEQ ID NOs: 64 and 65, and KOD-Plus-(manufactured by TOYOBO CO., LTD.), strains of *E. coli* JM109 were transformed, and a nucleotide sequence of DNA encoding the AnFX variant in the plasmid DNA carried on the grown colonies was determined. As a result, a recombinant plasmid encoding the AnFX gene comprising an amino acid sequence derived from the amino acid sequence as shown in SEQ ID NO: 62 by substitution of arginine at position 61 with aspartic acid (pET22b-AnFX-61D) was obtained.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid and glycine at position 105 with lysine (pET22b-AnFX-61D/105K) was obtained with the use of pET22b-AnFX-61D as a template and synthetic oligonucleotides as shown in SEQ ID NOs: 66 and 67.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, glycine at position 105 with lysine, and lysine at position 109 with leucine (pET22b-AnFX-61D/105K/109L) was obtained with the use of pET22b-AnFX-61D/105K as a template and synthetic oligonucleotides as shown in SEQ ID NOs: 68 and 69.

Strains of *E. coli* BL21 (DE3) were transformed under the same conditions as in Example 1 to obtain strains of *E. coli* BL21 (DE3) (pET22b-AnFX-61D/105K/109L).

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, glycine at position 105 with lysine, lysine at position 109 with leucine, and serine at position 112 with lysine (pET22b-AnFX-61D/105K/109L/112K) was obtained with the use of pET22b-AnFX-61D/105K/109L as a template and synthetic oligonucleotides as shown in SEQ ID NOs: 112 and 70.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, glycine at position 105 with lysine, lysine at position 109 with leucine, serine at position 112 with lysine, and alanine at position 355 with serine (pET22b-AnFX-61D/105K/109L/112K/355S) was obtained with the use of pET22b-AnFX-61D/105K/109L/112K as a template and synthetic oligonucleotides as shown in SEQ ID NOs: 71 and 72.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, leucine at position 62 with histidine, glycine at position 105 with lysine, lysine at position 109 with leucine, serine at position 112 with lysine, and alanine at position 355 with serine (pET22b-AnFX-61D/62H/105K/109L/112K/355S) was obtained with the use of pET22b-AnFX-61D/105K/109L/112K/355S as a template and synthetic oligonucleotides as shown in SEQ ID NOs: 73 and 74.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, leucine at position 62 with histidine, glutamic acid at position 101 with lysine, glycine at position 105 with lysine, lysine at position 109 with leucine, serine at position 112 with lysine, and alanine at position 355 with serine (pET22b-AnFX-61D/62H/101K/105K/109L/112K/355S) was obtained with the use of pET22b-AnFX-61D/62H/105K/109L/112K/355S as a template and synthetic oligonucleotides as shown in SEQ ID NOs: 75 and 76.

Strains of *E. coli* BL21 (DE3) were transformed under the same conditions as in Example 1 to obtain strains of *E. coli* BL21 (DE3) (pET22b-AnFX-61D/62H/101K/105K/109L/112K/355S).

4. Introduction of Point Mutation into Gene of Fructosyl Peptide Oxidase Derived from *Phaeosphaeria nodorum*

In order to introduce a mutation aimed at improvement of substrate specificity into PnFX, in the same manner as in Example 1, PCR was carried out with the use of the recombinant plasmid pET22b-PnFX prepared in the manner as described above as a template, synthetic oligonucleotides as shown in SEQ ID NOs: 77 and 78, and KOD-Plus-(manufactured by TOYOBO CO., LTD.), strains of *E. coli* JM109 were transformed, and a nucleotide sequence of DNA encoding the PnFX variant in the plasmid DNA carried on the grown colonies was determined. As a result, a recombinant plasmid encoding the PnFX gene comprising an amino acid sequence derived from the amino acid sequence as shown in SEQ ID NO: 38 by substitution of serine at position 62 with aspartic acid (pET22b-PnFX-62D) was obtained.

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid and aspartic acid at position 106 with lysine (pET22b-PnFX-62D/106K) was obtained with the use of pET22b-PnFX-62D as a template and synthetic oligonucleotides as shown in SEQ ID NOs: 79 and 80.

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid, aspartic acid at position 106 with lysine, and glycine at position 110 with leucine (pET22b-PnFX-62D/106K/110L) was obtained with the use of pET22b-PnFX-62D/106K as a template and synthetic oligonucleotides as shown in SEQ ID NOs: 81 and 82.

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid, aspartic acid at position 106 with lysine, glycine at position 110 with leucine, and alanine at position 113 with lysine (pET22b-PnFX-62D/106K/110L/113K) was obtained with the use of pET22b-PnFX-62D/106K/110L as a template and synthetic oligonucleotides as shown in SEQ ID NOs: 83 and 84.

Strains of *E. coli* BL21 (DE3) were transformed under the same conditions as in Example 1 to obtain strains of *E. coli* BL21 (DE3) (pET22b-PnFX-62D/106K/110L/113K).

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid, aspartic acid at position 106 with lysine, glycine at position 110 with leucine, alanine at position 113 with lysine, and alanine at position 351 with serine (pET22b-PnFX-62D/106K/110L/113K/351S) was obtained with the use of pET22b-PnFX-62D/106K/110L/113K as a template and synthetic oligonucleotides as shown in SEQ ID NOs: 85 and 86.

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid, leucine at position 63 with histidine, aspartic acid at position 106 with lysine, glycine at position 110 with leucine, alanine at position 113 with lysine, and alanine at position 351 with serine (pET22b-PnFX-62D/63H/106K/110L/113K/351S) was obtained with the use of pET22b-PnFX-62D/106K/110L/113K/351S as a template and synthetic oligonucleotides as shown in SEQ ID NOs: 87 and 88.

Strains of *E. coli* BL21 (DE3) were transformed under the same conditions as in Example 1 to obtain strains of *E. coli* BL21 (DE3) (pET22b-PnFX-62D/63H/106K/110L/113K/351S).

5. Introduction of Point Mutation into Gene of Fructosyl Peptide Oxidase Derived from *Cryptococcus neoformans*

SEQ ID NO: 89 shows the amino acid sequence of fructosyl amino acid oxidase derived from *Cryptococcus neoformans* (hereafter referred to as "CnFX"), and it can be prepared by *E. coli* strains carrying the recombinant plasmid pET22b-CnFX into which the gene (SEQ ID NO: 90) encoding the amino acid sequence as shown in SEQ ID NO: 89 has been inserted. CnFX is confirmed to exhibit oxidation activity on αFV and αFVH (see WO 2012/018094).

In order to introduce a mutation aimed at improvement of substrate specificity into CnFX, in the same manner as in Example 1, PCR was carried out with the use of the recombinant plasmid pET22b-CnFX prepared in the manner as described above as a template, synthetic oligonucleotides as shown in SEQ ID NOs: 91 and 92, and KOD-Plus-(manufactured by TOYOBO CO., LTD.), strains of *E. coli* JM109 were transformed, and a nucleotide sequence of DNA encoding the CnFX variant in the plasmid DNA carried on the grown colonies was determined. As a result, a recombinant plasmid encoding the CnFX gene comprising an amino acid sequence derived from the amino acid sequence as shown in SEQ ID NO: 89 by substitution of arginine at position 62 with aspartic acid (pET22b-CnFX-62D) was obtained.

Subsequently, in the same manner as described above, a recombinant plasmid encoding the CnFX gene comprising an amino acid sequence derived from the amino acid sequence as shown in SEQ ID NO: 89 by substitution of arginine at position 62 with aspartic acid and serine at position 106 with lysine (pET22b-CnFX-62D/106K) was obtained with the use of pET22b-CnFX-62D as a template and synthetic oligonucleotides as shown in SEQ ID NOs: 93 and 94.

Subsequently, in the same manner as described above, a recombinant plasmid encoding the CnFX gene comprising an amino acid sequence derived from the amino acid sequence as shown in SEQ ID NO: 89 by substitution of arginine at position 62 with aspartic acid, serine at position 106 with lysine, and serine at position 110 with leucine, (pET22b-CnFX-62D/106K/110L) was obtained with the use of pET22b-CnFX-62D/106K as a template and synthetic oligonucleotides as shown in SEQ ID NOs: 95 and 96.

Subsequently, in the same manner as described above, a recombinant plasmid encoding the CnFX gene comprising an amino acid sequence derived from the amino acid sequence as shown in SEQ ID NO: 89 by substitution of arginine at position 62 with aspartic acid, serine at position 106 with lysine, serine at position 110 with leucine, and alanine at position 113 with lysine (pET22b-CnFX-62D/106K/110L/113K) was obtained with the use of pET22b-PnFX-62D/106K/110L as a template and synthetic oligonucleotides as shown in SEQ ID NOs: 97 and 98.

Strains of *E. coli* BL21 (DE3) were transformed under the same conditions as in Example 1 to obtain strains of *E. coli* BL21 (DE3) (pET22b-CnFX-62D/106K/110L/113K). 6. Introduction of point mutation into amadoriase gene exhibiting 95% sequence identity with ketoamine oxidase derived from *Curvularia clavata*

(Preparation of Amadoriase-Producing Strain Exhibiting 95% Sequence Identity with Ketoamine Oxidase Derived from *Curvularia clavata*)

SEQ ID NO: 99 shows the amino acid sequence of an amadoriase exhibiting 95% sequence identity with ketoamine oxidase derived from *Curvularia clavata* (hereafter referred to as "Cc95FX"). The gene (SEQ ID NO: 100) encoding the amino acid sequence as shown in SEQ ID NO: 99 was obtained via total synthesis of cDNA by a conventional technique of PCR of a gene fragment. The NdeI site and the BamHI were added to the 5' terminus and the 3' terminus of SEQ ID NO: 100, respectively.

In order to express the gene as shown in SEQ ID NO: 100 in *E. coli*, subsequently, the following procedures were performed. The gene fully synthesized above was treated with two types of restriction enzymes, NdeI and BamHI (manufactured by Takara Bio Inc.) and inserted into the NdeI-BamHI site of the pET-22b(+) vector (manufactured by Novagen, Inc.). Thus, the recombinant plasmid pET22b-Cc95FX was obtained. Strains of *E. coli* BL21 (DE3) were transformed under the conditions as described above to obtain strains of *E. coli* BL21 (DE3) (pET22b-Cc95FX).

(Introduction of Point Mutation into Amadoriase Gene Exhibiting 95% Sequence Identity with Ketoamine Oxidase Derived from *Curvularia clavata*)

In order to introduce a mutation aimed at improvement of substrate specificity into Cc95FX, in the same manner as in Example 1, PCR was carried out with the use of the recombinant plasmid pET22b-Cc95FX prepared in the manner as described above as a template, synthetic oligonucleotides as shown in SEQ ID NOs: 101 and 102, and KOD-Plus-(manufactured by TOYOBO CO., LTD.), strains of *E. coli* JM109 were transformed, and a nucleotide sequence of DNA encoding the Cc95FX variant in the plasmid DNA carried on the grown colonies was determined. As a result, a recombinant plasmid encoding the Cc95FX gene comprising an amino acid sequence derived from the amino acid sequence as shown in SEQ ID NO: 99 by substitution of arginine at position 62 with aspartic acid (pET22b-Cc95FX-62D) was obtained.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid and aspartic acid at position 106 with lysine (pET22b-Cc95FX-62D/106K) was obtained with the use of pET22b-Cc95FX-62D as a template and synthetic oligonucleotides as shown in SEQ ID NOs: 103 and 104.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, aspartic acid at position 106 with lysine, and alanine at position 110 with leucine (pET22b-Cc95FX-62D/106K/110L) was obtained with the use of pET22b-Cc95FX-62D/106K as a template and synthetic oligonucleotides as shown in SEQ ID NOs: 105 and 106.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, aspartic acid at position 106 with lysine, alanine at position 110 with leucine, and alanine at position 113 with lysine (pET22b-Cc95FX-62D/106K/110L/113K) was obtained with the use of pET22b-Cc95FX-62D/106K/110L as a template and synthetic oligonucleotides as shown in SEQ ID NOs: 107 and 108.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, aspartic acid at position 106 with lysine, alanine at position 110 with leucine, alanine at position 113 with lysine, and alanine at position 353 with serine (pET22b-Cc95FX-62D/106K/110L/113K/353S) was obtained with the use of pET22b-Cc95FX-62D/106K/110L/113K as a template and synthetic oligonucleotides as shown in SEQ ID NOs: 109 and 110.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, leucine at position 63 with histidine, aspartic acid at position 106 with lysine, alanine at position 110 with leucine, alanine at position 113 with lysine, and alanine at position 353 with serine (pET22b-Cc95FX-62D/63H/106K/110L/113K/353S) was obtained with the use of pET22b-Cc95FX-62D/106K/110L/113K/353S as a template and synthetic oligonucleotides as shown in SEQ ID NOs: 111 and 102.

Strains of *E. coli* BL21 (DE3) were transformed under the same conditions as in Example 1 to obtain strains of *E. coli* BL21 (DE3) (pET22b-Cc95FX-621)/63H/106K/110L/113K/353S).

Example 4

Production and Purification of Various Types of Amadoriases (Production and Purification of Fructosyl Peptide Oxidase Derived from *Eupenicillium terrenum*)

Wild-type EFP-T5 strains and the strains of *E. coli* JM109 (pUTE100K'-EFP-T5), *E. coli* JM109 (pUTE100K'-EFP-T5-62D), and *E. coli* JM109 (pUTE100K'-EFP-T5-62D/63H/106K/110L/113K/355S) producing modified EFP-T5 obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare a crude enzyme solution.

To the prepared crude enzyme solution of wild-type or modified EFP-T5, ammonium sulfate was added to bring the concentration of the solution to 35% saturation, the mixture was agitated, and the resultant was centrifuged at 20,000×g for 10 minutes to collect a supernatant. Subsequently, ammonium sulfate was further added to the supernatant to bring the concentration of the solution to 70% saturation, the mixture was agitated, and the resultant was centrifuged at 20,000×g for 10 minutes. The supernatant was then discarded and the precipitate was dissolved in 10 mM potassium phosphate buffer (pH 7.0).

The prepared crude enzyme solution of wild-type or modified EFP-T5 was dialyzed against 10 mM potassium phosphate buffer (pH 6.5), the resultant was applied to 4 ml of Q Sepharose Fast Flow resin (manufactured by GE Healthcare) equilibrated with the buffer, and proteins that do not adsorb to the resin were eluted with the aid of the buffer. Subsequently, the prepared crude enzyme solution of wild-type or modified EFP-T5M was dialyzed against a 10 mM potassium phosphate buffer (pH 8.0), the resultant was allowed to adsorb to the HiLoad 26/10 Q Sepharose HP column (manufactured by GE Healthcare) equilibrated with the buffer, and the resin was washed with the same buffer. While linearly increasing the concentration of NaCl in the buffer from 0 mM to 100 mM, wild-type or modified EFP-T5 that had adsorbed to the resin was then eluted and collected.

The resulting crude enzyme solution containing wild-type or modified EFP-T5 was applied to the HiLoad 26/600 Superdex 200 column equilibrated with a 10 mM potassium phosphate buffer (pH 7.0) containing 150 mM NaCl so as to elute wild-type or modified EFP-T5 with the same buffer, and a fraction exhibiting activity of fructosyl amino acid oxidase (i.e., amadoriase activity) was collected. The obtained fraction was analyzed by SDS-PAGE to confirm that the fraction was sufficiently purified, so that no other contaminating proteins were present therein. The fraction was designated to be a purified sample of wild-type or modified EFP-T5.

(Production and Purification of Ketoamine Oxidase Derived from *Neocosmospora vasinfecta*)

Wild-type NvFX strains and the strains of *E. coli* BL21 (DE3) (pET22b-NvFX) and *E. coli* BL21 (DE3) (pET22b-NvFX-62D/106K/110L) producing modified NvFX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH8.0), the washed strains were suspended in the same buffer, the resulting suspension was ultrasonically disintegrated, and the resultant was centrifuged at 20,000×g for 10 minutes to prepare a crude enzyme solution.

The prepared crude enzyme solution was allowed to adsorb to Q Sepharose Fast Flow resin (manufactured by GE Healthcare) equilibrated with a 10 mM potassium phosphate buffer (pH8.0), the resin was washed with a 10 mM potassium phosphate buffer (pH8.0) containing 20 mM NaCl, and wild-type or modified NvFX adsorbed to the resin was then eluted and collected with the aid of a 10 mM potassium phosphate buffer (pH8.0) containing 300 mM NaCl.

The resulting crude enzyme solution containing wild-type NvFX or modified NvFX was applied to the HiLoad 26/600 Superdex 200 column equilibrated with a 20 mM MES-NaOH buffer (pH 7.0) containing 150 mM NaCl so as to elute wild-type NvFX or modified NvFX with the same buffer, and a fraction exhibiting activity of fructosyl amino acid oxidase (i.e., amadoriase activity) was collected. The obtained fraction was analyzed by SDS-PAGE to confirm that the fraction was sufficiently purified, so that no other contaminating proteins were present therein. The fraction was designated to be a purified sample of wild-type or modified NvFX.

(Production and Purification of Fructosyl Amino Acid Oxidase Derived from *Aspergillus nidulans*)

Wild-type AnFX strains and the strains of *E. coli* BL21 (DE3) (pET22b-AnFX-61D/105K/109L) and *E. coli* BL21 (DE3) (pET22b-AnFX-61D/62H/101K/105K/109L/112K/

355S) producing modified AnFX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 6.0), the washed strains were suspended in the same buffer, the resulting suspension was ultrasonically disintegrated, and the resultant was centrifuged at 20,000×g for 10 minutes to prepare a crude enzyme solution.

The prepared crude enzyme solution was allowed to adsorb to SP Sepharose Fast Flow resin (manufactured by GE Healthcare) equilibrated with a 10 mM potassium phosphate buffer (pH6.0), the resin was washed with a 10 mM potassium phosphate buffer (pH 6.0) containing 20 mM NaCl, and modified AnFX adsorbed to the resin was then eluted and collected with the aid of a 10 mM potassium phosphate buffer (pH 6.0) containing 100 mM NaCl.

The resulting crude enzyme solution containing modified AnFX was applied to the HiLoad 26/600 Superdex 200 column equilibrated with a 20 mM MES-NaOH buffer (pH 7.0) containing 150 mM NaCl so as to elute modified AnFX with the same buffer, and a fraction exhibiting activity of fructosyl amino acid oxidase (i.e., amadoriase activity) was collected. The obtained fraction was analyzed by SDS-PAGE to confirm that the fraction was sufficiently purified, so that no other contaminating proteins were present therein. The fraction was designated to be a purified sample of modified AnFX.

(Production and Purification of Fructosyl Peptide Oxidase Derived from *Phaeosphaeria nodorum*)

Strains of *E. coli* BL21 (DE3) (pET22b-PnFX-62D/106K/110L/113K) and *E. coli BL*21 (DE3) (pET22b-PnFX-62D/63H/106K/110L/113K/351S) producing modified AnFX obtained in the manner described above were purified in accordance with the method for purification of wild-type PnFX described above. After the completion of purification with the HiLoad 26/600 Superdex 200 column, the degree of purification was analyzed via SDS-PAGE, and the purified product was confirmed to be sufficiently purified, so that no other contaminating proteins were present therein. The resultant was designated to be a purified sample of modified PnFX.

(Production and Purification of Ketoamine Oxidase Derived from *Cryptococcus neoformans*)

Wild-type CnFX strains and the strains of *E. coli* BL21 (DE3) (pET22b-CnFX) and *E. coli* BL21 (DE3) (pET22b-CnFX-62D/106K/110L/113K) producing modified CnFX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The prepared crude enzyme solution was allowed to adsorb to Q Sepharose Fast Flow resin (manufactured by GE Healthcare) equilibrated with a 10 mM potassium phosphate buffer (pH 8.0), the resin was washed with a 10 mM potassium phosphate buffer (pH 8.0) containing 20 mM NaCl, and wild-type or modified CnFX adsorbed to the resin was then eluted and collected with the aid of a 10 mM potassium phosphate buffer (pH 8.0) containing 300 mM NaCl.

The resulting crude enzyme solution containing wild-type CnFX or modified CnFX was applied to the HiLoad 26/600 Superdex 200 column equilibrated with a 20 mM MES-NaOH buffer (pH 7.0) containing 150 mM NaCl so as to elute wild-type CnFX or modified CnFX with the same buffer, and a fraction exhibiting activity of fructosyl amino acid oxidase (i.e., amadoriase activity) was collected. The obtained fraction was analyzed by SDS-PAGE to confirm that the fraction was sufficiently purified, so that no other contaminating proteins were present therein. The fraction was designated to be a purified sample of wild-type or modified CnFX.

(Preparation of Amadoriase Exhibiting 95% Sequence Identity with Ketoamine Oxidase Derived from *Curvularia clavata*)

Wild-type Cc95FX strains and the strains of *E. coli* JM109 (pET22b-Cc95FX) and *E. coli* JM109 (pET22b-Cc95FX-62D/63H/106K/110L/113K/355S) producing modified Cc95FX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare a crude enzyme solution.

With the use of the purified samples of various types of wild-type amadoriases and modified enzymes, specific activity thereof relative to αF6P as substrates was measured. The results are shown in Table 15. Concentration of a protein used for calculation of specific activity was determined by the ultraviolet absorption method involving the use of the absorbance at 280 nm (see Protein Sci., 4, 2411-23, 1995).

A crude enzyme solution containing Cc95FX or Cc95FX-62D/63H/106K/110L/113K/355S was subjected to measurement of oxidation activity on αFV, αFVH, and αF6P by the method described in the "B: Method of activity measurement" above. Oxidation activity on substrates, αF6P/αFVH, and αF6P/FV of amadoriases relative to αFVH oxidation activity designated to be 100 are as shown in Table 16.

TABLE 15

| Amadoriase | Amino acid variation | Specific activity (U/mg) 1 mM αF6P |
|---|---|---|
| EFP-T5 (Comparative Example 4) | None | 0 |
| EFP-T5-R62D (Present Invention 27) | R62D | 0.0043 |
| EFP-T5-62D/63H/106K/110L/113K/355S (Present Invention 28) | R62D, L63H, N106K, K110L, T113K, A355S | 1.12 |
| NvFX (Comparative Example 5) | None | 0 |
| NvFX-62D/106K/110L (Present Invention 29) | R62D, G106K, E110L | 0.0030 |

TABLE 15-continued

| Amadoriase | Amino acid variation | Specific activity (U/mg) 1 mM αF6P |
|---|---|---|
| AnFX (Comparative Example 6) | None | 0 |
| AnFX-61D/105K/109L (Present Invention 30) | R61D, G105K, K109L | 0.106 |
| AnFX-61D/62H/101K/105K/109L/112K/355S (Present Invention 31) | R61D, L62H, E101K, G105K, K109L, S112K, A355S | 0.283 |
| PnFX (Comparative Example 3) | None | 0.0091 |
| PnFX-62D/106K/110L/113K (Present Invention 32) | S62D, D106K, G110L, A113K | 0.125 |
| PnFX-62D/63H/106K/110L/113K/351S (Present Invention 33) | S62D, L63H, D106K, G110L, A113K, A351S | 0.667 |
| CnFX (Comparative Example 7) | None | 0 |
| CnFX-62D/106K/110L/113K (Present Invention 34) | R62D, S106K, S110L, A113K | 0.342 |

TABLE 16

| Amadoriase | Amino acid substitution | αFV oxidation activity | αFVH oxidation activity | αF6P oxidation activity | αF6P/αFVH | αF6P/αFV |
|---|---|---|---|---|---|---|
| Cc95FX (Comparative Example 8) | None | | 100 | 0 | 0 | 0 |
| Cc95FX-62D/63H/106K/110L/113K/353S (Present Invention 35) | R62D/L63H/D106K/A110L/A113K/A353S | 16400 | 100 | 237 | 2.37 | 0.0144 |

As a result of introduction of amino acid substitution into various amadoriases aimed at addition or enhancement of reactivity with αF6P to the amadoriase derived from *Coniochaeta* obtained in the present invention (CFP-T7; Comparative Example 1), a new trait; i.e., reactivity with αF6P, was added to EFP-T5, NvFX, AnFX, and CnFX, as expected. While PnFX had exhibited a minor level of reactivity with αF6P, specific activity was elevated by 13.7 fold as a result of introduction of the amino acid substitution found in the present invention.

Also, amino acid substitution aimed at addition or enhancement of reactivity with αF6P to the amadoriase derived from *Coniochaeta* obtained in the present invention (CFP-T7; Comparative Example 1) was introduced into an amadoriase (Cc95FX; Comparative Example 8) exhibiting 95% sequence identity with the ketoamine oxidase derived from *Curvularia clavata* obtained in the present invention. As a result, a new trait; i.e., reactivity with αF6P, was added to Ce95FX, as expected, and αF6P oxidation activity of Cc95FX-62D/63H/106K/110L/113K/355S exceeded αFVH oxidation activity.

Specifically, the effects of amino acid substitution aimed at addition or enhancement of reactivity with αF6P to the amadoriase derived from *Coniochaeta* obtained in the present invention are not limited to the amadoriase derived from *Coniochaeta*. In general, similar effects were exerted on amadoriases exhibiting 74% or higher sequence identity with the amadoriase derived from *Coniochaeta* as shown in FIGS. 1 and 2.

Example 5

Quantification of αF6P

Reagents for measurement of αF6P of the formulations shown below were prepared, and, with the use of Bio Majesty JCA-BM1650 (JEOL Ltd.), measurement of αF6P was carried out in the manner as described below.

Sample 1: αF6P solution (final concentration: 0.5 to 10 μM)
0 μM, 4.0 μM, 8.0 μM, 12 μM, 16 μM, 24 μM, 32 μM, 40 μM, 48 μM, and 80 μM αF6P
Reagent 4: Leuco dye solution
24 mM HEPES-NaOH buffer (pH 7.8)
0.24 mM sodium N-(carboxymethylaminocarbonyl)-4,4'-bis(dimethylamino)diphenylamine (DA-64, manufactured by Wako Pure Chemical Industries, Ltd.)
Reagent 5: Peroxidase, αF6P oxidase solution
400 mM MES-NaOH buffer (pH 6.0)
20 U/ml peroxidase (manufactured by Kikkoman Corporation)
4.0 U/ml (0.94 mg/ml) CFP-T7-H35 (Present Invention 25)
Reagent 6: Peroxidase, amadoriase solution exhibiting no αF6P oxidation activity
400 mM MES-NaOH buffer (pH 6.0)
20 U/ml peroxidase (manufactured by Kikkoman Corporation)
0.94 g/ml CFP-T7 (Comparative Example 1)

Sample 1 (25 μl) was added to 125 μl of Reagent 4, the resultant was incubated at 37° C. for 5 minutes, and the absorbance at 751 nm was then measured ($A_0$). Subsequently, 50 μl of Reagent 5 or 6 was added, a quantitative reaction of hydrogen peroxide generated upon oxidation of αF6P was allowed to proceed at 37° C. for 5 minutes, and the absorbance at 751 nm was measured again ($A_5$). FIG. 5 shows a chart demonstrating the final concentration of αF6P derived from Sample 1 on the horizontal axis and differences in the absorbance before and after the quantitative reaction of hydrogen peroxide ΔA ($A_5-A_0$) on the vertical axis.

When Reagent 5 was used, a favorable correlation was developed between ΔA and αF6P concentration in the range of αF6P concentration from 0.5 μM to 10 μM (FIG. 5-1). When Reagent 6 was used, however, no correlation was observed between ΔA and αF6P concentration (FIG. 5-2). This indicates that incorporation of the αF6P oxidase of the present invention enables rapid (5 minutes) and highly sensitive (up to 0.5 μM) quantification of αF6P.

In order to diagnose diabetes mellitus, it is necessary to detect HbAlc of 6.5% (NGSP), which is the borderline for diabetes mellitus. An NGSP value of 6.5% is equivalent to 47 mmol/mol in terms of IFCC. When blood hemoglobin level is 13 g/dl and NGSP level is 6.5%, the hemoglobin β-chain level with the glycated amino terminus in the blood is approximately 190 μM. Specifically, it is necessary to quantify αF6P at 190 μM or lower in order to realize diagnosis of diabetes mellitus with the NGSP level. That is, it is difficult to approve the industrial applicability of the NGSP level. With the use of the αF6P oxidase of the present invention, however, αF6P derived from the amino terminus of the HbAlc β-chain can be detected even if the blood is diluted 380 fold. Thus, the αF6P oxidase of the present invention is very advantageous in terms of industrial applicability.

Example 6

Quantification of HbAlc

Reagents for measurement of HbAlc of the formulations shown below were prepared, and, with the use of Bio Majesty JCA-BM1650 (JEOL Ltd.), measurement of HbAlc was carried out in the manner as described below.

Sample 2: HbAlc solution

Reference Material for Measurement of HbAlc, JCCRM423-8 (manufactured by Reference Material Institute for Clinical Chemistry Standards)

Total hemoglobin level: 133 g/l 3 different HbAlc levels (NGSP levels: 5.56%, 7.74%, and 10.48%)

Reagent 7: Sample pretreatment solution 0.012% 1-dodecylpyridinium chloride (DPC, manufactured by Tokyo Chemical Industry Co., Ltd.)

Reagent 8: Leuco dye, Glu-C protease solution 24 mM HEPES-NaOH buffer (pH 7.8)

0.24 mM sodium N-(carboxymethylaminocarbonyl)-4,4'-bis (dimethylamino)diphenylamine (DA-64, manufactured by Wako Pure Chemical Industries, Ltd.)

8.0 U/ml V-8 protease (endoproteinase Glu-C, manufactured by Wako Pure Chemical Industries, Ltd.)

Reagent 9: Peroxidase, αF6P oxidase solution 400 mM MES-NaOH buffer (pH 6.0)

20 U/ml peroxidase (manufactured by Kikkoman Corporation)

8.0 U/ml (1.9 mg/ml) CFP-T7-H35 (Present Invention 25)

Reagent 10: Peroxidase, amadoriase solution exhibiting no αF6P oxidation activity 400 mM MES-NaOH buffer (pH 6.0)

20 U/ml peroxidase (manufactured by Kikkoman Corporation)

1.9 mg/ml CFP-T7 (Comparative Example 1)

Sample 2 diluted 20-fold with Reagent 7 (25 μl) was added to 125 μl of Reagent 8, the resultant was incubated at 37° C. for 5 minutes, 50 μl of Reagent 9 or 10 was added, and a quantitative reaction of hydrogen peroxide generated upon oxidation of αF6P, which had been released from the β-chain amino terminus of HbAlc, was allowed to proceed at 37° C. for 5 minutes. FIG. 6 shows a chart demonstrating the final concentration of HbAlc (NGSP) of Sample 2 on the horizontal axis and differences in the absorbance at 751 nm before and after the quantitative reaction of hydrogen peroxide (ΔA) on the vertical axis.

When Reagent 6 was used, a favorable correlation was developed between HbAlc level and ΔA (FIG. 6-1). When Reagent 7 was used, however, no correlation was observed between ΔA and HbAlc level (FIG. 6-2). This indicates that the use of the αF6P oxidase of the present invention in combination with Glu-C protease enables rapid (10 minutes) quantification of HbAlc.

As described above, the amadoriase of the present invention shows excellent reactivity (substrate specificity) with αF6P, and it is a very potential enzyme that enables rapid, simple, accurate, and satisfactory quantification of αF6P. Accordingly, industrial applicability thereof in measurement of HbAlc by an enzymatic method is expected.

Tables below show the amino acids at positions 62, 63, 102, 106, 110, 113, 355, and 419 of the variants of comparative examples and of the present invention. These tables also show amino acids after substitutions, in the presence of substitution.

TABLE 17

| | Comparative Example 1 | Comparative Example 3 | Comparative Example 5 | Comparative Example 6 | Comparative Example 4 | Comparative Example 7 | Comparative Example 8 | Comparative Example 2 |
|---|---|---|---|---|---|---|---|---|
| Name | CFP-T7 | PnFX | NvFX | AnFX | EFP-T5 | CnFX | Cc95FX | FAOAo2 |
| Origin | *Coniochaeta* sp. | *Phaeosphaeria nodorum* | *Neocosmospora vasinfecta* | *Aspergillus nidulans* | *Eupenicillium terrenum* | *Cryptococcus neoformans* | *Curvularia clavata* | *Aspergillus oryzae* |
| | SEQ ID NO | | | | | | | |
| aa position | SEQ 1 | SEQ 38 | SEQ 54 | SEQ 62 (SEQ 147) | SEQ 40 (SEQ 145) | SEQ 89 (SEQ 149) | SEQ 99 | SEQ 36 |
| 62 | R | S | R | R61 | R | R | R | |
| 63 | L | L | L | L62 | L | I | L | |
| 102 | E | K | E | E101 | E | E | E | |
| 106 | D | D | G | G105 | N | S | D | |
| 110 | Q | G | E | K109 | K | S | A | |
| 113 | A | A | K | S112 | T | A | A | |
| 355 | A | A351 | S | A | A | A | A353 | |
| 419 | A | S416 | A420 | A420 | G | A420 | S418 | |

TABLE 18

| Name<br>Origin | PyFX<br>*Pyrenochaeta* sp. | ArFX<br>*Arthrinium* sp. | CcFX<br>*Curuvlaria clavata* | EnFX<br>*Emericella nidulans* | UlFX<br>*Ulocladium* sp. | PjFX<br>*Penicillium janthineilum* |
|---|---|---|---|---|---|---|
| aa | SEQ ID NO | | | | | |
| position | SEQ 113 | SEQ 115 | SEQ 117 | SEQ 119 | SEQ 121 | SEQ 123 |
| 62 | R | R | R | R61 | R | R |
| 63 | L | L | L | L62 | L | L |
| 102 | K | K | E | E101 | K | E |
| 106 | D | A | D | K105 | D | S |
| 110 | A | Q | A | R109 | A | K |
| 113 | T | T | A | S112 | A | D |
| 355 | A353 | A356 | A353 | A | A353 | A |
| 419 | A418 | A421 | A418 | A420 | A418 | S |

TABLE 19

| | Present Invention 26 | Present Invention 1 | Present Invention 2 | Present Invention 4 | Present Invention 5 | Present Invention 6 | Present Invention 27 |
|---|---|---|---|---|---|---|---|
| Name<br>Origin | CFP-T7-62D<br>*Coniochaeta* sp. | CFP-T7-H1<br>*Coniochaeta* sp. | CFP-T7-H2<br>*Coniochaeta* sp. | CFP-T7-H4<br>*Coniochaeta* sp | CFP-T7-H2-62N<br>*Coniochaeta* sp. | CFP-T7-H6<br>*Coniochaeta* sp. | EFP-T5-R62D<br>*Eupenicillium terrenum* |
| aa | SEQ ID NO | | | | | | |
| position | SEQ 153 | SEQ 151 | SEQ 157 | SEQ 159 | SEQ 161 | SEQ 163 | SEQ 155 |
| 62 | R62D | R62A | R62A | R62A | R62N | R62D | R62D |
| 63 | | | | | | | |
| 102 | | | | | | | |
| 106 | | | | | | | |
| 110 | | | Q110L | Q110Y | Q110L | Q110L | |
| 113 | | | | | | | |
| 355 | | | | | | | |
| 419 | | | | | | | |

TABLE 20

| | Present Invention 12 | Present Invention 13 | Present Invention 14 | Present Invention 15 | Present Invention 16 | Present Invention 29 | Present Invention 30 |
|---|---|---|---|---|---|---|---|
| Name | CFP-T7-H10 | CFP-T7-H11 | CFP-T7-H12 | CFP-T7-H13 | CFP-T7-H14 | NvFX-62D/<br>106K/110L | AnFX-61D/<br>105K/109L |
| Origin | *Coniochaeta* sp. | *Coniochaeta* sp. | *Coniochaeta* sp. | *Coniochaeta* sp. | *Coniochaeta* sp. | Neocosmospora *vasinfecta* | *Aspergillus nidulans* |
| aa | SEQ ID NO | | | | | | |
| position | SEQ 165 | SEQ 167 | SEQ 169 | SEQ 171 | SEQ 173 | SEQ 137 | SEQ 139 |
| 62 | R62D | R62D | R62D | R62D | R62D | R62D | R61D |
| 63 | | | | | | | |
| 102 | | | | | | | |
| 106 | D106A | D106K | D106R | | | G106K | G105K |
| 110 | Q110L | Q110L | Q110L | Q110L | Q110L | E110L | K109L |
| 113 | | | | A113K | A113R | | |
| 355 | | | | | | | |
| 419 | | | | | | | |

TABLE 21

| | Present Invention 17 | Present Invention 18 | Present Invention 19 | Present Invention 21 | Present Invention 32 | Present Invention 34 |
|---|---|---|---|---|---|---|
| Name | CFP-T7-H20 | CFP-T7-H21 | CFP-T7-H24 | CFP-T7-H26 | PnFX-62D/<br>106K/110L/113K | CnFX-62D/<br>106K/110L/113K |
| Origin | *Coniochaeta* sp. | *Coniochaeta* sp. | *Coniochaeta* sp. | *Coniochaeta* sp. | *Phaeosphaeria nodrum* | *Cryptococcus neoformans* |

TABLE 21-continued

| aa | SEQ ID NO | | | | | |
|---|---|---|---|---|---|---|
| position | SEQ 133 | SEQ 175 | SEQ 177 | SEQ 179 | SEQ 135 | SEQ 189 |
| 62 | R62D | R62D | R62D | R62D | S62D | R62D |
| 63 | | | L63A | L63H | | |
| 102 | | | | | | |
| 106 | D106K | D106K | D106K | D106K | D106K | S106K |
| 110 | Q110L | Q110L | Q110L | Q110L | G110L | S110L |
| 113 | A113K | A113R | A113K | A113K | A113K | A113K |
| 355 | | | | | | |
| 419 | | | | | | |

TABLE 22

| | Present Invention 23 | Present Invention 24 | Present Invention 25 | Present Invention 33 | Present Invention 31 | Present Invention 28 | Present Invention 35 |
|---|---|---|---|---|---|---|---|
| Name | CFP-T7-H28 | CFP-T7-H29 | CFP-T7-H35 | PnFX-62D/106K/110L/113K/351S | AnFX-61D/62H/101K/105K/109L/112K/355S | EFP-T5-62D/63H/106K/110L/113K/355S | Cc95FX-62D/63H/106K/110L/113K/353S |
| Origin | *Coniochaeta* sp. | *Coniochaeta* sp. | *Coniochaeta* sp. | *Phaeosphaeria nodorum* | *Aspergillus nidulans* | *Eupenicillium terrenum* | *Curvularia clavata* |
| aa | SEQ ID NO | | | | | | |
| position | SEQ 181 | SEQ 183 | SEQ 141 | SEQ 187 | SEQ 185 | SEQ 143 | SEQ 191 |
| 62 | R62D | R62D | R62D | S62D | R61D | R62D | R62D |
| 63 | L63H | L63H | L63H | L63H | L62H | L63H | L63H |
| 102 | E102K | | E102K | | E101K | | |
| 106 | D106K | D106K | D106K | D106K | G105K | N106K | D106K |
| 110 | Q110L | Q110L | Q110L | G110L | K109L | K110L | A110L |
| 113 | A113K | A113K | A113K | A113K | S112K | T113K | A113K |
| 355 | | | A355S | A351S | A355S | A355S | A353S |
| 419 | | A419K | | | | | |

Sequence Listing Free Text

SEQ ID NO: 1: Amino acid sequence of amadoriase derived from *Coniochaeta* sp. NISL 9330

SEQ ID NO: 2: Nucleotide sequence of the amadoriase as shown in SEQ ID NO: 1

SEQ ID NOs: 3-33: PCR primers

SEQ ID NO: 34: PCR primer

SEQ ID NO: 35: PCR primer

SEQ ID NO: 36: Amino acid sequence of *Aspergillus oryzae* RIB40 (FAOAo2)

SEQ ID NO: 37: Nucleotide sequence of FAOAo2

SEQ ID NO: 38: Amino acid sequence of *Phaeosphaeria nodorum* (PnFX)

SEQ ID NO: 39: Nucleotide sequence of PnFX

SEQ ID NO: 40: Amino acid sequence of *Eupenicillium terrenum* (EFP-T5)

SEQ ID NO: 41: Nucleotide sequence of EFP-T5

SEQ ID NOs: 42-53: PCR primers

SEQ ID NO: 54: Amino acid sequence of *Neocosmospora vasinfecta* (NvFX)

SEQ ID NO: 55: Nucleotide sequence of NvFX

SEQ ID NOs: 56-61: PCR primers

SEQ ID NO: 62: Amino acid sequence with substitution S59G of *Aspergillus nidulans* (AnFX)

SEQ ID NO: 63: Nucleotide sequence of AnFX

SEQ ID NOs: 64-88: PCR primers

SEQ ID NO: 89: Amino acid sequence of *Cryptococcus neoformans* (CnFX)

SEQ ID NO: 90: Nucleotide sequence of CnFX

SEQ ID NOs: 91-98: PCR primers

SEQ ID NO: 99: Amino acid sequence of amadoriase (Cc95FX) exhibiting 95% sequence identity with ketoamine oxidase derived from *Curvularia clavata*

SEQ ID NO: 100: Nucleotide sequence of Cc95FX

SEQ ID NOs: 101-112: PCR primers

SEQ ID NO: 113: Amino acid sequence of amadoriase derived from *Pyrenochaeta* sp. (Py)

SEQ ID NO: 114: Nucleotide sequence of amadoriase derived from *Pyrenochaeta* sp. (Py)

SEQ ID NO: 115: Amino acid sequence of amadoriase derived from *Arthrinium* sp. (Ar)

SEQ ID NO: 116: Nucleotide sequence of amadoriase derived from *Arthrinium* sp. (Ar)

SEQ ID NO: 117: Amino acid sequence of amadoriase derived from *Curvularia clavata* (Cc)

SEQ ID NO: 118: Nucleotide sequence of amadoriase derived from *Curvularia clavata* (Cc)

SEQ ID NO: 119: Amino acid sequence of amadoriase derived from *Emericella nidulans* (En)

SEQ ID NO: 120: Nucleotide sequence of amadoriase derived from *Emericella nidulans* (En)

SEQ ID NO: 121: Amino acid sequence of amadoriase derived from *Ulocladium* sp. (Ul)

SEQ ID NO: 122: Nucleotide sequence of amadoriase derived from *Ulocladium* sp. (Ul)

SEQ ID NO: 123: Amino acid sequence of amadoriase derived from *Penicillium janthinellum* (Pj)

SEQ ID NO: 124: Nucleotide sequence of amadoriase derived from *Penicillium janthinellum* (Pj)

SEQ ID NO: 125: Amino acid sequence of Amadoriase I derived from *Aspergillus fumigatus*

SEQ ID NO: 126: Nucleotide sequence of Amadoriase I

SEQ ID NO: 127: Amino acid sequence of *Aspergillus oryzae* (FAOAo1)

SEQ ID NO: 128: Nucleotide sequence of FAOAo1

SEQ ID NO: 129: Amino acid sequence of Amadoriase II derived from *Aspergillus fumigatus*

SEQ ID NO: 130: Nucleotide sequence of Amadoriase II

SEQ ID NO: 131: Amino acid sequence of *Aspergillus terreus* (FAOD-A)

SEQ ID NO: 132: Nucleotide sequence of FAOD-A

SEQ ID NO: 133: Amino acid sequence of CFP-T7-H20 derived from *Coniochaeta* sp. (R62D, D106K, Q110L, and A113K)

SEQ ID NO: 134: Nucleotide sequence of CFP-T7-H20

SEQ ID NO: 135: Amino acid sequence of PnFPDX derived from *Phaeosphaeria nodorum* (S62D, D106K, G110L, and A113K)

SEQ ID NO: 136: Nucleotide sequence encoding the amino acid sequence as shown in SEQ ID NO: 135

SEQ ID NO: 137: Amino acid sequence of NvFX-62D/106K/110L derived from *Neocosmospora vasinfecta* (R62D, G106K, and E110L) (Present Invention 29)

SEQ ID NO: 138: Nucleotide sequence encoding the amino acid sequence as shown in SEQ ID NO: 137

SEQ ID NO: 139: Amino acid sequence of AnFX-61D/105K/109L derived from *Aspergillus nidulans* (S590, R61D, G105K and K1091L) (Present Invention 30)

SEQ ID NO: 140: Nucleotide sequence encoding the amino acid sequence as shown in SEQ ID NO: 139

SEQ ID NO: 141: Amino acid sequence of CFP-T7-H35 derived from *Coniochaeta* sp. (R62D, L63H, E102K, D106K, Q110L, A113K, and A355S)

SEQ ID NO: 142: Nucleotide sequence of CFP-T7-H35

SEQ ID NO: 143: Amino acid sequence of EFP-T5-62D/63H/106K/110L/113K/355S derived from *Eupenicillium terrenum*

SEQ ID NO: 144: Nucleotide sequence encoding the amino acid sequence as shown in SEQ ID NO: 143

SEQ ID NO: 145: Amino acid sequence of wild-type amadoriase derived from *Eupenicillium terrenum*

SEQ ID NO: 146: Nucleotide sequence of wild-type amadoriase derived from *Eupenicillium terrenum*

SEQ ID NO: 147: Amino acid sequence of wild-type amadoriase, AnFX

SEQ ID NO: 148: Nucleotide sequence of wild-type amadoriase, AnFX

SEQ ID NO: 149: Amino acid sequence of wild-type amadoriase, CnFX

SEQ ID NO: 150: Nucleotide sequence of wild-type amadoriase, CnFX

SEQ ID NO: 151: Amino acid sequence of CFP-T7-H1 derived from *Coniochaeta* sp. (R62A) (Present Invention 1)

SEQ ID NO: 152: Nucleotide sequence of CFP-T7-H1

SEQ ID NO: 153: Amino acid sequence of CFP-T7-62D derived from *Coniochaeta* sp. (R62D) (Present Invention 26)

SEQ ID NO: 154: Nucleotide sequence of CFP-T7-62D

SEQ ID NO: 155: Amino acid sequence of EFP-T5-R62D derived from *Eupenicillium terrenum* (R62D) (Present Invention 27)

SEQ ID NO: 156: Nucleotide sequence of EFP-T5-R62D

SEQ ID NO: 157: Amino acid sequence of CFP-T7-H2 derived from *Coniochaeta* sp. (R62A and Q110L) (Present Invention 2)

SEQ ID NO: 158: Nucleotide sequence of CFP-T7-H2

SEQ ID NO: 159: Amino acid sequence of CFP-T7-H4 derived from *Coniochaeta* sp. (R62A, Q110Y) (Present Invention 4)

SEQ ID NO: 160: Nucleotide sequence of CFP-T7-H4

SEQ ID NO: 161: Amino acid sequence of CFP-T7-H2-62N derived from *Coniochaeta* (R62N and Q110L) (Present Invention 5)

SEQ ID NO: 162: Nucleotide sequence of CFP-T7-H2-62N

SEQ ID NO: 163: Amino acid sequence of CFP-T7-H6 derived from *Coniochaeta* sp. (R62D, Q110L) (Present Invention 6)

SEQ ID NO: 164: Nucleotide sequence of CFP-T7-H6

SEQ ID NO: 165: Amino acid sequence of CFP-T7-H10 derived from *Coniochaeta* sp. (R62D, D106A, and Q110L) (Present Invention 12)

SEQ ID NO: 166: Nucleotide sequence of CFP-T7-H10

SEQ ID NO: 167: Amino acid sequence of CFP-T7-H11 derived from *Coniochaeta* sp. (R62D, D106K, and Q110L) (Present Invention 13)

SEQ ID NO: 168: Nucleotide sequence of CFP-T7-H11

SEQ ID NO: 169: Amino acid sequence of CFP-T7-H12 derived from *Coniochaeta* sp. (R62D, D106R, and Q110L) (Present Invention 14)

SEQ ID NO: 170: Nucleotide sequence of CFP-T7-H12

SEQ ID NO: 171: Amino acid sequence of CFP-T7-H13 derived from *Coniochaeta* sp. (R62D, Q110L, and A113K) (Present Invention 15)

SEQ ID NO: 172: Nucleotide sequence of CFP-T7-H13

SEQ ID NO: 173: Amino acid sequence of CFP-T7-H14 derived from *Coniochaeta* sp. (R62D, Q110L, and A113R) (Present Invention 16)

SEQ ID NO: 174: Nucleotide sequence of CFP-T7-H14

SEQ ID NO: 175: Amino acid sequence of CFP-T7-H21 derived from *Coniochaeta* sp. (R62D, D106K, Q110L, and A113R) (Present Invention 18)

SEQ ID NO: 176: Nucleotide sequence of CFP-T7-H21

SEQ ID NO: 177: Amino acid sequence of CFP-T7-H24 derived from *Coniochaeta* sp. (R62D, L63A, D106K, Q110L, and A113K) (Present Invention 19)

SEQ ID NO: 178: Nucleotide sequence of CFP-T7-H24

SEQ ID NO: 179: Amino acid sequence of CFP-T7-H26 derived from *Coniochaeta* sp. (R62D, L63H, D106K, Q110L, and A113K) (Present Invention 21)

SEQ ID NO: 180: Nucleotide sequence of CFP-T7-H26

SEQ ID NO: 181: Amino acid sequence of CFP-T7-H28 derived from *Coniochaeta* sp. (R62D, L63H, E102K, D106K, Q110L, and A113K) (Present Invention 23)

SEQ ID NO: 182: Nucleotide sequence of CFP-T7-H28

SEQ ID NO: 183: Amino acid sequence of CFP-T7-H29 derived from *Coniochaeta* sp. (R62D, L63H, D106K, Q110L, All 3K, and A419K) (Present Invention 24)

SEQ ID NO: 184: Nucleotide sequence of CFP-T7-H29

SEQ ID NO: 185: Amino acid sequence of *Aspergillus nidulans* (AnFX-61D/62H/101K/105K/109L/112K/355S) (Present Invention 31)

SEQ ID NO: 186: Nucleotide sequence encoding the amino acid sequence as shown in SEQ ID NO: 185

SEQ ID NO: 187: Amino acid sequence of *Phaeosphaeria nodorum* (PnFX-62D/63H/106K/110L/113K/351S) (Present Invention 33)

SEQ ID NO: 188: Nucleotide sequence encoding the amino acid sequence as shown in SEQ ID NO: 187

SEQ ID NO: 189: Amino acid sequence of *Cryptococcus neoformans* (CnFX-62D/106K/110L/113K) (Present Invention 34)

SEQ ID NO: 190: Nucleotide sequence encoding the amino acid sequence as shown in SEQ ID NO: 189

SEQ ID NO: 191: Amino acid sequence of *Curvularia clavata* (Cc95FX-62D/63H/106K/110L/113K/353S) (Present Invention 35)

SEQ ID NO: 192: Nucleotide sequence encoding the amino acid sequence as shown in SEQ ID NO: 191

All publications, patents, and patent applications cited herein are incorporated herein by reference in their entirety.

The invention claimed is:

1. A variant amadoriase comprising an amino acid sequence which exhibits 90% or higher sequence identity with the amino acid sequence as shown in SEQ ID NO: 1 over the full length in which, when said amino acid sequence is aligned with the amino acid sequence as shown in SEQ ID NO: 1, the amino acid at the position corresponding to position 62 of the amino acid sequence as shown in SEQ ID NO: 1 is alanine or aspartic acid and having activity on α-fructosyl hexapeptide (αF6P) greater than the activity of an amadoriase having the amino acid sequence as shown in SEQ ID NO: 1.

2. A kit used for measurement of hemoglobin Alc (HbAlc), which includes the variant amadoriase according to claim 1.

3. The variant amadoriase according to claim 1, wherein the variant amadoriase comprises an amino acid sequence having a substitution, deletion, or addition of one to fifteen amino acids, wherein the substitution, deletion, or addition occurs at positions other than that corresponding to position 62 in the amino acid sequence as shown in SEQ ID NO: 1.

4. A kit used for measurement of HbAlc, which includes the variant amadoriase according to claim 3.

* * * * *

SEQUENCE LISTING

```
<160> NUMBER OF SEQ ID NOS: 192

<210> SEQ ID NO 1
<211> LENGTH: 437
<212> TYPE: PRT
<213> ORGANISM: Coniochaeta sp.

<400> SEQUENCE: 1

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Arg Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335
```

```
Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 2
<211> LENGTH: 1314
<212> TYPE: DNA
<213> ORGANISM: Coniochaeta sp.

<400> SEQUENCE: 2

atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atacgactgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagcag taccaggcac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc ccccatctccg     900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg acgctgctct cttgatgtgt    1080

gaacacccca aatggaagaa tttcattcta gcgaccggcg acagcggaca ctcattcaaa    1140

atcttgccta acgtcggaaa atacgtagtc gagttgatag agggccgcct gccggaggaa    1200

atggcttatc aatggaggtg gcggccagga ggcgatgcac tcaagtctag acgtgcggca    1260

ccgccaaaag atcttgcaga catgccagga tggaaacatg atccgaaatt gtaa          1314


<210> SEQ ID NO 3
<211> LENGTH: 30
<212> TYPE: DNA
<213> ORGANISM: Artificial
```

<220> FEATURE:
<223> OTHER INFORMATION: primer

<400> SEQUENCE: 3
tcatgggaat agcactgcgc aacaaggtgg 30

<210> SEQ ID NO 4
<211> LENGTH: 29
<212> TYPE: DNA
<213> ORGANISM: Artificial
<220> FEATURE:
<223> OTHER INFORMATION: primer

<400> SEQUENCE: 4
tattcccatg atcttgttga gatcatggc 29

<210> SEQ ID NO 5
<211> LENGTH: 29
<212> TYPE: DNA
<213> ORGANISM: Artificial
<220> FEATURE:
<223> OTHER INFORMATION: primer

<400> SEQUENCE: 5
acctgaaaaa gctgtaccag gcactgcac 29

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
acctgaaaaa gttctaccag gcactgcac 29

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
acctgaaaaa gtattaccag gcactgcac 29

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
ctttttcagg tcctcgatac cctcaggc 28

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
tcatgggaat aaacctgcgc aacaaggtgg 30

-continued

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
tcatgggaat agatctgcgc aacaaggtgg 30

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
tcatgggaat acaactgcgc aacaaggtgg 30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
tcatgggaat agaactgcgc aacaaggtgg 30

<210> SEQ ID NO 13
<211> LENGTH: 30
<212> TYPE: DNA
<213> ORGANISM: Artificial
<220> FEATURE:
<223> OTHER INFORMATION: primer

<400> SEQUENCE: 13
tgggaataga tctggccaac aaggtggacc 30

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14
tgggaataga tctggaaaac aaggtggacc 30

<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
tgggaataga tctgcacaac aaggtggacc 30

<210> SEQ ID NO 16
<211> LENGTH: 27
<212> TYPE: DNA
<213> ORGANISM: Artificial
<220> FEATURE:
<223> OTHER INFORMATION: primer

<400> SEQUENCE: 16
cagatctatt cccatgatct tgttgag 27

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
tgagggtatc gaggccctga aaaagctg 28

<210> SEQ ID NO 18
<211> LENGTH: 28
<212> TYPE: DNA
<213> ORGANISM: Artificial
<220> FEATURE:
<223> OTHER INFORMATION: primer

<400> SEQUENCE: 18
tgagggtatc gagaaactga aaaagctg 28

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19
tgagggtatc gagcgcctga aaaagctg 28

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
ctcgataccc tcaggcgtgt gttcgcag 28

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21
aaaaagctgt accagaaact gcacgatgcc 30

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
gcatcgtgca gtttctggta cagctttttc 30

<210> SEQ ID NO 23

<211> LENGTH: 30
<212> TYPE: DNA
<213> ORGANISM: Artificial
<220> FEATURE:
<223> OTHER INFORMATION: primer

<400> SEQUENCE: 23
aaaaagctgt accagcgtct gcacgatgcc 30

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
gcatcgtgca gacgctggta cagctttttc 30

<210> SEQ ID NO 25
<211> LENGTH: 30
<212> TYPE: DNA
<213> ORGANISM: Artificial
<220> FEATURE:
<223> OTHER INFORMATION: primer

<400> SEQUENCE: 25
tcatgggaat agatgcgcgc aacaaggtgg 30

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
tcatgggaat agatgaccgc aacaaggtgg 30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
tcatgggaat agatcatcgc aacaaggtgg 30

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
tcatgggaat agataagcgc aacaaggtgg 30

<210> SEQ ID NO 29
<211> LENGTH: 29
<212> TYPE: DNA
<213> ORGANISM: Artificial
<220> FEATURE:
<223> OTHER INFORMATION: primer

<400> SEQUENCE: 29
atctattccc atgatcttgt tgagatcat 29

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
aggcgtgtgt tcgcagtcca ttctg 25

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
gcgaacacac gcctaagggt atcgagaaac 30

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32
acgtctagac ttgagtgcat cgcctcctg 29

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
tcaagtctag acgtaaggca ccgccaaaag 30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
acagacactg cggactctgc tctcttgatg 30

<210> SEQ ID NO 35
<211> LENGTH: 28
<212> TYPE: DNA
<213> ORGANISM: Artificial
<220> FEATURE:
<223> OTHER INFORMATION: primer

<400> SEQUENCE: 35
gtccgcagtg tctgtacacc agcacaag 28

<210> SEQ ID NO 36
<211> LENGTH: 436
<212> TYPE: PRT

<213> ORGANISM: Aspergillus oryzae

<400> SEQUENCE: 36

```
Met Thr Val Thr Lys Ser Ser Ser Ile Leu Ile Ile Gly Ala Gly Thr
1               5                   10                  15

Trp Gly Ala Ser Thr Ala Leu His Leu Gly Arg Arg Gly Tyr Thr Asn
            20                  25                  30

Val Thr Val Leu Asp Pro Tyr Thr Val Pro Ser Ala Ile Ser Ala Gly
        35                  40                  45

Asn Asp Val Asn Lys Ile Ile Ser Ser Gly Gln Tyr Ser Asn Lys Lys
    50                  55                  60

Asp Glu Ile Glu Val Asn Glu Ile Leu Ala Glu Glu Ala Phe Lys Gly
65                  70                  75                  80

Trp Thr Thr Asp Pro Leu Phe Lys Pro Tyr Tyr His Asp Thr Gly Val
                85                  90                  95

Val Met Ser Ala Cys Ser Ser Ala Gly Leu Asp Arg Leu Gly Ile Arg
            100                 105                 110

Val Arg Pro Glu Glu Glu Pro Asp Val Ser Glu Val Thr Lys Pro Glu
        115                 120                 125

His Phe Arg Gln Leu Ala Pro Ala Val Leu Lys Gly Asn Phe Pro Gly
    130                 135                 140

Trp Arg Gly Tyr His Ile Arg Ser Asn Ala Gly Trp Ala His Ala Arg
145                 150                 155                 160

Asn Ala Leu Val Ala Ala Ile Arg Glu Ala Glu Lys Leu Gly Val Lys
                165                 170                 175

Phe Val Thr Gly Thr Gln Gly Arg Val Ile Thr Leu Ile Phe Glu Asn
            180                 185                 190

Asn Asp Val Lys Gly Ala Val Thr Ala Asp Gly Lys Ile Trp Arg Ala
        195                 200                 205

Glu Gln Thr Val Leu Cys Ala Gly Ala Asn Ala Ala Gln Phe Leu Asp
    210                 215                 220

Phe Lys Asp Gln Leu Arg Pro Thr Ala Trp Thr Leu Ala His Ile Arg
225                 230                 235                 240

Leu Lys Pro Glu Glu Arg Ala Leu Tyr Lys Asn Leu Pro Val Ile Phe
                245                 250                 255

Asn Ile Glu Lys Gly Phe Phe Phe Glu Pro Asp Glu Glu Arg Gly Glu
            260                 265                 270

Ile Lys Ile Cys Asp Glu His Pro Gly Tyr Thr Asn Met Val Lys Ser
        275                 280                 285

Ala Asp Gly His Leu Thr Ser Leu Pro Phe Glu Lys Thr Gln Ile Pro
    290                 295                 300

Lys Glu Ser Glu Ala Arg Val Arg Ala Leu Leu Ser Glu Thr Met Pro
305                 310                 315                 320

Gln Leu Ala Asp Arg Pro Phe Ser Phe Ala Arg Val Cys Trp Cys Ala
                325                 330                 335

Asp Thr Ala Asn Arg Glu Phe Ile Ile Asp Arg His Pro Glu His Pro
            340                 345                 350

Ser Leu Val Leu Gly Cys Gly Ala Ser Gly Arg Gly Phe Lys Tyr Leu
        355                 360                 365

Pro Ser Ile Gly Asn Leu Ile Val Asp Ala Ile Glu Asp Lys Val Pro
    370                 375                 380

Glu Lys Val His Lys Leu Thr Arg Trp Ser Pro Asp Ile Ala Val Asp
385                 390                 395                 400
```

-continued

```
Arg Lys Trp Arg Asp Thr Leu Gly Arg Phe Gly Gly Pro Asn Arg Val
                405                 410                 415

Met Asp Phe His Asp Val Lys Glu Trp Thr Asn Val Gln Asn Lys Asp
            420                 425                 430

Thr Ala Lys Leu
        435


<210> SEQ ID NO 37
<211> LENGTH: 1311
<212> TYPE: DNA
<213> ORGANISM: Aspergillus oryzae

<400> SEQUENCE: 37

atgactgtca ccaaatcttc ctcaatcctg atcatcggcg caggcacttg gggcgcttca      60

actgcccttc accttggtcg cagaggatac accaatgtca ccgtcctaga cccttacaca     120

gtgccctcag caatttcagc tggaaatgac gtgaacaaga tcatctcctc ggggcaatac     180

agcaacaaaa aggatgagat tgaagttaac gaaattctcg ccgaggaggc attcaaaggc     240

tggacaaccg accctttgtt caagccatac taccacgaca ctggcgttgt aatgtctgct     300

tgcagcagcg ccggtctgga tcgcctcgga atccgagtaa ggccggaaga ggaacctgat     360

gtttccgaag tcacgaagcc ggagcacttc cgccaactgg cccccgctgt gctgaaagga     420

aacttcccgg ggtggagagg ctaccacatt cgttcgaacg ctggctgggc gcacgcccga     480

aatgccctcg tggccgctat acgcgaagca gagaaacttg gtgttaaatt cgtaacaggc     540

acccaaggaa gagtcatcac ccttatcttc gagaacaacg acgtcaaggg cgcagtcacc     600

gccgacggaa agatctggcg cgcggagcaa acagttctct gcgctggcgc aaatgctgcg     660

cagttcttgg attttaagga ccagctccgc ccaacggcat ggacactcgc ccatatccgg     720

ctcaaacctg aggaacgcgc gctctacaaa aacttgccgg tgattttcaa cattgagaaa     780

ggatttttct tcgagcctga tgaggagcgc ggggagatca agatctgcga cgaacatccg     840

ggatacacta acatggttaa atctgcggat ggccacttga cgagtttgcc ctttgagaag     900

acccagatcc ccaaggagtc tgaagctaga gtcagagctt tactatcgga gaccatgcct     960

caattagccg atcgcccatt tagcttcgcc cgcgtttgct ggtgtgcgga caccgcaaac    1020

cgtgaattca tcattgaccg ccaccctgaa cacccgtctc ttgttttggg atgcggtgct    1080

tccggaaggg gtttcaaata tctcccctca atcggcaacc tcattgttga cgccattgaa    1140

gacaaagtcc cagagaaagt tcacaagctt acgaggtgga gtccagacat tgctgttgac    1200

agaaagtgga gggacactct ggggcgcttt ggagggccta accgtgtcat ggacttccat    1260

gatgtcaagg aatggactaa cgtgcagaac aaggatactg cgaagctgta g             1311


<210> SEQ ID NO 38
<211> LENGTH: 437
<212> TYPE: PRT
<213> ORGANISM: Phaeosphaeria nodorum

<400> SEQUENCE: 38

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
        35                  40                  45

Gln Ser Ala Gly Asn Asp Leu Asn Lys Ile Met Gly Val Ser Leu Arg
```

-continued

```
    50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Phe Glu Pro Asn Glu His Gly Val
            260                 265                 270

Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
        355                 360                 365

Gly Asp Ser Gly His Ser Phe Lys Leu Leu Pro Asn Ile Gly Lys His
    370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435


<210> SEQ ID NO 39
<211> LENGTH: 1314
<212> TYPE: DNA
<213> ORGANISM: Phaeosphaeria nodorum
```

<400> SEQUENCE: 39

```
atggccccgt cgcgtgctaa tacgtcggtc attgtggttg gtggtggtgg tacgattggc     60
tcatctacgg ctctgcatct ggtccgctca ggctataccc cgtcgaacgt gacggttctg    120
gatgcatacc cgattccgag ctctcagagc gctggcaacg acctgaataa aatcatgggt    180
gtctctctgc gtaatccggt ggatctgcag ctggctctgg aagcgcgcca aatgtggaac    240
gaagacgaac tgttcaagaa gtttttccat aacaccggcc gtctggattg cgcgcacggt    300
gaaaaagata ttgccgacct gaagagcggc tatcaggctc tggtggatgc gggtctggac    360
gccacgaacg aatggctgga tagtgaagac gaaatcctga aacgtatgcc gctgctgtcc    420
cgcgatcaaa ttaaaggctg gaaggcgatc ttttcaaaag acggtggttg gctggcagca    480
gcaaaggcaa ttaatgcagt tggtgaatat ctgcgtgatc agggcgtccg cttcggtttt    540
tacggcgccg gttctttcaa agcaccgctg ctggctgaag gcgtctgcat cggtgtcgaa    600
accgtggatg gcacgcgcta ttacgcagac aaagtggttc tggctgcagg tgcatggtcg    660
ccgaccctgg ttgaactgca tgaacagtgt gtgagcaaag cgtgggttta cggccacatt    720
caactgacgc cggaagaagc cgcacgttat aagaacagcc cggtcgtgta caatggcgat    780
gtgggctttt tctttgaacc gaacgaacat ggcgttatca aagtctgcga tgaatttccg    840
ggttttaccc gcttcaagat gcaccagccg tttggtgcca aagcaccgaa gcgtattagt    900
gtgccgcgct cccatgccaa acacccgacc gatacgatcc cggatgcaag tgacgtttcc    960
attcgtcgcg ctatcgcgac ctttatgccg cagttcaaga acaaaaagat gttcaaccaa   1020
gcgatgtgct ggtgtaccga tacggccgac gctgcgctgc tgatttgtga acatccggaa   1080
tggaaaaact ttgttctggc gaccggcgat tcaggtcatt cgttcaaact gctgccgaat   1140
atcggcaagc acgttgtcga actgctggag ggtacgctgg cagatgacct ggcacacgca   1200
tggcgttggc gtccgggtag tggtgatgca ctgaaaagcc gtcgctctgc tccggcgaaa   1260
gacctggctg atatgccggg ctggaaccat gacaaaccgc gtgctaatct gtaa         1314
```

<210> SEQ ID NO 40
<211> LENGTH: 437
<212> TYPE: PRT
<213> ORGANISM: Eupenicillium terrenum

<400> SEQUENCE: 40

```
Met Ala His Ser Arg Ala Ser Thr Lys Val Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125
```

-continued

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asp
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435

<210> SEQ ID NO 41
<211> LENGTH: 1314
<212> TYPE: DNA
<213> ORGANISM: Eupenicillium terrenum

<400> SEQUENCE: 41
atggctcatt cgcgtgcaag caccaaagtc gtcgtggttg ggggaggtgg tacgatcggg 60
tcttcgacgg ctctgcactt aatccgctct ggatataccc cctcaaatat caccgtgctt 120
gacgtataca agacccccttc attgcaatct gcaggacatg atttgaacaa gatcatgggc 180
attcgattgc gcaacgggcc tgacttgcag ctttcgctgg aatcactcga catgtggcaa 240
aacgatgagt tgttcaagcc attctttcac caagtgggca tgattgattg ttcgtcatcc 300
aaagagggta ttgaaaatct tcgacgaaaa taccagaccc tcctcgatgc gggcattggg 360
ctggagaaga cgaacgtttg gctggaatct gaagatgaga tcctcgccaa agcgccgaat 420
ttcacgcgtg aacaagtcaa ggggtggaaa ggcttatttt gcactgatgg aggctggctt 480
gctgcagcca aggctatcaa tgcgatcgga attttcctcc aggacaaagg tgtcaagttt 540
ggctttggag atgctggtac ctttcagcaa cctctgttcg ccgctgatgg aaaaacttgc 600
atcggacttg aaactacaga cggaaccaag tactttgctg acaaggttgt cttggctgct 660
ggtgcgtgga gtcccacctt ggtggatcta gaagatcagt gtgtttcaaa ggcctgggtt 720
ttcgctcata ttcaactcac acccaaagaa gcggacgcgt acaagaatgt gcctgtggtc 780
tatgatggtg aatatgggtt ctttttcgaa cccgacgagt atggggtgat caaagtctgt 840
gacgagttcc ctggtttctc tcgcttcaaa ctgcatcaac cgtacggggc tgcatctccc 900
aagatgatat ccgtaccgcg atcacacgcc aagcatccca cagataccta ccctgatgcc 960
tccgaagtca ccatacgcaa agcgatcgca aggttcctgc cagaatttaa agacaaggag 1020
ctcttcaacc gtaccatgtg ctggtgtaca gatacggccg atgctaactt attgatttgc 1080
gaacacccga agtggaagaa tttcattctg gccactggag atagcggaca ttccttcaag 1140
ctgttgccaa acatcgggaa atacgtagtt gagcttttag agggatctct atcgcaggaa 1200
atggctggtg cctggagatg gagacccgga ggtgatgctc ttagatctag acgcggtgct 1260
ccggcaaagg atcttgctga gatgccggga tggaagcatg atgcacattt gtga 1314

<210> SEQ ID NO 42
<211> LENGTH: 30
<212> TYPE: DNA
<213> ORGANISM: Artificial
<220> FEATURE:
<223> OTHER INFORMATION: primer

<400> SEQUENCE: 42
aagatcatgg gcattgattt gcgcaacggg 30

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
aatgcccatg atcttgttca aatcatgtcc 30

<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44
gagggtattg aaaaacttcg acgaaaatac 30

<210> SEQ ID NO 45
<211> LENGTH: 26
<212> TYPE: DNA
<213> ORGANISM: Artificial
<220> FEATURE:
<223> OTHER INFORMATION: primer

<400> SEQUENCE: 45
ttcaataccc tctttggatg acgaac 26

<210> SEQ ID NO 46
<211> LENGTH: 30
<212> TYPE: DNA
<213> ORGANISM: Artificial
<220> FEATURE:
<223> OTHER INFORMATION: primer

<400> SEQUENCE: 46
aaaaacttcg acgattatac cagaccctcc 30

<210> SEQ ID NO 47
<211> LENGTH: 29
<212> TYPE: DNA
<213> ORGANISM: Artificial
<220> FEATURE:
<223> OTHER INFORMATION: primer

<400> SEQUENCE: 47
tcgtcgaagt tttcaatac cctctttgg 29

<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
cgacgattat accagaaact cctcgatgcg 30

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
ctggtataat cgtcgaagtt tttcaatacc 30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
agatacggcc gattctaact tattgatttg 30

<210> SEQ ID NO 51
<211> LENGTH: 29
<212> TYPE: DNA
<213> ORGANISM: Artificial
<220> FEATURE:
<223> OTHER INFORMATION: primer

<400> SEQUENCE: 51
atcggccgta tctgtacacc agcacatgg 29

<210> SEQ ID NO 52
<211> LENGTH: 30
<212> TYPE: DNA
<213> ORGANISM: Artificial

<220> FEATURE:
<223> OTHER INFORMATION: primer

<400> SEQUENCE: 52
tcatgggcat tgatcatcgc aacgggcctg 30

<210> SEQ ID NO 53
<211> LENGTH: 29
<212> TYPE: DNA
<213> ORGANISM: Artificial
<220> FEATURE:
<223> OTHER INFORMATION: primer

<400> SEQUENCE: 53
atcaatgccc atgatcttgt tcaaatcat 29

<210> SEQ ID NO 54
<211> LENGTH: 441
<212> TYPE: PRT
<213> ORGANISM: Neocosmospora vasinfecta

<400> SEQUENCE: 54

```
Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe Phe His Asn Thr Gly Arg Leu Asp
                85                  90                  95

Cys Glu Ser Ser Ala Glu Gly Val Glu Gly Leu Arg Arg Glu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Glu Gly Gly Trp Leu
145                 150                 155                 160

Ala Ala Ala Lys Ala Ile Asn Ala Ile Gly Glu Glu Leu Gln Arg Gln
                165                 170                 175

Gly Val Arg Phe Gly Phe Gly Gly Ala Gly Ser Phe Lys Arg Pro Leu
            180                 185                 190

Phe Ala Asp Asp Gly Thr Thr Cys Ile Gly Val Glu Thr Val Asp Gly
        195                 200                 205

Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
                245                 250                 255

Cys Pro Val Val Tyr His Gly Asp Val Gly Phe Phe Phe Glu Pro Asn
            260                 265                 270

Glu Asn Gly Val Ile Lys Val Cys Asp Glu Phe Pro Gly Phe Thr Arg
```

```
        275                 280                 285

Phe Lys Gln His Gln Pro Tyr Gly Ala Pro Ala Pro Lys Pro Val Ser
    290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
        355                 360                 365

Ile Leu Ala Thr Gly Asp Ser Gly His Ser Phe Lys Leu Leu Pro Ile
    370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
        435                 440
```

<210> SEQ ID NO 55
<211> LENGTH: 1326
<212> TYPE: DNA
<213> ORGANISM: Neocosmospora vasinfecta

<400> SEQUENCE: 55

```
atgacgaccc cgcgtaaaga aacgacggtc ctgattattg gtggtggtgg cacgattggt      60

agctcgacgg ctctgcatct gctgcgtgcc ggctataccc cgtctaacat taccgtgctg     120

gatacgtacc cgatcccgag tgcccagtcc gcaggcaacg acctgaataa aattatgggt     180

atccgtctgc gcaataaagt tgatctgcaa ctgagcctgg aagcccgtga tatgtggcgc     240

aacgacgcac tgtttcgtcc gtttttccat aataccggcc gcctggactg cgaaagctct     300

gctgaaggcg tggaaggtct gcgtcgcgaa tatcagaaac tggtggaagc aggcgttggt     360

ctggaagaaa cgcacgaatg gctggatagc gaagaagcta ttctggaaaa agcgccgctg     420

ctgcaacgtg aagaaattga aggttggaaa gccatctggt ctgaagaagg cggttggctg     480

gcggccgcaa aagctattaa cgcgatcggc gaagaactgc agcgtcaagg cgttcgcttc     540

ggttttggcg gtgccggtag ttttaaacgc ccgctgttcg cagatgacgg caccacgtgt     600

atcggtgtcg aaaccgtgga tggcacgcag tatcatgcgg acaaagtggt tctggctgca     660

ggtgcttggt caccggcgct ggtcgatctg gaagaacagt gctgttcgaa agcctgggtg     720

tacgcacaca tgcaactgac cccggaagaa gccgcagttt ataaaggctg cccggtcgtg     780

taccacggcg atgtcggctt tttctttgaa ccgaacgaaa atggcgttat taaagtctgt     840

gacgaattcc cgggttttac gcgtttcaaa cagcatcaac cgtatggtgc ccccggcaccg    900

aaacctgtga gtgttccgcg ctcccatgcg aaacacccga ccgatacgta cccggacgct     960

tcagaagaat cgatcaaacg tgccgtgagt acctttctgc cgcgcttcaa agataaaccg    1020

ctgtttaacc gtgcactgtg ctggtgtacc gatacggccg actccgcact gctgatttgc    1080

gaacacccgc gctggaaaaa ttttatcctg gcgaccggcg atagcggtca ttctttcaaa    1140

ctgctgccga ttatcggcaa acacgttgtc gaactggttg aaggtcgtct ggcggatgac    1200
```

ctggctgaag cgtggcgttg gcgtccgggt cagggtgatg cacgtaaaag cattcgcgct 1260
gcgccggcga aagacctggc ggatatgccg ggctggaaac acgaccaaga ctcggaatca 1320
cgctga 1326

<210> SEQ ID NO 56
<211> LENGTH: 29
<212> TYPE: DNA
<213> ORGANISM: Artificial
<220> FEATURE:
<223> OTHER INFORMATION: primer

<400> SEQUENCE: 56
ttatgggtat cgatctgcgc aataaagtt 29

<210> SEQ ID NO 57
<211> LENGTH: 30
<212> TYPE: DNA
<213> ORGANISM: Artificial
<220> FEATURE:
<223> OTHER INFORMATION: primer

<400> SEQUENCE: 57
gctcagttgc agatcaactt tattgcgcag 30

<210> SEQ ID NO 58
<211> LENGTH: 30
<212> TYPE: DNA
<213> ORGANISM: Artificial
<220> FEATURE:
<223> OTHER INFORMATION: primer

<400> SEQUENCE: 58
gaaggcgtgg aaaaactgcg tcgcgaatat 30

<210> SEQ ID NO 59
<211> LENGTH: 30
<212> TYPE: DNA
<213> ORGANISM: Artificial
<220> FEATURE:
<223> OTHER INFORMATION: primer

<400> SEQUENCE: 59
ttccaccagt ttctgatatt cgcgacgcag 30

<210> SEQ ID NO 60
<211> LENGTH: 27
<212> TYPE: DNA
<213> ORGANISM: Artificial
<220> FEATURE:
<223> OTHER INFORMATION: primer

<400> SEQUENCE: 60
ctgcgtcgcc tgtatcagaa actggtg 27

<210> SEQ ID NO 61
<211> LENGTH: 30
<212> TYPE: DNA
<213> ORGANISM: Artificial
<220> FEATURE:
<223> OTHER INFORMATION: primer

<400> SEQUENCE: 61
accaacgcct gcttccacca gtttctgata 30

<210> SEQ ID NO 62
<211> LENGTH: 438
<212> TYPE: PRT
<213> ORGANISM: Aspergillus nidulans

<400> SEQUENCE: 62

Met Thr Pro Arg Ala Asn Thr Lys Ile Ile Val Val Gly Gly Gly Gly
1 5 10 15

Thr Met Gly Ser Ser Thr Ala Leu His Leu Leu Arg Ala Gly Tyr Thr
20 25 30

Pro Ser Asn Ile Thr Val Leu Asp Thr Cys Pro Ile Pro Ser Ala Gln
35 40 45

Ser Ala Gly Tyr Asp Leu Asn Lys Ile Met Gly Ile Arg Leu Arg Asn
50 55 60

Lys Pro Asp Leu Gln Leu Ser Leu Glu Ala Leu Asp Met Trp Lys Asn
65 70 75 80

Asp Pro Leu Phe Lys Pro Phe Phe His Asn Val Gly Met Ile Asp Val
85 90 95

Ser Ser Thr Glu Glu Gly Ile Glu Gly Leu Arg Lys Lys Tyr Gln Ser
100 105 110

Leu Leu Asp Ala Gly Ile Gly Leu Glu Lys Thr Asn Phe Met Leu Glu
115 120 125

Ser Glu Asp Glu Ile Leu Ala Lys Ala Pro His Phe Thr Gln Glu Gln
130 135 140

Ile Lys Gly Trp Lys Gly Leu Phe Cys Gly Asp Gly Gly Trp Leu Ala
145 150 155 160

Ala Ala Lys Ala Ile Asn Ala Ile Gly Gln Phe Leu Lys Glu Gln Gly
165 170 175

Val Lys Phe Gly Phe Gly Gly Ala Gly Thr Phe Lys Lys Pro Leu Phe
180 185 190

Ala Asp Ala His Glu Lys Thr Cys Ile Gly Val Glu Thr Val Asp Gly
195 200 205

Thr Lys Tyr Tyr Ala Asp Lys Val Val Leu Ala Ala Gly Ala Trp Ser
210 215 220

Ser Thr Leu Val Asp Leu Glu Glu Gln Cys Val Ser Lys Ala Trp Val
225 230 235 240

Phe Ala His Ile Gln Leu Thr Pro Ala Glu Ala Ala Ala Tyr Lys Asn
245 250 255

Thr Pro Val Ile Tyr Asp Gly Asp Tyr Gly Phe Phe Phe Glu Pro Asn
260 265 270

Glu Asn Gly Ile Ile Lys Val Cys Asp Glu Phe Pro Gly Phe Thr His
275 280 285

Phe Lys Met His Gln Pro Tyr Gly Ser Pro Ala Pro Lys Pro Ile Ser
290 295 300

Val Pro Arg Ser His Ala Lys His Pro Thr Asp Thr Tyr Pro His Ala
305 310 315 320

Ser Glu Val Thr Ile Lys Lys Ala Ile Asn Arg Phe Leu Pro Arg Phe
325 330 335

Asn Asp Lys Glu Leu Phe Asn Arg Ala Met Cys Trp Cys Thr Asp Thr
340 345 350

Ala Asp Ala Asn Leu Leu Val Cys Glu His Pro Arg Trp Lys Gly Phe
355 360 365

Tyr Leu Ala Thr Gly Asp Ser Gly His Ser Phe Lys Leu Leu Pro Asn
370 375 380

Ile Gly Lys His Val Val Glu Leu Leu Glu Glu Arg Leu Glu Ser Val
385 390 395 400

Phe Lys Asp Ala Trp Arg Trp Arg Pro Gly Ser Gly Asp Ala Leu Lys
405 410 415

Ser Arg Arg Ala Ala Pro Ala Lys Asp Leu Ala Asp Met Pro Gly Trp
420 425 430

Arg Asn Glu Ala Lys Met
435

<210> SEQ ID NO 63
<211> LENGTH: 1317
<212> TYPE: DNA
<213> ORGANISM: Aspergillus nidulans

<400> SEQUENCE: 63
atgacgcccc gagccaacac caaaatcatt gtcgtcggcg gcggcggcac aatgggctcg 60
tcgacagccc tacacctcct gcgcgccggc tacacgccgt ccaacattac agtgctcgac 120
acgtgcccta tcccctccgc acagtctgca ggctacgacc tgaacaaaat catggggatc 180
cgtctgcgca acaagcctga tttacagctc tctcttgagg cgctggacat gtggaaaaat 240
gatcctctct tcaagccgtt tttccacaat gttggaatga tcgacgtctc ttcaacagag 300
gaaggcatcg agggtcttcg gaagaaatac cagtctcttc tcgacgcagg cattgggctc 360
gagaagacga atttcatgct ggaaagtgaa gacgagatcc tggctaaagc gccgcatttc 420
acgcaggagc agattaaagg ctggaaaggc ctgttctgtg gcgacggcgg ctggctcgct 480
gcagccaaag ccatcaatgc cattgggcag ttcctcaagg aacagggcgt caagtttgga 540
ttcggcggcg ccggcacgtt caaaaagcca ctcttcgccg atgcccacga gaagacgtgc 600
atcggcgtcg agactgtaga cggcacaaag tactacgccg acaaggtcgt tctagcagct 660
ggtgcctgga gttcgacgtt ggtcgatctg gaggagcagt gcgtttcaaa ggcctgggtc 720
tttgcccaca tccaactgac gcccgctgaa gcagccgcgt ataagaacac tcctgttata 780
tacgacggtg actatgggtt tttctttgag ccgaatgaaa acggcatcat aaaagtctgt 840
gacgaattcc ctggcttcac gcatttcaaa atgcaccagc cgtacggctc gccggcgccc 900
aaacccatct ctgtgcctcg ttcccatgcg aagcacccca cagatacata cccgcacgcg 960
tcggaggtca cgatcaaaaa ggctatcaac cggttcctgc cgaggttcaa tgacaaggaa 1020
ctgtttaaca gggccatgtg ctggtgcacc gataccgcgg atgcaaatct gcttgtttgt 1080
gagcatccac gctggaaggg gttttatctt gcaacagggg acagtgggca ttcgttcaag 1140
ttgctgccga atattggaaa gcatgttgtc gagttattgg aggagaggct ggaaagtgtg 1200
tttaaggatg cttggaggtg gaggcctggc agtggggatg cattaaaaag tagacgggct 1260
gcgcctgcga aggacctggc ggatatgccg gggtggagga atgaggcaaa gatgtag 1317

<210> SEQ ID NO 64
<211> LENGTH: 30
<212> TYPE: DNA
<213> ORGANISM: Artificial
<220> FEATURE:
<223> OTHER INFORMATION: primer

<400> SEQUENCE: 64
atcatgggca tcgatctgcg caacaagcct 30

<210> SEQ ID NO 65

<211> LENGTH: 30
<212> TYPE: DNA
<213> ORGANISM: Artificial
<220> FEATURE:
<223> OTHER INFORMATION: primer

<400> SEQUENCE: 65
agagagctgt aaatcaggct tgttgcgcag 30

<210> SEQ ID NO 66
<211> LENGTH: 30
<212> TYPE: DNA
<213> ORGANISM: Artificial
<220> FEATURE:
<223> OTHER INFORMATION: primer

<400> SEQUENCE: 66
gaaggcatcg agaaacttcg gaagaaatac 30

<210> SEQ ID NO 67
<211> LENGTH: 30
<212> TYPE: DNA
<213> ORGANISM: Artificial
<220> FEATURE:
<223> OTHER INFORMATION: primer

<400> SEQUENCE: 67
gtcgagaaga gactggtatt tcttccgaag 30

<210> SEQ ID NO 68
<211> LENGTH: 27
<212> TYPE: DNA
<213> ORGANISM: Artificial
<220> FEATURE:
<223> OTHER INFORMATION: primer

<400> SEQUENCE: 68
cttcggaagc tgtaccagtc tcttctc 27

<210> SEQ ID NO 69
<211> LENGTH: 30
<212> TYPE: DNA
<213> ORGANISM: Artificial
<220> FEATURE:
<223> OTHER INFORMATION: primer

<400> SEQUENCE: 69
cccaatgcct gcgtcgagaa gagactggta 30

<210> SEQ ID NO 70
<211> LENGTH: 30
<212> TYPE: DNA
<213> ORGANISM: Artificial
<220> FEATURE:
<223> OTHER INFORMATION: primer

<400> SEQUENCE: 70
cttctcgagc ccaatgcctg cgtcgagaag 30

<210> SEQ ID NO 71
<211> LENGTH: 30
<212> TYPE: DNA
<213> ORGANISM: Artificial
<220> FEATURE:
<223> OTHER INFORMATION: primer

<400> SEQUENCE: 71
gataccgcgg atagcaatct gcttgtttgt 30

<210> SEQ ID NO 72
<211> LENGTH: 30
<212> TYPE: DNA
<213> ORGANISM: Artificial
<220> FEATURE:
<223> OTHER INFORMATION: primer

<400> SEQUENCE: 72
ccagcgtgga tgctcacaaa caagcagatt 30

<210> SEQ ID NO 73
<211> LENGTH: 30
<212> TYPE: DNA
<213> ORGANISM: Artificial
<220> FEATURE:
<223> OTHER INFORMATION: primer

<400> SEQUENCE: 73
atcatgggca tcgatcatcg caacaagcct 30

<210> SEQ ID NO 74
<211> LENGTH: 27
<212> TYPE: DNA
<213> ORGANISM: Artificial
<220> FEATURE:
<223> OTHER INFORMATION: primer

<400> SEQUENCE: 74
agagagctgt aaatcaggct tgttgcg 27

<210> SEQ ID NO 75
<211> LENGTH: 30
<212> TYPE: DNA
<213> ORGANISM: Artificial
<220> FEATURE:
<223> OTHER INFORMATION: primer

<400> SEQUENCE: 75
tcttcaacag agaaaggcat cgagaaactt 30

<210> SEQ ID NO 76
<211> LENGTH: 27
<212> TYPE: DNA
<213> ORGANISM: Artificial
<220> FEATURE:
<223> OTHER INFORMATION: primer

<400> SEQUENCE: 76
gtacagcttc cgaagtttct cgatgcc 27

<210> SEQ ID NO 77
<211> LENGTH: 29
<212> TYPE: DNA
<213> ORGANISM: Artificial
<220> FEATURE:
<223> OTHER INFORMATION: primer

<400> SEQUENCE: 77
atcatgggtg tcgatctgcg taatccggt 29

<210> SEQ ID NO 78
<211> LENGTH: 30
<212> TYPE: DNA

<213> ORGANISM: Artificial
<220> FEATURE:
<223> OTHER INFORMATION: primer

<400> SEQUENCE: 78
agccagctgc agatccaccg gattacgcag 30

<210> SEQ ID NO 79
<211> LENGTH: 30
<212> TYPE: DNA
<213> ORGANISM: Artificial
<220> FEATURE:
<223> OTHER INFORMATION: primer

<400> SEQUENCE: 79
aaagatattg ccaaactgaa gagcggctat 30

<210> SEQ ID NO 80
<211> LENGTH: 30
<212> TYPE: DNA
<213> ORGANISM: Artificial
<220> FEATURE:
<223> OTHER INFORMATION: primer

<400> SEQUENCE: 80
atccaccaga gcctgatagc cgctcttcag 30

<210> SEQ ID NO 81
<211> LENGTH: 27
<212> TYPE: DNA
<213> ORGANISM: Artificial
<220> FEATURE:
<223> OTHER INFORMATION: primer

<400> SEQUENCE: 81
ctgaagagcc tgtatcaggc tctggtg 27

<210> SEQ ID NO 82
<211> LENGTH: 30
<212> TYPE: DNA
<213> ORGANISM: Artificial
<220> FEATURE:
<223> OTHER INFORMATION: primer

<400> SEQUENCE: 82
gtccagaccc gcatccacca gagcctgata 30

<210> SEQ ID NO 83
<211> LENGTH: 30
<212> TYPE: DNA
<213> ORGANISM: Artificial
<220> FEATURE:
<223> OTHER INFORMATION: primer

<400> SEQUENCE: 83
agcctgtatc agaaactggt ggatgcgggt 30

<210> SEQ ID NO 84
<211> LENGTH: 30
<212> TYPE: DNA
<213> ORGANISM: Artificial
<220> FEATURE:
<223> OTHER INFORMATION: primer

<400> SEQUENCE: 84
gttcgtggcg tccagacccg catccaccag 30

<210> SEQ ID NO 85
<211> LENGTH: 30
<212> TYPE: DNA
<213> ORGANISM: Artificial
<220> FEATURE:
<223> OTHER INFORMATION: primer

<400> SEQUENCE: 85
gatacggccg acagcgcgct gctgatttgt 30

<210> SEQ ID NO 86
<211> LENGTH: 30
<212> TYPE: DNA
<213> ORGANISM: Artificial
<220> FEATURE:
<223> OTHER INFORMATION: primer

<400> SEQUENCE: 86
ccattccgga tgttcacaaa tcagcagcgc 30

<210> SEQ ID NO 87
<211> LENGTH: 29
<212> TYPE: DNA
<213> ORGANISM: Artificial
<220> FEATURE:
<223> OTHER INFORMATION: primer

<400> SEQUENCE: 87
atgggtgtcg atcatcgtaa tccggtgga 29

<210> SEQ ID NO 88
<211> LENGTH: 30
<212> TYPE: DNA
<213> ORGANISM: Artificial
<220> FEATURE:
<223> OTHER INFORMATION: primer

<400> SEQUENCE: 88
cagagccagc tgcagatcca ccggattacg 30

<210> SEQ ID NO 89
<211> LENGTH: 443
<212> TYPE: PRT
<213> ORGANISM: Cryptococcus neoformans

<400> SEQUENCE: 89

Met Pro Pro Ser Arg Ala Ser Thr Lys Val Ile Val Ile Gly Gly Gly
1 5 10 15

Gly Thr Leu Gly Ser Ser Thr Ala Leu His Leu Leu Arg Ala Gly Tyr
20 25 30

Thr Pro Ser Asn Ile Thr Val Leu Asp Thr Tyr Leu Ile Pro Ser Ala
35 40 45

Gln Ser Ala Gly Asn Asp Leu Asn Lys Ile Met Gly Ile Arg Ile Arg
50 55 60

Asn Pro Val Asp Lys Gln Leu Ser Leu Glu Ala Arg Asp Met Trp Arg
65 70 75 80

Asn Asp Glu Val Phe Lys Pro Tyr Phe His Asn Thr Gly Arg Leu Asp
85 90 95

Cys Ala His Thr Pro Glu Ser Ile Ala Ser Leu Arg Lys Ser Tyr Glu
100 105 110

Ala Ile Leu Lys Ala Gly Ser Gly Leu Glu Lys Thr His His Trp Leu

-continued

```
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Asp Met Asp
        435                 440
```

<210> SEQ ID NO 90
<211> LENGTH: 1332
<212> TYPE: DNA
<213> ORGANISM: Cryptococcus neoformans

<400> SEQUENCE: 90

```
atgccgccgt cccgtgcttc aacgaaagtg attgtcattg gtggtggtgg tacgctgggc      60

tcctcaaccg ccctgcatct gctgcgcgcg ggctataccc cgagtaacat taccgtgctg     120

gatacgtacc tgatcccgag tgcccagtcc gcaggcaacg acctgaataa aattatgggt     180

attcgtatcc gcaatccggt ggataaacaa ctgagcctgg aagcccgtga tatgtggcgc     240

aacgacgaag ttttcaaacc gtacttccat aacaccggtc gtctggactg cgctcacacg     300
```

```
ccggaatcaa ttgcgtcgct gcgtaaaagc tacgaagcca tcctgaaagc aggctcaggt    360

ctggaaaaaa cccatcactg gctgtcgacg gaagatgaaa tcctggcacg tgcaccgctg    420

ctggaccgta aacagattaa aggttggaaa gcaatctata gtgaagatgg cggttggctg    480

gcggccgcaa aagctattaa ctccatcggc caagtcctga aagaaaaagg tgtgaccttc    540

ggctttggta gcgcaggctc ttttaaaaaa ccgctgttcg atgaagacgg cacgaaagcc    600

attggtatcg aaaccgttga tggtacgcag tattttgccg acaaagtggt tctggctgca    660

ggtgcatgga gcccgaccct ggttgatctg gaaggccagt gctgttctaa agcttgggtc    720

tacgcgcaca tgcaactgac gccggaagaa gccgcagaat ataaagaatg cccggtcgtg    780

tacaacagcg aactgggctt tttctttgaa ccgaacgaaa aaggtgtgat caaagtttgt    840

gatgaattcc cgggctttac ccgtttcaaa cagcatcaac cgtacggtgc tagctctacg    900

aaacacatta gctttccgcg ctctcatgcg aaacacccga ccgatacgat cccggatgaa    960

agtgacgcct ccattcgtcg cgctatctct gcgtttctgc cgcgtttcaa agaaaaagaa   1020

ctgtttaacc gcgcgctgtg ctggtgtacc gatacggctg acgcgaacct gctgatttgt   1080

gaacacccga aatggaaaaa ttttatcctg gccaccggcg attcaggtca ttcgttcaaa   1140

attctgccga atatcggcaa acacgttgtc gaactgattg aaggtaccct ggccgaagat   1200

ctggcagaaa gctggcgttg gcgtccgggc agtggtgacc cgctgatctc ccgtcgcgct   1260

gcgccggcgc gcgacctggc ggacctgccg ggctggaacc acgacgaacc gagcgacgat   1320

gacatggact ga                                                       1332
```

```
<210> SEQ ID NO 91
<211> LENGTH: 30
<212> TYPE: DNA
<213> ORGANISM: Artificial
<220> FEATURE:
<223> OTHER INFORMATION: primer

<400> SEQUENCE: 91

attatgggta ttgatatccg caatccggtg                                      30


<210> SEQ ID NO 92
<211> LENGTH: 30
<212> TYPE: DNA
<213> ORGANISM: Artificial
<220> FEATURE:
<223> OTHER INFORMATION: primer

<400> SEQUENCE: 92

gctcagttgt ttatccaccg gattgcggat                                      30


<210> SEQ ID NO 93
<211> LENGTH: 30
<212> TYPE: DNA
<213> ORGANISM: Artificial
<220> FEATURE:
<223> OTHER INFORMATION: primer

<400> SEQUENCE: 93

gaatcaattg cgaaactgcg taaaagctac                                      30


<210> SEQ ID NO 94
<211> LENGTH: 30
<212> TYPE: DNA
<213> ORGANISM: Artificial
<220> FEATURE:
```

<223> OTHER INFORMATION: primer

<400> SEQUENCE: 94
tttcaggatg gcttcgtagc ttttacgcag 30

<210> SEQ ID NO 95
<211> LENGTH: 30
<212> TYPE: DNA
<213> ORGANISM: Artificial
<220> FEATURE:
<223> OTHER INFORMATION: primer

<400> SEQUENCE: 95
ctgcgtaaac tgtacgaagc catcctgaaa 30

<210> SEQ ID NO 96
<211> LENGTH: 30
<212> TYPE: DNA
<213> ORGANISM: Artificial
<220> FEATURE:
<223> OTHER INFORMATION: primer

<400> SEQUENCE: 96
acctgagcct gctttcagga tggcttcgta 30

<210> SEQ ID NO 97
<211> LENGTH: 30
<212> TYPE: DNA
<213> ORGANISM: Artificial
<220> FEATURE:
<223> OTHER INFORMATION: primer

<400> SEQUENCE: 97
aaactgtacg aaaaaatcct gaaagcaggc 30

<210> SEQ ID NO 98
<211> LENGTH: 30
<212> TYPE: DNA
<213> ORGANISM: Artificial
<220> FEATURE:
<223> OTHER INFORMATION: primer

<400> SEQUENCE: 98
tttttccaga cctgagcctg ctttcaggat 30

<210> SEQ ID NO 99
<211> LENGTH: 440
<212> TYPE: PRT
<213> ORGANISM: Curvularia clavata

<400> SEQUENCE: 99

Met Ala Pro Ser Arg Ala Asn Thr Ser Val Ile Val Val Gly Gly Gly
1 5 10 15

Gly Thr Ile Gly Ser Ser Thr Ala Leu His Leu Val Arg Ser Gly Tyr
20 25 30

Thr Pro Ser Asn Ile Thr Val Leu Asp Ala Tyr Pro Ile Pro Ser Ser
35 40 45

Gln Ser Ala Gly Asn Asp Leu Asn Lys Ile Met Gly Ile Arg Leu Arg
50 55 60

Asn Lys Val Asp Leu Gln Leu Ser Leu Glu Ala Arg Gln Met Trp Arg
65 70 75 80

Glu Asp Asp Leu Phe Lys Glu Tyr Phe His Asn Thr Gly Arg Leu Asp
85 90 95

-continued

```
Cys Ala His Gly Glu Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Ser Arg Asp
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Thr
    210                 215                 220

Leu Val Glu Leu His Glu Gln Cys Val Ser Lys Ala Trp Val Tyr Gly
225                 230                 235                 240

His Ile Gln Leu Thr Pro Glu Glu Ala Ala Glu Tyr Lys Asn Ser Pro
                245                 250                 255

Val Val Tyr Asn Gly Asp Val Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Met His Gln Pro Phe Gly Ala Lys Ala Pro Lys Arg Ile Ser Val Pro
    290                 295                 300

Arg Ser His Ala Lys His Pro Thr Asp Thr Ile Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ala Ala Leu Leu Ile Cys Glu His Pro Glu Trp Lys Asn Phe Val Leu
        355                 360                 365

Ala Thr Gly Asp Ser Gly His Ser Phe Lys Leu Leu Pro Asn Ile Gly
    370                 375                 380

Lys His Val Val Glu Leu Leu Glu Gly Thr Leu Ala Asp Asp Leu Ala
385                 390                 395                 400

His Ala Trp Arg Trp Arg Pro Gly Ser Gly Asp Ala Leu Lys Ser Arg
                405                 410                 415

Arg Ser Ala Pro Ala Lys Asp Leu Ala Asp Met Pro Gly Trp Lys His
            420                 425                 430

Asp Asp Val Val Lys Ser Lys Leu
        435                 440
```

<210> SEQ ID NO 100
<211> LENGTH: 1323
<212> TYPE: DNA
<213> ORGANISM: Curvularia clavata

<400> SEQUENCE: 100

```
atggccccgt cgcgtgctaa tacgtcggtc attgtggttg gtggtggtgg tacgattggc      60

tcatctacgg ctctgcatct ggtccgctca ggctataccc cgtcgaacat tacggttctg     120
```

-continued

```
gatgcatacc cgattccgag ctctcagagc gctggcaacg acctgaataa aatcatgggt    180
atccgtctgc gtaataaggt ggatctgcag ctgtctctgg aagcgcgcca aatgtggcgc    240
gaagacgatc tgttcaagga gtatttccat aacaccggcc gtctggattg cgcgcacggt    300
gaagaaggtc ttgccgacct gcgtcaagcc tatcaggctc tgctggatgc gaatgcgggt    360
ctggaagaga cgaccgaatg gctggatagt gaagacgaaa tcctgaaaaa aatgccgctg    420
ctgtcccgcg atcaaattaa aggctggaag gcggtgtatt cacaggacgg tggttggctg    480
gcagcagcaa aggcaattaa tgcaattggt gaatatctgc gtgctcaggg cgtcaaattc    540
ggttttggcg gcgccggttc tttcaaacaa ccgctgctgg ctgaaggcgt ctgcatcggt    600
gtcgaaaccg tggatggcac gcgctattac gcagacaaag tggttctggc tgcaggtgca    660
tggtcgccga ccctggttga actgcatgaa cagtgtgtga gcaaagcgtg ggtttacggc    720
cacattcaac tgacgccgga agaagccgca gaatataaga acagcccggt cgtgtacaat    780
ggcgatgtgg gctttttctt tgaaccgaac gaacatggcg ttatcaaagt ctgcgatgaa    840
tttccgggtt ttacccgctt caagatgcac cagccgtttg gtgccaaagc accgaagcgt    900
attagtgtgc cgcgctccca tgccaaacac ccgaccgata cgatcccgga tgcaagtgaa    960
aaatccattc gtaaagctat cgcgaccttt ctgccgaagt tcacggagaa agagctgttc   1020
aaccgtcatc tgtgctggtg taccgatacg gccgacgctg cgctgctgat ttgtgaacat   1080
ccggaatgga aaaactttgt tctggcgacc ggcgattcag gtcattcgtt caaactgctg   1140
ccgaatatcg gcaagcacgt tgtcgaactg ctggagggta cgctggcaga tgacctggca   1200
cacgcatggc gttggcgtcc gggtagtggt gatgcactga aaagccgtcg ctctgctccg   1260
gcgaaagacc tggctgatat gccgggctgg aaacatgacg atgtggtgaa aagcaaactg   1320
taa                                                                1323
```

<210> SEQ ID NO 101
<211> LENGTH: 30
<212> TYPE: DNA
<213> ORGANISM: Artificial
<220> FEATURE:
<223> OTHER INFORMATION: primer

<400> SEQUENCE: 101

```
atcatgggta tcgatctgcg taataaggtg                                     30
```

<210> SEQ ID NO 102
<211> LENGTH: 30
<212> TYPE: DNA
<213> ORGANISM: Artificial
<220> FEATURE:
<223> OTHER INFORMATION: primer

<400> SEQUENCE: 102

```
cagagacagc tgcagatcca ccttattacg                                     30
```

<210> SEQ ID NO 103
<211> LENGTH: 30
<212> TYPE: DNA
<213> ORGANISM: Artificial
<220> FEATURE:
<223> OTHER INFORMATION: primer

<400> SEQUENCE: 103

```
gaaggtcttg ccaaactgcg tcaagcctat                                     30
```

<210> SEQ ID NO 104
<211> LENGTH: 30
<212> TYPE: DNA
<213> ORGANISM: Artificial
<220> FEATURE:
<223> OTHER INFORMATION: primer

<400> SEQUENCE: 104
atccagcaga gcctgatagg cttgacgcag 30

<210> SEQ ID NO 105
<211> LENGTH: 30
<212> TYPE: DNA
<213> ORGANISM: Artificial
<220> FEATURE:
<223> OTHER INFORMATION: primer

<400> SEQUENCE: 105
cttgccaaac tgcgtcaact gtatcaggct 30

<210> SEQ ID NO 106
<211> LENGTH: 30
<212> TYPE: DNA
<213> ORGANISM: Artificial
<220> FEATURE:
<223> OTHER INFORMATION: primer

<400> SEQUENCE: 106
acccgcattc gcatccagca gagcctgata 30

<210> SEQ ID NO 107
<211> LENGTH: 30
<212> TYPE: DNA
<213> ORGANISM: Artificial
<220> FEATURE:
<223> OTHER INFORMATION: primer

<400> SEQUENCE: 107
cgtcaactgt atcagaaact gctggatgcg 30

<210> SEQ ID NO 108
<211> LENGTH: 30
<212> TYPE: DNA
<213> ORGANISM: Artificial
<220> FEATURE:
<223> OTHER INFORMATION: primer

<400> SEQUENCE: 108
ctcttccaga cccgcattcg catccagcag 30

<210> SEQ ID NO 109
<211> LENGTH: 30
<212> TYPE: DNA
<213> ORGANISM: Artificial
<220> FEATURE:
<223> OTHER INFORMATION: primer

<400> SEQUENCE: 109
gatacggccg acagcgcgct gctgatttgt 30

<210> SEQ ID NO 110
<211> LENGTH: 30
<212> TYPE: DNA
<213> ORGANISM: Artificial
<220> FEATURE:
<223> OTHER INFORMATION: primer

<400> SEQUENCE: 110
ccattccgga tgttcacaaa tcagcagcgc 30

<210> SEQ ID NO 111
<211> LENGTH: 30
<212> TYPE: DNA
<213> ORGANISM: Artificial
<220> FEATURE:
<223> OTHER INFORMATION: primer

<400> SEQUENCE: 111
atcatgggta tcgatcatcg taataaggtg 30

<210> SEQ ID NO 112
<211> LENGTH: 30
<212> TYPE: DNA
<213> ORGANISM: Artificial
<220> FEATURE:
<223> OTHER INFORMATION: primer

<400> SEQUENCE: 112
aagctgtacc agaaacttct cgacgcaggc 30

<210> SEQ ID NO 113
<211> LENGTH: 440
<212> TYPE: PRT
<213> ORGANISM: Pyrenochaeta sp.

<400> SEQUENCE: 113

```
Met Ala Ala Ser Arg Ala Lys Thr Thr Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Pro Ser Asn Ile Thr Val Leu Asp Thr Tyr Pro Ile Pro Ser Leu
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Glu Met Trp Arg
65                  70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110

Thr Leu Leu Asp Ala Asn Ala Gly Leu Glu Glu Thr Asn Glu Trp Leu
        115                 120                 125

Asp Ser Glu Asp Glu Ile Leu Ala Arg Met Pro Leu Leu Ser Arg Glu
    130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Gly Ala Gly Ser Phe Gln Gln Pro Leu
            180                 185                 190

Leu Ala Glu Gly Ile Cys Ile Gly Val Glu Thr Thr Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Glu Asp Gln Cys Val Ser Lys Ala Trp Val Tyr Ala
```

-continued

```
225                 230                 235                 240

His Met Gln Leu Thr Pro Lys Glu Ala Ala Ala Tyr Lys Asp Thr Pro
                245                 250                 255

Val Val Tyr Asn Gly Asp Leu Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Lys His Gln Pro Phe Gly Ala Arg Ala Pro Lys Arg Ile Ser Val Pro
    290                 295                 300

Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
                325                 330                 335

Lys Glu Leu Phe Asn Arg Ala Met Cys Trp Cys Thr Asp Thr Ala Asp
            340                 345                 350

Ala Ala Leu Leu Ile Cys Glu His Pro Gln Trp Lys Asn Phe Met Leu
        355                 360                 365

Ala Thr Gly Asp Ser Gly His Ser Phe Lys Leu Leu Pro Asn Ile Gly
    370                 375                 380

Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415

Arg Ala Ala Pro Ala Lys Asp Leu Ala Asp Met Pro Gly Trp Asn His
            420                 425                 430

Asp Glu Ser Pro Arg Ala Lys Leu
        435                 440
```

<210> SEQ ID NO 114
<211> LENGTH: 1323
<212> TYPE: DNA
<213> ORGANISM: Pyrenochaeta sp.

<400> SEQUENCE: 114

```
atggccgctt cacgagcaaa gacgacagtg atcgtcgtgg gtggcggcgg taccattggg      60

tcatcaacag cgctccacct tctacgttca ggttatactc catcgaatat cacagttttg     120

gacacatatc caattccttc attacagtcc gcgggcaatg atttaaacaa gattatgggc     180

attcgcttgc gaaacaaagt cgacctccaa ttgagtttag aggctaggga gatgtggaga     240

gaagatgaac tttttagaga ttttttttcac aatactgggc gactggattg tgcccatggc     300

gaaaaaggaa tcaatgatct taggcaggca tatcaaacac tactcgacgc caatgccggt     360

ttggaagaga cgaacgagtg gctggactct gaggacgaaa ttctggcaag aatgccgctc     420

ttgagtcgag agcagatcaa gggctggaaa gcggtcttca gccgagacgg cggttggctc     480

gccgcaggta aggccatcaa tgcaattggc gagtatctgc gcaaggaagg agtcaagttt     540

ggctttggcg gcgcgggatc gttccagcag ccgcttcttg cagagggtat ttgcattggc     600

gtggaaacaa cggatggaac tagatactac gccgacaaag ttgtcctggc agctggtgca     660

tggagtcctg cattggtgga cttggaagac cagtgtgttt caaaagcatg ggtctatgct     720

cacatgcagc tcaccccgaa ggaggctgcg gcatacaaag acacaccagt agtctacaat     780

ggcgatctgg gatttttctt tgaaccaaac gagcatggcg tgatcaaagt ctgcgacgag     840

ttcccaggct tcacacgttt taagaagcat caaccatttg gtgcaagggc accaaaacgg     900
```

-continued

```
atatcggttc ccagatctca tgccaaacac cctactgata cttatcctca cgcatccgaa    960

gccagtatca agaaagctat tgcggcattc ttaccacagt tcaaggacaa ggagctgttc   1020

aaccgcgcaa tgtgctggtg cacagataca gctgatgcag ccttgttgat ctgcgaacac   1080

ccgcaatgga agaatttcat gcttgctact ggagacagcg ggcactcatt taagctctta   1140

ccaaatatcg gcaagcatgt agttgaactg attgaaggca ctctggcggc agatcttgcc   1200

catgcttgga ggtggcgacc tgggattggt gacgctttgc agtcaaggcg agcggcacct   1260

gcgaaggatc tggcggacat gccaggatgg aatcatgatg aatctcctag ggcgaaattg   1320

taa                                                                 1323


<210> SEQ ID NO 115
<211> LENGTH: 452
<212> TYPE: PRT
<213> ORGANISM: Arthrinium sp.

<400> SEQUENCE: 115

Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Ala Thr Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Pro Val Asp Lys Gln Leu Ser Leu Glu Ala Gln Asp Met Trp Cys
65                  70                  75                  80

His Asp Glu Leu Phe Lys Pro Tyr Phe His Asn Thr Gly Arg Met Asp
                85                  90                  95

Cys Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
        115                 120                 125

Asp Ser Glu Asp Ala Ile Leu Ala Lys Met Pro Leu Leu Glu Arg Asp
    130                 135                 140

Gln Ile Lys Gly Trp Lys Ala Ile Phe Ser Gln Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Gly Ala Gly Ala Phe Lys Lys Pro Leu
            180                 185                 190

Phe Ala Pro Asp Gly Ser Thr Cys Ile Gly Val Glu Thr Val Asp Gly
        195                 200                 205

Thr Lys Tyr Tyr Gly Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
                245                 250                 255

Cys Pro Val Val Tyr His Gly Asp Leu Gly Phe Phe Phe Glu Pro Asn
            260                 265                 270

Glu His Gly Val Ile Lys Val Cys Asp Glu Phe Pro Gly Phe Thr Arg
        275                 280                 285

Phe Leu Glu Gln His Gln Ser Tyr Gly Ala Pro Ala Pro Thr Arg Val
```

```
    290                 295                 300

Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
                325                 330                 335

Phe Gln Ser Lys Glu Leu Phe Asn Arg Ala Met Cys Trp Cys Thr Asp
            340                 345                 350

Thr Ala Asp Ala Ala Leu Leu Ile Cys Glu His Pro Arg Trp Arg Asn
        355                 360                 365

Phe Ile Leu Ala Thr Gly Asp Ser Gly His Ser Phe Lys Leu Leu Pro
    370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gly Gln Gly Asp Ala Leu
                405                 410                 415

Lys Ser Arg Arg Ala Ala Pro Ala Lys Asp Leu Ala Asp Met Pro Gly
            420                 425                 430

Trp Asn His Asp Gly Asp Ser Gly Asn Ala Thr Ser Gly Thr Ser Ser
        435                 440                 445

Glu His Lys Leu
    450


<210> SEQ ID NO 116
<211> LENGTH: 1359
<212> TYPE: DNA
<213> ORGANISM: Arthrinium sp.

<400> SEQUENCE: 116

atggcggcgt cacgaaagac caccaaagtg attgtcgtgg gcggcggagg caccatcggc     60

tcatccacgg ctctacatct tctccggtcg ggtatacgg ccaccaacat taccgtcctg     120

gacacctacc ccatcccctc ggcgcagtcg gccggcaacg acctgaacaa gattatgggg    180

atccgcctgc ggaacccggt cgacaagcag ctcagccttg aagcccagga catgtggtgc    240

catgacgagc tcttcaagcc ctacttccac aacaccggca ggatggactg cgagggcacc    300

gagaagggca tcgcggcgct caagcagcag taccagacct tgcttgacgc cgacgtgggc    360

ctcgagaaga cgacggagtg gctcgacagt gaggatgcca tcctggcaaa gatgccactc    420

ctggagcgcg accaaatcaa aggatggaaa gcgatattta gccaggacgg cggttggctg    480

gccgcagcta aagccatcaa cgcgataggc gaggaactga agaggcaggg cgtcaacttc    540

gggttcggcg gggcgggcgc cttcaagaag cccctttttcg ccccggacgg atccacctgc   600

atcggcgtcg agacggtgga tggaaccaag tactacggcg acaaggtcgt cctggccgcg    660

ggcgcgtgga gccctgcgct ggtcgacctg gaagagcagt gctgctccaa ggcctgggtg    720

tacgcccaca tgcagctgac gccgcacgag gcagccgagt accagggctg tccggtcgtg    780

taccacggcg acctcggctt cttcttcgag cccaacgagc acggcgtcat caaggtgtgc    840

gacgagttcc ccggcttcac gcggttcctc gagcagcacc agtcgtacgg cgcgccggcg    900

ccgacgcgcg tctcggtgcc ccggtcgcac gcgaagcacc ccaccgacac atacccggac    960

gcgtcggagc agtcgatccg gcgggccgtg gccgcgttcc tgccgcgatt ccaaagcaaa   1020

gagcttttca accgcgccat gtgctggtgc accgacacgg ccgacgccgc gctgctgatc   1080

tgcgagcacc cccgctggcg caattttatt ctggctacgg gcgacagcgg acactcgttc   1140

aagctcctgc ccaacatcgg caagcacgtg gtcgagctgc tggaaggccg gctagcggat   1200
```

```
gacctggcgc aggcgtggag gtggcgcccc ggtcaggggg atgcgttgaa gtctagacgg   1260

gcggctccgg ctaaggatct ggcggatatg ccagggtgga atcatgacgg ggattcaggg   1320

aatgctacgt ctggaacaag ctcggagcac aaattgtag                          1359


<210> SEQ ID NO 117
<211> LENGTH: 440
<212> TYPE: PRT
<213> ORGANISM: Curvularia clavata

<400> SEQUENCE: 117

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Asp Arg Glu
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Val
    210                 215                 220

Leu Val Asp Leu Glu Asp Gln Cys Val Ser Lys Ala Trp Val Tyr Ala
225                 230                 235                 240

His Ile Gln Leu Thr Pro Glu Glu Ala Ala Glu Tyr Lys Asn Val Pro
                245                 250                 255

Val Val Tyr Asn Gly Asp Val Gly Phe Phe Phe Glu Pro Asp Glu His
            260                 265                 270

Gly Val Ile Lys Val Cys Asp Glu Phe Pro Gly Phe Thr Arg Phe Lys
        275                 280                 285

Gln His Gln Pro Tyr Gly Ala Lys Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
```

```
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
    370                 375                 380

Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415

Arg Ala Ala Pro Ala Lys Asp Leu Ala Asp Met Pro Gly Trp Lys His
            420                 425                 430

Asp Asp Val Val Lys Ser Lys Leu
        435                 440


<210> SEQ ID NO 118
<211> LENGTH: 1323
<212> TYPE: DNA
<213> ORGANISM: Curvularia clavata

<400> SEQUENCE: 118

atggcgccct caagagcaaa cacttctgtt atcgttgtcg gtggcggtgg cactattggc     60

tcttcaaccg ctcttcatct agtccgctcg ggctacacac catctaacat caccgttctt    120

gacacatacc ctatcccatc agcgcagtca gctggaaatg acctgaataa gatcatgggt    180

atccgcttgc ggaacaaggt cgatctccaa ttgagtctag aagccaggca gatgtggaga    240

gaggatgacc tattcaaaga gtatttccac aacactggaa gactcgactg tgcacatggg    300

gaagagggac ttgcagattt gagacaggca taccaggctc tgctcgacgc taacgcgggt    360

ctcgaagaaa caacagaatg gcttgactcc gaagacgaaa ttctaaagaa aatgccgctt    420

ctggaccgcg agcaaatcaa gggctggaaa gcggtttaca gccaagacgg cggctggctg    480

gctgcagcaa aagccatcaa tgctataggc gagtacttgc gagcccaagg agttaagttt    540

ggttttggtg gtgctggatc gttcaagcag cctcttttgg ccgagggagt gtgcattggc    600

gtagagacag tcgacgggac gaggtactac gccgataaag ttgtgcttgc agctggtgct    660

tggagtccgg tattggtcga cctggaagat caatgcgttt caaaagcttg ggtatatgct    720

cacatacagc ttacgcctga ggaagcagca gagtacaaaa acgtgcctgt ggtatacaac    780

ggcgacgtcg gcttcttctt cgagcctgac gagcacggcg ttatcaaggt ttgtgacgaa    840

tttccaggtt ttacacgctt caagcaacat cagccatatg gcgccaaagc accgaaacgt    900

atctccgtgc ccagatcggc agcgaagcac ccgacggata cttaccccga tgcgtcggag    960

aagagcatcc gcaaggccat tgcaactttc ctgcccaagt tcacagagaa ggagctattc   1020

aaccggcatc tatgttggtg tacggatacg gctgacgctg cgctattgat gtgtgagcat   1080

cccgagtgga agaactttgt gctggcgaca ggggacagcg ggcacacatt caaacttttg   1140

ccaaatatcg gcaagcatgt ggttgagctt ctcgagggta cactcgcgga ggatctggca   1200

catgcatgga gatggcggcc tggtactggc gatgcgctga aatcaagaag agcggcaccg   1260

gcgaaggatt tagcagatat gcctggctgg aagcatgacg atgttgtcaa gtccaagtta   1320

tag                                                                 1323


<210> SEQ ID NO 119
<211> LENGTH: 438
<212> TYPE: PRT
<213> ORGANISM: Emericella nidulans
```

<400> SEQUENCE: 119

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Arg Leu Arg Asn
    50                  55                  60

Lys Pro Asp Leu Gln Leu Tyr Leu Glu Ala Leu Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
```

-continued 405 410 415

Ser Arg Arg Ala Ala Pro Ala Lys Asp Leu Ala Asp Met Pro Gly Trp
420 425 430

Arg Asn Glu Ala Lys Met
435

<210> SEQ ID NO 120
<211> LENGTH: 1317
<212> TYPE: DNA
<213> ORGANISM: Emericella nidulans

<400> SEQUENCE: 120
atggcgcccc gagccaacac caaaatcatc gtcgtcggcg gcggcggcac aatgggctcg 60
tcgacagccc tacacctcct gcgcgccggc tacacgccgt ccaacatcac agtgctcgac 120
acgtacccta tcccttccgc acagtctgca ggctacgacc tgaacaaaat cttcggcatc 180
aggctgcgca acaagcctga cttacaactc tatcttgagg cgctggacat gtggaaaaat 240
gatcctctat tcaagccgtt tttccacaat gttggacaga tggacgtctc ttcaacagaa 300
gaaggcatca aaaagcttcg catgagatac cagtctcttc tcgacgcagg cattgggctc 360
gagaagacga atttcctgct ggaaagtgaa gacgagatcc tggctaaagc gccgcatttc 420
acgcgggagc agattaaagg ctggaaaggg ctgttctgtg gcgacggcgg ttggctcgct 480
gcagccaaag ccatcaatgc catcgggcag ttcctcaagg aacagggcgt caagtttgga 540
tttggcgagg ccggcacgtt caaaaagcca ctcttcgccg atgccgacga gaagacgtgc 600
atcggcgtcg aaactgtaga cggcacaaaa tactacgccg acaaggtcgt tctagcagct 660
ggtgcctgga gttcgacgtt ggtcgatctg gaggagcagt gcgtttcaaa ggcctgggtc 720
tttgcccaca tccaactgac gcccgctgaa gcagccgcgt acaagaacac tcctgttata 780
tacgacggtg actatgggtt tttcattgag ccggacgaga acggcatcat aaaagtctgc 840
gacgaattcc ctggcttcac gcacttcaag atgcaccagc cgtacggctc accggtgccc 900
aaattgatct ctgtgcctcg ctcccatgcg aagcacccca cagatacata cccgcacgcg 960
tcggaggtca ccatcaaaaa ggctatcaac cggttcctgc cgaggttcaa tgacaaggaa 1020
ctgtttaaca gggccatgtg ctggtgcacc gataccgcgg atgcaaatct gcttgtttgt 1080
gagcatccac gctggaaggg gttttatctt gcaacagggg acagcgggca ttcgttcaag 1140
ttgctgccga atattggaaa gcacgttgtc gagttattgg aggggaggct ggaaagtgtg 1200
tttaaggatg cttggaggtg gaggcctggc agtggggatg cattaaagag tagacgggct 1260
gcgcctgcga aggacctggc ggatatgccg gggtggagga atgaggcaaa gatgtag 1317

<210> SEQ ID NO 121
<211> LENGTH: 441
<212> TYPE: PRT
<213> ORGANISM: Ulocladium sp.

<400> SEQUENCE: 121

Met Ala Pro Asn Arg Ala Asn Ile Ser Val Ile Val Val Gly Gly Gly
1 5 10 15

Gly Thr Ile Gly Ser Ser Thr Ala Leu His Leu Val Arg Ser Gly Tyr
20 25 30

Thr Pro Ser Asn Ile Thr Val Leu Asp Thr Tyr Pro Ile Pro Ser Ala
35 40 45

Gln Ser Ala Gly Asn Asp Leu Asn Lys Ile Met Gly Ile Arg Leu Arg
50 55 60

```
Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
    130                 135                 140

Gln Ile Lys Gly Trp Lys Ala Val Phe Ser Glu Asp Gly Gly Trp Leu
145                 150                 155                 160

Ala Ala Ala Lys Ala Ile Asn Ala Ile Gly Arg Phe Leu Arg Asp Gln
                165                 170                 175

Gly Val Lys Phe Gly Phe Gly Gly Ala Gly Ser Phe Lys Gln Pro Leu
            180                 185                 190

Leu Ala Glu Gly Val Cys Val Gly Val Glu Thr Val Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
                245                 250                 255

Val Val Tyr Asn Gly Asp Val Gly Phe Phe Phe Glu Pro Asp Glu Tyr
            260                 265                 270

Gly Val Ile Lys Val Cys Asp Glu Phe Pro Gly Phe Thr Arg Phe Lys
        275                 280                 285

Gln His Gln Pro Phe Gly Ala Ser Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
                325                 330                 335

Lys Glu Val Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
    370                 375                 380

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
                405                 410                 415

Arg Ala Ala Arg Ala Lys Asp Leu Ala Asp Met Pro Gly Trp Asn His
            420                 425                 430

Asp Gly Glu Ala Pro Arg Ala Lys Leu
        435                 440
```

<210> SEQ ID NO 122
<211> LENGTH: 1326
<212> TYPE: DNA
<213> ORGANISM: Ulocladium sp.

<400> SEQUENCE: 122

```
atggcaccta acagagctaa tatttctgtc atcgtcgtgg gtggtggcgg caccattggg     60
tcttcaacgg cccttcatct cgtacgctcg ggatacacac cgtcgaatat cacggttctg    120
gacacttatc caattccatc agcgcaatca gctggcaatg acttgaacaa gatcatgggt    180
atccgtttgc ggaacaaggt ggatttgcag ttgagcttag aggcgagaca aatgtggaca    240
gaagacgatc tgttcaagga gtactttcat aaaaccgggc ggctcgactg cgcacatggc    300
gagaaaggcc ttgcagatct caaacaagcc taccaagccc ttcttgatgc gaacgctggc    360
ctggaggcga cgacagaatg gttagattcc gaggacaaga ttcttgagaa gatgccgctt    420
ctcaatcgcg atcagatcaa aggatggaaa gccgtcttca gcgaagacgg cggatggctc    480
gctgcggcaa aagccatcaa cgctatcggt agatttctgc gcgatcaagg cgtcaagttt    540
ggctttggcg gagcaggatc attcaaacaa cctcttcttg ccgagggtgt ttgtgttggt    600
gttgaaacag ttgacgggac gagatattat gctgacaagg ttgtgttggc ggctggtgcg    660
tggagtcctg cattggtcga tctacaagac caatgtgtgt cgaaagcatg ggtatacgct    720
cacatccaac tgtccccgag cgaggcggcg gaatacaaaa atgttcctgt agtctataat    780
ggcgacgtgg gcttcttctt cgagcctgac gaatacggcg tcatcaaagt ctgtgacgag    840
tttccaggtt ttacgcgctt caagcagcat caacctttcg gcgcatcggc tccaaagcgc    900
atttctgtgc ctcgatctgc cgcaaaacac cccacagata cctatccgga cgcctcggaa    960
gtcagtatcc gcaaggccat cgcgacgttc ctgcccaagt tcacagaaaa ggaagtgttc   1020
aacaggcatc tgtgttggtg tactgatacg gctgatgcgg cgcttttgat gtgcgaacat   1080
cctgagtgga agaactttgt tttggccacg ggtgacagtg gtcacacctt caagcttcta   1140
cctaacatcg gtaagcatgt ggtcgagcta ctagagggta cattagcaga cgacctagcg   1200
catgcgtgga gatggcgtcc cggtaccggc gatgcgctga agtcgcgaag ggcggcgcgt   1260
gcgaaagacc ttgcagatat gccaggatgg aatcatgacg gggaagcccc cagagcgaag   1320
ctgtga                                                              1326
```

<210> SEQ ID NO 123
<211> LENGTH: 437
<212> TYPE: PRT
<213> ORGANISM: Penicillium janthinellum

<400> SEQUENCE: 123

```
Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
            20                  25                  30

Thr Pro Ser Asn Ile Thr Val Leu Asp Val Tyr Pro Ile Pro Ser Leu
        35                  40                  45

Gln Ser Ala Gly Tyr Asp Leu Asn Lys Ile Met Ser Ile Arg Leu Arg
    50                  55                  60

Asn Gly Pro Asp Leu Gln Leu Ser Leu Glu Ala Leu Asp Met Trp Lys
65                  70                  75                  80

Asn Asp Pro Leu Phe Lys Pro Phe Phe His Asn Val Gly Met Leu Asp
                85                  90                  95

Cys Ser Ser Ser Gln Glu Gly Ile Ala Ser Leu Arg Arg Lys His Gln
            100                 105                 110

Asp Leu Ile Asp Ala Asn Ile Gly Leu Glu Lys Thr Asn Ile Trp Leu
        115                 120                 125
```

-continued

```
Glu Ser Glu Asp Asp Ile Leu Ala Lys Ala Pro His Phe Thr Arg Glu
    130                 135                 140

Gln Ile Lys Gly Trp Lys Gly Leu Phe Cys Gly Asp Gly Gly Trp Leu
145                 150                 155                 160

Ala Ala Ala Lys Ala Ile Asn Ala Ile Gly Thr Phe Leu Lys Ser Gln
                165                 170                 175

Gly Val Lys Phe Gly Phe Gly Ser Ala Gly Thr Phe Lys Arg Pro Leu
            180                 185                 190

Phe Ala Pro Asp Gly Ala Thr Cys Ser Gly Val Glu Thr Val Asp Gly
        195                 200                 205

Thr Lys Tyr Phe Ala Asp Lys Val Val Leu Ala Ala Gly Ala Trp Ser
    210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Phe Glu Pro Asn
            260                 265                 270

Glu His Gly Val Ile Lys Val Cys Asp Glu Phe Pro Gly Phe Ser Arg
        275                 280                 285

Phe Lys Leu His Gln Pro Tyr Gly Ala Thr Ser Pro Lys Leu Ile Ser
    290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Val Leu Pro Asn
    370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Gly Asp Ala Leu Lys Ser
                405                 410                 415

Lys Arg Ser Ala Pro Ala Lys Asp Leu Ala Glu Met Pro Gly Trp Lys
            420                 425                 430

His Asp Ala Lys Leu
        435
```

<210> SEQ ID NO 124
<211> LENGTH: 1314
<212> TYPE: DNA
<213> ORGANISM: Penicillium janthinellum

<400> SEQUENCE: 124

```
atggctcatt cgcgagaaag cacaaagatt gtcattgtcg ggggaggtgg cacaatggga      60

tcttcaaccg cgctacacct gatacgctct ggatacaccc cgtcaaacat caccgtcctt     120

gatgtatacc caattccatc cttgcaatcc gcaggatatg atcttaacaa gatcatgagc     180

atccgattac gcaacgggcc tgacttgcaa ctttccctgg aggctctcga tatgtggaaa     240

aacgatccgt tgttcaagcc tttctttcac aacgttggca tgctagactg ttcatcgtca     300
```

-continued

```
caagagggta ttgcaagcct tcgacggaag caccaagacc tcatagacgc gaatatcgga    360

ctagagaaga cgaatatctg gttagagagt gaagatgata ttctggcaaa agccccgcac    420

ttcacgcggg aacagatcaa ggggtggaag ggcttgtttt gcggcgatgg aggatggctt    480

gctgcagcca aggccatcaa tgcgatcgga acctttctaa aaagtcaagg cgtcaagttc    540

ggatttggaa gtgccgggac tttcaagcga cctttgtttg ctccagatgg ggcgacatgc    600

agcggtgttg agacagtaga tggaacaaaa tacttcgccg acaaggtggt tttggccgct    660

ggtgcttgga gttcgacgtt agtagatttg gaggaccaat gtgtttcgaa ggcctgggtc    720

ttcgctcata tccaactcac gccccaagaa tcggcccagt acaaggacgt gcccgtagta    780

tacgacggtg attatggctt tttcttcgag cccaacgaac acggagtaat caaagtctgc    840

gatgagttcc ccgggttctc ccgcttcaag ctgcatcaac cttacggtgc cacctctcct    900

aagcttatat ccgttcctcg atcacacgcc aagcatccca ccgataccta cccagattct    960

tctgaagaga ccattcgaaa agcgattgcg aggtttatgc cacgcttcaa ggataaggag   1020

ctttttaata ggagcatgtg ctggtgcacc gatactgctg atgccaactt gttgatctgc   1080

gagcacccca agtggaagaa ctttatcttg gccacaggag acagcggcca tagtttcaag   1140

gttttgccca atataggaaa acatgtcgtt gagttgatag aaggacgcct accacaagac   1200

ctggctggtg cgtggagatg gagaccaggg ggagatgccc ttaagtccaa acgcagtgct   1260

ccggcaaagg accttgctga aatgccgggc tggaagcatg atgcgaagct ctga         1314
```

```
<210> SEQ ID NO 125
<211> LENGTH: 445
<212> TYPE: PRT
<213> ORGANISM: Aspergillus fumigatus

<400> SEQUENCE: 125

Met Ala Pro Ser Ile Leu Ser Thr Glu Ser Ser Ile Ile Val Ile Gly
1               5                   10                  15

Ala Gly Thr Trp Gly Cys Ser Thr Ala Leu His Leu Ala Arg Arg Gly
            20                  25                  30

Tyr Lys Asp Val Thr Val Leu Asp Pro His Pro Val Pro Ser Pro Ile
        35                  40                  45

Ala Ala Gly Asn Asp Ile Asn Lys Ile Met Glu His Ser Glu Leu Lys
    50                  55                  60

Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                85                  90                  95

His Glu Thr Gly Phe Ile Ile Ser Gly His Thr Pro Ala Leu Ile Asp
            100                 105                 110

His Ile Arg Lys Asp Glu Val Glu Pro Ser Glu Thr Asn Phe Val Lys
        115                 120                 125

Leu Glu Thr Ala Glu Asp Phe Arg Arg Thr Met Pro Pro Gly Val Leu
    130                 135                 140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                165                 170                 175

Lys Arg Leu Gly Val Arg Phe Val Thr Gly Ser Pro Glu Gly Asn Val
            180                 185                 190

Val Ser Leu Val Tyr Glu Asp Gly Asp Val Val Gly Ala Arg Thr Ala
```

-continued

```
        195                 200                 205

Asp Gly Arg Val His Lys Ala His Arg Thr Ile Leu Ser Ala Gly Ala
    210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                245                 250                 255

Arg Asn Leu Pro Val Leu Phe Asn Ile Ala Lys Gly Phe Phe Met Glu
            260                 265                 270

Pro Asp Glu Asp Lys His Glu Leu Lys Ile Cys Asp Glu His Pro Gly
        275                 280                 285

Tyr Cys Asn Phe Leu Pro Asp Pro Asn Arg Pro Gly Gln Glu Lys Ser
    290                 295                 300

Val Pro Phe Ala Lys His Gln Ile Pro Leu Glu Ala Glu Ala Arg Ala
305                 310                 315                 320

Arg Asp Phe Leu His Asp Thr Met Pro His Leu Ala Asp Arg Pro Leu
                325                 330                 335

Ser Phe Ala Arg Ile Cys Trp Asp Ala Asp Thr Pro Asp Arg Ala Phe
            340                 345                 350

Leu Ile Asp Arg His Pro Glu His Pro Ser Leu Leu Val Ala Val Gly
        355                 360                 365

Gly Ser Gly Asn Gly Ala Met Gln Met Pro Thr Ile Gly Gly Phe Ile
    370                 375                 380

Ala Asp Ala Leu Glu Ser Lys Leu Gln Lys Glu Val Lys Asp Ile Val
385                 390                 395                 400

Arg Trp Arg Pro Glu Thr Ala Val Asp Arg Asp Trp Arg Ala Thr Gln
                405                 410                 415

Asn Arg Phe Gly Gly Pro Asp Arg Ile Met Asp Phe Gln Gln Val Gly
            420                 425                 430

Glu Asp Gln Trp Thr Lys Ile Gly Glu Ser Arg Gly Pro
        435                 440                 445
```

<210> SEQ ID NO 126
<211> LENGTH: 1338
<212> TYPE: DNA
<213> ORGANISM: Aspergillus fumigatus

<400> SEQUENCE: 126

```
atggcgcctt caattttgag cactgaatct tccattatcg ttatcggagc aggcacatgg      60

ggctgctcaa ctgctctgca cctcgctcgt cgaggctaca aagatgtcac tgttctcgac     120

cctcatccag ttccttcgcc cattgcagca ggcaatgaca tcaacaagat tatggagcac     180

agcgagctga aagatggctc atccgaccct cgaagcgcag ccttctcgac atttacgcga     240

gctgctctta aggcgtggaa aactgacccg gttttccagc cttactttca cgaaactggc     300

tttatcatat cggggcacac acctgctctg attgaccaca tacgaaaaga cgaggtagaa     360

ccgtcagaaa caaacttcgt caagctggag acagccgagg acttccgccg gaccatgccg     420

ccaggtgtac tgacaggcga cttccctggc tggaaaggct ggttgcacaa gtctggtgct     480

gggtggattc atgccaaaaa ggctatgatc tctgctttca atgaagctaa gcgcttggga     540

gtcagatttg tcactggctc tccggaaggg aatgttgtat cgttggtata cgaggacgga     600

gacgtcgttg gagccagaac tgccgatggt cgcgtgcaca aagcccatcg cactattctt     660

tcggcaggtg ctggcagtga cagtctccta gacttcaaga agcagcttcg gcctaccgcg     720
```

tggactctct gtcatattca gatgggccct gaagaggtca agcaatatcg gaaccttcct 780
gtgttgttca acatcgccaa agggttcttc atggagcctg atgaggataa acacgagctc 840
aagatttgtg acgagcatcc agggtactgc aactttctcc ctgacccaaa cagaccgggc 900
caggagaaga gtgtcccctt cgcaaagcat cagatcccgc tcgaggccga agcccgcgca 960
cgagactttc tccatgatac aatgccgcat ctggctgacc ggccactgtc tttcgcgcgt 1020
atttgctggg atgctgatac cccagaccgt gctttcttga tcgatagaca tcctgaacac 1080
ccctcactgc tagtcgctgt tggaggttcc ggcaatggcg ccatgcaaat gcctacaatt 1140
ggcggtttta tcgcagatgc tctagagagt aaactacaga aggaggtgaa ggacatcgtt 1200
cgatggaggc cagagacggc tgtcgatcga gattggagag cgactcagaa tcgctttggc 1260
gggcctgaca ggatcatgga ttttcagcag gtcggagagg atcagtggac caagattgga 1320
gagagcagag gtccgtaa 1338

<210> SEQ ID NO 127
<211> LENGTH: 445
<212> TYPE: PRT
<213> ORGANISM: Aspergillus oryzae

<400> SEQUENCE: 127

Met Thr Ser Ser Lys Leu Thr Pro Thr Ser Ser Ile Leu Ile Val Gly
1 5 10 15

Ala Gly Thr Trp Gly Cys Ser Thr Ala Leu His Leu Ala Arg Arg Gly
20 25 30

Tyr Lys Asn Val Thr Val Leu Asp Pro His Pro Val Pro Ser Pro Ile
35 40 45

Ala Ala Gly Asn Asp Ile Asn Lys Ile Met Glu His Arg Glu Val Lys
50 55 60

Ala Ser Glu Thr Asp Pro Trp Ser Ile Ala Phe Ser Thr Cys Thr Arg
65 70 75 80

Ala Ala Leu Lys Gly Trp Lys Asn Asp Pro Val Phe Gln Pro Tyr Phe
85 90 95

His Glu Thr Gly Ala Ile Val Ser Gly His Thr Ala Ser Leu Ile Lys
100 105 110

His Ile Gln Glu His Glu Ile Asp Ser Ser Asp Ala Glu Phe Ile Lys
115 120 125

Leu Asn Thr Ala Glu Asp Phe Arg Lys Thr Met Pro Pro Gly Ile Leu
130 135 140

Thr Gly Asn Phe Pro Gly Trp Lys Gly Trp Leu Asn Lys Thr Gly Ala
145 150 155 160

Gly Trp Ile His Ala Lys Lys Ala Met Phe Ser Ala Tyr Thr Glu Ala
165 170 175

Lys Arg Leu Gly Val Thr Phe Ile Thr Gly Ser Pro Glu Gly Asp Val
180 185 190

Val Ser Leu Ile Tyr Glu Asn Gly Asp Val Val Gly Ala Arg Thr Ala
195 200 205

Asp Gly Thr Val His Arg Ala Asp His Thr Ile Leu Ser Ala Gly Ala
210 215 220

Gly Ser Asp Arg Leu Leu Asp Phe Lys Lys Gln Leu Arg Pro Thr Ala
225 230 235 240

Trp Thr Leu Cys His Ile Arg Met Thr Pro Asp Glu Ala Lys Lys Tyr
245 250 255

Arg Asn Leu Pro Val Leu Phe Asn Val Ala Lys Gly Phe Phe Met Glu

-continued

```
            260                 265                 270

Pro Asp Glu Asp Asn His Glu Leu Lys Ile Cys Asp Glu His Pro Gly
        275                 280                 285

Tyr Cys Asn Phe Val Pro Asp Pro Lys His Gly Gly Glu Val Arg Ser
    290                 295                 300

Ile Pro Phe Ala Lys His Gln Ile Pro Leu Glu Ala Glu Ala Arg Ala
305                 310                 315                 320

Arg Asp Phe Leu Arg Asp Thr Met Pro His Leu Ala Asp Arg Pro Leu
                325                 330                 335

Ser Phe Ala Arg Ile Cys Trp Asp Ala Asp Thr Val Asp Arg Ala Phe
            340                 345                 350

Leu Ile Asp Arg His Pro Glu Tyr Arg Ser Leu Leu Leu Ala Val Gly
        355                 360                 365

Gly Ser Gly Asn Gly Ala Met Gln Met Pro Thr Ile Gly Gly Phe Ile
    370                 375                 380

Ala Asp Ala Leu Glu Gly Asn Leu Gln Lys Glu Leu Lys His Ala Leu
385                 390                 395                 400

Arg Trp Arg Pro Glu Ile Ala Ala Gln Arg Asp Trp Lys Asp Thr Gln
                405                 410                 415

Asn Arg Phe Gly Gly Pro Asn Lys Val Met Asp Phe Gln Lys Val Gly
            420                 425                 430

Glu Asn Glu Trp Thr Lys Ile Gly Asp Lys Ser Arg Leu
        435                 440                 445


<210> SEQ ID NO 128
<211> LENGTH: 1338
<212> TYPE: DNA
<213> ORGANISM: Aspergillus oryzae

<400> SEQUENCE: 128

atgacatcct ccaagttgac tcccacatca tctatcttaa ttgtcggtgc agggacctgg     60

ggttgttcta ctgctttaca tcttgcccgt cgaggataca aaaatgtcac ggtcctagat    120

ccgcacccgg tcccttctcc cattgcagct ggcaatgaca ttaacaagat tatggagcac    180

agggaggtaa aagcctctga aaccgatcct tggagtatcg ccttctcaac atgcacacga    240

gctgcactga aaggttggaa aaacgaccca gtattccagc catacttcca tgaaacgggg    300

gcaatagttt ctggccacac cgcctctttg attaaacata tacaagaaca cgaaatcgac    360

tcgtcagacg ccgagttcat aaaattgaac accgcagagg atttccgcaa aactatgccc    420

ccgggaatcc tcactggcaa cttccccggc tggaagggct ggctgaacaa gaccggcgcc    480

ggatggatcc acgccaagaa ggccatgttc tccgcataca ccgaagcaaa gcgcctagga    540

gtcactttca tcaccggctc ccctgaagga gacgttgtat ctctaattta cgagaatgga    600

gacgtagtcg gagccagaac ggccgacggc accgtccacc gagcagacca taccattctt    660

tccgcagggg ctggcagtga tcgtctcctg gactttaaga aacagctccg tcctaccgcc    720

tggacgctct gccacatcag aatgacgccc gacgaggcca agaagtaccg gaatcttcct    780

gtgctgttca acgtcgctaa ggggttcttc atggaacctg atgaggataa tcatgagctt    840

aagatctgcg acgagcatcc tggatattgc aacttcgtcc cggacccgaa gcacggcggt    900

gaggtgcgca gtatcccatt tgcaaagcat cagattcctc ttgaagccga ggcccgtgca    960

agggacttcc tccgtgatac gatgcctcat cttgctgatc gaccactgtc ttttgctcgt   1020

atatgctggg atgctgatac agtggatcgc gccttcttga tcgataggca tcctgagtat   1080
```

```
cgctctttac tgcttgctgt cggtggatct ggtaatggag ccatgcaaat gcctaccatt   1140

ggtgggttca tagcggatgc tctggaggga aacctgcaaa aggaactgaa gcatgcacta   1200

cggtggaggc ctgagattgc cgcccaacga gactggaagg atacgcaaaa tagattcgga   1260

ggtccgaata aagtaatgga tttccaaaag gttggagaga atgagtggac caagattggc   1320

gataagagtc ggctttaa                                                 1338
```

<210> SEQ ID NO 129
<211> LENGTH: 438
<212> TYPE: PRT
<213> ORGANISM: Aspergillus fumigatus

<400> SEQUENCE: 129

```
Met Ala Val Thr Lys Ser Ser Ser Leu Leu Ile Val Gly Ala Gly Thr
1               5                   10                  15

Trp Gly Thr Ser Thr Ala Leu His Leu Ala Arg Arg Gly Tyr Thr Asn
            20                  25                  30

Val Thr Val Leu Asp Pro Tyr Pro Val Pro Ser Ala Ile Ser Ala Gly
        35                  40                  45

Asn Asp Val Asn Lys Val Ile Ser Ser Gly Gln Tyr Ser Asn Asn Lys
    50                  55                  60

Asp Glu Ile Glu Val Asn Glu Ile Leu Ala Glu Glu Ala Phe Asn Gly
65                  70                  75                  80

Trp Lys Asn Asp Pro Leu Phe Lys Pro Tyr Tyr His Asp Thr Gly Leu
                85                  90                  95

Leu Met Ser Ala Cys Ser Gln Glu Gly Leu Asp Arg Leu Gly Val Arg
            100                 105                 110

Val Arg Pro Gly Glu Asp Pro Asn Leu Val Glu Leu Thr Arg Pro Glu
        115                 120                 125

Gln Phe Arg Lys Leu Ala Pro Glu Gly Val Leu Gln Gly Asp Phe Pro
    130                 135                 140

Gly Trp Lys Gly Tyr Phe Ala Arg Ser Gly Ala Gly Trp Ala His Ala
145                 150                 155                 160

Arg Asn Ala Leu Val Ala Ala Ala Arg Glu Ala Gln Arg Met Gly Val
                165                 170                 175

Lys Phe Val Thr Gly Thr Pro Gln Gly Arg Val Val Thr Leu Ile Phe
            180                 185                 190

Glu Asn Asn Asp Val Lys Gly Ala Val Thr Gly Asp Gly Lys Ile Trp
        195                 200                 205

Arg Ala Glu Arg Thr Phe Leu Cys Ala Gly Ala Ser Ala Gly Gln Phe
    210                 215                 220

Leu Asp Phe Lys Asn Gln Leu Arg Pro Thr Ala Trp Thr Leu Val His
225                 230                 235                 240

Ile Ala Leu Lys Pro Glu Glu Arg Ala Leu Tyr Lys Asn Ile Pro Val
                245                 250                 255

Ile Phe Asn Ile Glu Arg Gly Phe Phe Phe Glu Pro Asp Glu Glu Arg
            260                 265                 270

Gly Glu Ile Lys Ile Cys Asp Glu His Pro Gly Tyr Thr Asn Met Val
        275                 280                 285

Gln Ser Ala Asp Gly Thr Met Met Ser Ile Pro Phe Glu Lys Thr Gln
    290                 295                 300

Ile Pro Lys Glu Ala Glu Thr Arg Val Arg Ala Leu Leu Lys Glu Thr
305                 310                 315                 320

Met Pro Gln Leu Ala Asp Arg Pro Phe Ser Phe Ala Arg Ile Cys Trp
```

```
            325                 330                 335

Cys Ala Asp Thr Ala Asn Arg Glu Phe Leu Ile Asp Arg His Pro Gln
        340                 345                 350

Tyr His Ser Leu Val Leu Gly Cys Gly Ala Ser Gly Arg Gly Phe Lys
    355                 360                 365

Tyr Leu Pro Ser Ile Gly Asn Leu Ile Val Asp Ala Met Glu Gly Lys
    370                 375                 380

Val Pro Gln Lys Ile His Glu Leu Ile Lys Trp Asn Pro Asp Ile Ala
385                 390                 395                 400

Ala Asn Arg Asn Trp Arg Asp Thr Leu Gly Arg Phe Gly Gly Pro Asn
                405                 410                 415

Arg Val Met Asp Phe His Asp Val Lys Glu Trp Thr Asn Val Gln Tyr
            420                 425                 430

Arg Asp Ile Ser Lys Leu
        435
```

<210> SEQ ID NO 130
<211> LENGTH: 1317
<212> TYPE: DNA
<213> ORGANISM: Aspergillus fumigatus

<400> SEQUENCE: 130

```
atggcggtaa ccaagtcatc ttccctttg atcgtggggg caggcacctg gggcacatcg      60

actgctctcc acctggcacg aagaggatac acaaatgtga cggttctaga tccctacccc     120

gttccctcag ccatctcggc tgggaatgat gtgaacaagg tcatctcctc cggccaatat     180

agcaacaaca aggacgaaat tgaggtcaac gagattctgg ctgaagaagc gttcaatggc     240

tggaagaacg accccttgtt caaaccatac tatcacgata ctggattgct catgtccgcc     300

tgctcccagg aaggcttgga ccgccttgga gtccgtgtca ggcccggtga ggaccccaac     360

cttgtggaac tgacacggcc ggagcaattc cgcaaattag ctcctgaggg tgttctacag     420

ggagatttcc ccggctggaa gggctacttt gcgcgttcag gagctggttg ggcccatgct     480

cgcaatgcac tcgtggctgc tgcaagggag gctcagagaa tgggcgtgaa gttcgtaact     540

ggcactcctc agggcagagt agtcactcta atatttgaga ataacgatgt caaaggtgcc     600

gttaccggag acggcaagat ttggcgtgca gagcgcacat tcctctgcgc cggtgccagc     660

gctggtcagt tcctcgactt caagaatcag ttgcgtccaa cggcatggac gctggttcat     720

attgctctga agcctgagga gcgggctctt tacaagaata tcccagttat cttcaacatt     780

gagaggggggt tcttcttcga accagatgag gagcgcggtg agattaagat ctgcgacgaa     840

catccggggt ataccaatat ggtacagtct gccgacggca cgatgatgag cattcctttt     900

gaaaagactc agattcctaa agaagccgag acgagggtta gagctctgct taaagagacg     960

atgccacagc ttgcagaccg tccattcagt ttcgccagga tttgctggtg cgccgacact    1020

gccaaccggg agttcttgat cgatcgccat cctcagtacc attcgcttgt gctgggctgc    1080

ggcgcttccg gcagaggatt caaatatcta ccttcaattg gcaatctcat cgttgatgct    1140

atggaaggca aggtccctca aaagatccac gaactgatta aatggaaccc agatattgct    1200

gccaatcgca actggaggga tactttgggg agattcgggg gtcccaacag agtaatggac    1260

ttccacgacg tcaaggagtg gacaaatgta caatatagag atatttccaa gttataa       1317
```

<210> SEQ ID NO 131
<211> LENGTH: 437
<212> TYPE: PRT

<213> ORGANISM: Aspergillus terreus

<400> SEQUENCE: 131

Met Pro Val Thr Lys Ser Ser Ser Ile Leu Ile Ile Gly Ala Gly Thr
1 5 10 15

Trp Gly Cys Ser Thr Ala Leu His Leu Ala Arg Arg Gly Tyr Thr Asn
20 25 30

Val Thr Val Leu Asp Pro Tyr Pro Val Pro Ser Ala Ile Ser Ala Gly
35 40 45

Asn Asp Val Asn Lys Ile Ile Ser Ser Gly Gln Tyr Ser Ser Lys Lys
50 55 60

Asp Glu Val Glu Val Asn Glu Ile Ile Ala Glu Gln Ala Phe Asn Gly
65 70 75 80

Trp Lys Asn Asp Pro Ile Phe Lys Pro Tyr Tyr His Asp Thr Gly Val
85 90 95

Val Met Ser Ala Thr Thr Gln Glu Gly Leu Glu Arg Leu Gly Val Arg
100 105 110

Val Arg Pro Glu Asp Glu Pro Asp Val Ala Glu Leu Thr Arg Pro Glu
115 120 125

Gln Phe Arg Gln Leu Ala Pro Gly Val Leu Lys Gly Asn Phe Pro Gly
130 135 140

Trp Arg Gly Tyr His Ile Arg Ser Asn Ala Gly Trp Ala His Ala Arg
145 150 155 160

Asn Ala Leu Val Ala Ala Ala Arg Glu Ala Gln Arg Leu Gly Val Arg
165 170 175

Phe Val Ala Gly Ser Pro Gln Gly Arg Val Ile Thr Leu Ile Phe Glu
180 185 190

Asn Asn Asp Val Lys Gly Ala Val Thr Ala Asp Gly Lys Ile Trp Arg
195 200 205

Ala Glu Gln Thr Ile Leu Cys Ala Gly Ala Ala Ala Gly Gln Phe Leu
210 215 220

Asp Phe Lys Asp Gln Leu Arg Pro Thr Ala Trp Thr Leu Val His Ile
225 230 235 240

Gln Leu Lys Pro Glu Glu Arg Ala Gln Tyr Lys Asn Met Pro Val Val
245 250 255

Phe Asn Ile Glu Lys Gly Phe Phe Phe Glu Pro Asp Glu Glu Arg Gly
260 265 270

Glu Ile Lys Ile Cys Asp Glu His Pro Gly Tyr Thr Asn Met Thr Thr
275 280 285

Gly Ala Asp Gly Arg Val Arg Ser Ile Pro Phe Glu Lys Thr Gln Val
290 295 300

Pro Arg Glu Ala Glu Met Arg Val Arg Lys Leu Leu Ser Glu Thr Met
305 310 315 320

Pro Gln Leu Ala Asp Arg Pro Phe Ser Phe Ala Arg Ile Cys Trp Cys
325 330 335

Ala Asp Thr Pro Asn Arg Glu Phe Ile Ile Asp Arg His Pro Glu Tyr
340 345 350

Pro Ser Leu Val Leu Gly Cys Gly Ala Ser Gly Arg Gly Phe Lys Tyr
355 360 365

Leu Pro Ser Ile Gly Ser Ile Ile Ala Asp Ala Met Glu Asp Lys Thr
370 375 380

Pro Ala Lys Ile His Lys Leu Ile Arg Trp Ser Pro Glu Ile Ala Ile
385 390 395 400

```
Asn Arg Asn Trp Gly Asp Arg Leu Gly Arg Phe Gly Gly Pro Asn Arg
                405                 410                 415

Val Met Asp Phe Asn Glu Val Lys Glu Trp Thr Asn Val Thr Gln Arg
            420                 425                 430

Asp Ile Ser Lys Leu
        435


<210> SEQ ID NO 132
<211> LENGTH: 1314
<212> TYPE: DNA
<213> ORGANISM: Aspergillus terreus

<400> SEQUENCE: 132

atgccagtca ccaagtcttc gtcgatattg atcatcgggg cgggcacctg gggttgctca     60

actgccctgc atcttgcccg cagaggatac accaatgtca ctgtccttga cccgtacccg    120

gttccatcag ccatttcggc cggcaacgac gtcaacaaga tcatctcgtc cggccagtac    180

agcagcaaga aggacgaggt cgaagtcaat gagattatcg ccgaacaggc cttcaatggc    240

tggaaaaatg accccatctt caagccgtac taccacgaca ccggcgtcgt gatgtccgcc    300

accacacagg aaggattgga gcgtctgggg gtccgcgtgc gacctgaaga tgaacccgat    360

gtagccgaat tgactcggcc ggagcagttc cgccagctgg cccccggcgt cttgaagggt    420

aacttccccg gttggagggg gtaccacatt cgctcaaacg cgggctgggc gcatgcgcgc    480

aacgccctgg tcgccgcggc gcgggaggca cagcgcctgg gtgtgcgctt cgtcgcggga    540

tcgccgcagg gcagagtcat cacgttgatt tttgagaaca acgatgtgaa gggtgccgtc    600

acggcggacg gcaagatctg gcgggccgag cagactatcc tctgcgctgg tgcggccgcc    660

ggccagtttc tggatttcaa ggaccaactg cgtcccactg cgtggactct ggtccacatc    720

cagttgaagc cggaagagcg tgcccagtat aaaaacatgc cggtggtctt caacatcgag    780

aaggggttct tcttcgagcc ggatgaggag cgtggtgaaa tcaagatctg cgacgaacac    840

cccgggtaca cgaatatgac cacgggggcc gacggccgcg tgaggagcat tcccttcgag    900

aagacgcagg ttcctcgaga agcggagatg cgcgtccgca agcttctgtc tgaaacgatg    960

cctcagcttg cggaccggcc gttcagtttc gcaaggatct gctggtgtgc ggataccccc   1020

aatcgcgagt ttatcattga ccgtcatccc gaatacccgt cgcttgttct tgggtgtggt   1080

gcttcaggac gaggcttcaa atatcttccc tcgatcggaa gcatcatcgc agacgccatg   1140

gaggacaaaa ccccggcaaa aatccacaag ctgatccgct ggagcccgga aatcgcgatc   1200

aaccgtaact gggggacag attaggtcga tttggagggc ccaaccgggt catggatttc   1260

aatgaagtga aggagtggac taatgtcacc caaagggaca tctcgaagtt atag         1314


<210> SEQ ID NO 133
<211> LENGTH: 437
<212> TYPE: PRT
<213> ORGANISM: Coniochaeta sp.

<400> SEQUENCE: 133

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
```

-continued

```
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 134
<211> LENGTH: 1314
<212> TYPE: DNA
<213> ORGANISM: Coniochaeta sp.

<400> SEQUENCE: 134

```
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagaaact gaaaaagctg taccagaaac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga aagaacgtgg tgtaaagttc     540
ggattcggcg gcgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaaccct ggtggacctg gaagatcaat gttgctcgaa ggcttgggtg     720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta tccagacgca     960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca aatggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 135
<211> LENGTH: 437
<212> TYPE: PRT
<213> ORGANISM: Phaeosphaeria nodorum

<400> SEQUENCE: 135

```
Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
        35                  40                  45

Gln Ser Ala Gly Asn Asp Leu Asn Lys Ile Met Gly Val Asp Leu Arg
    50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Lys Leu Lys Ser Leu Tyr Gln
            100                 105                 110

Lys Leu Val Asp Ala Gly Leu Asp Ala Thr Asn Glu Trp Leu Asp Ser
        115                 120                 125
```

-continued

```
Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Phe Glu Pro Asn Glu His Gly Val
            260                 265                 270

Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
        355                 360                 365

Gly Asp Ser Gly His Ser Phe Lys Leu Leu Pro Asn Ile Gly Lys His
    370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435
```

<210> SEQ ID NO 136
<211> LENGTH: 1314
<212> TYPE: DNA
<213> ORGANISM: Phaeosphaeria nodorum

<400> SEQUENCE: 136

```
atggccccgt cgcgtgctaa tacgtcggtc attgtggttg gtggtggtgg tacgattggc      60

tcatctacgg ctctgcatct ggtccgctca ggctataccc cgtcgaacgt gacggttctg     120

gatgcatacc cgattccgag ctctcagagc gctggcaacg acctgaataa aatcatgggt     180

gtcgatctgc gtaatccggt ggatctgcag ctggctctgg aagcgcgcca aatgtggaac     240

gaagacgaac tgttcaagaa gtttttccat aacaccggcc gtctggattg cgcgcacggt     300

gaaaaagata ttgccaaact gaagagcctg tatcagaaac tggtggatgc gggtctggac     360
```

```
gccacgaacg aatggctgga tagtgaagac gaaatcctga aacgtatgcc gctgctgtcc    420

cgcgatcaaa ttaaaggctg gaaggcgatc ttttcaaaag acggtggttg gctggcagca    480

gcaaaggcaa ttaatgcagt tggtgaatat ctgcgtgatc agggcgtccg cttcggtttt    540

tacggcgccg gttctttcaa agcaccgctg ctggctgaag gcgtctgcat cggtgtcgaa    600

accgtggatg gcacgcgcta ttacgcagac aaagtggttc tggctgcagg tgcatggtcg    660

ccgaccctgg ttgaactgca tgaacagtgt gtgagcaaag cgtgggttta cggccacatt    720

caactgacgc cggaagaagc cgcacgttat aagaacagcc cggtcgtgta caatggcgat    780

gtgggctttt tctttgaacc gaacgaacat ggcgttatca aagtctgcga tgaatttccg    840

ggttttaccc gcttcaagat gcaccagccg tttggtgcca aagcaccgaa gcgtattagt    900

gtgccgcgct cccatgccaa acacccgacc gatacgatcc cggatgcaag tgacgtttcc    960

attcgtcgcg ctatcgcgac ctttatgccg cagttcaaga acaaaaagat gttcaaccaa   1020

gcgatgtgct ggtgtaccga tacggccgac gctgcgctgc tgatttgtga acatccggaa   1080

tggaaaaact ttgttctggc gaccggcgat tcaggtcatt cgttcaaact gctgccgaat   1140

atcggcaagc acgttgtcga actgctggag ggtacgctgg cagatgacct ggcacacgca   1200

tggcgttggc gtccgggtag tggtgatgca ctgaaaagcc gtcgctctgc tccggcgaaa   1260

gacctggctg atatgccggg ctggaaccat gacaaaccgc gtgctaatct gtaa         1314
```

<210> SEQ ID NO 137
<211> LENGTH: 441
<212> TYPE: PRT
<213> ORGANISM: Neocosmospora vasinfecta

<400> SEQUENCE: 137

```
Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Asp Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe Phe His Asn Thr Gly Arg Leu Asp
                85                  90                  95

Cys Glu Ser Ser Ala Glu Gly Val Glu Lys Leu Arg Arg Leu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Glu Gly Gly Trp Leu
145                 150                 155                 160

Ala Ala Ala Lys Ala Ile Asn Ala Ile Gly Glu Glu Leu Gln Arg Gln
                165                 170                 175

Gly Val Arg Phe Gly Phe Gly Gly Ala Gly Ser Phe Lys Arg Pro Leu
            180                 185                 190

Phe Ala Asp Asp Gly Thr Thr Cys Ile Gly Val Glu Thr Val Asp Gly
        195                 200                 205
```

```
Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
                245                 250                 255

Cys Pro Val Val Tyr His Gly Asp Val Gly Phe Phe Phe Glu Pro Asn
            260                 265                 270

Glu Asn Gly Val Ile Lys Val Cys Asp Glu Phe Pro Gly Phe Thr Arg
        275                 280                 285

Phe Lys Gln His Gln Pro Tyr Gly Ala Pro Ala Pro Lys Pro Val Ser
    290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
        355                 360                 365

Ile Leu Ala Thr Gly Asp Ser Gly His Ser Phe Lys Leu Leu Pro Ile
    370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
        435                 440
```

<210> SEQ ID NO 138
<211> LENGTH: 1326
<212> TYPE: DNA
<213> ORGANISM: Neocosmospora vasinfecta

<400> SEQUENCE: 138

```
atgacgaccc cgcgtaaaga aacgacggtc ctgattattg gtggtggtgg cacgattggt     60

agctcgacgg ctctgcatct gctgcgtgcc ggctataccc cgtctaacat taccgtgctg    120

gatacgtacc cgatcccgag tgcccagtcc gcaggcaacg acctgaataa aattatgggt    180

atcgatctgc gcaataaagt tgatctgcaa ctgagcctgg aagcccgtga tatgtggcgc    240

aacgacgcac tgtttcgtcc gtttttccat aataccggcc gcctggactg cgaaagctct    300

gctgaaggcg tggaaaaact gcgtcgcctg tatcagaaac tggtggaagc aggcgttggt    360

ctggaagaaa cgcacgaatg gctggatagc gaagaagcta ttctggaaaa agcgccgctg    420

ctgcaacgtg aagaaattga aggttggaaa gccatctggt ctgaagaagg cggttggctg    480

gcggccgcaa aagctattaa cgcgatcggc gaagaactgc agcgtcaagg cgttcgcttc    540

ggttttggcg gtgccggtag ttttaaacgc ccgctgttcg cagatgacgg caccacgtgt    600

atcggtgtcg aaaccgtgga tggcacgcag tatcatgcgg acaaagtggt tctggctgca    660

ggtgcttggt caccggcgct ggtcgatctg gaagaacagt gctgttcgaa agcctgggtg    720

tacgcacaca tgcaactgac cccggaagaa gccgcagttt ataaaggctg cccggtcgtg    780
```

taccacggcg atgtcggctt tttctttgaa ccgaacgaaa atggcgttat taaagtctgt 840
gacgaattcc cgggttttac gcgtttcaaa cagcatcaac cgtatggtgc cccggcaccg 900
aaacctgtga gtgttccgcg ctcccatgcg aaacacccga ccgatacgta cccggacgct 960
tcagaagaat cgatcaaacg tgccgtgagt acctttctgc cgcgcttcaa agataaaccg 1020
ctgtttaacc gtgcactgtg ctggtgtacc gatacggccg actccgcact gctgatttgc 1080
gaacacccgc gctggaaaaa ttttatcctg gcgaccggcg atagcggtca ttctttcaaa 1140
ctgctgccga ttatcggcaa acacgttgtc gaactggttg aaggtcgtct ggcggatgac 1200
ctggctgaag cgtggcgttg gcgtccgggt cagggtgatg cacgtaaaag cattcgcgct 1260
gcgccggcga aagacctggc ggatatgccg ggctggaaac acgaccaaga ctcggaatca 1320
cgctga 1326

<210> SEQ ID NO 139
<211> LENGTH: 438
<212> TYPE: PRT
<213> ORGANISM: Aspergillus nidulans

<400> SEQUENCE: 139

Met Thr Pro Arg Ala Asn Thr Lys Ile Ile Val Val Gly Gly Gly Gly
1 5 10 15

Thr Met Gly Ser Ser Thr Ala Leu His Leu Leu Arg Ala Gly Tyr Thr
20 25 30

Pro Ser Asn Ile Thr Val Leu Asp Thr Cys Pro Ile Pro Ser Ala Gln
35 40 45

Ser Ala Gly Tyr Asp Leu Asn Lys Ile Met Gly Ile Asp Leu Arg Asn
50 55 60

Lys Pro Asp Leu Gln Leu Ser Leu Glu Ala Leu Asp Met Trp Lys Asn
65 70 75 80

Asp Pro Leu Phe Lys Pro Phe Phe His Asn Val Gly Met Ile Asp Val
85 90 95

Ser Ser Thr Glu Glu Gly Ile Glu Lys Leu Arg Lys Leu Tyr Gln Ser
100 105 110

Leu Leu Asp Ala Gly Ile Gly Leu Glu Lys Thr Asn Phe Met Leu Glu
115 120 125

Ser Glu Asp Glu Ile Leu Ala Lys Ala Pro His Phe Thr Gln Glu Gln
130 135 140

Ile Lys Gly Trp Lys Gly Leu Phe Cys Gly Asp Gly Gly Trp Leu Ala
145 150 155 160

Ala Ala Lys Ala Ile Asn Ala Ile Gly Gln Phe Leu Lys Glu Gln Gly
165 170 175

Val Lys Phe Gly Phe Gly Gly Ala Gly Thr Phe Lys Lys Pro Leu Phe
180 185 190

Ala Asp Ala His Glu Lys Thr Cys Ile Gly Val Glu Thr Val Asp Gly
195 200 205

Thr Lys Tyr Tyr Ala Asp Lys Val Val Leu Ala Ala Gly Ala Trp Ser
210 215 220

Ser Thr Leu Val Asp Leu Glu Glu Gln Cys Val Ser Lys Ala Trp Val
225 230 235 240

Phe Ala His Ile Gln Leu Thr Pro Ala Glu Ala Ala Ala Tyr Lys Asn
245 250 255

Thr Pro Val Ile Tyr Asp Gly Asp Tyr Gly Phe Phe Phe Glu Pro Asn
260 265 270

```
Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435


<210> SEQ ID NO 140
<211> LENGTH: 1317
<212> TYPE: DNA
<213> ORGANISM: Aspergillus nidulans

<400> SEQUENCE: 140

atgacgcccc gagccaacac caaaatcatt gtcgtcggcg gcggcggcac aatgggctcg      60

tcgacagccc tacacctcct gcgcgccggc tacacgccgt ccaacattac agtgctcgac     120

acgtgcccta tcccctccgc acagtctgca ggctacgacc tgaacaaaat catgggcatc     180

gatctgcgca acaagcctga tttacagctc tctcttgagg cgctggacat gtggaaaaat     240

gatcctctct tcaagccgtt tttccacaat gttggaatga tcgacgtctc ttcaacagag     300

gaaggcatcg agaaacttcg gaagctgtac cagtctcttc tcgacgcagg cattgggctc     360

gagaagacga atttcatgct ggaaagtgaa gacgagatcc tggctaaagc gccgcatttc     420

acgcaggagc agattaaagg ctggaaaggc ctgttctgtg gcgacggcgg ctggctcgct     480

gcagccaaag ccatcaatgc cattgggcag ttcctcaagg aacagggcgt caagtttgga     540

ttcggcggcg ccggcacgtt caaaaagcca ctcttcgccg atgcccacga gaagacgtgc     600

atcggcgtcg agactgtaga cggcacaaag tactacgccg acaaggtcgt tctagcagct     660

ggtgcctgga gttcgacgtt ggtcgatctg gaggagcagt gcgtttcaaa ggcctgggtc     720

tttgcccaca tccaactgac gcccgctgaa gcagccgcgt ataagaacac tcctgttata     780

tacgacggtg actatgggtt tttctttgag ccgaatgaaa acggcatcat aaaagtctgt     840

gacgaattcc ctggcttcac gcatttcaaa atgcaccagc cgtacggctc gccggcgccc     900

aaacccatct ctgtgcctcg ttcccatgcg aagcacccca cagatacata cccgcacgcg     960

tcggaggtca cgatcaaaaa ggctatcaac cggttcctgc cgaggttcaa tgacaaggaa    1020

ctgtttaaca gggccatgtg ctggtgcacc gataccgcgg atgcaaatct gcttgtttgt    1080

gagcatccac gctggaaggg gttttatctt gcaacagggg acagtgggca ttcgttcaag    1140
```

-continued

```
ttgctgccga atattggaaa gcatgttgtc gagttattgg aggagaggct ggaaagtgtg   1200

tttaaggatg cttggaggtg gaggcctggc agtggggatg cattaaaaag tagacgggct   1260

gcgcctgcga aggacctggc ggatatgccg gggtggagga atgaggcaaa gatgtag      1317


<210> SEQ ID NO 141
<211> LENGTH: 437
<212> TYPE: PRT
<213> ORGANISM: Coniochaeta sp.

<400> SEQUENCE: 141

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
```

```
            340                 345                 350

Ala Asp Ser Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 142
<211> LENGTH: 1314
<212> TYPE: DNA
<213> ORGANISM: Coniochaeta sp.

<400> SEQUENCE: 142

atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatcatc gcaacaaggt ggacctgcaa atgagtctag aggctagaca gatgtggaag     240

gaggatgagt tattccagcc cttctttcac aataccggca gaatggactg cgaacacacg     300

cctaagggta tcgagaaact gaaaaagctg taccagaaac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc cccatctccg     900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg actctgctct cttgatgtgt    1080

gaacacccca aatggaagaa tttcattcta gcgaccggcg acagcggaca ctcattcaaa    1140

atcttgccta acgtcggaaa atacgtagtc gagttgatag agggccgcct gccggaggaa    1200

atggcttatc aatggaggtg gcggccagga ggcgatgcac tcaagtctag acgtgcggca    1260

ccgccaaaag atcttgcaga catgccagga tggaaacatg atccgaaatt gtaa          1314


<210> SEQ ID NO 143
<211> LENGTH: 437
<212> TYPE: PRT
<213> ORGANISM: Eupenicillium terrenum

<400> SEQUENCE: 143
```

```
Met Ala His Ser Arg Ala Ser Thr Lys Val Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Asp His Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Lys Leu Arg Arg Leu Tyr Gln
            100                 105                 110

Lys Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asp
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ser Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415
```

-continued

Arg Arg Gly Ala Pro Ala Lys Asp Leu Ala Glu Met Pro Gly Trp Lys
            420                 425                 430

His Asp Ala His Leu
        435

<210> SEQ ID NO 144
<211> LENGTH: 1314
<212> TYPE: DNA
<213> ORGANISM: Eupenicillium terrenum

<400> SEQUENCE: 144
atggctcatt cgcgtgcaag caccaaagtc gtcgtggttg ggggaggtgg tacgatcggg 60
tcttcgacgg ctctgcactt aatccgctct ggatataccc cctcaaatat caccgtgctt 120
gacgtataca agaccccttc attgcaatct gcaggacatg atttgaacaa gatcatgggc 180
attgatcatc gcaacgggcc tgacttgcag ctttcgctgg aatcactcga catgtggcaa 240
aacgatgagt tgttcaagcc attctttcac caagtgggca tgattgattg ttcgtcatcc 300
aaagagggta ttgaaaaact tcgacgatta taccagaaac tcctcgatgc gggcattggg 360
ctggagaaga cgaacgtttg gctggaatct gaagatgaga tcctcgccaa agcgccgaat 420
ttcacgcgtg aacaagtcaa ggggtggaaa ggcttatttt gcactgatgg aggctggctt 480
gctgcagcca aggctatcaa tgcgatcgga attttcctcc aggacaaagg tgtcaagttt 540
ggctttggag atgctggtac ctttcagcaa cctctgttcg ccgctgatgg aaaaacttgc 600
atcggacttg aaactacaga cggaaccaag tactttgctg acaaggttgt cttggctgct 660
ggtgcgtgga gtcccacctt ggtggatcta gaagatcagt gtgtttcaaa ggcctgggtt 720
ttcgctcata ttcaactcac acccaaagaa gcggacgcgt acaagaatgt gcctgtggtc 780
tatgatggtg aatatgggtt ctttttcgaa cccgacgagt atggggtgat caaagtctgt 840
gacgagttcc ctggtttctc tcgcttcaaa ctgcatcaac cgtacggggc tgcatctccc 900
aagatgatat ccgtaccgcg atcacacgcc aagcatccca cagataccta ccctgatgcc 960
tccgaagtca ccatacgcaa agcgatcgca aggttcctgc cagaatttaa agacaaggag 1020
ctcttcaacc gtaccatgtg ctggtgtaca gatacggccg attctaactt attgatttgc 1080
gaacacccga agtggaagaa tttcattctg gccactggag atagcggaca ttccttcaag 1140
ctgttgccaa acatcgggaa atacgtagtt gagcttttag agggatctct atcgcaggaa 1200
atggctggtg cctggagatg gagacccgga ggtgatgctc ttagatctag acgcggtgct 1260
ccggcaaagg atcttgctga gatgccggga tggaagcatg atgcacattt gtga 1314

<210> SEQ ID NO 145
<211> LENGTH: 437
<212> TYPE: PRT
<213> ORGANISM: Eupenicillium terrenum

<400> SEQUENCE: 145

Met Ala His Ser Arg Ala Ser Thr Lys Val Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln

-continued

```
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Gly Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asn
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys His Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435
```

<210> SEQ ID NO 146
<211> LENGTH: 1314
<212> TYPE: DNA
<213> ORGANISM: Eupenicillium terrenum

<400> SEQUENCE: 146

-continued

```
atggctcatt cgcgtgcaag caccaaagtc gtcgtggttg ggggaggtgg tacgatcggg      60
tcttcgacgg ctctgcactt aatccgctct ggatataccc cctcaaatat caccgtgctt     120
gacgtataca agaccccttc attgcaatct gcaggacatg atttgaacaa gatcatgggc     180
attcgattgc gcaacgggcc tgacttgcag ctttcgctgg aatcactcga catgtggcaa     240
aacgatgagt tgttcaagcc attctttcac caagtgggca tgattgattg ttcgtcatcc     300
aaagagggta ttgaaaatct tcgacgaaaa taccagaccc tcctcgatgc gggcattggg     360
ctggagaaga cgaacgtttg gctggaatct gaagatgaga tcctcgccaa agcgccgaat     420
ttcacgcgtg aacaagtcaa ggggtggaaa ggcttatttt gcactgatgg aggctggctt     480
gctgcagcca aggctatcaa tgcgatcgga attttcctcc aggacaaagg tgtcaagttt     540
ggctttggag gtgctggaac atttcagcaa cctctgttcg ccgctgatgg aaaaacttgc     600
atcggacttg aaactacaga cggaaccaag tactttgctg acaaggttgt cttggctgct     660
ggtgcgtgga gtcccacctt ggtggatcta gaagatcagt gtgtttcaaa ggcctgggtt     720
ttcgctcata ttcaactcac acccaaagaa gcggacgcgt acaagaatgt gcctgtggtc     780
tatgatggtg aatatgggtt ctttttgag cccaacgagt atggggtgat caaagtctgt      840
gacgagttcc ctggtttctc tcgcttcaaa ctgcatcaac cgtacggggc tgcatctccc     900
aagatgatat ccgtaccgcg atcacacgcc aagcatccca cagataccta ccctgatgcc     960
tccgaagtca ccatacgcaa agcgatcgca aggttcctgc cagaatttaa agacaaggag    1020
ctcttcaacc gtaccatgtg ctggtgtaca gatacggccg atgctaactt attgatttgc    1080
gaacacccga agtggaagaa tttcattctg gccactggag atagcggaca ttccttcaag    1140
ctgttgccaa acatcgggaa acacgttgtt gagcttttag agggatctct atcgcaggaa    1200
atggctggtg cctggagatg gagacccgga ggtgatgctc ttagatctag acgcggtgct    1260
ccggcaaagg atcttgctga gatgccggga tggaagcatg atgcacattt gtga          1314
```

<210> SEQ ID NO 147
<211> LENGTH: 438
<212> TYPE: PRT
<213> ORGANISM: Aspergillus nidulans

<400> SEQUENCE: 147

```
Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Ser Ile Arg Leu Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Met Ile Asp Val
                85                  90                  95

Ser Ser Thr Glu Glu Gly Ile Glu Gly Leu Arg Lys Lys Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140
```

```
Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Ala Tyr Lys Asn
                245                 250                 255

Thr Pro Val Ile Tyr Asp Gly Asp Tyr Gly Phe Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435
```

<210> SEQ ID NO 148
<211> LENGTH: 1317
<212> TYPE: DNA
<213> ORGANISM: Aspergillus nidulans

<400> SEQUENCE: 148

```
atgacgcccc gagccaacac caaaatcatt gtcgtcggcg gcggcggcac aatgggctcg      60

tcgacagccc tacacctcct gcgcgccggc tacacgccgt ccaacattac agtgctcgac     120

acgtgcccta tcccctccgc acagtctgca ggctacgacc tgaacaaaat catgagcatc     180

aggctgcgca acaagcctga tttacagctc tctcttgagg cgctggacat gtggaaaaat     240

gatcctctct tcaagccgtt tttccacaat gttggaatga tcgacgtctc ttcaacagag     300

gaaggcatcg agggtcttcg gaagaaatac cagtctcttc tcgacgcagg cattgggctc     360

gagaagacga atttcatgct ggaaagtgaa gacgagatcc tggctaaagc gccgcatttc     420
```

-continued

```
acgcaggagc agattaaagg ctggaaaggc ctgttctgtg gcgacggcgg ctggctcgct    480

gcagccaaag ccatcaatgc cattgggcag ttcctcaagg aacagggcgt caagtttgga    540

ttcggcggcg ccggcacgtt caaaaagcca ctcttcgccg atgcccacga gaagacgtgc    600

atcggcgtcg agactgtaga cggcacaaag tactacgccg acaaggtcgt tctagcagct    660

ggtgcctgga gttcgacgtt ggtcgatctg gaggagcagt gcgtttcaaa ggcctgggtc    720

tttgcccaca tccaactgac gcccgctgaa gcagccgcgt ataagaacac tcctgttata    780

tacgacggtg actatgggtt tttctttgag ccgaatgaaa acggcatcat aaaagtctgt    840

gacgaattcc ctggcttcac gcatttcaaa atgcaccagc cgtacggctc gccggcgccc    900

aaacccatct ctgtgcctcg ttcccatgcg aagcacccca cagatacata cccgcacgcg    960

tcggaggtca cgatcaaaaa ggctatcaac cggttcctgc cgaggttcaa tgacaaggaa   1020

ctgtttaaca gggccatgtg ctggtgcacc gataccgcgg atgcaaatct gcttgtttgt   1080

gagcatccac gctggaaggg gttttatctt gcaacagggg acagtgggca ttcgttcaag   1140

ttgctgccga atattggaaa gcatgttgtc gagttattgg aggagaggct ggaaagtgtg   1200

tttaaggatg cttggaggtg gaggcctggc agtggggatg cattaaaaag tagacgggct   1260

gcgcctgcga aggacctggc ggatatgccg ggtggagga atgaggcaaa gatgtag       1317
```

```
<210> SEQ ID NO 149
<211> LENGTH: 477
<212> TYPE: PRT
<213> ORGANISM: Cryptococcus neoformans

<400> SEQUENCE: 149

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Arg Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220
```

```
Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Asp Met Asp Val Lys Asp Val Ala
        435                 440                 445

Val Ser Leu Ala Ser Val Lys Ile Gly Glu Asn Ile Gly Glu Lys Val
    450                 455                 460

Val Glu Asp Gly Ala Arg Val Gly Val Lys Val Leu Ala
465                 470                 475
```

<210> SEQ ID NO 150
<211> LENGTH: 1434
<212> TYPE: DNA
<213> ORGANISM: Cryptococcus neoformans

<400> SEQUENCE: 150

```
atgccacctt cgcgcgccag tactaaggtc atagttatcg ggggcggtgg tactctcggg      60

tcctctactg ctcttcacct tttacgagcc ggttacactc catccaacat cactgtgctt     120

gacacgtatc taatcccatc agcacagtcg gctggcaatg acctcaataa gatcatgggt     180

attcgtatca ggaatcctgt agataaacag ttgagcctgg aagcaagaga catgtggagg     240

aatgatgaag ttttcaagcc ttatttccac aacacgggaa gacttgattg tgctcataca     300

ccggagagca ttgcatcttt gcgtaaatcg tacgaggcta tcttaaaggc cgggagcggg     360

ctcgagaaga cccaccattg gctgagtaca gaagatgaaa tactggctag agcccctttg     420

ttggatcgga aacagatcaa aggatggaaa gctatttaca gcgaagatgg gggctggctt     480

gcggcggcga aagctatcaa cagtatcggc caggtgttga aagagaaagg tgtgacattc     540

ggattcggga gtgcgggctc attcaagaaa cccttgtttg acgaagacgg taccaaggcc     600

atcggcattg agacagttga tggtacgcaa tattttgccg acaaggtcgt tctggctgcc     660
```

-continued

```
ggagcttgga gtcctaccct cgtggatttg gaagggcaat gctgttcaaa ggcttgggtt     720

tacgcccata tgcaattgac accagaagag gctgccgaat acaaggagtg tcctgtggtg     780

tacaactctg aacttgggtt cttcttcgag cccaatgaaa aaggagtcat caaagtgtgc     840

gacgaattcc cagggttcac ccgtttcaag caacatcaac cttacggcgc ctcctctact     900

aaacacatct ctttcccgcg ctcccatgcc aaacacccta ccgataccat tccggacgag     960

tcggacgcat ctatccgccg tgctatctct gcctttttac cgagattcaa agaaaaagaa    1020

ctgttcaaca gagcactgtg ctggtgtaca gataccgccg atgccaatct tttgatatgc    1080

gaacatccca aatggaaaaa ttttatctta gctacagggg atagtggaca ttcattcaaa    1140

attcttccca atatcggtaa acatgtcgtt gaacttatag aaggtaccct tgccgaggac    1200

ttggctgaga gctggagatg gagacctgga agcggtgacc ccctgatctc tcgtcgggca    1260

gcccctgcaa gggatcttgc tgatcttcca ggatggaacc atgatgagcc ctcggatgac    1320

gatatggatg taaaggatgt cgctgtatcg cttgcttctg tgaaaattgg cgaaaacatc    1380

ggggagaagg ttgtggaaga tggagcacga gtcggagtca aagttctagc ttag          1434
```

```
<210> SEQ ID NO 151
<211> LENGTH: 437
<212> TYPE: PRT
<213> ORGANISM: Coniochaeta sp.

<400> SEQUENCE: 151

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Ala Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240
```

-continued

```
Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 152
<211> LENGTH: 1314
<212> TYPE: DNA
<213> ORGANISM: Coniochaeta sp.

<400> SEQUENCE: 152

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagcactgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagcag taccaggcac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc ccccatctccg    900

aaacggatat cagtaccacg atcgcacgcc aagcatccca cagacactta tccagacgca     960
```

-continued

```
tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314


<210> SEQ ID NO 153
<211> LENGTH: 437
<212> TYPE: PRT
<213> ORGANISM: Coniochaeta sp.

<400> SEQUENCE: 153

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320
```

```
Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 154
<211> LENGTH: 1314
<212> TYPE: DNA
<213> ORGANISM: Coniochaeta sp.

<400> SEQUENCE: 154

atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagcag taccaggcac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc cccatctccg     900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg acgctgctct cttgatgtgt    1080

gaacacccca aatggaagaa tttcattcta gcgaccggcg acagcggaca ctcattcaaa    1140

atcttgccta acgtcggaaa atacgtagtc gagttgatag agggccgcct gccggaggaa    1200

atggcttatc aatggaggtg gcggccagga ggcgatgcac tcaagtctag acgtgcggca    1260

ccgccaaaag atcttgcaga catgccagga tggaaacatg atccgaaatt gtaa          1314


<210> SEQ ID NO 155
```

<211> LENGTH: 437
<212> TYPE: PRT
<213> ORGANISM: Eupenicillium terrenum

<400> SEQUENCE: 155

Met Ala His Ser Arg Ala Ser Thr Lys Val Val Val Val Gly Gly Gly
1 5 10 15

Gly Thr Ile Gly Ser Ser Thr Ala Leu His Leu Ile Arg Ser Gly Tyr
20 25 30

Thr Pro Ser Asn Ile Thr Val Leu Asp Val Tyr Lys Thr Pro Ser Leu
35 40 45

Gln Ser Ala Gly His Asp Leu Asn Lys Ile Met Gly Ile Asp Leu Arg
50 55 60

Asn Gly Pro Asp Leu Gln Leu Ser Leu Glu Ser Leu Asp Met Trp Gln
65 70 75 80

Asn Asp Glu Leu Phe Lys Pro Phe Phe His Gln Val Gly Met Ile Asp
85 90 95

Cys Ser Ser Ser Lys Glu Gly Ile Glu Asn Leu Arg Arg Lys Tyr Gln
100 105 110

Thr Leu Leu Asp Ala Gly Ile Gly Leu Glu Lys Thr Asn Val Trp Leu
115 120 125

Glu Ser Glu Asp Glu Ile Leu Ala Lys Ala Pro Asn Phe Thr Arg Glu
130 135 140

Gln Val Lys Gly Trp Lys Gly Leu Phe Cys Thr Asp Gly Gly Trp Leu
145 150 155 160

Ala Ala Ala Lys Ala Ile Asn Ala Ile Gly Ile Phe Leu Gln Asp Lys
165 170 175

Gly Val Lys Phe Gly Phe Gly Asp Ala Gly Thr Phe Gln Gln Pro Leu
180 185 190

Phe Ala Ala Asp Gly Lys Thr Cys Ile Gly Leu Glu Thr Thr Asp Gly
195 200 205

Thr Lys Tyr Phe Ala Asp Lys Val Val Leu Ala Ala Gly Ala Trp Ser
210 215 220

Pro Thr Leu Val Asp Leu Glu Asp Gln Cys Val Ser Lys Ala Trp Val
225 230 235 240

Phe Ala His Ile Gln Leu Thr Pro Lys Glu Ala Asp Ala Tyr Lys Asn
245 250 255

Val Pro Val Val Tyr Asp Gly Glu Tyr Gly Phe Phe Phe Glu Pro Asp
260 265 270

Glu Tyr Gly Val Ile Lys Val Cys Asp Glu Phe Pro Gly Phe Ser Arg
275 280 285

Phe Lys Leu His Gln Pro Tyr Gly Ala Ala Ser Pro Lys Met Ile Ser
290 295 300

Val Pro Arg Ser His Ala Lys His Pro Thr Asp Thr Tyr Pro Asp Ala
305 310 315 320

Ser Glu Val Thr Ile Arg Lys Ala Ile Ala Arg Phe Leu Pro Glu Phe
325 330 335

Lys Asp Lys Glu Leu Phe Asn Arg Thr Met Cys Trp Cys Thr Asp Thr
340 345 350

Ala Asp Ala Asn Leu Leu Ile Cys Glu His Pro Lys Trp Lys Asn Phe
355 360 365

Ile Leu Ala Thr Gly Asp Ser Gly His Ser Phe Lys Leu Leu Pro Asn
370 375 380

Ile Gly Lys Tyr Val Val Glu Leu Leu Glu Gly Ser Leu Ser Gln Glu

```
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435


<210> SEQ ID NO 156
<211> LENGTH: 1314
<212> TYPE: DNA
<213> ORGANISM: Eupenicillium terrenum

<400> SEQUENCE: 156

atggctcatt cgcgtgcaag caccaaagtc gtcgtggttg gggaggtgg tacgatcggg     60

tcttcgacgg ctctgcactt aatccgctct ggatataccc cctcaaatat caccgtgctt    120

gacgtataca agaccccttc attgcaatct gcaggacatg atttgaacaa gatcatgggc    180

attgatttgc gcaacgggcc tgacttgcag ctttcgctgg aatcactcga catgtggcaa    240

aacgatgagt tgttcaagcc attctttcac caagtgggca tgattgattg ttcgtcatcc    300

aaagagggta ttgaaaatct tcgacgaaaa taccagaccc tcctcgatgc gggcattggg    360

ctggagaaga cgaacgtttg gctggaatct gaagatgaga tcctcgccaa agcgccgaat    420

ttcacgcgtg aacaagtcaa ggggtggaaa ggcttatttt gcactgatgg aggctggctt    480

gctgcagcca aggctatcaa tgcgatcgga attttcctcc aggacaaagg tgtcaagttt    540

ggctttggag atgctggtac ctttcagcaa cctctgttcg ccgctgatgg aaaaacttgc    600

atcggacttg aaactacaga cggaaccaag tactttgctg acaaggttgt cttggctgct    660

ggtgcgtgga gtcccacctt ggtggatcta gaagatcagt gtgtttcaaa ggcctgggtt    720

ttcgctcata ttcaactcac acccaaagaa gcggacgcgt acaagaatgt gcctgtggtc    780

tatgatggtg aatatgggtt ctttttcgaa cccgacgagt atggggtgat caaagtctgt    840

gacgagttcc ctggtttctc tcgcttcaaa ctgcatcaac cgtacggggc tgcatctccc    900

aagatgatat ccgtaccgcg atcacacgcc aagcatccca cagataccta ccctgatgcc    960

tccgaagtca ccatacgcaa agcgatcgca aggttcctgc cagaatttaa agacaaggag   1020

ctcttcaacc gtaccatgtg ctggtgtaca gatacggccg atgctaactt attgatttgc   1080

gaacacccga agtggaagaa tttcattctg gccactggag atagcggaca ttccttcaag   1140

ctgttgccaa acatcgggaa atacgtagtt gagcttttag agggatctct atcgcaggaa   1200

atggctggtg cctggagatg gagacccgga ggtgatgctc ttagatctag acgcggtgct   1260

ccggcaaagg atcttgctga gatgccggga tggaagcatg atgcacattt gtga         1314


<210> SEQ ID NO 157
<211> LENGTH: 437
<212> TYPE: PRT
<213> ORGANISM: Coniochaeta sp.

<400> SEQUENCE: 157

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45
```

```
Gln Ser Ala Gly His Asp Leu Asn Lys Ile Met Gly Ile Ala Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 158
<211> LENGTH: 1314

<212> TYPE: DNA
<213> ORGANISM: Coniochaeta sp.

<400> SEQUENCE: 158
atgacgtcga atcgtgcaga tacaagggtg attgtcgtcg gtggcggagg aacgattggt 60
tcctcgacag cgctgcatct tgtgaggagt ggttatgctc ccgcaaatat cacggtcttg 120
gacacatttg agattccatc ggctcaatca gccggccatg atctcaacaa gatcatggga 180
atagcactgc gcaacaaggt ggacctgcaa atgagtctag aggctagaca gatgtggaag 240
gaggatgagt tattccagcc cttctttcac aataccggca gaatggactg cgaacacacg 300
cctgagggta tcgaggacct gaaaaagctg taccaggcac tgcacgatgc cggtgcgggt 360
ctggagaaga ctcatgcctg gttggacaac gaggatgaga tcttatccaa gatgccgttg 420
cttcaacgtg accaaataca aggatggaaa gcaatatgga gtcaagatgg cggctggtta 480
gctgcggcaa aggccatcaa tgcgatcgga cagttcttga aagaacgtgg tgtaaagttc 540
ggattcggcg gcgctggatc cttcaagcaa ccccttttcg acgatgaagg cacaacttgc 600
attggcgttg agacggcaga tggtaccaaa tattacgctg acaaggtggt cttagcagct 660
ggcgcatgga gcccaaccct ggtggacctg gaagatcaat gttgctcgaa ggcttgggtg 720
tatgctcata ttcagttgac gcctgaagag gccgctgagt ataagggtgt cccagttgtg 780
tataatggcg aatttggctt cttctttgag cctgatgagt ttggtgtaat aaaggtgtgc 840
gacgagttcc caggattctc gcgcttcaag gaacatcaac cctatggcgc cccatctccg 900
aaacggatat cagtaccacg atcgcacgcc aagcatccca cagacactta tccagacgca 960
tccgaagtca gcatcaaaaa agcaatcgcg acgtttctcc ctcgatttca ggacaaggag 1020
ctcttcaatc gcgccttgtg ctggtgtaca gacactgcgg acgctgctct cttgatgtgt 1080
gaacacccca aatggaagaa tttcattcta gcgaccggcg acagcggaca ctcattcaaa 1140
atcttgccta acgtcggaaa atacgtagtc gagttgatag agggccgcct gccggaggaa 1200
atggcttatc aatggaggtg gcggccagga ggcgatgcac tcaagtctag acgtgcggca 1260
ccgccaaaag atcttgcaga catgccagga tggaaacatg atccgaaatt gtaa 1314

<210> SEQ ID NO 159
<211> LENGTH: 437
<212> TYPE: PRT
<213> ORGANISM: Coniochaeta sp.

<400> SEQUENCE: 159

Met Thr Ser Asn Arg Ala Asp Thr Arg Val Ile Val Val Gly Gly Gly
1 5 10 15

Gly Thr Ile Gly Ser Ser Thr Ala Leu His Leu Val Arg Ser Gly Tyr
20 25 30

Ala Pro Ala Asn Ile Thr Val Leu Asp Thr Phe Glu Ile Pro Ser Ala
35 40 45

Gln Ser Ala Gly His Asp Leu Asn Lys Ile Met Gly Ile Ala Leu Arg
50 55 60

Asn Lys Val Asp Leu Gln Met Ser Leu Glu Ala Arg Gln Met Trp Lys
65 70 75 80

Glu Asp Glu Leu Phe Gln Pro Phe Phe His Asn Thr Gly Arg Met Asp
85 90 95

Cys Glu His Thr Pro Glu Gly Ile Glu Asp Leu Lys Lys Tyr Tyr Gln
100 105 110

Ala Leu His Asp Ala Gly Ala Gly Leu Glu Lys Thr His Ala Trp Leu

```
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 160
<211> LENGTH: 1314
<212> TYPE: DNA
<213> ORGANISM: Coniochaeta sp.

<400> SEQUENCE: 160

atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagcactgc gcaacaaggt ggacctgcaa atgagtctag aggctagaca gatgtggaag     240

gaggatgagt tattccagcc cttctttcac aataccggca gaatggactg cgaacacacg     300
```

-continued

```
cctgagggta tcgaggacct gaaaaagtat taccaggcac tgcacgatgc cggtgcgggt    360

ctggagaaga ctcatgcctg gttggacaac gaggatgaga tcttatccaa gatgccgttg    420

cttcaacgtg accaaataca aggatggaaa gcaatatgga gtcaagatgg cggctggtta    480

gctgcggcaa aggccatcaa tgcgatcgga cagttcttga aagaacgtgg tgtaaagttc    540

ggattcggcg gcgctggatc cttcaagcaa cccctttcg acgatgaagg cacaacttgc    600

attggcgttg agacggcaga tggtaccaaa tattacgctg acaaggtggt cttagcagct    660

ggcgcatgga gcccaaccct ggtggacctg gaagatcaat gttgctcgaa ggcttgggtg    720

tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc cccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa          1314
```

```
<210> SEQ ID NO 161
<211> LENGTH: 437
<212> TYPE: PRT
<213> ORGANISM: Coniochaeta sp.

<400> SEQUENCE: 161

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asn Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190
```

```
Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 162
<211> LENGTH: 1314
<212> TYPE: DNA
<213> ORGANISM: Coniochaeta sp.

<400> SEQUENCE: 162

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

ataaacctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagctg taccaggcac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720
```

```
tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc cccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314
```

<210> SEQ ID NO 163
<211> LENGTH: 437
<212> TYPE: PRT
<213> ORGANISM: Coniochaeta sp.

<400> SEQUENCE: 163

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270
```

```
Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 164
<211> LENGTH: 1314
<212> TYPE: DNA
<213> ORGANISM: Coniochaeta sp.

<400> SEQUENCE: 164

atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagctg taccaggcac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc ccccatctccg    900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg acgctgctct cttgatgtgt    1080

gaacacccca aatggaagaa tttcattcta gcgaccggcg acagcggaca ctcattcaaa    1140
```

atcttgccta acgtcggaaa atacgtagtc gagttgatag agggccgcct gccggaggaa 1200
atggcttatc aatggaggtg gcggccagga ggcgatgcac tcaagtctag acgtgcggca 1260
ccgccaaaag atcttgcaga catgccagga tggaaacatg atccgaaatt gtaa 1314

<210> SEQ ID NO 165
<211> LENGTH: 437
<212> TYPE: PRT
<213> ORGANISM: Coniochaeta sp.

<400> SEQUENCE: 165

Met Thr Ser Asn Arg Ala Asp Thr Arg Val Ile Val Val Gly Gly Gly
1 5 10 15

Gly Thr Ile Gly Ser Ser Thr Ala Leu His Leu Val Arg Ser Gly Tyr
20 25 30

Ala Pro Ala Asn Ile Thr Val Leu Asp Thr Phe Glu Ile Pro Ser Ala
35 40 45

Gln Ser Ala Gly His Asp Leu Asn Lys Ile Met Gly Ile Asp Leu Arg
50 55 60

Asn Lys Val Asp Leu Gln Met Ser Leu Glu Ala Arg Gln Met Trp Lys
65 70 75 80

Glu Asp Glu Leu Phe Gln Pro Phe Phe His Asn Thr Gly Arg Met Asp
85 90 95

Cys Glu His Thr Pro Glu Gly Ile Glu Ala Leu Lys Lys Leu Tyr Gln
100 105 110

Ala Leu His Asp Ala Gly Ala Gly Leu Glu Lys Thr His Ala Trp Leu
115 120 125

Asp Asn Glu Asp Glu Ile Leu Ser Lys Met Pro Leu Leu Gln Arg Asp
130 135 140

Gln Ile Gln Gly Trp Lys Ala Ile Trp Ser Gln Asp Gly Gly Trp Leu
145 150 155 160

Ala Ala Ala Lys Ala Ile Asn Ala Ile Gly Gln Phe Leu Lys Glu Arg
165 170 175

Gly Val Lys Phe Gly Phe Gly Gly Ala Gly Ser Phe Lys Gln Pro Leu
180 185 190

Phe Asp Asp Glu Gly Thr Thr Cys Ile Gly Val Glu Thr Ala Asp Gly
195 200 205

Thr Lys Tyr Tyr Ala Asp Lys Val Val Leu Ala Ala Gly Ala Trp Ser
210 215 220

Pro Thr Leu Val Asp Leu Glu Asp Gln Cys Cys Ser Lys Ala Trp Val
225 230 235 240

Tyr Ala His Ile Gln Leu Thr Pro Glu Glu Ala Ala Glu Tyr Lys Gly
245 250 255

Val Pro Val Val Tyr Asn Gly Glu Phe Gly Phe Phe Phe Glu Pro Asp
260 265 270

Glu Phe Gly Val Ile Lys Val Cys Asp Glu Phe Pro Gly Phe Ser Arg
275 280 285

Phe Lys Glu His Gln Pro Tyr Gly Ala Pro Ser Pro Lys Arg Ile Ser
290 295 300

Val Pro Arg Ser His Ala Lys His Pro Thr Asp Thr Tyr Pro Asp Ala
305 310 315 320

Ser Glu Val Ser Ile Lys Lys Ala Ile Ala Thr Phe Leu Pro Arg Phe
325 330 335

Gln Asp Lys Glu Leu Phe Asn Arg Ala Leu Cys Trp Cys Thr Asp Thr

```
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 166
<211> LENGTH: 1314
<212> TYPE: DNA
<213> ORGANISM: Coniochaeta sp.

<400> SEQUENCE: 166

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggccct gaaaaagctg taccaggcac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc cccatctccg     900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg acgctgctct cttgatgtgt    1080

gaacacccca aatggaagaa tttcattcta gcgaccggcg acagcggaca ctcattcaaa    1140

atcttgccta acgtcggaaa atacgtagtc gagttgatag agggccgcct gccggaggaa    1200

atggcttatc aatggaggtg gcggccagga ggcgatgcac tcaagtctag acgtgcggca    1260

ccgccaaaag atcttgcaga catgccagga tggaaacatg atccgaaatt gtaa          1314
```

<210> SEQ ID NO 167
<211> LENGTH: 437
<212> TYPE: PRT
<213> ORGANISM: Coniochaeta sp.

<400> SEQUENCE: 167

-continued

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415
```

-continued

Arg Arg Ala Ala Pro Pro Lys Asp Leu Ala Asp Met Pro Gly Trp Lys
            420                 425                 430

His Asp Pro Lys Leu
        435

<210> SEQ ID NO 168
<211> LENGTH: 1314
<212> TYPE: DNA
<213> ORGANISM: Coniochaeta sp.

<400> SEQUENCE: 168
atgacgtcga atcgtgcaga tacaagggtg attgtcgtcg gtggcggagg aacgattggt 60
tcctcgacag cgctgcatct tgtgaggagt ggttatgctc ccgcaaatat cacggtcttg 120
gacacatttg agattccatc ggctcaatca gccggccatg atctcaacaa gatcatggga 180
atagatctgc gcaacaaggt ggacctgcaa atgagtctag aggctagaca gatgtggaag 240
gaggatgagt tattccagcc cttctttcac aataccggca gaatggactg cgaacacacg 300
cctgagggta tcgagaaact gaaaaagctg taccaggcac tgcacgatgc cggtgcgggt 360
ctggagaaga ctcatgcctg gttggacaac gaggatgaga tcttatccaa gatgccgttg 420
cttcaacgtg accaaataca aggatggaaa gcaatatgga gtcaagatgg cggctggtta 480
gctgcggcaa aggccatcaa tgcgatcgga cagttcttga aagaacgtgg tgtaaagttc 540
ggattcggcg gcgctggatc cttcaagcaa ccccttttcg acgatgaagg cacaacttgc 600
attggcgttg agacggcaga tggtaccaaa tattacgctg acaaggtggt cttagcagct 660
ggcgcatgga gcccaaccct ggtggacctg gaagatcaat gttgctcgaa ggcttgggtg 720
tatgctcata ttcagttgac gcctgaagag gccgctgagt ataagggtgt cccagttgtg 780
tataatggcg aatttggctt cttctttgag cctgatgagt ttggtgtaat aaaggtgtgc 840
gacgagttcc caggattctc gcgcttcaag gaacatcaac cctatggcgc cccatctccg 900
aaacggatat cagtaccacg atcgcacgcc aagcatccca cagacactta tccagacgca 960
tccgaagtca gcatcaaaaa agcaatcgcg acgtttctcc ctcgatttca ggacaaggag 1020
ctcttcaatc gcgccttgtg ctggtgtaca gacactgcgg acgctgctct cttgatgtgt 1080
gaacacccca aatggaagaa tttcattcta gcgaccggcg acagcggaca ctcattcaaa 1140
atcttgccta acgtcggaaa atacgtagtc gagttgatag agggccgcct gccggaggaa 1200
atggcttatc aatggaggtg gcggccagga ggcgatgcac tcaagtctag acgtgcggca 1260
ccgccaaaag atcttgcaga catgccagga tggaaacatg atccgaaatt gtaa 1314

<210> SEQ ID NO 169
<211> LENGTH: 437
<212> TYPE: PRT
<213> ORGANISM: Coniochaeta sp.

<400> SEQUENCE: 169

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys

-continued

```
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Arg Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 170
<211> LENGTH: 1314
<212> TYPE: DNA
<213> ORGANISM: Coniochaeta sp.

<400> SEQUENCE: 170
```

-continued

```
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagcgcct gaaaaagctg taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga aagaacgtgg tgtaaagttc     540
ggattcggcg gcgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaaccct ggtggacctg gaagatcaat gttgctcgaa ggcttgggtg     720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta tccagacgca     960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca aatggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

```
<210> SEQ ID NO 171
<211> LENGTH: 437
<212> TYPE: PRT
<213> ORGANISM: Coniochaeta sp.

<400> SEQUENCE: 171

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140
```

-continued

```
Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 172
<211> LENGTH: 1314
<212> TYPE: DNA
<213> ORGANISM: Coniochaeta sp.

<400> SEQUENCE: 172

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagctg taccagaaac tgcacgatgc cggtgcgggt     360

ctggagaaga ctcatgcctg gttggacaac gaggatgaga tcttatccaa gatgccgttg     420
```

-continued

```
cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa cccctttcg acgatgaagg cacaacttgc      600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc cccatctccg     900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg acgctgctct cttgatgtgt    1080

gaacacccca aatggaagaa tttcattcta gcgaccggcg acagcggaca ctcattcaaa    1140

atcttgccta acgtcggaaa atacgtagtc gagttgatag agggccgcct gccggaggaa    1200

atggcttatc aatggaggtg gcggccagga ggcgatgcac tcaagtctag acgtgcggca    1260

ccgccaaaag atcttgcaga catgccagga tggaaacatg atccgaaatt gtaa          1314
```

```
<210> SEQ ID NO 173
<211> LENGTH: 437
<212> TYPE: PRT
<213> ORGANISM: Coniochaeta sp.

<400> SEQUENCE: 173

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

Arg Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220
```

```
Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 174
<211> LENGTH: 1314
<212> TYPE: DNA
<213> ORGANISM: Coniochaeta sp.

<400> SEQUENCE: 174

atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagctg taccagcgtc tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840
```

```
gacgagttcc caggattctc gcgcttcaag gaacatcaac cctatggcgc cccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314


<210> SEQ ID NO 175
<211> LENGTH: 437
<212> TYPE: PRT
<213> ORGANISM: Coniochaeta sp.

<400> SEQUENCE: 175

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Arg Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
```

```
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 176
<211> LENGTH: 1314
<212> TYPE: DNA
<213> ORGANISM: Coniochaeta sp.

<400> SEQUENCE: 176

atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgagaaact gaaaaagctg taccagcgtc tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc cccatctccg     900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg acgctgctct cttgatgtgt    1080

gaacacccca aatggaagaa tttcattcta gcgaccggcg acagcggaca ctcattcaaa    1140

atcttgccta acgtcggaaa atacgtagtc gagttgatag agggccgcct gccggaggaa    1200

atggcttatc aatggaggtg gcggccagga ggcgatgcac tcaagtctag acgtgcggca    1260
```

-continued ccgccaaaag atcttgcaga catgccagga tggaaacatg atccgaaatt gtaa 1314

<210> SEQ ID NO 177
<211> LENGTH: 437
<212> TYPE: PRT
<213> ORGANISM: Coniochaeta sp.

<400> SEQUENCE: 177

Met Thr Ser Asn Arg Ala Asp Thr Arg Val Ile Val Val Gly Gly Gly
1 5 10 15

Gly Thr Ile Gly Ser Ser Thr Ala Leu His Leu Val Arg Ser Gly Tyr
20 25 30

Ala Pro Ala Asn Ile Thr Val Leu Asp Thr Phe Glu Ile Pro Ser Ala
35 40 45

Gln Ser Ala Gly His Asp Leu Asn Lys Ile Met Gly Ile Asp Ala Arg
50 55 60

Asn Lys Val Asp Leu Gln Met Ser Leu Glu Ala Arg Gln Met Trp Lys
65 70 75 80

Glu Asp Glu Leu Phe Gln Pro Phe Phe His Asn Thr Gly Arg Met Asp
85 90 95

Cys Glu His Thr Pro Glu Gly Ile Glu Lys Leu Lys Lys Leu Tyr Gln
100 105 110

Lys Leu His Asp Ala Gly Ala Gly Leu Glu Lys Thr His Ala Trp Leu
115 120 125

Asp Asn Glu Asp Glu Ile Leu Ser Lys Met Pro Leu Leu Gln Arg Asp
130 135 140

Gln Ile Gln Gly Trp Lys Ala Ile Trp Ser Gln Asp Gly Gly Trp Leu
145 150 155 160

Ala Ala Ala Lys Ala Ile Asn Ala Ile Gly Gln Phe Leu Lys Glu Arg
165 170 175

Gly Val Lys Phe Gly Phe Gly Gly Ala Gly Ser Phe Lys Gln Pro Leu
180 185 190

Phe Asp Asp Glu Gly Thr Thr Cys Ile Gly Val Glu Thr Ala Asp Gly
195 200 205

Thr Lys Tyr Tyr Ala Asp Lys Val Val Leu Ala Ala Gly Ala Trp Ser
210 215 220

Pro Thr Leu Val Asp Leu Glu Asp Gln Cys Cys Ser Lys Ala Trp Val
225 230 235 240

Tyr Ala His Ile Gln Leu Thr Pro Glu Glu Ala Ala Glu Tyr Lys Gly
245 250 255

Val Pro Val Val Tyr Asn Gly Glu Phe Gly Phe Phe Phe Glu Pro Asp
260 265 270

Glu Phe Gly Val Ile Lys Val Cys Asp Glu Phe Pro Gly Phe Ser Arg
275 280 285

Phe Lys Glu His Gln Pro Tyr Gly Ala Pro Ser Pro Lys Arg Ile Ser
290 295 300

Val Pro Arg Ser His Ala Lys His Pro Thr Asp Thr Tyr Pro Asp Ala
305 310 315 320

Ser Glu Val Ser Ile Lys Lys Ala Ile Ala Thr Phe Leu Pro Arg Phe
325 330 335

Gln Asp Lys Glu Leu Phe Asn Arg Ala Leu Cys Trp Cys Thr Asp Thr
340 345 350

Ala Asp Ala Ala Leu Leu Met Cys Glu His Pro Lys Trp Lys Asn Phe
355 360 365

```
Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 178
<211> LENGTH: 1314
<212> TYPE: DNA
<213> ORGANISM: Coniochaeta sp.

<400> SEQUENCE: 178

atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatgcgc gcaacaaggt ggacctgcaa atgagtctag aggctagaca gatgtggaag     240

gaggatgagt tattccagcc cttctttcac aataccggca gaatggactg cgaacacacg     300

cctgagggta tcgagaaact gaaaaagctg taccagaaac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc cccatctccg     900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg acgctgctct cttgatgtgt    1080

gaacacccca aatggaagaa tttcattcta gcgaccggcg acagcggaca ctcattcaaa    1140

atcttgccta acgtcggaaa atacgtagtc gagttgatag agggccgcct gccggaggaa    1200

atggcttatc aatggaggtg gcggccagga ggcgatgcac tcaagtctag acgtgcggca    1260

ccgccaaaag atcttgcaga catgccagga tggaaacatg atccgaaatt gtaa          1314


<210> SEQ ID NO 179
<211> LENGTH: 437
<212> TYPE: PRT
<213> ORGANISM: Coniochaeta sp.

<400> SEQUENCE: 179

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
```

-continued

```
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 180
<211> LENGTH: 1314
<212> TYPE: DNA
<213> ORGANISM: Coniochaeta sp.

<400> SEQUENCE: 180
atgacgtcga atcgtgcaga tacaagggtg attgtcgtcg gtggcggagg aacgattggt 60
tcctcgacag cgctgcatct tgtgaggagt ggttatgctc ccgcaaatat cacggtcttg 120
gacacatttg agattccatc ggctcaatca gccggccatg atctcaacaa gatcatggga 180
atagatcatc gcaacaaggt ggacctgcaa atgagtctag aggctagaca gatgtggaag 240
gaggatgagt tattccagcc cttctttcac aataccggca gaatggactg cgaacacacg 300
cctgagggta tcgagaaact gaaaaagctg taccagaaac tgcacgatgc cggtgcgggt 360
ctggagaaga ctcatgcctg gttggacaac gaggatgaga tcttatccaa gatgccgttg 420
cttcaacgtg accaaataca aggatggaaa gcaatatgga gtcaagatgg cggctggtta 480
gctgcggcaa aggccatcaa tgcgatcgga cagttcttga aagaacgtgg tgtaaagttc 540
ggattcggcg gcgctggatc cttcaagcaa ccccttttcg acgatgaagg cacaacttgc 600
attggcgttg agacggcaga tggtaccaaa tattacgctg acaaggtggt cttagcagct 660
ggcgcatgga gcccaaccct ggtggacctg gaagatcaat gttgctcgaa ggcttgggtg 720
tatgctcata ttcagttgac gcctgaagag gccgctgagt ataagggtgt cccagttgtg 780
tataatggcg aatttggctt cttctttgag cctgatgagt ttggtgtaat aaaggtgtgc 840
gacgagttcc caggattctc gcgcttcaag gaacatcaac cctatggcgc ccccatctccg 900 aaacggatat cagtaccacg atcgcacgcc aagcatccca cagacactta tccagacgca 960
tccgaagtca gcatcaaaaa agcaatcgcg acgtttctcc ctcgatttca ggacaaggag 1020
ctcttcaatc gcgccttgtg ctggtgtaca gacactgcgg acgctgctct cttgatgtgt 1080
gaacacccca aatggaagaa tttcattcta gcgaccggcg acagcggaca ctcattcaaa 1140
atcttgccta acgtcggaaa atacgtagtc gagttgatag agggccgcct gccggaggaa 1200
atggcttatc aatggaggtg gcggccagga ggcgatgcac tcaagtctag acgtgcggca 1260
ccgccaaaag atcttgcaga catgccagga tggaaacatg atccgaaatt gtaa 1314

<210> SEQ ID NO 181
<211> LENGTH: 437
<212> TYPE: PRT
<213> ORGANISM: Coniochaeta sp.

<400> SEQUENCE: 181

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

-continued

```
Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 182
<211> LENGTH: 1314
<212> TYPE: DNA
<213> ORGANISM: Coniochaeta sp.

<400> SEQUENCE: 182

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180
```

```
atagatcatc gcaacaaggt ggacctgcaa atgagtctag aggctagaca gatgtggaag    240

gaggatgagt tattccagcc cttctttcac aataccggca gaatggactg cgaacacacg    300

cctaagggta tcgagaaact gaaaaagctg taccagaaac tgcacgatgc cggtgcgggt    360

ctggagaaga ctcatgcctg gttggacaac gaggatgaga tcttatccaa gatgccgttg    420

cttcaacgtg accaaataca aggatggaaa gcaatatgga gtcaagatgg cggctggtta    480

gctgcggcaa aggccatcaa tgcgatcgga cagttcttga aagaacgtgg tgtaaagttc    540

ggattcggcg gcgctggatc cttcaagcaa ccccttttcg acgatgaagg cacaacttgc    600

attggcgttg agacggcaga tggtaccaaa tattacgctg acaaggtggt cttagcagct    660

ggcgcatgga gcccaaccct ggtggacctg gaagatcaat gttgctcgaa ggcttgggtg    720

tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc cccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314
```

```
<210> SEQ ID NO 183
<211> LENGTH: 437
<212> TYPE: PRT
<213> ORGANISM: Coniochaeta sp.

<400> SEQUENCE: 183

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175
```

```
Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Lys Ala Pro Pro Lys Asp Leu Ala Asp Met Pro Gly Trp Lys
            420                 425                 430

His Asp Pro Lys Leu
        435
```

<210> SEQ ID NO 184
<211> LENGTH: 1314
<212> TYPE: DNA
<213> ORGANISM: Coniochaeta sp.

<400> SEQUENCE: 184

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatcatc gcaacaaggt ggacctgcaa atgagtctag aggctagaca gatgtggaag     240

gaggatgagt tattccagcc cttctttcac aataccggca gaatggactg cgaacacacg     300

cctgagggta tcgagaaact gaaaaagctg taccagaaac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600
```

```
attggcgttg agacggcaga tggtaccaaa tattacgctg acaaggtggt cttagcagct    660

ggcgcatgga gcccaaccct ggtggacctg gaagatcaat gttgctcgaa ggcttgggtg    720

tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc ccatctccg     900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtaaggca   1260

ccgccaaaag atcttgcaga catgccagga tggaaacatg atccgaaatt gtaa         1314
```

<210> SEQ ID NO 185
<211> LENGTH: 438
<212> TYPE: PRT
<213> ORGANISM: Aspergillus nidulans

<400> SEQUENCE: 185

```
Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Gly Ile Asp His Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Met Ile Asp Val
                85                  90                  95

Ser Ser Thr Glu Lys Gly Ile Glu Lys Leu Arg Lys Leu Tyr Gln Lys
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Ala Tyr Lys Asn
```

-continued

```
                245                 250                 255

Thr Pro Val Ile Tyr Asp Gly Asp Tyr Gly Phe Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435


<210> SEQ ID NO 186
<211> LENGTH: 1317
<212> TYPE: DNA
<213> ORGANISM: Aspergillus nidulans

<400> SEQUENCE: 186

atgacgcccc gagccaacac caaaatcatt gtcgtcggcg gcggcggcac aatgggctcg      60

tcgacagccc tacacctcct gcgcgccggc tacacgccgt ccaacattac agtgctcgac     120

acgtgcccta tcccctccgc acagtctgca ggctacgacc tgaacaaaat catgggcatc     180

gatcatcgca acaagcctga tttacagctc tctcttgagg cgctggacat gtggaaaaat     240

gatcctctct tcaagccgtt tttccacaat gttggaatga tcgacgtctc ttcaacagag     300

aaaggcatcg agaaacttcg gaagctgtac cagaaacttc tcgacgcagg cattgggctc     360

gagaagacga atttcatgct ggaaagtgaa gacgagatcc tggctaaagc gccgcatttc     420

acgcaggagc agattaaagg ctggaaaggc ctgttctgtg gcgacggcgg ctggctcgct     480

gcagccaaag ccatcaatgc cattgggcag ttcctcaagg aacagggcgt caagtttgga     540

ttcggcggcg ccggcacgtt caaaaagcca ctcttcgccg atgcccacga gaagacgtgc     600

atcggcgtcg agactgtaga cggcacaaag tactacgccg acaaggtcgt tctagcagct     660

ggtgcctgga gttcgacgtt ggtcgatctg gaggagcagt gcgtttcaaa ggcctgggtc     720

tttgcccaca tccaactgac gcccgctgaa gcagccgcgt ataagaacac tcctgttata     780

tacgacggtg actatgggtt tttctttgag ccgaatgaaa acggcatcat aaaagtctgt     840

gacgaattcc ctggcttcac gcatttcaaa atgcaccagc cgtacggctc gccggcgccc     900

aaacccatct ctgtgcctcg ttcccatgcg aagcacccca cagatacata cccgcacgcg     960

tcggaggtca cgatcaaaaa ggctatcaac cggttcctgc cgaggttcaa tgacaaggaa    1020
```

ctgtttaaca gggccatgtg ctggtgcacc gataccgcgg atagcaatct gcttgtttgt 1080
gagcatccac gctggaaggg gttttatctt gcaacagggg acagtgggca ttcgttcaag 1140
ttgctgccga atattggaaa gcatgttgtc gagttattgg aggagaggct ggaaagtgtg 1200
tttaaggatg cttggaggtg gaggcctggc agtggggatg cattaaaaag tagacgggct 1260
gcgcctgcga aggacctggc ggatatgccg gggtggagga atgaggcaaa gatgtag 1317

<210> SEQ ID NO 187
<211> LENGTH: 437
<212> TYPE: PRT
<213> ORGANISM: Phaeosphaeria nodorum

<400> SEQUENCE: 187

Met Ala Pro Ser Arg Ala Asn Thr Ser Val Ile Val Val Gly Gly Gly
1 5 10 15

Gly Thr Ile Gly Ser Ser Thr Ala Leu His Leu Val Arg Ser Gly Tyr
20 25 30

Thr Pro Ser Asn Val Thr Val Leu Asp Ala Tyr Pro Ile Pro Ser Ser
35 40 45

Gln Ser Ala Gly Asn Asp Leu Asn Lys Ile Met Gly Val Asp His Arg
50 55 60

Asn Pro Val Asp Leu Gln Leu Ala Leu Glu Ala Arg Gln Met Trp Asn
65 70 75 80

Glu Asp Glu Leu Phe Lys Lys Phe Phe His Asn Thr Gly Arg Leu Asp
85 90 95

Cys Ala His Gly Glu Lys Asp Ile Ala Lys Leu Lys Ser Leu Tyr Gln
100 105 110

Lys Leu Val Asp Ala Gly Leu Asp Ala Thr Asn Glu Trp Leu Asp Ser
115 120 125

Glu Asp Glu Ile Leu Lys Arg Met Pro Leu Leu Ser Arg Asp Gln Ile
130 135 140

Lys Gly Trp Lys Ala Ile Phe Ser Lys Asp Gly Gly Trp Leu Ala Ala
145 150 155 160

Ala Lys Ala Ile Asn Ala Val Gly Glu Tyr Leu Arg Asp Gln Gly Val
165 170 175

Arg Phe Gly Phe Tyr Gly Ala Gly Ser Phe Lys Ala Pro Leu Leu Ala
180 185 190

Glu Gly Val Cys Ile Gly Val Glu Thr Val Asp Gly Thr Arg Tyr Tyr
195 200 205

Ala Asp Lys Val Val Leu Ala Ala Gly Ala Trp Ser Pro Thr Leu Val
210 215 220

Glu Leu His Glu Gln Cys Val Ser Lys Ala Trp Val Tyr Gly His Ile
225 230 235 240

Gln Leu Thr Pro Glu Glu Ala Ala Arg Tyr Lys Asn Ser Pro Val Val
245 250 255

Tyr Asn Gly Asp Val Gly Phe Phe Phe Glu Pro Asn Glu His Gly Val
260 265 270

Ile Lys Val Cys Asp Glu Phe Pro Gly Phe Thr Arg Phe Lys Met His
275 280 285

Gln Pro Phe Gly Ala Lys Ala Pro Lys Arg Ile Ser Val Pro Arg Ser
290 295 300

His Ala Lys His Pro Thr Asp Thr Ile Pro Asp Ala Ser Asp Val Ser
305 310 315 320

```
Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ser Ala
            340                 345                 350

Leu Leu Ile Cys Glu His Pro Glu Trp Lys Asn Phe Val Leu Ala Thr
        355                 360                 365

Gly Asp Ser Gly His Ser Phe Lys Leu Leu Pro Asn Ile Gly Lys His
    370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435


<210> SEQ ID NO 188
<211> LENGTH: 1314
<212> TYPE: DNA
<213> ORGANISM: Phaeosphaeria nodorum

<400> SEQUENCE: 188

atggccccgt cgcgtgctaa tacgtcggtc attgtggttg gtggtggtgg tacgattggc      60

tcatctacgg ctctgcatct ggtccgctca ggctataccc cgtcgaacgt gacggttctg     120

gatgcatacc cgattccgag ctctcagagc gctggcaacg acctgaataa aatcatgggt     180

gtcgatcatc gtaatccggt ggatctgcag ctggctctgg aagcgcgcca aatgtggaac     240

gaagacgaac tgttcaagaa gtttttccat aacaccggcc gtctggattg cgcgcacggt     300

gaaaaagata ttgccaaact gaagagcctg tatcagaaac tggtggatgc gggtctggac     360

gccacgaacg aatggctgga tagtgaagac gaaatcctga aacgtatgcc gctgctgtcc     420

cgcgatcaaa ttaaaggctg gaaggcgatc ttttcaaaag acggtggttg gctggcagca     480

gcaaaggcaa ttaatgcagt tggtgaatat ctgcgtgatc agggcgtccg cttcggtttt     540

tacggcgccg gttctttcaa agcaccgctg ctggctgaag gcgtctgcat cggtgtcgaa     600

accgtggatg gcacgcgcta ttacgcagac aaagtggttc tggctgcagg tgcatggtcg     660

ccgaccctgg ttgaactgca tgaacagtgt gtgagcaaag cgtgggttta cggccacatt     720

caactgacgc cggaagaagc cgcacgttat aagaacagcc cggtcgtgta caatggcgat     780

gtgggctttt tctttgaacc gaacgaacat ggcgttatca aagtctgcga tgaatttccg     840

ggttttaccc gcttcaagat gcaccagccg tttggtgcca aagcaccgaa gcgtattagt     900

gtgccgcgct cccatgccaa acacccgacc gatacgatcc cggatgcaag tgacgtttcc     960

attcgtcgcg ctatcgcgac ctttatgccg cagttcaaga acaaaaagat gttcaaccaa    1020

gcgatgtgct ggtgtaccga tacggccgac agcgcgctgc tgatttgtga acatccggaa    1080

tggaaaaact ttgttctggc gaccggcgat tcaggtcatt cgttcaaact gctgccgaat    1140

atcggcaagc acgttgtcga actgctggag ggtacgctgg cagatgacct ggcacacgca    1200

tggcgttggc gtccgggtag tggtgatgca ctgaaaagcc gtcgctctgc tccggcgaaa    1260

gacctggctg atatgccggg ctggaaccat gacaaaccgc gtgctaatct gtaa          1314


<210> SEQ ID NO 189
<211> LENGTH: 443
```

<212> TYPE: PRT
<213> ORGANISM: Cryptococcus neoformans

<400> SEQUENCE: 189

```
Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Asp Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Lys Leu Arg Lys Leu Tyr Glu
            100                 105                 110

Lys Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Ile Gly Lys His Val Val Glu Leu Ile Glu Gly Thr Leu Ala Glu Asp
385                 390                 395                 400
```

```
Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Asp Met Asp
        435                 440


<210> SEQ ID NO 190
<211> LENGTH: 1332
<212> TYPE: DNA
<213> ORGANISM: Cryptococcus neoformans

<400> SEQUENCE: 190

atgccgccgt cccgtgcttc aacgaaagtg attgtcattg gtggtggtgg tacgctgggc      60

tcctcaaccg ccctgcatct gctgcgcgcg ggctataccc cgagtaacat taccgtgctg     120

gatacgtacc tgatcccgag tgcccagtcc gcaggcaacg acctgaataa aattatgggt     180

attgatatcc gcaatccggt ggataaacaa ctgagcctgg aagcccgtga tatgtggcgc     240

aacgacgaag ttttcaaacc gtacttccat aacaccggtc gtctggactg cgctcacacg     300

ccggaatcaa ttgcgaaact gcgtaaactg tacgaaaaaa tcctgaaagc aggctcaggt     360

ctggaaaaaa cccatcactg gctgtcgacg gaagatgaaa tcctggcacg tgcaccgctg     420

ctggaccgta aacagattaa aggttggaaa gcaatctata gtgaagatgg cggttggctg     480

gcggccgcaa aagctattaa ctccatcggc caagtcctga aagaaaaagg tgtgaccttc     540

ggctttggta gcgcaggctc ttttaaaaaa ccgctgttcg atgaagacgg cacgaaagcc     600

attggtatcg aaaccgttga tggtacgcag tattttgccg acaaagtggt tctggctgca     660

ggtgcatgga gcccgaccct ggttgatctg gaaggccagt gctgttctaa agcttgggtc     720

tacgcgcaca tgcaactgac gccggaagaa gccgcagaat ataaagaatg cccggtcgtg     780

tacaacagcg aactgggctt tttctttgaa ccgaacgaaa aaggtgtgat caaagtttgt     840

gatgaattcc cgggctttac ccgtttcaaa cagcatcaac cgtacggtgc tagctctacg     900

aaacacatta gctttccgcg ctctcatgcg aaacacccga ccgatacgat cccggatgaa     960

agtgacgcct ccattcgtcg cgctatctct gcgtttctgc cgcgtttcaa agaaaaagaa    1020

ctgtttaacc gcgcgctgtg ctggtgtacc gatacggctg acgcgaacct gctgatttgt    1080

gaacacccga aatggaaaaa ttttatcctg gccaccggcg attcaggtca ttcgttcaaa    1140

attctgccga atatcggcaa acacgttgtc gaactgattg aaggtaccct ggccgaagat    1200

ctggcagaaa gctggcgttg gcgtccgggc agtggtgacc cgctgatctc ccgtcgcgct    1260

gcgccggcgc gcgacctggc ggacctgccg ggctggaacc acgacgaacc gagcgacgat    1320

gacatggact ga                                                        1332


<210> SEQ ID NO 191
<211> LENGTH: 440
<212> TYPE: PRT
<213> ORGANISM: Curvularia clavata

<400> SEQUENCE: 191

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Ala Tyr Pro Ile Pro Ser Ser
```

-continued

```
        35                  40                  45

Gln Ser Ala Gly Asn Asp Leu Asn Lys Ile Met Gly Ile Asp His Arg
    50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Lys Leu Arg Gln Leu Tyr Gln
            100                 105                 110

Lys Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Ser Arg Asp
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Thr
    210                 215                 220

Leu Val Glu Leu His Glu Gln Cys Val Ser Lys Ala Trp Val Tyr Gly
225                 230                 235                 240

His Ile Gln Leu Thr Pro Glu Glu Ala Ala Glu Tyr Lys Asn Ser Pro
                245                 250                 255

Val Val Tyr Asn Gly Asp Val Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Met His Gln Pro Phe Gly Ala Lys Ala Pro Lys Arg Ile Ser Val Pro
    290                 295                 300

Arg Ser His Ala Lys His Pro Thr Asp Thr Ile Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ser Ala Leu Leu Ile Cys Glu His Pro Glu Trp Lys Asn Phe Val Leu
        355                 360                 365

Ala Thr Gly Asp Ser Gly His Ser Phe Lys Leu Leu Pro Asn Ile Gly
    370                 375                 380

Lys His Val Val Glu Leu Leu Glu Gly Thr Leu Ala Asp Asp Leu Ala
385                 390                 395                 400

His Ala Trp Arg Trp Arg Pro Gly Ser Gly Asp Ala Leu Lys Ser Arg
                405                 410                 415

Arg Ser Ala Pro Ala Lys Asp Leu Ala Asp Met Pro Gly Trp Lys His
            420                 425                 430

Asp Asp Val Val Lys Ser Lys Leu
        435                 440
```

<210> SEQ ID NO 192

-continued

```
<211> LENGTH: 1323
<212> TYPE: DNA
<213> ORGANISM: Curvularia clavata

<400> SEQUENCE: 192

atggccccgt cgcgtgctaa tacgtcggtc attgtggttg gtggtggtgg tacgattggc      60

tcatctacgg ctctgcatct ggtccgctca ggctataccc cgtcgaacat tacggttctg     120

gatgcatacc cgattccgag ctctcagagc gctggcaacg acctgaataa aatcatgggt     180

atcgatcatc gtaataaggt ggatctgcag ctgtctctgg aagcgcgcca aatgtggcgc     240

gaagacgatc tgttcaagga gtatttccat aacaccggcc gtctggattg cgcgcacggt     300

gaagaaggtc ttgccaaact gcgtcaactg tatcagaaac tgctggatgc gaatgcgggt     360

ctggaagaga cgaccgaatg gctggatagt gaagacgaaa tcctgaaaaa aatgccgctg     420

ctgtcccgcg atcaaattaa aggctggaag gcggtgtatt cacaggacgg tggttggctg     480

gcagcagcaa aggcaattaa tgcaattggt gaatatctgc gtgctcaggg cgtcaaattc     540

ggttttggcg gcgccggttc tttcaaacaa ccgctgctgg ctgaaggcgt ctgcatcggt     600

gtcgaaaccg tggatggcac gcgctattac gcagacaaag tggttctggc tgcaggtgca     660

tggtcgccga ccctggttga actgcatgaa cagtgtgtga gcaaagcgtg ggtttacggc     720

cacattcaac tgacgccgga agaagccgca gaatataaga acagcccggt cgtgtacaat     780

ggcgatgtgg gctttttctt tgaaccgaac gaacatggcg ttatcaaagt ctgcgatgaa     840

tttccgggtt ttacccgctt caagatgcac cagccgtttg gtgccaaagc accgaagcgt     900

attagtgtgc cgcgctccca tgccaaacac ccgaccgata cgatcccgga tgcaagtgaa     960

aaatccattc gtaaagctat cgcgaccttt ctgccgaagt tcacggagaa agagctgttc    1020

aaccgtcatc tgtgctggtg taccgatacg gccgacagcg cgctgctgat ttgtgaacat    1080

ccggaatgga aaaactttgt tctggcgacc ggcgattcag gtcattcgtt caaactgctg    1140

ccgaatatcg gcaagcacgt tgtcgaactg ctggagggta cgctggcaga tgacctggca    1200

cacgcatggc gttggcgtcc gggtagtggt gatgcactga aaagccgtcg ctctgctccg    1260

gcgaaagacc tggctgatat gccgggctgg aaacatgacg atgtggtgaa aagcaaactg    1320

taa                                                                  1323
```